United States Patent
Yu et al.

(10) Patent No.: US 11,858,879 B2
(45) Date of Patent: Jan. 2, 2024

(54) PARG INHIBITORS AND METHOD OF USE THEREOF

(71) Applicant: City of Hope, Duarte, CA (US)

(72) Inventors: Xiaochun Yu, Glendora, CA (US); Shih-Hsun Chen, Duarte, CA (US); Yate-Ching Yuan, Duarte, CA (US); Hongzhi Li, Duarte, CA (US); David Horne, Altadena, CA (US)

(73) Assignee: CITY OF HOPE, Duarte, CA (US)

( * ) Notice: Subject to any disclaimer, the term of this patent is extended or adjusted under 35 U.S.C. 154(b) by 263 days.

(21) Appl. No.: 16/625,511

(22) PCT Filed: Jun. 22, 2018

(86) PCT No.: PCT/US2018/039053
§ 371 (c)(1),
(2) Date: Dec. 20, 2019

(87) PCT Pub. No.: WO2018/237296
PCT Pub. Date: Dec. 27, 2018

(65) Prior Publication Data
US 2022/0002231 A1 Jan. 6, 2022

Related U.S. Application Data

(60) Provisional application No. 62/592,043, filed on Nov. 29, 2017, provisional application No. 62/524,182, filed on Jun. 23, 2017.

(51) Int. Cl.
C07C 251/86 (2006.01)
C07C 311/17 (2006.01)
C07C 311/29 (2006.01)
A61P 35/00 (2006.01)

(52) U.S. Cl.
CPC ............ *C07C 251/86* (2013.01); *A61P 35/00* (2018.01); *C07C 311/17* (2013.01); *C07C 311/29* (2013.01)

(58) Field of Classification Search
CPC .... C07C 251/86; C07C 311/17; C07C 311/29
See application file for complete search history.

(56) References Cited

U.S. PATENT DOCUMENTS

| | | | | |
|---|---|---|---|---|
| 2,818,367 A | * | 12/1957 | Jaworski | C07C 251/72 564/310 |
| 4,187,317 A | * | 2/1980 | Nuss, Jr. | A61K 31/135 514/533 |
| 8,071,623 B2 | | 12/2011 | Jones et al. | |
| 2006/0178527 A1 | * | 8/2006 | Kelly | A61P 9/10 562/439 |
| 2009/0137681 A1 | | 5/2009 | Sinclair et al. | |
| 2011/0172234 A1 | | 7/2011 | Srivaslav et al. | |

FOREIGN PATENT DOCUMENTS

| GB | 1333027 A | * 10/1973 | ........... C07C 251/72 |
|---|---|---|---|
| WO | WO-2016/007993 A1 | 1/2016 | |

OTHER PUBLICATIONS

CAS Registry No. 1799181-70-6, which entered STN on Jul. 12, 2015 (Year: 2015).*
Hisaindee et al. Arabian Journal of Chemistry 2015, 8, 828-836 (Year: 2015).*
Eloh et al. J. Agric. Food Chem. 2015, 63, 9970-9976 (Year: 2015).*
Sharghi et al. Arkivoc 2007, xv, 255-264 (Year: 2007).*
Tokunaga et al. J. Am. Chem. Soc. 2004, 126, 13584-13585 (Year: 2004).*
Rajeshkumar et al. Eur. J. Org. Chem. 2012, 3795-3805 (Year: 2012).*
Ohshima et al. Bull. Chem. Soc. Jpn. 2006, 79, 305-311 (Year: 2006).*
CAS Registry No. 907167-34-4, which entered STN on Sep. 17, 2006 (Year: 2006).*
CAS Registry No. 906629-78-5, which entered STN on Sep. 14, 2006 (Year: 2006).*
CAS Registry No. 325699-39-6, which entered STN on Mar. 5, 2001 (Year: 2001).*
Chohan et al. Journal of Enzyme Inhibition and Medicinal Chemistry 2008, 23, 369-379 (Year: 2008).*
International Search Report dated Nov. 2, 2018, for PCT Application No. PCT/US2018/039053, filed Jun. 22, 2018, 4 pages.
Written Opinion dated Nov. 2, 2018, for PCT Application No. PCT/US2018/039053, filed Jun. 22, 2018, 4 pages.

* cited by examiner

*Primary Examiner* — Matthew P Coughlin
(74) *Attorney, Agent, or Firm* — Irina E. Britva; Mintz, Levin, Cohn, Ferris, Glovsky and Popeo, P.C.

(57) ABSTRACT

Provided herein are, inter alia, compounds inhibiting poly (ADP-ribose) Glycohydrolase (PARG) in a cancer cell and methods of treating cancer using compounds of the invention.

11 Claims, 13 Drawing Sheets

| PC | NC | 1 | 2 | 3 | 4 |
| 5 | 6 | 7 | 8 | 9 | 10 |
| 11 | 12 | 13 | 14 | 15 | 16 |
| 17 | 18 | 19 | 20 | 21 | 22 |
| 23 | 24 | 25 | 26 | 27 | 28 |
| 29 | 30 | 31 | 32 | 33 | 34 |
| 35 | 36 | 37 | 38 | 39 | 40 |

5        34

[Inhibitor] = 1 nM

| PC | NC | #34 | 2 | 3 | 6 |
|----|----|-----|---|---|---|
| 7  | 8  | 9   | 12| 15|   |

2

6

12

9

15

| Compounds | CHP20 | CHP21 | CHP22 | CHP23 | CHP24 | CHP25 |
|---|---|---|---|---|---|---|
| $IC_{50}$ (nM) | 62.5 | 17.8 | 65.6 | 7.8 | 15.6 | 11.7 |
| [a]$EC_{50}$ (µM) | 18.1 | 5.7 | 17.3 | 8.2 | 9.8 | 5.2 |
| [b]$EC_{50}$ (µM) | 17.3 | 3.8 | 16.5 | 5.8 | 5.6 | 3.1 | a: BRCA1-mutant TNBC (HCC1937)
b: PARPi-resistant UWB1.289

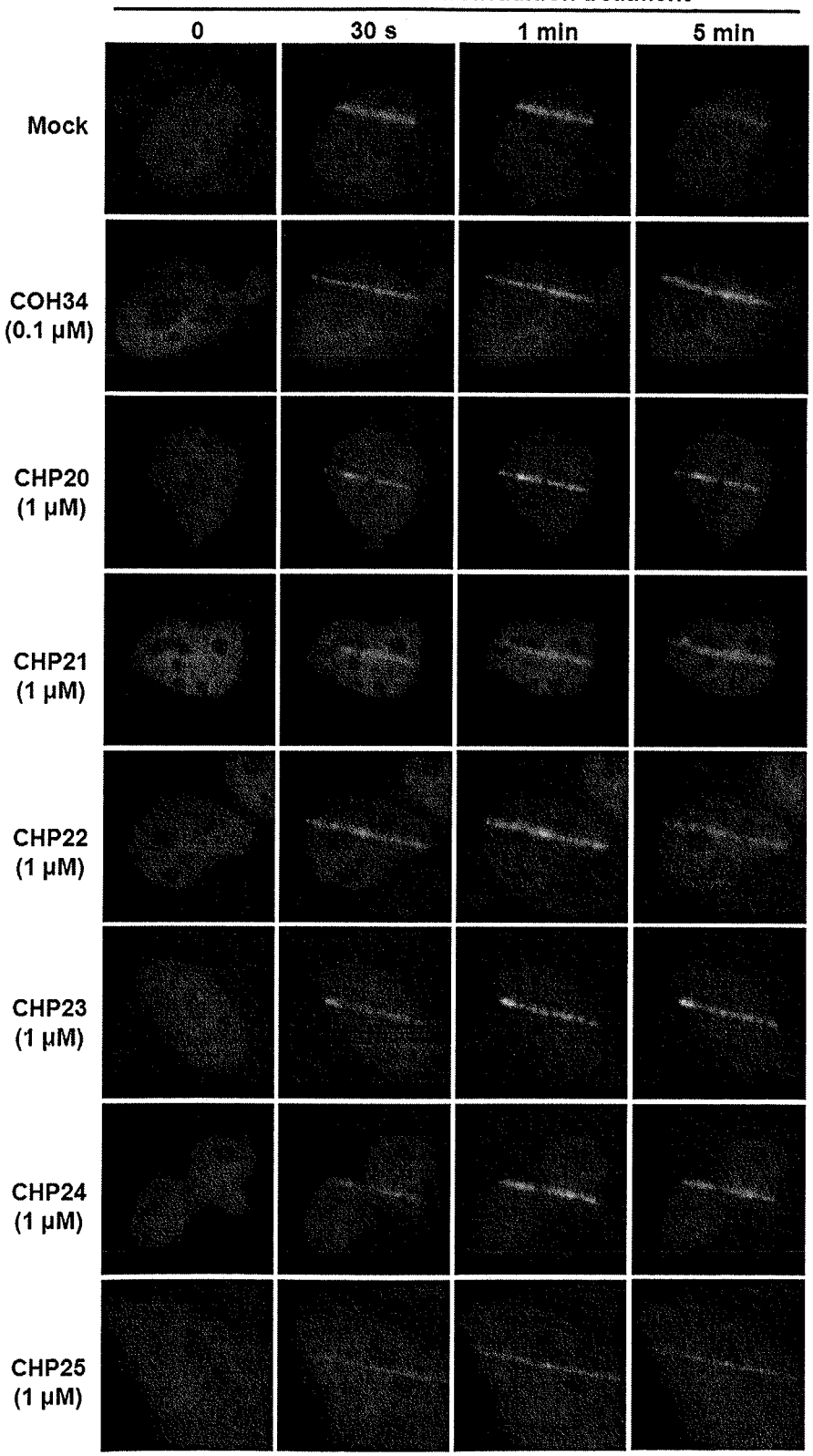

PARG INHIBITORS AND METHOD OF USE THEREOF

CROSS-REFERENCES TO RELATED APPLICATIONS

This application is a U.S. national phase application, pursuant to 35 U.S.C. § 371, of PCT/US2018/039053, filed Jun. 22, 2018, which claims the benefit of priority of U.S. Provisional Application No. 62/524,182 filed on Jun. 23, 2017 and U.S. Provisional Application No. 62/592,043 filed on Nov. 29, 2017, which are incorporated herein by reference in their entirety and for all purposes.

This invention was made with government support under R01 CA130899 and R01 CA132755 awarded by the National Institutes of Health. The government has certain rights in the invention.

BACKGROUND OF THE INVENTION

Poly(ADP-ribosyl)ation polymerase (PARP) inhibitors have been identified as a potential cancer drug to treat various cancers. For instance, PARP inhibitors suppress poly(ADP-ribosyl)ation (PARylation), which is induced by DNA damage. Interestingly, DNA damage repair system ensures genomic stability and suppresses tumorigenesis in cells, whereas mutations DNA damage repair system cause genomic instability and induce tumorigenesis. Thus, many DNA damage repair machineries, e.g., BRCA1, ATM and CHK2 are important tumor suppressors and are often mutated in cancers. As suppression of PARylation weakens DNA damage repair, PARP inhibitor treatment further disrupts DNA damage repair in tumor cells with defective DNA repair machinery, which eventually leads to apoptosis and kill tumor cells when tumor cells lose essential repair capability for survival.

Depoly(ADP-ribosyl)ation (dePARylation) is a sequential step following the PARylation in DNA damage repair system and poly(ADP-ribose) glycohydrolase (PARG) is a major dePARylation enzyme degrading the PARylated DNA. Since transient PARylation and immediate dePARylation are sequential events to mediate the recruitment of DNA damage machineries to the sites of DNA damage, suppression of dePARylation also can abolish PARP-dependent DNA damage repair in tumor cells. Therefore, suppression of dePARylation pathway and/or inhibiting PARG can be targeted in cancer treatment.

BRIEF SUMMARY OF THE INVENTION

Herein is provided, inter alia, a compound inhibiting a poly(ADP-ribose) glycohydrolase (PARG). In an aspect, the compound has a formula (I):

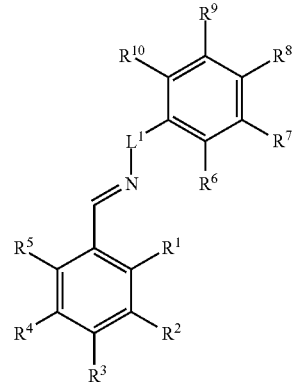

(I)

$L^1$ is a bond, —$CR^{11}R^{12}$—, —$NR^{13}$—, —O—, —S—, —S(O)—, —S(O)$_2$—, —$NR^{13}$S(O)—, —$NR^{13}$S(O)$_2$—, —$NR^{13}$C(O)—, —S(O)$NR^{13}$—, —S(O)$_2NR^{13}$—, or —C(O)$NR^{13}$—.

$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$—$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, C(O)—$OR^{4C}$, —C(O)$NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, —$CX^5_3$, —$CHX^5_2$, —$CH_2X^5$, —$OCX^5_3$, —$OCH_2X^5$, —$OCHX^5_2$, —$N_3$, —CN, —$SO_{n5}R^{5D}$, —$SO_{v5}NR^{5A}R^{5B}$, —$NHC(O)NR^{5A}R^{5B}$, —$N(O)_{m5}$, —$NR^{5A}R^{5B}$, —$C(O)R^{5C}$, C(O)—$OR^{5C}$, —C(O)$NR^{5A}R^{5B}$, —$OR^{5D}$, —$NR^{5A}SO_2R^{5D}$, —$NR^{5A}C(O)R^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^6$ is hydrogen, halogen, —CX$^6_3$, —CHX$^6_2$, —CH$_2$X$^6$, —OCX$^6_3$, —OCH$_2$X$^6$, —OCHX$^6_2$, —N$_3$, —CN, —SO$_{n6}$R$^{6D}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted cycloalkyl, substituted or unsubstituted heterocycloalkyl, substituted or unsubstituted aryl, or substituted or unsubstituted heteroaryl.

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O) NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)O R$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{7D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl.

n1, n2, n3, n4, n5, n6, n7, n8, n9, n10, n11 and n12 are independently an integer from 0 to 4 (e.g. 0). m1, m2, m3, m4, m5, m6, m7, m8, m9, m10, m11, m12, v1, v2, v3, v4, v5, v6, v7, v8, v9, v10, v11 and v12 are independently an integer from 1 to 2. X, X$^1$, X$^2$, X$^3$, X$^4$, X$^5$, X$^6$, X$^7$, X$^8$, X$^9$, X$^{10}$, X$^{11}$, X$^{12}$, and X$^{13}$ are independently —F, —Cl, —Br, or —I.

In embodiments, the compound has a formula (IIA):

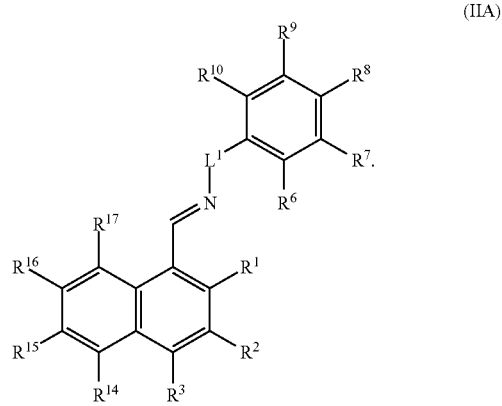

(IIA)

R$^{14}$ is hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —N$_3$, —CN, —SO$_{n14}$R$^{14D}$, —SO$_{v14}$NR$^{14A}$R$^{14B}$, —NHC(O) NR$^{14A}$R$^{14B}$, —N(O)$_{m14}$, —NR$^{14A}$R$^{14B}$, —C(O)R$^{14C}$, —C(O)—OR$^{14C}$, —C(O)NR$^{14A}$R$^{14B}$, —OR$^{14D}$, —NR$^{14A}$SO$_2$R$^{14D}$, —NR$^{14A}$C(O)R$^{14C}$, —NR$^{14A}$C(O)O R$^{14C}$, —NR$^{14A}$OR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —N$_3$, —CN, —SO$_{n15}$R$^{15D}$, —SO$_{v15}$NR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{16}$ is hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —N$_3$, —CN, —SO$_{n16}$R$^{16D}$, —SO$_{v16}$NR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{17}$ is hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —N$_3$, —CN, —SO$_{n17}$R$^{17D}$, —SO$_{v17}$NR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, and R$^{17D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n14, n15, n16, and n17 are independently an integer from 0 to 4 (e.g. 0). m14, m15, m16, m17, v14, v15, v16, and v17 are independently an integer from 1 to 2. X$^{14}$, X$^{15}$, X$^{16}$, and X$^{17}$ are independently —F, —Cl, —Br, or —I.

In an aspect is provided a pharmaceutical composition including a compound as described herein, and a pharmaceutically acceptable carrier thereof.

In an aspect is provided is a method of treating a cancer. The method includes administering to the subject an effective amount of a compound or a salt thereof as described herein.

Further provided herein is a method of inhibiting a poly(ADP-ribose) glycohydrolase (PARG). The method includes contacting the PARG with a compound or a salt thereof as described herein.

Other aspects are disclosed infra.

BRIEF DESCRIPTION OF THE DRAWINGS

FIG. 8 shows laser microirradiation and imaging of U2OS cells with transfection of GFP-CHFR that were treated with compounds (CHP20-25) according to Example 12.

DETAILED DESCRIPTION OF THE INVENTION

I. Definitions

Figure 1A:
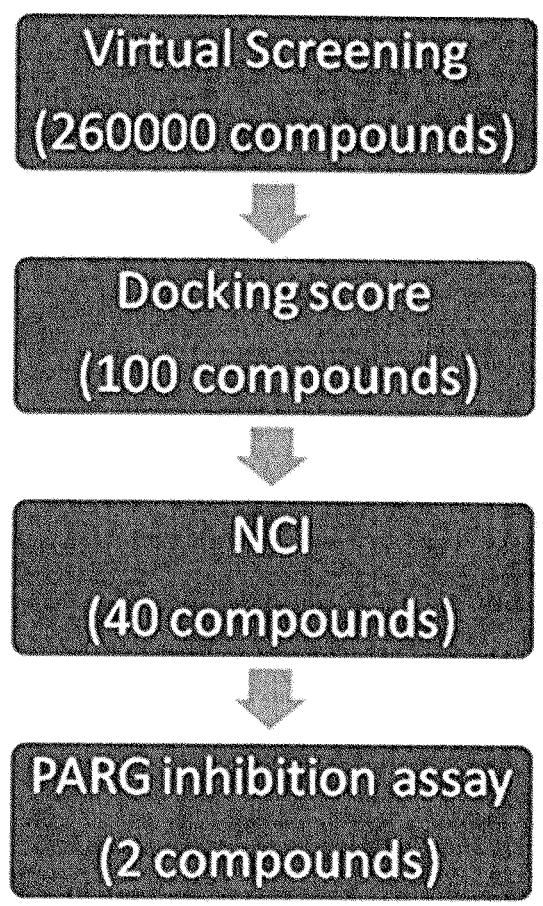
FIG. 1A shows an exemplary screening for identifying potential PARG inhibitors.
Figures 1B, 1C:
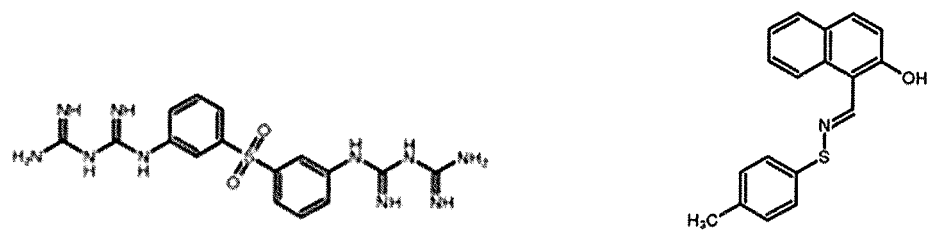
FIG. 1B shows results of dot blotting with anti-PAR antibody.
FIG. 1C shows two compounds (compounds 5 and 34) having inhibitory activity for PARG from the dot blotting in FIG. 1B.
Figure 1D:
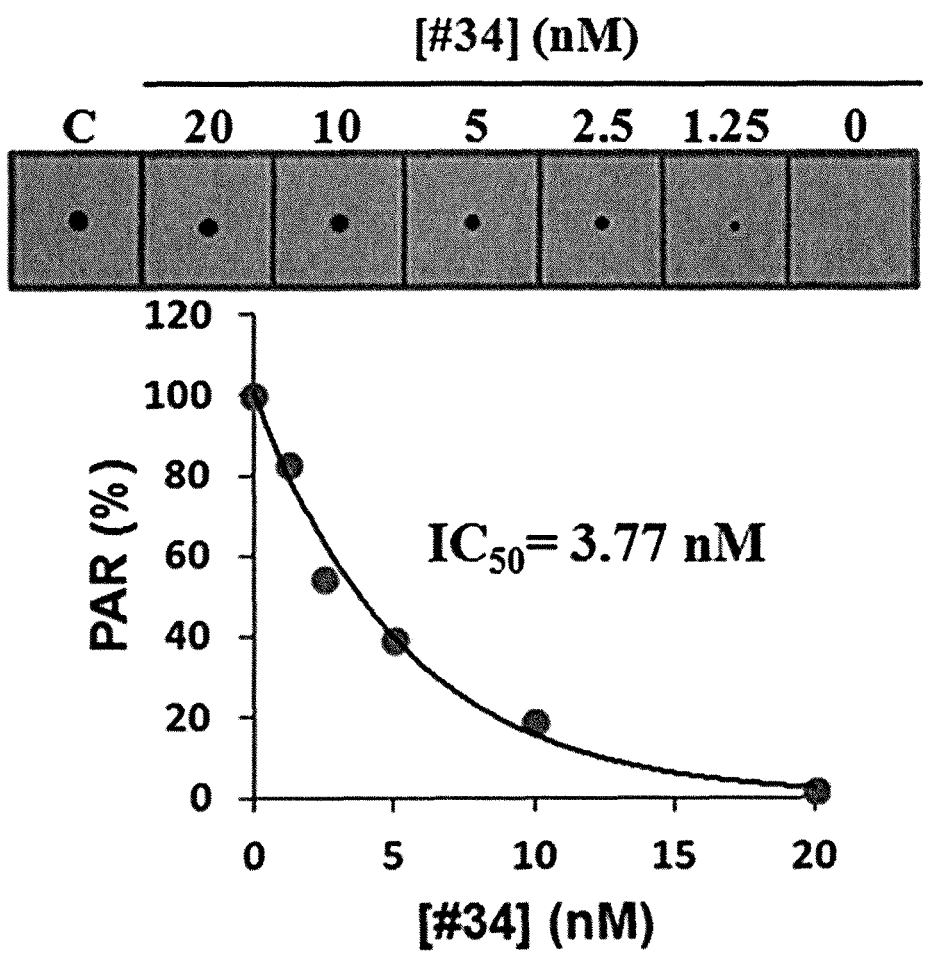
FIG. 1D shows IC$_{50}$ measurement of compound 34 by dot blotting with anti-PAR antibody in a dose course of compound 34.
Figure 2A:
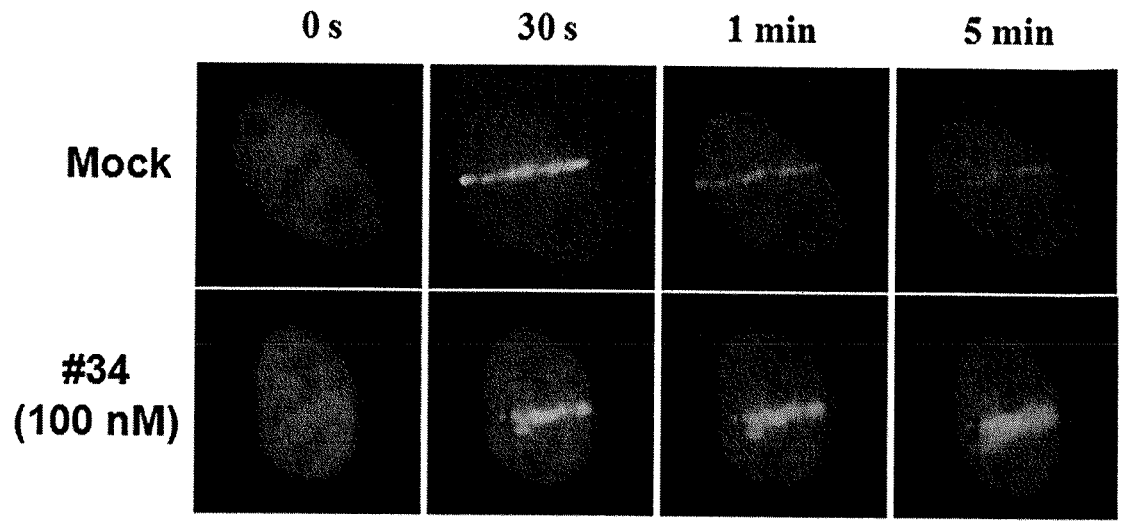
FIG. 2A shows laser microirradiation and imaging of cells which were non-treated or treated with compound 34 in dose dependent manner.
Figure 2B:
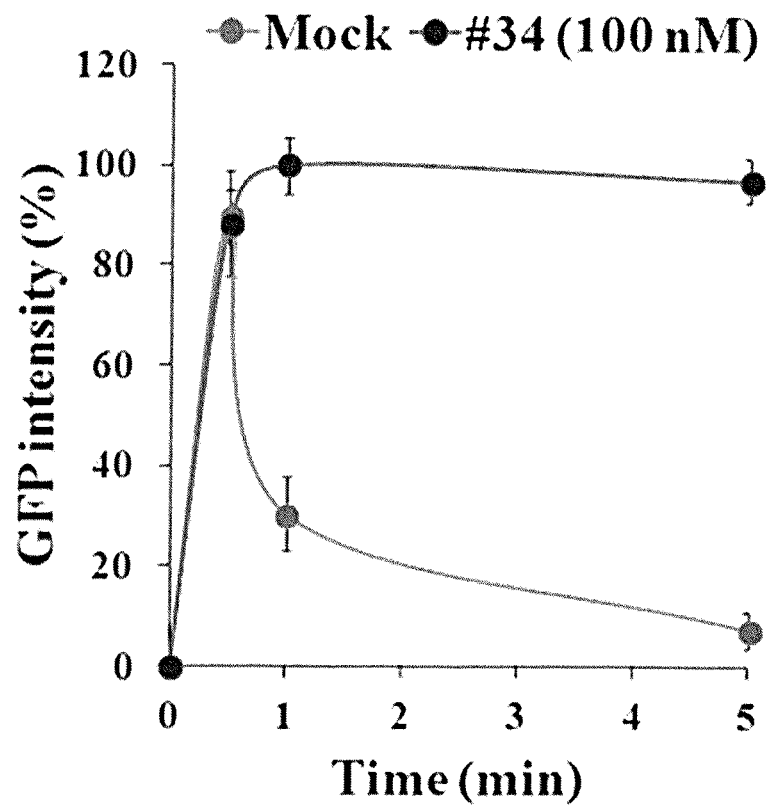
FIG. 2B is a graph of numerical values of GFP fluorescence at the laser line, which were averaged values using CellSens software (Olympus) from 50 cells from three independent experiments.
Figure 3A:
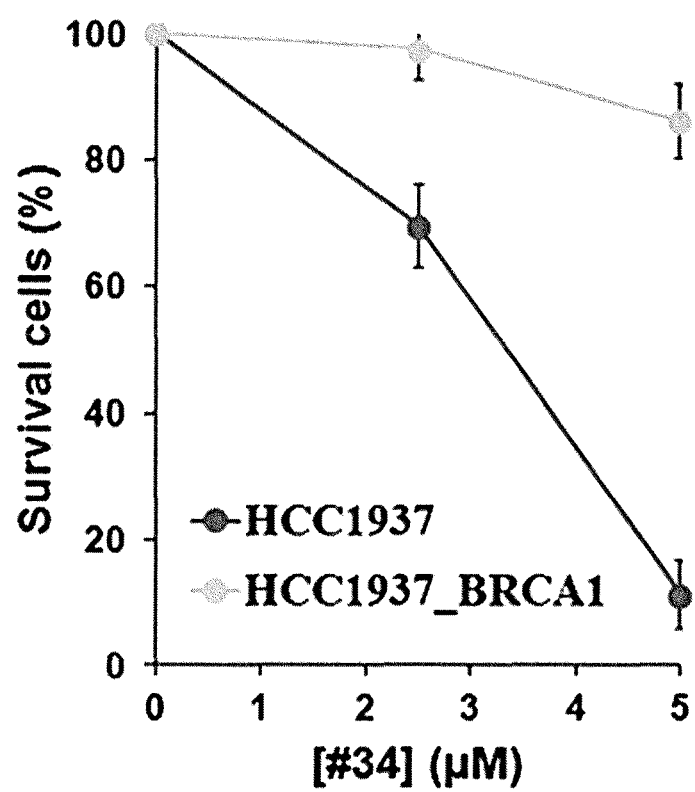
FIG. 3A is a graph showing survival rates of HCC1937 (BRCA1-deficient breast cancer cells), and HCC1937 BRCA1 (BRCA1-reconstituted HCC1937 cells) treated with compound 34 in dose dependent manner.
Figure 3B:
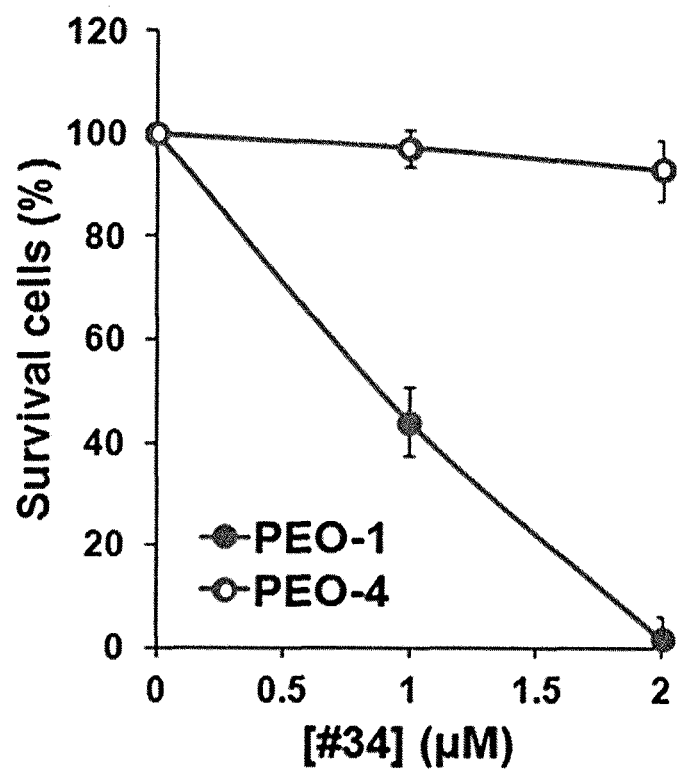
FIG. 3B is a graph showing survival rates of PEO-1 (BRCA2-deficient ovarian cancer cells) and PEO-4 (BRCA2-reconstituted PEO-1 cells) treated with compound 34 in dose dependent manner.
Figure 4A:
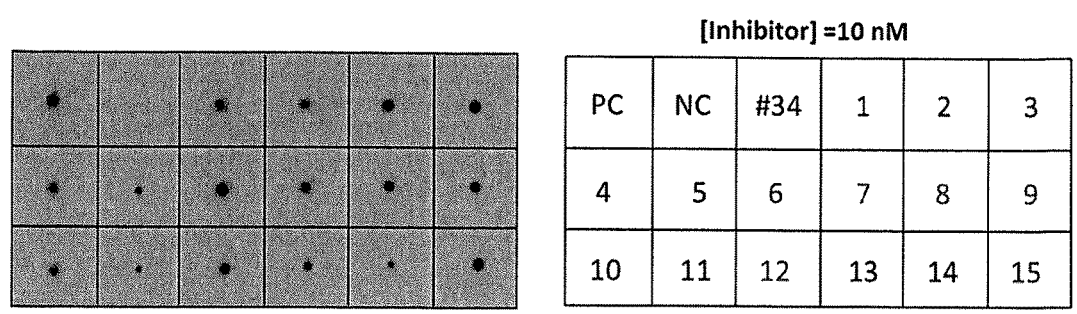
FIG. 4A shows results of dot blotting with anti-PAR antibody using compounds at a concentration of 10 nM and FIG. 4B shows the tested compounds in FIG. 4A.
Figure 4B:
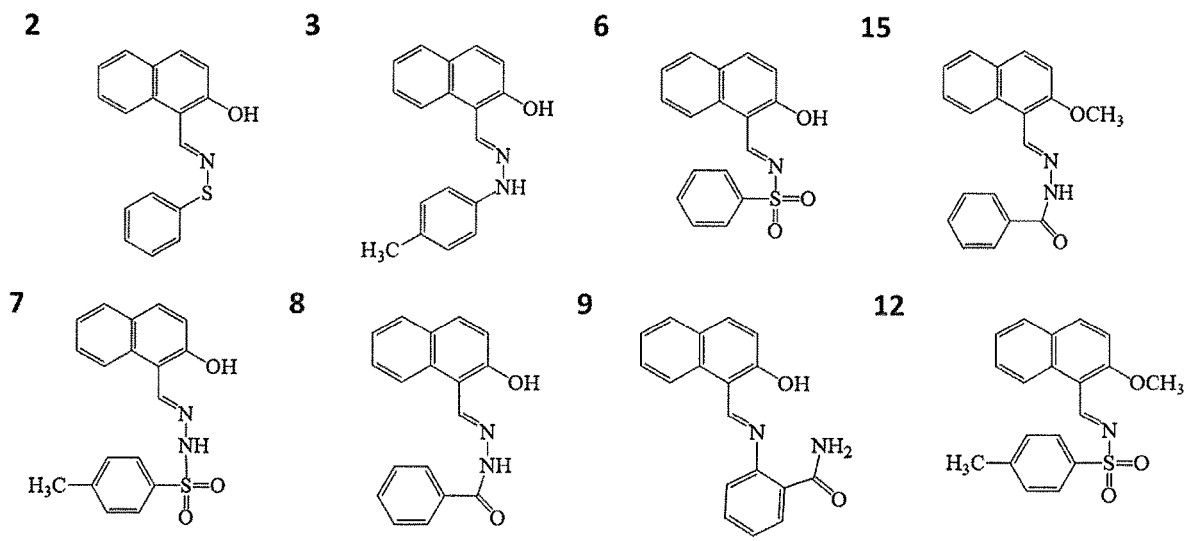
Figure 5A:
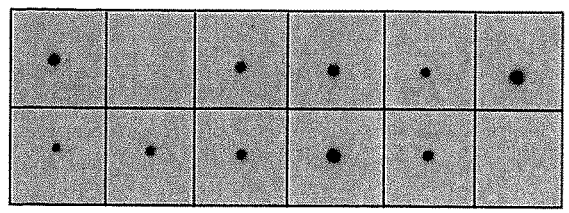
FIG. 5A shows results of dot blotting with anti-PAR antibody using compounds at a concentration of 1 nM and FIG. 5B shows the tested compounds in FIG. 5A.
Figure 5B:
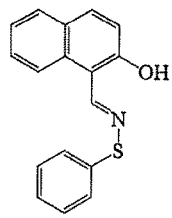
Figure 5B:
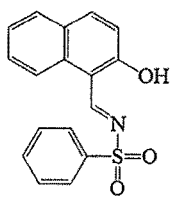
Figure 5B:
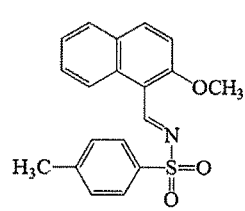
Figure 5B:
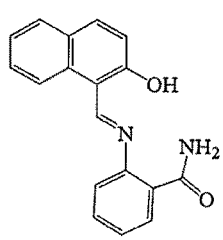
Figure 5B:
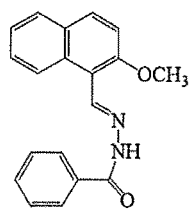

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3 dioxanyl, 1,3 dioxolanyl, 1,3 dithiolanyl, 1,3 dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1 dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3 dihydrobenzofuran 2 yl, 2,3 dihydrobenzofuran 3 yl, indolin 1 yl, indolin 2 yl, indolin 3 yl, 2,3 dihydrobenzothien 2 yl, decahydroquinolinyl, decahydroisoquinolinyl, octahydro 1H indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "alkylene," by itself or as part of another substituent, means, unless otherwise stated, a divalent radical derived from an alkyl, as exemplified, but not limited by, —CH$_2$CH$_2$CH$_2$CH$_2$— Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—S—CH$_2$, —S(O)—CH$_3$, —CH$_2$—CH$_2$—S(O)$_2$—CH$_3$, —CH═CHO—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " ~~~ " denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

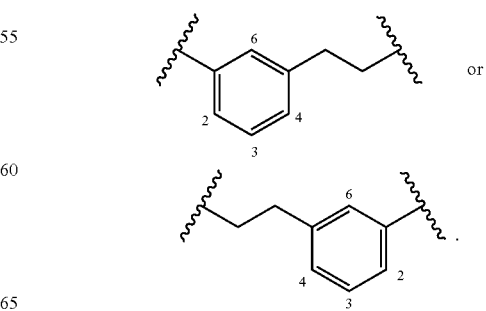

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$ SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', —O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C(O)NR"NR'''R'''', —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from:

(i) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from:

(a) oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In embodiments of the compounds herein, each substituted or unsubstituted alkyl may be a substituted (e.g., substituted with a substituent group, a size-limited substituent group, or lower substituent group) or unsubstituted $C_1$-$C_{20}$ alkyl, each substituted or unsubstituted heteroalkyl is a substituted (e.g., substituted with a substituent group, a size-limited substituent group, or lower substituent group) or unsubstituted 2 to 20 membered heteroalkyl, each substituted or unsubstituted cycloalkyl is a substituted (e.g., substituted with a substituent group, a size-limited substituent group, or lower substituent group) or unsubstituted $C_3$-$C_8$ cycloalkyl, each substituted or unsubstituted heterocycloalkyl is a substituted (e.g., substituted with a substituent group, a size-limited substituent group, or lower substituent group) or unsubstituted 3 to 8 membered heterocycloalkyl, each or unsubstituted aryl is a substituted (e.g., substituted with a substituent group, a size-limited substituent group, or lower substituent group) or unsubstituted $C_6$-$C_{10}$ aryl, and/or each substituted or unsubstituted heteroaryl is a substituted (e.g., substituted with a substituent group, a size-limited substituent group, or lower substituent group) or unsubstituted 5 to 10 membered heteroaryl. In embodiments herein, each substituted or unsubstituted alkylene is a substituted (e.g., substituted with a substituent group, a size-limited substituent group, or lower substituent group) or unsubstituted $C_1$-$C_{20}$ alkylene, each substituted or unsubstituted heteroalkylene is a substituted (e.g., substituted with a substituent group, a size-limited substituent group, or lower substituent group) or unsubstituted 2 to 20 membered heteroalkylene, each substituted or unsubstituted cycloalkylene is a substituted (e.g., substituted with a substituent group, a size-limited substituent group, or lower substituent group) or unsubstituted $C_3$-$C_8$ cycloalkylene, each substituted or unsubstituted heterocycloalkylene is a substituted (e.g., substituted with a substituent group, a size-limited substituent group, or lower substituent group) or unsubstituted 3 to 8 membered heterocycloalkylene, each substituted or unsubstituted arylene is a substituted (e.g., substituted with a substituent group, a size-limited substituent group, or lower substituent group) or unsubstituted $C_6$-$C_{10}$ arylene, and/or each substituted or unsubstituted heteroarylene is a substituted (e.g., substituted with a substituent group, a size-limited substituent group, or lower substituent group) or unsubstituted 5 to 10 membered heteroarylene.

In some embodiments, each substituted or unsubstituted alkyl is a substituted (e.g., substituted with a substituent group, a size-limited substituent group, or lower substituent group) or unsubstituted $C_1$-$C_8$ alkyl, each substituted or unsubstituted heteroalkyl is a substituted (e.g., substituted with a substituent group, a size-limited substituent group, or lower substituent group) or unsubstituted 2 to 8 membered heteroalkyl, each substituted or unsubstituted cycloalkyl is a substituted (e.g., substituted with a substituent group, a size-limited substituent group, or lower substituent group) or unsubstituted $C_3$-$C_7$ cycloalkyl, each substituted or unsubstituted heterocycloalkyl is a substituted (e.g., substituted with a substituent group, a size-limited substituent group, or lower substituent group) or unsubstituted 3 to 7 membered heterocycloalkyl, each substituted or unsubstituted aryl is a substituted (e.g., substituted with a substituent group, a size-limited substituent group, or lower substituent group) or unsubstituted $C_6$-$C_{10}$ aryl, and/or each substituted or unsubstituted heteroaryl is a substituted (e.g., substituted with a substituent group, a size-limited substituent group, or lower substituent group) or unsubstituted 5 to 9 membered heteroaryl. In some embodiments, each substituted or unsubstituted alkylene is a substituted (e.g., substituted with a substituent group, a size-limited substituent group, or lower substituent group) or unsubstituted $C_1$-$C_8$ alkylene, each substituted or unsubstituted heteroalkylene is a substituted (e.g., substituted with a substituent group, a size-limited substituent group, or lower substituent group) or unsubstituted 2 to 8 membered heteroalkylene, each substituted or unsubstituted cycloalkylene is a substituted (e.g., substituted with a substituent group, a size-limited substituent group, or lower substituent group) or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted (e.g., substituted with a substituent group, a size-limited substituent group, or lower substituent group) or unsubstituted $C_6$-$C_{10}$ arylene, and/or each substituted or unsubstituted heteroarylene is a substituted (e.g., substituted with a substituent group, a size-limited substituent group, or lower substituent group) or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the (R) and (S) configurations for each asymmetric center. Therefore, single stereochemical isomers as well as enantiomeric and diastereomeric mixtures of the present compounds, generally recognized as stable by those skilled in the art, are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, replacement of fluoride by $^{18}F$, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman decimal symbol may be used to distinguish each appearance of that particular R group. For example, where multiple $R^{13}$ substituents are present, each $R^{13}$ substituent may be distinguished as $R^{13.1}$, $R^{13.2}$, $R^{13.3}$, $R^{13.4}$, etc., wherein each of $R^{13.1}$, $R^{13.2}$, $R^{13.3}$, $R^{13.4}$, etc. is defined within the scope of the definition of $R^{13}$ and optionally differently. The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As defined herein, a term "poly (ADP-ribose) polymerase" or "PARP" refers to an enzyme that can be found in cell nucleus and is typically involved in various cellular functions, such as DNA repair, inflammatory response and the like, cvarious 16 isoforms, i.e. PARP1 (e.g., UniProtKB: P11103, P09874, and P18493); PARP2 (e.g., UniProtKB: Q9UGN5, O88554, and Q11207); PARP3 (e.g., UniProtKB: Q9Y6F1, Q3ULW8, and E1BD56); PARP4 (e,g, UniProtKB: Q9UKK3, E9PYK3, and E1BD73); PARP-5a (e,g, UniProtKB: Q95271); PARP-5b (e,g, UniProtKB: Q9H2K2); PARP6 (e,g UniProtKB: Q2NL67, Q6P6P7, and F1N1A4); PARP7 (e,g UniProtKB: Q7Z3E1); PARP8 (e,g, UniProtKB: Q8N3A8); PARP9 (e,g UniProtKB: Q8IXQ6, Q8CAS9, and Q08DN9); PARP10 (e,g, UniProtKB: Q53GL7, Q8CIE4, and F6Z9X8), PARP11 (e,g, UniProtKB: Q9NR21, Q8CFF0, and A2VE05; PARP12 (e,g, UniProtKB: Q9H0J9, Q8BZ20, and D4A3V3); PARP14 (e,g, UniProtKB: Q460N5, Q2EMV9 and F1LZ05); PARP15 (e,g, UniProtKB: Q460N3, F1SQ35, and F6S617); and PARP16 (e,g, UniProtKB: Q8N5Y8, Q7TMM8, and Q5U2Q4). PARP can detect and initiate an immediate cellular response to single-strand DNA breaks (SSB), for example, by binding to the DNA, changing its structure, and synthesizing polymeric adenosine diphosphate ribose (poly (ADP-ribose) or PAR) chain, which acts as a signal for the other DNA-repairing enzymes. In addition, as defined herein, a term "poly ADP-ribosylation" or "PARylation" means a type of post-translational modification of protein, for example, by attaching or covalently bonding poly (ADP-ribose) to the protein, which is typically mediated by PARPs. During the damaged DNA repair, PARylation occurs at single-strand DNA breaks (SSB) or DNA lesions.

As defined herein, a term "poly-(ADP-ribose) glycohydrolase" or "PARG" refers to an enzyme that can be found in cell nucleus and typically is involved in various cellular functions, such as DNA repair, inflammatory response and the like, particularly as a downstream process of PARylation. The family of PARP may include several isoforms, e.g., PARG1 (e.g., UniProtKB: Q86W56, Q867X0, and Q9SKB3), and PARG2 (e.g., UniProtKB: Q9N5L4, Q8VYA1, A0A178VXC5), which can hydrolyze glycosidic bond in the PARylated protein, thereby cleaving mono or poly (ADP-ribose) from the PARylated protein. In addition, as defined herein, a term "de-poly ADP-ribosylation" or "dePARylation" means a first step of hydrolysis of the poly (ADP-ribose) modified or PARylated protein, e.g. cleaving mono or poly (ADP-ribose) from the modified or PARylated protein. DePARylation is typically mediated by PARG during the damaged DNA repair.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation). The term "inhibitor" may include synthetic or biological molecule (e.g. small molecule, nucleic acid, peptide or antibody) inhibiting or negatively affecting (e.g. decreasing) the activity or function of the protein relative to the activity or function of the protein in the absence of the inhibitor. In embodiments, the inhibitor is a small molecule.

The term "small molecule" or the like as used herein refers, unless indicated otherwise, to a molecule having a molecular weight of less than about 700 Dalton, e.g., less than about 700, 650, 600, 550, 500, 450, 400, 350, 300, 250, 200, 100, or even 50 Dalton.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (-)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. The term "treating" and conjugations thereof, may include prevention of an injury, pathology, condition, or disease. In embodiments, treating is preventing. In embodiments, treating does not include preventing.

The term "prevent" refers to a decrease in the occurrence of disease (e.g., PARG associated disease) symptoms in a patient. As indicated above, the prevention may be complete (e.g., no detectable symptoms) or partial, such that fewer symptoms are observed than would likely occur absent treatment.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g. achieve the effect for which it is administered, treat a disease, reduce enzyme activity, increase enzyme activity, reduce a catabolic enzyme activity, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may also include allowing two species to react, interact, or physically touch, wherein the two species may be a compound as described herein and a protein or enzyme. Contacting may include allowing a compound described herein to interact with a protein or enzyme that is involved in a catabolism.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The term "modulate" is used in accordance with its plain ordinary meaning and refers to the act of changing or varying one or more properties. "Modulation" refers to the process of changing or varying one or more properties. For example, as applied to the effects of a modulator on a target protein (e.g., poly(ADP-ribose) glycohydrolase (PARG)), to modulate means to change by increasing or decreasing a property or function (e.g., activity or catabolic activity) of the target molecule or the amount of the target molecule.

The term "modulate" is used in accordance with its plain ordinary meaning and refers to the act of changing or varying one or more properties. "Modulation" refers to the process of changing or varying one or more properties. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g, intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

The compounds described herein can be used in combination with one another, with other active drugs known to be useful in treating a disease (e.g. cancer) or with adjunctive agents that may not be effective alone, but may contribute to the efficacy of the active agent. Thus, the compounds described herein may be co-administered with one another or with other active drugs known to be useful in treating a disease.

By "co-administer" it is meant that a compound described herein is administered at the same time, just prior to, or just after the administration of one or more additional therapies, for example, an anticancer or antitumor agent as described herein. The compounds described herein can be administered alone or can be co-administered to the patient. Co-administration is meant to include simultaneous or sequential administration of the compound individually or in combination (more than one compound or agent). Thus, the preparations can also be combined, when desired, with other active substances (e.g. anticancer agents).

Co-administration includes administering one active agent (e.g. a complex described herein) within 0.5, 1, 2, 4, 6, 8, 10, 12, 16, 20, or 24 hours of a second active agent (e.g. anticancer or antitumor agents). Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for cancer (e.g., breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia).

As used herein, the term "cancer" refers to all types of cancer, neoplasm, or malignant tumors found in mammals, including leukemia, lymphomas, carcinomas and sarcomas. Exemplary cancers include acute myeloid leukemia ("AML"), chronic myelogenous leukemia ("CML"), and cancer of the brain, breast, pancreas, colon, liver, kidney, lung, non-small cell lung, melanoma, ovary, sarcoma, and prostate. Additional examples include, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, uterine cancer, urinary bladder cancer, bladder cancer, esophagus cancer, gastric cancer, head and neck cancer, cholangiocarcinoma, mesothelioma, premalignant skin lesions, testicular cancer, lymphomas, thyroid cancer, neuroblastoma, esophageal cancer, genitourinary tract cancer, malignant hypercalcemia, endometrial cancer, adrenal cortical cancer, fallopian tube cancer, neoplasms of the endocrine and exocrine pancreas cancer, prostate cancer, breast cancer including triple negative breast cancer, and cutaneous T-cell lymphoma.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma. In embodiments, "lymphoma" refers to a group of blood cell tumors that develop from cells of the immune system found in lymph, i.e. lymphocytes (e.g. natural killer cells (NK cells), T cells, and B cells). Lymphoma is typically classified into Hodgkin's lymphomas (HL) and the non-Hodgkin lymphomas (NHL) or based on whether it develops in B-lymphocytes (B-cells) or T-lymphocytes (T-cells). In embodiments, lymphoma is developed in B-cells. In embodiments, lymphoma is developed in T-cell.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid, antibody) used to treat cancer through destruction or inhibition of cancer cells or tissues. Anticancer agents may be selective for certain cancers or certain tissues. In embodiments, anticancer agents herein may include epigenetic inhibitors and multi- or specific kinase inhibitors.

The term "associated" or "associated with" in the context of a substance or substance activity or function associated with a disease (e.g. a protein associated disease, a cancer associated with PARG activity, PARG associated cancer, PARG associated disease (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. For example, a cancer associated with PARG activity or function may be a cancer that results (entirely or partially) from aberrant PARG function (e.g. catabolic enzyme activity, protein-protein interaction, signaling pathway) or a cancer wherein a particular symptom of the disease is caused (entirely or partially) by aberrant PARG activity or function. As used herein, what is described as being associated with a disease, if a causative agent, could be a target for treatment of the disease. For example, a cancer associated with PARG activity or function or a PARG associated disease (e.g., cancer, inflammatory disease, autoimmune disease, or infectious disease), may be treated with a PARG modulator or PARG inhibitor, in the instance where increased PARG activity or function (e.g. catabolic enzyme activity) causes the disease (e.g., cancer, inflammatory disease, autoimmune disease, or infectious disease). For example, an inflammatory disease associated with PARG activity or function or a PARG associated inflammatory disease, may be treated with a PARG modulator or PARG inhibitor, in the instance where increased PARG activity or function (e.g. catabolic enzyme activity) causes the disease.

"Disease" or "condition" refer to a state of being or health status of a patient or subject capable of being treated with the compounds or methods provided herein. In certain embodiments, disease as used herein may refer to cancer (e.g. breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia).

II. Compounds

Provided herein are compounds having a structure of Formula (I):

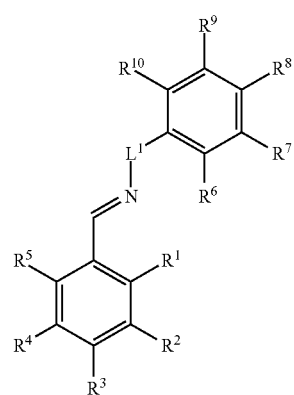

(I)

$L^1$ is a bond, $-CR^{11}R^{12}-$, $-NR^{13}-$, $-O-$, $-S-$, $-S(O)-$, $-S(O)_2-$, $-NR^{13}S(O)-$, $-NR^{13}S(O)_2-$, $-NR^{13}C(O)-$, $-S(O)NR^{13}-$, $-S(O)_2NR^{13}-$, or $-C(O)NR^{13}-$.

$R^1$ is hydrogen, halogen, $-CX^1_3$, $-CHX^1_2$, $-CH_2X^1$, $-OCX^1_3$, $-OCH_2X^1$, $-OCHX^1_2$, $-N_3$, $-CN$, $-SO_{n1}R^{1D}$, $-SO_{v1}NR^{1A}R^{1B}$, $-NHC(O)NR^{1A}R^{1B}$, $-N(O)_{m1}$, $NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)$ $R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, $-CX^2_3$, $-CHX^2_2$, $-CH_2X^2$, $-OCX^2_3$, $-OCH_2X^2$, $-OCHX^2_2$, $-N_3$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)$ $R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, $-CX^3_3$, $-CHX^3_2$, $-CH_2X^3$, $-OCX^3_3$, $-OCH_2X^3$, $-OCHX^3_2$, $-N_3$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, $-CX^4_3$, $-CHX^4_2$, $-CH_2X^4$, $-OCX^4_3$, $-OCH_2X^4$, $-OCHX^4_2$, $-N_3$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, $-CX^5_3$, $-CHX^5_2$, $-CH_2X^5$, $-OCX^5_3$, $-OCH_2X^5$, $-OCHX^5_2$, $-N_3$, $-CN$, $-SO_{n5}R^{5D}$, $-SO_{v5}NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^6$ is hydrogen, halogen, $-CX^6_3$, $-CHX^6_2$, $-CH_2X^6$, $-OCX^6_3$, $-OCH_2X^6$, $-OCHX^6_2$, $-N_3$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is hydrogen, halogen, $-CX^7_3$, $-CHX^7_2$, $-CH_2X^7$, $-OCX^7_3$, $-OCH_2X^7$, $-OCHX^7_2$, $-N_3$, $-CN$, $-SO_{n7}R^{7D}$, $-SO_{v7}NR^{7A}R^{7B}$, $-NHC(O)NR^{7A}R^{7B}$, —N(O)$_{m7}$, —NR$^{7A}$R$^{7B}$, —C(O)R$^{7C}$, C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10C}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O) R$^{10C}$, —NR$^{10A}$C(O) OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O) R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O) OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)O R$^{12C}$. —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In embodiments, when R$^4$ and R$^5$ together with atoms attached thereto are joined to form unsubstituted phenyl, L$^1$ is a bond, R$^1$ is —OH or —OCH$_3$, and R$^7$, R$^8$ and R$^9$ are hydrogen, then R$^6$ or R$^{10}$ is not —C(O)NH$_2$. In embodiments, when R$^4$ and R$^5$ together with atoms attached thereto are joined to form unsubstituted phenyl, L$^1$ is —S— or —S(O)$_2$—, R$^1$ is —OH, and R$^6$, R$^7$, R$^9$ and R$^{10}$ are hydrogen, then R$^8$ is not hydrogen, —Cl or —CH$_3$. In embodiments, when R$^4$ and R$^5$ together with atoms attached thereto are joined to form unsubstituted phenyl, L$^1$ is —S(O)$_2$—, R$^1$ is —OCH$_3$, and R$^6$, R$^7$, R$^9$ and R$^{10}$ are hydrogen, then R$^8$ is not hydrogen or —CH$_3$. In embodiments, when R$^4$ and R$^5$ together with atoms attached thereto are joined to form unsubstituted phenyl, L$^1$ is —NHS(O)$_2$— or —NH—, R$^1$ is —OH or —OCH$_3$, and R$^6$, R$^7$, R$^9$ and R$^{10}$ are hydrogen, then R$^8$ is not hydrogen, —Cl or —CH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^8$ and R$^{10}$ are hydrogen, then R$^7$ or R$^9$ is not —Cl, —Br, —CH$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^7$, R$^8$ and R$^9$ are hydrogen, then R$^6$ or R$^{10}$ is not —Cl, —Br, —CH$_3$, —OH, or —OCH$_3$. In embodiments, when R$^4$ and R$^5$ together with atoms attached thereto are joined to form unsubstituted phenyl, L$^1$ is —NHC(O)—, and R$^1$ is —OH or —OCH$_3$, then at least one of R$^6$, R$^7$ and R$^8$ are not —OCH$_3$, or at least one of R$^8$, R$^9$ and R$^{10}$ are not —OCH$_3$.

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. R$^2$ and R$^3$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. R$^3$ and R$^4$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl. The symbols n1, n2, n3, n4, n5, n6, n7, n8, n9, n10, n11 and n12 are independently an integer from 0 to 4 (e.g. 0). m1, m2, m3, m4, m5, m6, m7, m8, m9, m10, m11, m12, v1, v2, v3, v4, v5, v6, v7, v8, v9, v10, v11 and v12 are independently an integer from 1 to 2. X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently —F, —Cl, —Br, or —I.

In embodiments, $R^1$ and $R^2$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^1$ and $R^2$ together with atoms attached thereto are joined to form substituted (e.g., substituted with a substituent group, a size-limited substituent group, or lower substituent group) or unsubstituted cyclopentyl. In embodiments, $R^1$ and $R^2$ together with atoms attached thereto are joined to form substituted (e.g., substituted with a substituent group, a size-limited substituent group, or lower substituent group) or unsubstituted cyclohexyl. In embodiments, $R^1$ and $R^2$ together with atoms attached thereto are joined to form substituted (e.g., substituted with a substituent group, a size-limited substituent group, or lower substituent group) or unsubstituted pyridyl. In embodiments, $R^1$ and $R^2$ together with atoms attached thereto are joined to form substituted (e.g., substituted with a substituent group, a size-limited substituent group, or lower substituent group) or unsubstituted piperidinyl. In embodiments, $R^1$ and $R^2$ together with atoms attached thereto are joined to form substituted (e.g., substituted with a substituent group, a size-limited substituent group, or lower substituent group) or unsubstituted morpholinyl. In embodiments, $R^1$ and $R^2$ together with atoms attached thereto are joined to form substituted (e.g., substituted with a substituent group, a size-limited substituent group, or lower substituent group) or unsubstituted phenyl. In embodiments, $R^1$ and $R^2$ together with atoms attached thereto are joined to form substituted (e.g., substituted with a substituent group, a size-limited substituent group, or lower substituent group) or unsubstituted pyrrolyl. In embodiments, $R^1$ and $R^2$ together with atoms attached thereto are joined to form substituted (e.g., substituted with a substituent group, a size-limited substituent group, or lower substituent group) or unsubstituted pyrimidinyl. In embodiments, $R^1$ and $R^2$ together with atoms attached thereto are joined to form substituted (e.g., substituted with a substituent group, a size-limited substituent group, or lower substituent group) or unsubstituted thiophenyl.

In embodiments, $R^2$ and $R^3$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^2$ and $R^3$ together with atoms attached thereto are joined to form substituted (e.g., substituted with a substituent group, a size-limited substituent group, or lower substituent group) or unsubstituted cyclopentyl. In embodiments, $R^2$ and $R^3$ together with atoms attached thereto are joined to form substituted (e.g., substituted with a substituent group, a size-limited substituent group, or lower substituent group) or unsubstituted cyclohexyl. In embodiments, $R^2$ and $R^3$ together with atoms attached thereto are joined to form substituted (e.g., substituted with a substituent group, a size-limited substituent group, or lower substituent group) or unsubstituted pyridyl. In embodiments, $R^2$ and $R^3$ together with atoms attached thereto are joined to form substituted (e.g., substituted with a substituent group, a size-limited substituent group, or lower substituent group) or unsubstituted piperidinyl. In embodiments, $R^2$ and $R^3$ together with atoms attached thereto are joined to form substituted (e.g., substituted with a substituent group, a size-limited substituent group, or lower substituent group) or unsubstituted morpholinyl. In embodiments, $R^2$ and $R^3$ together with atoms attached thereto are joined to form substituted (e.g., substituted with a substituent group, a size-limited substituent group, or lower substituent group) or unsubstituted phenyl. In embodiments, $R^2$ and $R^3$ together with atoms attached thereto are joined to form substituted (e.g., substituted with a substituent group, a size-limited substituent group, or lower substituent group) or unsubstituted pyrrolyl. In embodiments, $R^2$ and $R^3$ together with atoms attached thereto are joined to form substituted (e.g., substituted with a substituent group, a size-limited substituent group, or lower substituent group) or unsubstituted pyrimidinyl. In embodiments, $R^2$ and $R^3$ together with atoms attached thereto are joined to form substituted (e.g., substituted with a substituent group, a size-limited substituent group, or lower substituent group) or unsubstituted thiophenyl.

In embodiments, $R^3$ and $R^4$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^3$ and $R^4$ together with atoms attached thereto are joined to form substituted (e.g., substituted with a substituent group, a size-limited substituent group, or lower substituent group) or unsubstituted cyclopentyl. In embodiments, $R^3$ and $R^4$ together with atoms attached thereto are joined to form substituted (e.g., substituted with a substituent group, a size-limited substituent group, or lower substituent group) or unsubstituted cyclohexyl. In embodiments, $R^3$ and $R^4$ together with atoms attached thereto are joined to form substituted (e.g., substituted with a substituent group, a size-limited substituent group, or lower substituent group) or unsubstituted pyridyl. In embodiments, $R^3$ and $R^4$ together with atoms attached thereto are joined to form substituted (e.g., substituted with a substituent group, a size-limited substituent group, or lower substituent group) or unsubstituted piperidinyl. In embodiments, $R^3$ and $R^4$ together with atoms attached thereto are joined to form substituted (e.g., substituted with a substituent group, a size-limited substituent group, or lower substituent group) or unsubstituted morpholinyl. In embodiments, $R^3$ and $R^4$ together with atoms attached thereto are joined to form substituted (e.g., substituted with a substituent group, a size-limited substituent group, or lower substituent group) or unsubstituted phenyl. In embodiments, $R^3$ and $R^4$ together with atoms attached thereto are joined to form substituted (e.g., substituted with a substituent group, a size-limited substituent group, or lower substituent group) or unsubstituted pyrrolyl. In embodiments, $R^3$ and $R^4$ together with atoms attached thereto are joined to form substituted (e.g., substituted with a substituent group, a size-limited substituent group, or lower substituent group) or unsubstituted pyrimidinyl. In embodiments, $R^3$ and $R^4$ together with atoms attached thereto are joined to form substituted (e.g., substituted with a substituent group, a size-limited substituent group, or lower substituent group) or unsubstituted thiophenyl.

In embodiments, $R^4$ and $R^5$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^4$ and $R^5$ together with atoms attached thereto are joined to form substituted (e.g., substituted with a substituent group, a size-limited substituent group, or lower substituent group) or unsubstituted cyclopentyl. In embodiments, $R^4$ and $R^5$ together with atoms attached thereto are joined to form substituted (e.g., substituted with a substituent group, a size-limited substituent group, or lower substituent group) or unsubstituted cyclohexyl. In embodiments, $R^4$ and $R^5$ together with atoms attached thereto are joined to form substituted (e.g., substituted with a substituent group, a size-limited substituent group, or lower substituent group) or unsubstituted pyridyl. In embodiments, $R^4$ and $R^5$ together with atoms attached thereto are joined to form substituted (e.g., substituted with a substituent group, a size-limited substituent group, or lower substituent group) or unsubstituted piperidinyl. In embodiments, $R^4$ and $R^5$ together with atoms attached thereto are joined to form substituted (e.g., substituted with a substituent group, a size-limited substituent group, or lower substituent group) or unsubstituted morpholinyl. In embodiments, $R^4$ and $R^5$ together with atoms attached thereto are joined to form substituted (e.g., substituted with a substituent group, a size-limited substituent group, or lower substituent group) or unsubstituted phenyl. In embodiments, $R^4$ and $R^5$ together with atoms attached thereto are joined to form substituted (e.g., substituted with a substituent group, a size-limited substituent group, or lower substituent group) or unsubstituted pyrrolyl. In embodiments, $R^4$ and $R^5$ together with atoms attached thereto are joined to form substituted (e.g., substituted with a substituent group, a size-limited substituent group, or lower substituent group) or unsubstituted pyrimidinyl. In embodiments, $R^4$ and $R^5$ together with atoms attached thereto are joined to form substituted (e.g., substituted with a substituent group, a size-limited substituent group, or lower substituent group) or unsubstituted thiophenyl.

In embodiments, $R^6$ and $R^7$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^6$ and $R^7$ together with atoms attached thereto are joined to form substituted (e.g., substituted with a substituent group, a size-limited substituent group, or lower substituent group) or unsubstituted cyclopentyl. In embodiments, $R^6$ and $R^7$ together with atoms attached thereto are joined to form substituted (e.g., substituted with a substituent group, a size-limited substituent group, or lower substituent group) or unsubstituted cyclohexyl. In embodiments, $R^6$ and $R^7$ together with atoms attached thereto are joined to form substituted (e.g., substituted with a substituent group, a size-limited substituent group, or lower substituent group) or unsubstituted pyridyl. In embodiments, $R^6$ and $R^7$ together with atoms attached thereto are joined to form substituted (e.g., substituted with a substituent group, a size-limited substituent group, or lower substituent group) or unsubstituted piperidinyl. In embodiments, $R^6$ and $R^7$ together with atoms attached thereto are joined to form substituted (e.g., substituted with a substituent group, a size-limited substituent group, or lower substituent group) or unsubstituted morpholinyl. In embodiments, $R^6$ and $R^7$ together with atoms attached thereto are joined to form substituted (e.g., substituted with a substituent group, a size-limited substituent group, or lower substituent group) or unsubstituted phenyl. In embodiments, $R^6$ and $R^7$ together with atoms attached thereto are joined to form substituted (e.g., substituted with a substituent group, a size-limited substituent group, or lower substituent group) or unsubstituted pyrrolyl. In embodiments, $R^6$ and $R^7$ together with atoms attached thereto are joined to form substituted (e.g., substituted with a substituent group, a size-limited substituent group, or lower substituent group) or unsubstituted pyrimidinyl. In embodiments, $R^6$ and $R^7$ together with atoms attached thereto are joined to form substituted (e.g., substituted with a substituent group, a size-limited substituent group, or lower substituent group) or unsubstituted thiophenyl.

In embodiments, $R^7$ and $R^8$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^7$ and $R^8$ together with atoms attached thereto are joined to form substituted (e.g., substituted with a substituent group, a size-limited substituent group, or lower substituent group) or unsubstituted cyclopentyl. In embodiments, $R^7$ and $R^8$ together with atoms attached thereto are joined to form substituted (e.g., substituted with a substituent group, a size-limited substituent group, or lower substituent group) or unsubstituted cyclohexyl. In embodiments, $R^7$ and $R^8$ together with atoms attached thereto are joined to form substituted (e.g., substituted with a substituent group, a size-limited substituent group, or lower substituent group) or unsubstituted pyridyl. In embodiments, $R^7$ and $R^8$ together with atoms attached thereto are joined to form substituted (e.g., substituted with a substituent group, a size-limited substituent group, or lower substituent group) or unsubstituted piperidinyl. In embodiments, $R^7$ and $R^8$ together with atoms attached thereto are joined to form substituted (e.g., substituted with a substituent group, a size-limited substituent group, or lower substituent group) or unsubstituted morpholinyl. In embodiments, $R^7$ and $R^8$ together with atoms attached thereto are joined to form substituted (e.g., substituted with a substituent group, a size-limited substituent group, or lower substituent group) or unsubstituted phenyl. In embodiments, $R^7$ and $R^8$ together with atoms attached thereto are joined to form substituted (e.g., substituted with a substituent group, a size-limited substituent group, or lower substituent group) or unsubstituted pyrrolyl. In embodiments, $R^7$ and $R^8$ together with atoms attached thereto are joined to form substituted (e.g., substituted with a substituent group, a size-limited substituent group, or lower substituent group) or unsubstituted pyrimidinyl. In embodiments, $R^7$ and $R^8$ together with atoms attached thereto are joined to form substituted (e.g., substituted with a substituent group, a size-limited substituent group, or lower substituent group) or unsubstituted thiophenyl.

In embodiments, $R^8$ and $R^9$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^8$ and $R^9$ together with atoms attached thereto are joined to form substituted (e.g., substituted with a substituent group, a size-limited substituent group, or lower substituent group) or unsubstituted cyclopentyl. In embodiments, $R^8$ and $R^9$ together with atoms attached thereto are joined to form substituted (e.g., substituted with a substituent group, a size-limited substituent group, or lower substituent group) or unsubstituted cyclohexyl. In embodiments, $R^8$ and $R^9$ together with atoms attached thereto are joined to form substituted (e.g., substituted with a substituent group, a size-limited substituent group, or lower substituent group) or unsubstituted pyridyl. In embodiments, $R^8$ and $R^9$ together with atoms attached thereto are joined to form substituted (e.g., substituted with a substituent group, a size-limited substituent group, or lower substituent group) or unsubstituted piperidinyl. In embodiments, $R^8$ and $R^9$ together with atoms attached thereto are joined to form substituted (e.g., substituted with a substituent group, a size-limited substituent group, or lower substituent group) or unsubstituted morpholinyl. In embodiments, $R^8$ and $R^9$ together with atoms attached thereto are joined to form substituted (e.g., substituted with a substituent group, a size-limited substituent group, or lower substituent group) or unsubstituted phenyl. In embodiments, $R^8$ and $R^9$ together with atoms attached thereto are joined to form substituted (e.g., substituted with a substituent group, a size-limited substituent group, or lower substituent group) or unsubstituted pyrrolyl. In embodiments, $R^8$ and $R^9$ together with atoms attached thereto are joined to form substituted (e.g., substituted with a substituent group, a size-limited substituent group, or lower substituent group) or unsubstituted pyrimidinyl. In embodiments, $R^8$ and $R^9$ together with atoms attached thereto are joined to form substituted (e.g., substituted with a substituent group, a size-limited substituent group, or lower substituent group) or unsubstituted thiophenyl.

In embodiments, $R^9$ and $R^{10}$ together with atoms attached thereto are joined to form substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). In embodiments, $R^9$ and $R^{10}$ together with atoms attached thereto are joined to form substituted (e.g., substituted with a substituent group, a size-limited substituent group, or lower substituent group) or unsubstituted cyclopentyl. In embodiments, $R^9$ and $R^{10}$ together with atoms attached thereto are joined to form substituted (e.g., substituted with a substituent group, a size-limited substituent group, or lower substituent group) or unsubstituted cyclohexyl. In embodiments, $R^9$ and $R^{10}$ together with atoms attached thereto are joined to form substituted (e.g., substituted with a substituent group, a size-limited substituent group, or lower substituent group) or unsubstituted pyridyl. In embodiments, $R^9$ and $R^{10}$ together with atoms attached thereto are joined to form substituted (e.g., substituted with a substituent group, a size-limited substituent group, or lower substituent group) or unsubstituted piperidinyl. In embodiments, $R^9$ and $R^{10}$ together with atoms attached thereto are joined to form substituted (e.g., substituted with a substituent group, a size-limited substituent group, or lower substituent group) or unsubstituted morpholinyl. In embodiments, $R^9$ and $R^{10}$ together with atoms attached thereto are joined to form substituted (e.g., substituted with a substituent group, a size-limited substituent group, or lower substituent group) or unsubstituted phenyl. In embodiments, $R^9$ and $R^{10}$ together with atoms attached thereto are joined to form substituted (e.g., substituted with a substituent group, a size-limited substituent group, or lower substituent group) or unsubstituted pyrrolyl. In embodiments, $R^9$ and $R^{10}$ together with atoms attached thereto are joined to form substituted (e.g., substituted with a substituent group, a size-limited substituent group, or lower substituent group) or unsubstituted pyrimidinyl. In embodiments, $R^9$ and $R^{10}$ together with atoms attached thereto are joined to form substituted (e.g., substituted with a substituent group, a size-limited substituent group, or lower substituent group) or unsubstituted thiophenyl.

In embodiments, the compound has a formula (IIA):

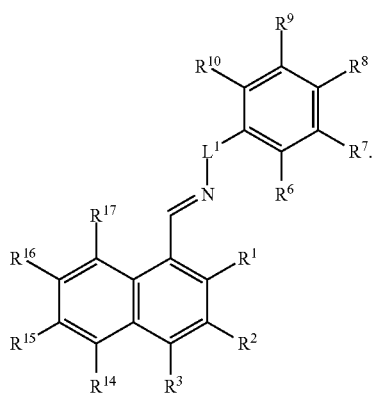

In formula (IIA), $L^1$, $R^1$, $R^2$, $R^3$, $R^6$, $R^7$, $R^8$, $R^9$, and $R^{10}$ are as described herein.

In embodiments, the compound has a formula (IIB):

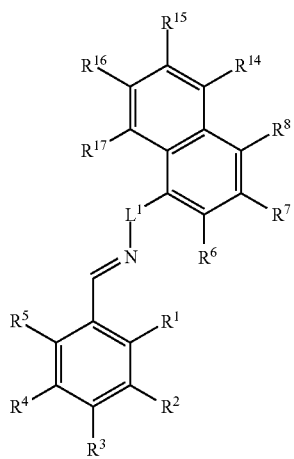

In formula (IIB), $L^1$, $R^1$, $R^2$, $R^3$, $R^6$, $R^7$, $R^8$, $R^9$, and $R^{10}$ are as described herein.

$R^{14}$ is hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-N_3$, $-CN$, $-SO_{n14}R^{14D}$, $-SO_{v14}NR^{14A}R^{14B}$, $-NHC(O)NR^{14A}R^{14B}$, $-N(O)_{m14}$, $-NR^{14A}R^{14B}$, $-C(O)R^{14C}$, $-C(O)-OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)OR^{14C}$, $-NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $-CX^{15}_3$, $-CHX^{15}_2$, $-CH_2X^{15}$, $-OCX^{15}_3$, $-OCH_2X^{15}$, $-OCHX^{15}_2$, $-N_3$, $-CN$, $-SO_{n15}R^{15D}$, $-SO_{v15}NR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is hydrogen, halogen, $-CX^{16}_3$, $-CHX^{16}_2$, $-CH_2X^{16}$, $-OCX^{16}_3$, $-OCH_2X^{16}$, $-OCHX^{16}_2$, $-N_3$, $-CN$, $-SO_{n16}R^{16D}$, $-SO_{v16}NR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{17}$ is hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-N_3$, $-CN$, $-SO_{n17}R^{17D}$, $-SO_{v17}NR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols n14, n15, n16, and n17 are independently an integer from 0 to 4 (e.g. 0). The symbols m14, m15, m16, m17, v14, v15, v16, and v17 are independently an integer from 1 to 2. The symbols $X^{14}$, $X^{15}$, $X^{16}$, and $X^{17}$ are independently $-F$, $-Cl$, $-Br$, or $-I$.

In embodiments, $L^1$ is $-CR^{11}R^{12}-$, $-NR^{13}-$, $-O-$, or $-S-$. In embodiments, $L^1$ is $-NR^{13}-$, $-O-$, or $-S-$. In embodiments, $L^1$ is $-CR^{11}R^{12}-$, $-O-$, or $-S-$. In embodiments, $L^1$ is $-O-$, or $-S-$. In embodiments, $L^1$ is $-O-$. In embodiments, $L^1$ is $-S-$. In embodiments, $L^1$ is $-NR^{13}-$. In embodiments, $L^1$ is $-NH-$. In embodiments, $L^1$ is a bond. In embodiments, $L^1$ is $-S(O)-$. In embodiments, $L^1$ is $-S(O)_2-$. In embodiments, $L^1$ is $-NR^{13}S(O)_2-$. In embodiments, $L^1$ is $-NR^{13}C(O)-$. In embodiments, $L^1$ is $-NHS(O)_2-$. In embodiments, $L^1$ is $-NHC(O)-$. In embodiments, $L^1$ is $-NCH_3S(O)_2-$. In embodiments, $L^1$ is $-NCH_3C(O)-$. In embodiments, $L^1$ is $-CH_2-$. In embodiments, $L^1$ is $-S(O)NR^{13}-$. In embodiments, $L^1$ is $-S(O)_2NR^{13}-$. In embodiments, $L^1$ is $-C(O)NR^{13}-$. In embodiments, $L^1$ is not a bond.

In embodiments, $R^{11}$ is hydrogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-N_3$, $-CN$, $-SH$, $-SCH_3$, $-SO_2H$, $-NO_2$, $-NH_2$, $-OH$, $-OCH_3$, substituted or unsubstituted $C_1$-$C_6$ alkyl, or substituted or unsubstituted 2 to 6 membered heteroalkyl. In embodiments, $R^{11}$ is hydrogen. In embodiments, $R^{11}$ is $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, or $-CH_2I$. In embodiments, $R^{11}$ is $-N_3$. In embodiments, $R^{11}$ is $-CN$. In embodiments, $R^{11}$ is $-SH$. In embodiments, $R^{11}$ is $-SCH_3$. In embodiments, $R^{11}$ is $-SO_2H$. In embodiments, $R^{11}$ is $-NO_2$. In embodiments, $R^{11}$ is $-NH_2$. In embodiments, $R^{11}$ is $-OH$. In embodiments, $R^{11}$ is $-OCH_3$. In embodiments, $R^{11}$ is substituted or unsubstituted $C_1$-$C_6$ alkyl. In embodiments, $R^{11}$ is substituted or unsubstituted $C_1$-$C_4$ alkyl. In embodiments, $R^{11}$ is substituted or unsubstituted $C_1$-$C_2$ alkyl. In embodiments, $R^{11}$ is substituted methyl. In embodiments, $R^{11}$ is unsubstituted methyl. In embodiments, $R^{11}$ is substituted ethyl. In embodiments, $R^{11}$ is unsubstituted ethyl. In embodiments, $R^{11}$ is substituted or unsubstituted 2 to 6 membered heteroalkyl. In embodiments, $R^{11}$ is substituted or unsubstituted 2 to 4 membered heteroalkyl. In embodiments, $R^{11}$ is substituted or unsubstituted 2 to 3 membered heteroalkyl. In embodiments, $R^{11}$ is substituted 2 membered heteroalkyl. In embodiments, $R^{11}$ is unsubstituted 2 membered heteroalkyl. In embodiments, $R^{11}$ is substituted 3 membered heteroalkyl. In embodiments, $R^{11}$ is unsubstituted 3 membered heteroalkyl.

In embodiments, $R^{12}$ is hydrogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-CH_2I$, $-N_3$, $-CN$, $-SH$, $-SCH_3$, $-SO_2H$, $-NO_2$. $-NH_2$, $-OH$, $-OCH_3$, substituted or unsubstituted $C_1$-$C_6$ alkyl, or substituted or unsubstituted 2 to 6 membered heteroalkyl. In embodiments, $R^{12}$ is hydrogen. In embodiments, $R^{12}$ is $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, or $-CH_2I$. In embodiments, $R^{12}$ is $-N_3$. In embodiments, $R^{12}$ is $-CN$. In embodiments, $R^{12}$ is $-SH$. In embodiments, $R^{12}$ is $-SCH_3$. In embodiments, $R^{12}$ is $-SO_2H$. In embodiments, $R^{12}$ is $-NO_2$. In embodiments, $R^{12}$ is $-NH_2$. In embodiments, $R^{12}$ is $-OH$. In embodiments, $R^{12}$ is $-OCH_3$. In embodiments, $R^{12}$ is substituted or unsubstituted $C_1$-$C_6$ alkyl. In embodiments, $R^{12}$ is substituted or unsubstituted $C_1$-$C_4$ alkyl. In embodiments, $R^{12}$ is substituted or unsubstituted $C_1$-$C_2$ alkyl. In embodiments, $R^{12}$ is substituted methyl. In embodiments, $R^{12}$ is unsubstituted methyl. In embodiments, $R^{12}$ is substituted ethyl. In embodiments, $R^{12}$ is unsubstituted ethyl. In embodiments, $R^{12}$ is substituted or unsubstituted 2 to 6 membered heteroalkyl. In embodiments, $R^{12}$ is substituted or unsubstituted 2 to 4 membered heteroalkyl. In embodiments, $R^{12}$ is substituted or unsubstituted 2 to 3 membered heteroalkyl. In embodiments, $R^{12}$ is substituted 2 membered heteroalkyl. In embodiments, $R^{12}$ is unsubstituted 2 membered heteroalkyl. In embodiments, $R^{12}$ is substituted 3 membered heteroalkyl. In embodiments, $R^{12}$ is unsubstituted 3 membered heteroalkyl.

In embodiments, $R^{13}$ is hydrogen, $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, $-CHI_2$, $-COOH$, $-CONH_2$, substituted or unsubstituted $C_1$-$C_6$, alkyl, or substituted or unsubstituted 2 to 6 membered heteroalkyl. In embodiments, $R^{13}$ is hydrogen. In embodiments, $R^{13}$ is $-CF_3$, $-CHF_2$, $-CH_2F$, $-CCl_3$, $-CHCl_2$, $-CH_2Cl$, $-CBr_3$, $-CHBr_2$, $-CH_2Br$, $-CI_3$, or $-CHI_2$. In embodiments, $R^{13}$ is $-COOH$. In embodiments, $R^{13}$ is $-CONH_2$. In embodiments, $R^{13}$ is substituted or unsubstituted $C_1$-$C_6$, alkyl. In embodiments, $R^{13}$ is substituted or unsubstituted $C_1$-$C_4$ alkyl. In embodiments, $R^{13}$ is substituted or unsubstituted $C_1$-$C_2$ alkyl. In embodiments, $R^{13}$ is substituted methyl. In embodiments, $R^{13}$ is unsubstituted methyl. In embodiments, $R^{13}$ is substituted ethyl. In embodiments, $R^{13}$ is unsubstituted ethyl. In embodiments, $R^{13}$ is substituted or unsubstituted 2 to 6 membered heteroalkyl. In embodiments, $R^{13}$ is substituted or unsubstituted 2 to 4 membered heteroalkyl. In embodiments, $R^{13}$ is substituted or unsubstituted 2 to 3 membered heteroalkyl. In embodiments, $R^{13}$ is substituted 2 membered heteroalkyl. In embodiments, $R^{13}$ is unsubstituted 2 membered heteroalkyl. In embodiments, $R^{13}$ is substituted 3 membered heteroalkyl. In embodiments, $R^{13}$ is unsubstituted 3 membered heteroalkyl.

In embodiments, $R^1$ is hydrogen, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-SH$, $-NO_2$, $-NH_2$, $-C(O)H$, $-C(O)OH$, $-C(O)OCH_3$, $-OH$, $-OCH_3$, substituted or unsubstituted $C_1$-$C_4$ alkyl, or substituted or unsubstituted 2 to 6 membered heteroalkyl. In embodiments, $R^1$ is hydrogen. In embodiments, $R^1$ is $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, or $-OCH_2I$. In embodiments, $R^1$ is $-SH$. In embodiments, $R^1$ is $-NO_2$. In embodiments, $R^1$ is $-NH_2$. In embodiments, $R^1$ is $-C(O)H$. In embodiments, $R^1$ is $-C(O)OH$. In embodiments, $R^1$ is $-C(O)OCH_3$. In embodiments, $R^1$ is $-OH$. In embodiments, $R^1$ is $-OCH_3$. In embodiments, $R^1$ is substituted or unsubstituted $C_1$-$C_4$ alkyl. In embodiments, $R^1$ is substituted or unsubstituted $C_1$-$C_4$ alkyl. In embodiments, $R^1$ is substituted methyl. In embodiments, $R^1$ is unsubstituted methyl. In embodiments, $R^1$ is substituted ethyl. In embodiments, $R^1$ is unsubstituted ethyl. In embodiments, $R^1$ is substituted or unsubstituted 2 to 6 membered heteroalkyl. In embodiments, $R^1$ is substituted or unsubstituted 2 to 4 membered heteroalkyl. In embodiments, $R^1$ is substituted or unsubstituted 2 to 3 membered heteroalkyl. In embodiments, $R^1$ is substituted 2 membered heteroalkyl. In embodiments, $R^1$ is unsubstituted 2 membered heteroalkyl. In embodiments, $R^1$ is substituted 3 membered heteroalkyl. In embodiments, $R^1$ is unsubstituted 3 membered heteroalkyl.

In embodiments, $R^2$ is hydrogen, $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, $-OCH_2I$, $-SH$, $-NO_2$, $-NH_2$, $-C(O)H$, $-C(O)OH$, $-C(O)OCH_3$, $-OH$, $-OCH_3$, substituted or unsubstituted $C_1$-$C_4$ alkyl, or substituted or unsubstituted 2 to 6 membered heteroalkyl. In embodiments, $R^2$ is hydrogen. In embodiments, $R^2$ is $-OCF_3$, $-OCCl_3$, $-OCBr_3$, $-OCI_3$, $-OCHF_2$, $-OCHCl_2$, $-OCHBr_2$, $-OCHI_2$, $-OCH_2F$, $-OCH_2Cl$, $-OCH_2Br$, or $-OCH_2I$. In embodiments, $R^2$ is $-SH$. In embodiments, $R^2$ is $-NO_2$. In embodiments, $R^2$ is $-NH_2$. In embodiments, $R^2$ is $-C(O)H$. In embodiments, $R^2$ is $-C(O)OH$. In embodiments, $R^2$ is $-C(O)OCH_3$. In embodiments, $R^2$ is $-OH$. In embodiments, $R^2$ is $-OCH_3$. In embodiments, $R^2$ is substituted or unsubstituted $C_1$-$C_4$ alkyl. In embodiments, $R^2$ is substituted or unsubstituted $C_1$-$C_2$ alkyl. In embodiments, $R^2$ is substituted methyl. In embodiments, $R^2$ is unsubstituted methyl. In embodiments, $R^2$ is substituted ethyl. In embodiments, $R^2$ is unsubstituted ethyl. In embodiments, $R^2$ is substituted or unsubstituted 2 to 6 membered heteroalkyl. In embodiments, $R^2$ is substituted or unsubstituted 2 to 4 membered heteroalkyl. In embodiments, $R^2$ is substituted or unsubstituted 2 to 3 membered heteroalkyl. In embodiments, $R^2$ is substituted 2 membered heteroalkyl. In embodiments, $R^2$ is unsubstituted 2 membered heteroalkyl. In embodiments, $R^2$ is substituted 3 membered heteroalkyl. In embodiments, $R^2$ is unsubstituted 3 membered heteroalkyl.

In embodiments, $R^3$ is hydrogen, —OCF$_3$, —OCCl$_3$, —OCBr$_2$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —NO$_2$, —NH$_2$, —C(O)H, —C(O)OH, —C(O)OCH$_3$, —OH, —OCH$_3$, substituted or unsubstituted C$_1$-C$_4$ alkyl, or substituted or unsubstituted 2 to 6 membered heteroalkyl. In embodiments, $R^3$ is hydrogen. In embodiments, $R^3$ is —OCF$_3$, —OCCl$_3$, —OCBr$_2$, —OCI$_3$, —OCHF$_2$, —OCHCl$_2$, —OCHBr$_2$, —OCHI$_2$, —OCH$_2$F, —OCH$_2$Cl, —OCH$_2$Br, or —OCH$_2$I. In embodiments, $R^3$ is —SH. In embodiments, $R^3$ is —NO$_2$. In embodiments, $R^3$ is —NH$_2$. In embodiments, $R^3$ is —C(O)H. In embodiments, $R^3$ is —C(O)OH. In embodiments, $R^3$ is —C(O)OCH$_3$. In embodiments, $R^3$ is —OH. In embodiments, $R^3$ is —OCH$_3$. In embodiments, $R^3$ is substituted or unsubstituted C$_1$-C$_4$ alkyl. In embodiments, $R^3$ is substituted or unsubstituted C$_1$-C$_2$ alkyl. In embodiments, $R^3$ is substituted methyl. In embodiments, $R^3$ is unsubstituted methyl. In embodiments, $R^3$ is substituted ethyl. In embodiments, $R^3$ is unsubstituted ethyl. In embodiments, $R^3$ is substituted or unsubstituted 2 to 6 membered heteroalkyl. In embodiments, $R^3$ is substituted or unsubstituted 2 to 4 membered heteroalkyl. In embodiments, $R^3$ is substituted or unsubstituted 2 to 3 membered heteroalkyl. In embodiments, $R^3$ is substituted 2 membered heteroalkyl. In embodiments, $R^3$ is unsubstituted 2 membered heteroalkyl. In embodiments, $R^3$ is substituted 3 membered heteroalkyl. In embodiments, $R^3$ is unsubstituted 3 membered heteroalkyl.

In embodiments, at least one of $R^1$, $R^2$ and $R^3$ are —OH. In embodiments, $R^1$ is —OH. In embodiments, $R^2$ is —OH. In embodiments, $R^3$ is —OH. In embodiments, at least two of $R^1$, $R^2$ and $R^3$ are —OH. In embodiments, $R^1$ and $R^2$ are —OH. In embodiments, $R^2$ and $R^3$ are —OH. In embodiments, $R^1$ and $R^3$ are —OH. In embodiments, $R^1$, $R^2$ and $R^3$ are —OH.

In embodiments, at least one of $R^1$, $R^2$ and $R^3$ are —OCH$_3$. In embodiments, $R^1$ is —OCH$_3$. In embodiments, $R^2$ is —OCH$_3$. In embodiments, $R^3$ is —OCH$_3$. In embodiments, at least two of $R^1$, $R^2$ and $R^3$ are —OCH$_3$. In embodiments, $R^1$ and $R^2$ are —OCH$_3$. In embodiments, $R^2$ and $R^3$ are —OCH$_3$. In embodiments, $R^1$ and $R^3$ are —OCH$_3$. In embodiments, $R^1$, $R^2$ and $R^3$ are —OCH$_3$.

In embodiments, $L^1$ is —S—, and $R^1$ is —OH. In embodiments, $L^1$ is —O—, and $R^1$ is —OH. In embodiments, $L^1$ is —S—, and $R^2$ is —OH. In embodiments, $L^1$ is —O—, and $R^2$ is —OH. In embodiments, $L^1$ is —S—, and $R^3$ is —OH. In embodiments, $L^1$ is —O—, and $R^3$ is —OH. In embodiments, $L^1$ is —NH—, and $R^1$ is —OH. In embodiments, $L^1$ is —S(O)—, and $R^1$ is —OH. In embodiments, $L^1$ is —S(O)$_2$—, and $R^1$ is —OH. In embodiments, $L^1$ is —NHC(O)—, and $R^1$ is —OH. In embodiments, $L^1$ is —NHS(O)—, and $R^1$ is —OH. In embodiments, $L^1$ is —NHS(O)$_2$—, and $R^1$ is —OH. In embodiments, $L^1$ is a bond, and $R^1$ is —OH.

In embodiments, $L^1$ is —S—, and $R^1$ is —OCH$_3$. In embodiments, $L^1$ is —O—, and $R^1$ is —OCH$_3$. In embodiments, $L^1$ is —NH—, and $R^1$ is —OCH$_3$. In embodiments, $L^1$ is —S(O)—, and $R^1$ is —OCH$_3$. In embodiments, $L^1$ is —S(O)$_2$—, and $R^1$ is —OCH$_3$. In embodiments, $L^1$ is —NHC(O)—, and $R^1$ is —OCH$_3$. In embodiments, $L^1$ is —NHS(O)—, and $R^1$ is —OCH$_3$. In embodiments, $L^1$ is —NHS(O)$_2$—, and $R^1$ is —OCH$_3$. In embodiments, $L^1$ is a bond, and $R^1$ is —OCH$_3$.

In embodiments, $R^7$ is hydrogen, —OCF$_3$, —OCCl$_3$, —OCBr$_2$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —NO$_2$, —NH$_2$, —C(O)H, —C(O)OH, —C(O)OCH$_3$, —OH, —OCH$_3$, substituted or unsubstituted C$_1$-C$_4$ alkyl, or substituted or unsubstituted 2 to 6 membered heteroalkyl. In embodiments, $R^7$ is hydrogen. In embodiments, $R^7$ is —OCF$_3$, —OCCl$_3$, —OCBr$_2$, —OCI$_3$, —OCHF$_2$, —OCHCl$_2$, —OCHBr$_2$, —OCHI$_2$, —OCH$_2$F, —OCH$_2$Cl, —OCH$_2$Br, or —OCH$_2$I. In embodiments, $R^7$ is —SH. In embodiments, $R^7$ is —NO$_2$. In embodiments, $R^7$ is —NH$_2$. In embodiments, $R^7$ is —C(O)H. In embodiments, $R^7$ is —C(O)OH. In embodiments, $R^7$ is —C(O)OCH$_3$. In embodiments, $R^7$ is —OH. In embodiments, $R^7$ is —OCH$_3$. In embodiments, $R^7$ is substituted or unsubstituted C$_1$-C$_4$ alkyl. In embodiments, $R^7$ is substituted or unsubstituted C$_1$-C$_2$ alkyl. In embodiments, $R^7$ is substituted methyl. In embodiments, $R^7$ is unsubstituted methyl. In embodiments, $R^7$ is substituted ethyl. In embodiments, $R^7$ is unsubstituted ethyl. In embodiments, $R^7$ is substituted or unsubstituted 2 to 6 membered heteroalkyl. In embodiments, $R^7$ is substituted or unsubstituted 2 to 4 membered heteroalkyl. In embodiments, $R^7$ is substituted or unsubstituted 2 to 3 membered heteroalkyl. In embodiments, $R^7$ is substituted 2 membered heteroalkyl. In embodiments, $R^7$ is unsubstituted 2 membered heteroalkyl. In embodiments, $R^7$ is substituted 3 membered heteroalkyl. In embodiments, $R^7$ is unsubstituted 3 membered heteroalkyl.

In embodiments, $R^9$ is hydrogen, —OCF$_3$, —OCCl$_3$, —OCBr$_2$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —SH, —NO$_2$, —NH$_2$, —C(O)H, —C(O)OH, —C(O)OCH$_3$, —OH, —OCH$_3$, substituted or unsubstituted C$_1$-C$_4$ alkyl, or substituted or unsubstituted 2 to 6 membered heteroalkyl. In embodiments, $R^9$ is hydrogen. In embodiments, $R^9$ is —OCF$_3$, —OCCl$_3$, —OCBr$_2$, —OCI$_3$, —OCHF$_2$, —OCHCl$_2$, —OCHBr$_2$, —OCHI$_2$, —OCH$_2$F, —OCH$_2$Cl, —OCH$_2$Br, or —OCH$_2$I. In embodiments, $R^9$ is —SH. In embodiments, $R^9$ is —NO$_2$. In embodiments, $R^9$ is —NH$_2$. In embodiments, $R^9$ is —C(O)H. In embodiments, $R^9$ is —C(O)OH. In embodiments, $R^9$ is —C(O)OCH$_3$. In embodiments, $R^9$ is —OH. In embodiments, $R^9$ is —OCH$_3$. In embodiments, $R^9$ is substituted or unsubstituted C$_1$-C$_4$ alkyl. In embodiments, $R^9$ is substituted or unsubstituted C$_1$-C$_2$ alkyl. In embodiments, $R^9$ is substituted methyl. In embodiments, $R^9$ is unsubstituted methyl. In embodiments, $R^9$ is substituted ethyl. In embodiments, $R^9$ is unsubstituted ethyl. In embodiments, $R^9$ is substituted or unsubstituted 2 to 6 membered heteroalkyl. In embodiments, $R^9$ is substituted or unsubstituted 2 to 4 membered heteroalkyl. In embodiments, $R^9$ is substituted or unsubstituted 2 to 3 membered heteroalkyl. In embodiments, $R^9$ is substituted 2 membered heteroalkyl. In embodiments, $R^9$ is unsubstituted 2 membered heteroalkyl. In embodiments, $R^9$ is substituted 3 membered heteroalkyl. In embodiments, $R^9$ is unsubstituted 3 membered heteroalkyl.

In embodiments, at least one of $R^7$ and $R^9$ are hydrogen. In embodiments, $R^7$ is hydrogen. In embodiments, $R^9$ is hydrogen. In embodiments, $R^7$ and $R^9$ are hydrogen. In embodiments, $R^7$ is not hydrogen. In embodiments, $R^9$ is not hydrogen.

In embodiments, $R^6$ is hydrogen, halogen, —N$_3$, —CN, —NO$_2$, —NH$_2$, —C(O)H, —C(O)CH$_3$, —C(O)OH, —C(O)OCH$_3$, —C(O)NH$_2$, —OH, —OCH$_3$, substituted or unsubstituted C$_1$-C$_4$ alkyl, or substituted or unsubstituted 2 to 6 membered heteroalkyl. In embodiments, $R^6$ is hydrogen. In embodiments, $R^6$ is —F, —Cl, —Br, or —I. In embodiments, $R^6$ is —$N_3$. In embodiments, $R^6$ is —CN. In embodiments, $R^6$ is —$NO_2$. In embodiments, $R^6$ is —$NH_2$, —C(O)H, —C(O)$CH_3$. In embodiments, $R^6$ is —C(O)OH, —C(O)$OCH_3$. In embodiments, $R^6$ is —C(O)$NH_2$. In embodiments, $R^6$ is —OH. In embodiments, $R^6$ is —$OCH_3$. In embodiments, $R^6$ is substituted or unsubstituted $C_1$-$C_4$ alkyl. In embodiments, $R^6$ is substituted or unsubstituted $C_1$-$C_2$ alkyl. In embodiments, $R^6$ is substituted methyl. In embodiments, $R^6$ is unsubstituted methyl. In embodiments, $R^6$ is substituted ethyl. In embodiments, $R^6$ is unsubstituted ethyl. In embodiments, $R^6$ is substituted or unsubstituted 2 to 6 membered heteroalkyl. In embodiments, $R^6$ is substituted or unsubstituted 2 to 4 membered heteroalkyl. In embodiments, $R^6$ is substituted or unsubstituted 2 to 3 membered heteroalkyl. In embodiments, $R^6$ is substituted 2 membered heteroalkyl. In embodiments, $R^6$ is unsubstituted 2 membered heteroalkyl. In embodiments, $R^6$ is substituted 3 membered heteroalkyl. In embodiments, $R^6$ is unsubstituted 3 membered heteroalkyl.

In embodiments, $R^8$ is hydrogen, halogen, —$N_3$, —CN, —$NO_2$, —$NH_2$, —C(O)H, —C(O)$CH_3$, —C(O)OH, —C(O)$OCH_3$, —C(O)$NH_2$, —OH, —$OCH_3$, substituted or unsubstituted $C_1$-$C_4$ alkyl, or substituted or unsubstituted 2 to 6 membered heteroalkyl. In embodiments, $R^8$ is hydrogen. In embodiments, $R^8$ is halogen. In embodiments, $R^8$ is —F, —Cl, —Br, or —I. In embodiments, $R^8$ is —$N_3$. In embodiments, $R^8$ is —CN. In embodiments, $R^8$ is —$NO_2$. In embodiments, $R^8$ is —$NH_2$, —C(O)H, —C(O)$CH_3$. In embodiments, $R^8$ is —C(O)OH, —C(O)$OCH_3$. In embodiments, $R^8$ is —C(O)$NH_2$. In embodiments, $R^8$ is —OH. In embodiments, $R^8$ is —$OCH_3$. In embodiments, $R^8$ is substituted or unsubstituted $C_1$-$C_4$ alkyl. In embodiments, $R^8$ is substituted or unsubstituted $C_1$-$C_2$ alkyl. In embodiments, $R^8$ is substituted methyl. In embodiments, $R^8$ is unsubstituted methyl. In embodiments, $R^8$ is substituted ethyl. In embodiments, $R^8$ is unsubstituted ethyl. In embodiments, $R^8$ is substituted or unsubstituted 2 to 6 membered heteroalkyl. In embodiments, $R^8$ is substituted or unsubstituted 2 to 4 membered heteroalkyl. In embodiments, $R^8$ is substituted or unsubstituted 2 to 3 membered heteroalkyl. In embodiments, $R^8$ is substituted 2 membered heteroalkyl. In embodiments, $R^8$ is unsubstituted 2 membered heteroalkyl. In embodiments, $R^8$ is substituted 3 membered heteroalkyl. In embodiments, $R^8$ is unsubstituted 3 membered heteroalkyl.

In embodiments, $R^{10}$ is hydrogen, halogen, —$N_3$, —CN, —$NO_2$, —$NH_2$, —C(O)H, —C(O)$CH_3$, —C(O)OH, —C(O)$OCH_3$, —C(O)$NH_2$, —OH, —$OCH_3$, substituted or unsubstituted $C_1$-$C_4$ alkyl, or substituted or unsubstituted 2 to 6 membered heteroalkyl. In embodiments, $R^{10}$ is hydrogen. In embodiments, $R^{10}$ is halogen. In embodiments, $R^{10}$ is —F, —Cl, —Br, or —I. In embodiments, $R^{10}$ is —$N_3$. In embodiments, $R^{10}$ is —CN. In embodiments, $R^{10}$ is —$NO_2$. In embodiments, $R^{10}$ is —$NH_2$, —C(O)H, —C(O)$CH_3$. In embodiments, $R^{10}$ is —C(O)OH, —C(O)$OCH_3$. In embodiments, $R^{10}$ is —C(O)$NH_2$. In embodiments, $R^{10}$ is —OH. In embodiments, $R^{10}$ is —$OCH_3$. In embodiments, $R^{10}$ is substituted or unsubstituted $C_1$-$C_4$ alkyl. In embodiments, $R^{10}$ is substituted or unsubstituted $C_1$-$C_2$ alkyl. In embodiments, $R^{10}$ is substituted methyl. In embodiments, $R^{10}$ is unsubstituted methyl. In embodiments, $R^{10}$ is substituted ethyl. In embodiments, $R^{10}$ is unsubstituted ethyl. In embodiments, $R^{10}$ is substituted or unsubstituted 2 to 6 membered heteroalkyl. In embodiments, $R^{10}$ is substituted or unsubstituted 2 to 4 membered heteroalkyl. In embodiments, $R^{10}$ is substituted or unsubstituted 2 to 3 membered heteroalkyl. In embodiments, $R^{10}$ is substituted 2 membered heteroalkyl. In embodiments, $R^{10}$ is unsubstituted 2 membered heteroalkyl. In embodiments, $R^{10}$ is substituted 3 membered heteroalkyl. In embodiments, $R^{10}$ is unsubstituted 3 membered heteroalkyl.

In embodiments, each $R^6$, $R^8$, and $R^{10}$ is independently hydrogen, halogen, —$N_3$, —CN, —$NO_2$, —$NH_2$, —C(O)H, —C(O)$CH_3$, —C(O)OH, —C(O)$OCH_3$, —C(O)$NH_2$, —OH, —$OCH_3$, or substituted or unsubstituted $C_1$-$C_3$ alkyl. In embodiments, each $R^6$ and $R^{10}$ is independently hydrogen, halogen, —$N_3$, —CN, —$NO_2$, —$NH_2$, —C(O)H, —C(O)$CH_3$, —C(O)OH, —C(O)$OCH_3$, —C(O)$NH_2$, —OH, —$OCH_3$, or substituted or unsubstituted $C_1$-$C_3$ alkyl. In embodiments, each $R^6$ and $R^8$ is independently hydrogen, halogen, —$N_3$, —CN, —$NO_2$, —$NH_2$, —C(O)H, —C(O)$CH_3$, —C(O)OH, —C(O)$OCH_3$, —C(O)$NH_2$, —OH, —$OCH_3$, or substituted or unsubstituted $C_1$-$C_3$ alkyl. In embodiments, each $R^8$, and $R^{10}$ is independently hydrogen, halogen, —$N_3$, —CN, —$NO_2$, —$NH_2$, —C(O)H, —C(O)$CH_3$, —C(O)OH, —C(O)$OCH_3$, —C(O)$NH_2$, —OH, —$OCH_3$, or substituted or unsubstituted $C_1$-$C_3$ alkyl.

In embodiments, at least one of $R^6$, $R^8$, and $R^{10}$ are hydrogen. In embodiments, $R^6$ is hydrogen. In embodiments, $R^8$ is hydrogen. In embodiments, $R^{10}$ is hydrogen. In embodiments, at least two of $R^6$, $R^8$, and $R^{10}$ are hydrogen. In embodiments, $R^6$ and $R^{10}$ are hydrogen. In embodiments, $R^8$ and $R^{10}$ are hydrogen. In embodiments, $R^6$ and $R^8$ are hydrogen. In embodiments, $R^6$, $R^8$, and $R^{10}$ are hydrogen.

In embodiments, the compound has a formula:

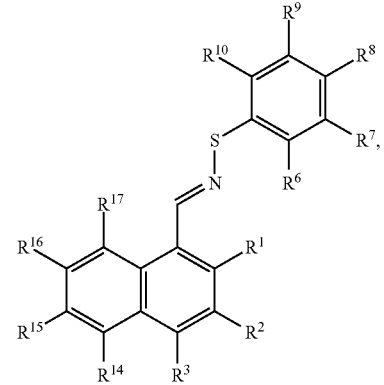

wherein $R^1$, $R^2$, $R^3$, $R^6$, $R^7$, $R^8$, $R^9$, $R^{10}$, $R^{15}$, $R^{16}$, and $R^{17}$ are as described herein.

In embodiments, the compound has a formula:

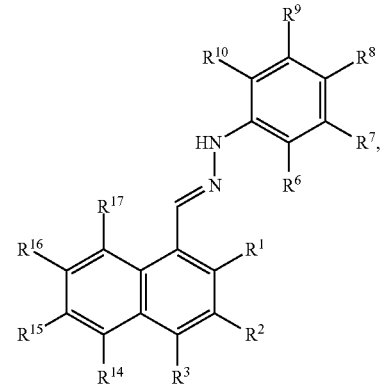

wherein $R^1$, $R^2$, $R^3$, $R^6$, $R^7$, $R^8$, $R^9$, $R^{10}$, $R^{15}$, $R^{16}$, and $R^{17}$ are as described herein.

In embodiments, the compound has a formula:

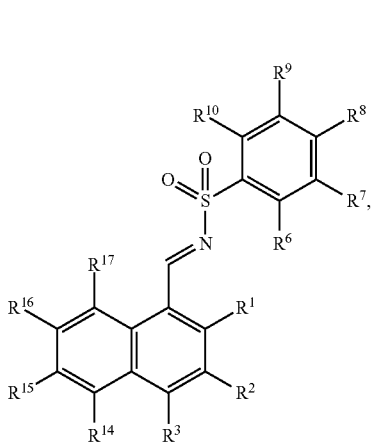

wherein $R^1$, $R^2$, $R^3$, $R^6$, $R^7$, $R^8$, $R^9$, $R^{10}$, $R^{15}$, $R^{16}$, and $R^{17}$ are as described herein.

In embodiments, the compound has a formula:

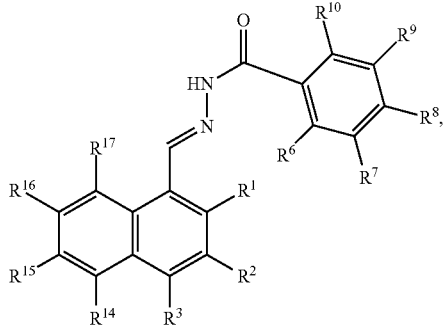

wherein $R^1$, $R^2$, $R^3$, $R^6$, $R^7$, $R^8$, $R^9$, $R^{10}$, $R^{15}$, $R^{16}$, and $R^{17}$ are as described herein.

In embodiments, the compound has a formula:

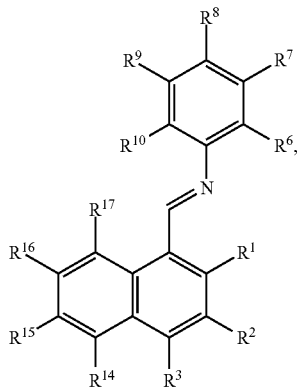

wherein $R^1$, $R^2$, $R^3$, $R^6$, $R^7$, $R^8$, $R^9$, $R^{10}$, $R^{15}$, $R^{16}$, and $R^{17}$ are as described herein.

In embodiments, the compound has a formula:

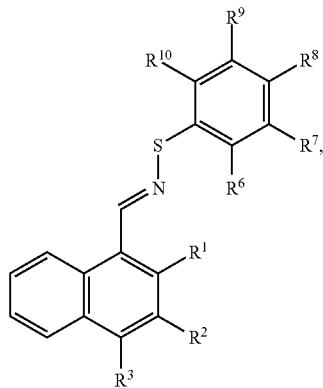

wherein $R^1$, $R^2$, $R^3$, $R^6$, $R^7$, $R^8$, $R^9$, and $R^{10}$ are as described herein.

In embodiments, the compound has a formula:

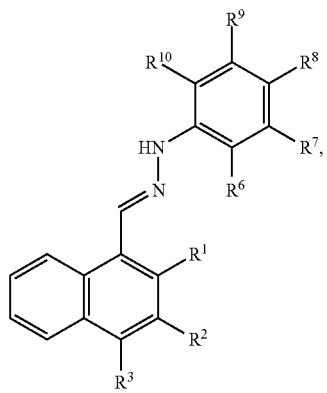

wherein $R^1$, $R^2$, $R^3$, $R^6$, $R^7$, $R^8$, $R^9$, and $R^{10}$ are as described herein.

In embodiments, the compound has a formula:

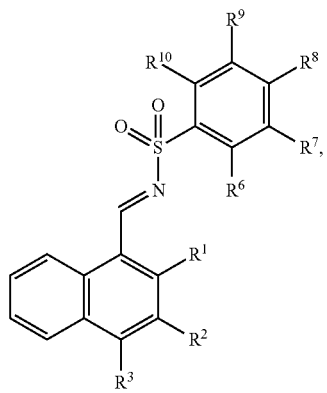

wherein $R^1$, $R^2$, $R^3$, $R^6$, $R^7$, $R^8$, $R^9$, and $R^{10}$ are as described herein.

In embodiments, the compound has a formula:

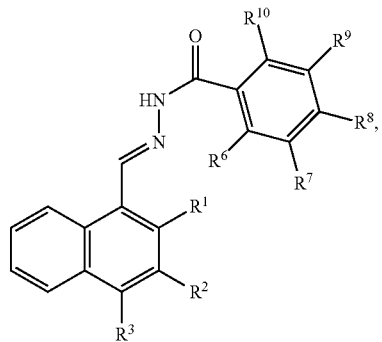

wherein $R^1$, $R^2$, $R^3$, $R^6$, $R^7$, $R^8$, $R^9$, and $R^{10}$ are as described herein.

In embodiments, the compound has a formula:

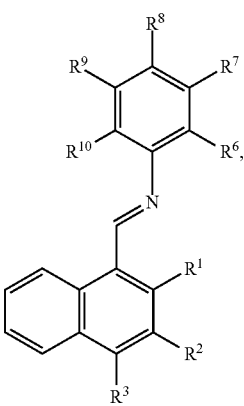

wherein $R^1$, $R^2$, $R^3$, $R^6$, $R^7$, $R^8$, $R^9$, and $R^{10}$ are as described herein.

In embodiments, the compound has a formula (III),

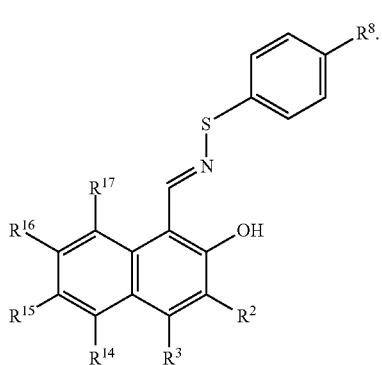

(III)

In formula (III), $R^2$, $R^3$, $R^8$, $R^{14}$, $R^{15}$, $R^{16}$, and $R^{17}$ are as described herein.

In embodiments, the compound has a formula (IV),

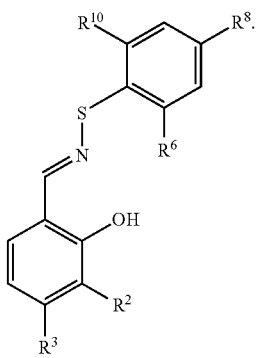

(IV)

In formula (IV), $R^2$, $R^3$, $R^6$, $R^8$, and $R^{10}$ are as described herein.

In embodiments, the compound has a formula (V),

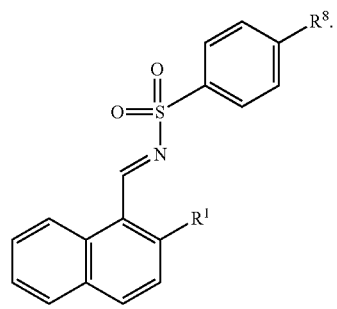

(V)

In formula (V), $R^1$ and $R^8$ are as described herein.

In embodiments, the compound has a formula (VI),

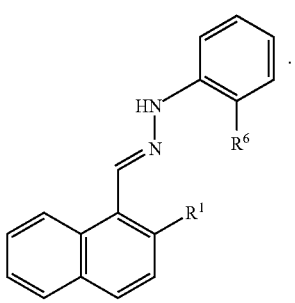

(VI)

In formula (VI), $R^1$ and $R^6$ are as described herein.

In embodiments, the compound has a formula (VII),

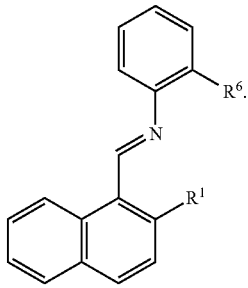

In formula (VII), $R^1$ and $R^6$ are as described herein.

In embodiments, the compound has a formula (VIII),

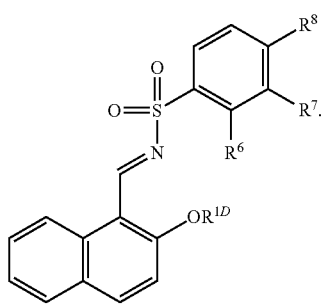

In formula (VIII), $R^{1D}$, $R^6$, $R^7$ and $R^8$ are as described herein.

In embodiments, $R^{1D}$ is hydrogen or unsubstituted $C_1$-$C_4$ alkyl and $R^6$ is hydrogen or —C(O)—$OR^{6C}$. In embodiments, $R^{1D}$ is hydrogen or unsubstituted $C_1$-$C_4$ alkyl and $R^7$ is hydrogen or halogen. In embodiments, $R^{1D}$ is hydrogen or unsubstituted $C_1$-$C_4$ alkyl and $R_8$ is halogen, —$OR^{8D}$, —C(O)—$OR^{8C}$, or unsubstituted $C_2$-$C_4$ alkyl. In embodiments, $R^{1D}$ is hydrogen or unsubstituted $C_1$-$C_4$ alkyl; $R^6$ is hydrogen or —C(O)—$OR^{6C}$; and $R^7$ is hydrogen or halogen. In embodiments, $R^{1D}$ is hydrogen or unsubstituted $C_1$-$C_4$ alkyl; $R^6$ is hydrogen or —C(O)—$OR^{6C}$; and $R_8$ is halogen, —$OR^{8D}$, —C(O)—$OR^{8C}$, or unsubstituted $C_2$-$C_4$ alkyl. In embodiments, $R^{1D}$ is hydrogen or unsubstituted $C_1$-$C_4$ alkyl; $R^7$ is hydrogen or halogen; and $R_8$ is halogen, —$OR^{8D}$, —C(O)—$OR^{8C}$, or unsubstituted $C_2$-$C_4$ alkyl. In embodiments, $R^{1D}$ is hydrogen or unsubstituted $C_1$-$C_4$ alkyl; $R^6$ is hydrogen or —C(O)—$OR^{6C}$; $R^7$ is hydrogen or halogen; and $R^8$ is halogen, —$OR^{8D}$, —C(O)—$OR^{8C}$, or unsubstituted $C_2$-$C_4$ alkyl.

In embodiments, $R^{1D}$ is hydrogen or unsubstituted $C_1$-$C_4$ alkyl. In embodiments, $R^{1D}$ is hydrogen. In embodiments, $R^{1D}$ is unsubstituted $C_1$-$C_4$ alkyl. In embodiments, $R^{1D}$ is unsubstituted methyl. In embodiments, $R^{1D}$ is unsubstituted ethyl. In embodiments, $R^{1D}$ is unsubstituted propyl. In embodiments, $R^{1D}$ is unsubstituted isopropyl. In embodiments, $R^{1D}$ is unsubstituted butyl. In embodiments, $R^{1D}$ is unsubstituted t-butyl.

In embodiments, $R^6$ is hydrogen or —C(O)—$OR^{6C}$. In embodiments, $R^6$ is hydrogen. In embodiments, $R^6$ is —C(O)—$OR^{6C}$. In embodiments, $R^6$ is —C(O)—OH. In embodiments, $R^6$ is —C(O)—$OCH_3$. In embodiments, $R^6$ is —C(O)—$OCH_2CH_3$.

In embodiments, $R^7$ is hydrogen or halogen. In embodiments, $R^7$ is hydrogen. In embodiments, $R^7$ halogen. In embodiments, $R^7$ is —F. In embodiments, $R^7$ is —Cl. In embodiments, $R^7$ is —Br. In embodiments, $R^7$ is —I.

In embodiments, $R^8$ is halogen, —$OR^{8D}$, —C(O)—$OR^{8C}$, or unsubstituted $C_2$-$C_4$ alkyl. In embodiments, $R^8$ is halogen. In embodiments, $R^8$ is —F. In embodiments, $R^8$ is —Cl. In embodiments, $R^8$ is —Br. In embodiments, $R^8$ is —I. In embodiments, $R^8$ is —$OR^{8D}$. In embodiments, $R^8$ is —OH. In embodiments, $R^8$ is —$OCH_3$. In embodiments, $R^8$ is —$OCH_2CH_3$. In embodiments, $R^8$ is —C(O)—$OR^{8C}$. In embodiments, $R^8$ is —C(O)—OH. In embodiments, $R^8$ is —C(O)—$OCH_3$. In embodiments, $R^8$ is —C(O)—$OCH_2CH_3$. In embodiments, $R^8$ is —C(O)—$OC(CH_3)_3$. In embodiments, $R^8$ is unsubstituted $C_2$-$C_4$ alkyl. In embodiments, $R^8$ is unsubstituted ethyl. In embodiments, $R^8$ is unsubstituted propyl. In embodiments, $R^8$ is unsubstituted propyl. In embodiments, $R^8$ is unsubstituted butyl. In embodiments, $R^8$ is unsubstituted t-butyl.

In embodiments, $R^{1D}$, $R^{6C}$, $R^{8C}$, and $R^{8D}$ are independently hydrogen or unsubstituted $C_1$-$C_3$ alkyl. In embodiments, $R^{1D}$ is hydrogen or unsubstituted $C_1$-$C_3$ alkyl. In embodiments, $R^{1D}$ is hydrogen. In embodiments, $R^{1D}$ is unsubstituted $C_1$-$C_3$ alkyl. In embodiments, $R^{1D}$ is —$CH_3$. In embodiments, $R^{1D}$ is —$CH_3$. In embodiments, $R^{1D}$ is —$CH_2CH_3$. In embodiments, $R^{1D}$ is —$C(CH_3)_3$. In embodiments, $R^{1D}$ is —$CH_2CH_2CH_3$. In embodiments, $R^{1D}$ is —$CH(CH_3)_2$. In embodiments, $R^{6C}$ is hydrogen or unsubstituted $C_1$-$C_3$ alkyl. In embodiments, $R^{6C}$ is hydrogen. In embodiments, $R^{6C}$ is unsubstituted $C_1$-$C_3$ alkyl. In embodiments, $R^{6C}$ is —$CH_3$. In embodiments, $R^{6C}$ is —$CH_3$. In embodiments, $R^{6C}$ is —$CH_2CH_3$. In embodiments, $R^{6C}$ is —$C(CH_3)_3$. In embodiments, $R^{6C}$ is —$CH_2CH_2CH_3$. In embodiments, $R^{6C}$ is —$CH(CH_3)_2$. In embodiments, $R^{8C}$ is hydrogen or unsubstituted $C_1$-$C_3$ alkyl. In embodiments, $R^{8C}$ is hydrogen. In embodiments, $R^{8C}$ is unsubstituted $C_1$-$C_3$ alkyl. In embodiments, $R^{8C}$ is —$CH_3$. In embodiments, $R^{8C}$ is —$CH_3$. In embodiments, $R^{8C}$ is —$CH_2CH_3$. In embodiments, $R^{8C}$ is —$CH_2CH_2CH_3$. In embodiments, $R^{8C}$ is —$CH(CH_3)_2$. In embodiments, $R^{8D}$ is hydrogen or unsubstituted $C_1$-$C_3$ alkyl. In embodiments, $R^{8D}$ is hydrogen. In embodiments, $R^{8D}$ is unsubstituted $C_1$-$C_3$ alkyl. In embodiments, $R^{8D}$ is —$CH_3$. In embodiments, $R^{8D}$ is —$CH_3$. In embodiments, $R^{8D}$ is —$CH_2CH_3$. In embodiments, $R^{8D}$ is —$C(CH_3)_3$. In embodiments, $R^{8D}$ is —$CH_2CH_2CH_3$. In embodiments, $R^{8D}$ is —$CH(CH_3)_2$.

In embodiments, $R^{1D}$ is hydrogen; $R^6$ and $R^7$ are hydrogen; and $R^8$ is —OH, —$OCH_3$, —COOH, —Br, or —$C(CH_3)_3$. In embodiments, $R^{1D}$ is hydrogen; $R^6$ is hydrogen; and $R^8$ is —OH, —$OCH_3$, —COOH, —Br, or —$C(CH_3)_3$. In embodiments, $R^{1D}$ is hydrogen; $R^7$ is hydrogen; and $R^8$ is —OH, —$OCH_3$, —COOH, —Br, or —$C(CH_3)_3$. In embodiments, $R^{1D}$ is hydrogen; and $R^8$ is —OH, —$OCH_3$, —COOH, —Br, or —$C(CH_3)_3$. In embodiments, $R^{1D}$ is hydrogen and $R^6$ and $R^7$ are hydrogen. In embodiments, $R^6$ and $R^7$ are hydrogen; and $R^8$ is —OH, —$OCH_3$, —COOH, —Br, or —$C(CH_3)_3$. In embodiments, $R^6$ is hydrogen; and $R^8$ is —OH, —$OCH_3$, —COOH, —Br, or —$C(CH_3)_3$. In embodiments, $R^7$ is hydrogen; and $R^8$ is —OH, —$OCH_3$, —COOH, —Br, or —$C(CH_3)_3$.

In embodiments, $R^{1D}$ is hydrogen; $R^6$ and $R^7$ are hydrogen; and $R^8$ is —$OR^{8D}$, —$COOR^{8C}$, halogen, or unsubstituted $C_2$-$C_4$ alkyl. In embodiments, $R^{1D}$ is hydrogen. In embodiments, $R^6$ and $R^7$ are hydrogen. In embodiments, $R^6$ is hydrogen. In embodiments, $R^7$ is hydrogen. In embodiments, $R^8$ is —$OR^{8D}$. In embodiments, $R^8$ is —OH. In embodiments, $R^8$ is —$OCH_3$. In embodiments, $R^8$ is —$OCH_2CH_3$. In embodiments, $R^8$ is —COOH. In embodiments, $R^8$ is —$COOCH_3$. In embodiments, $R^8$ is —$COOCH_2CH_3$. In embodiments, $R^8$ is —$COOC(CH_3)_3$. In embodiments, $R^8$ is halogen. In embodiments, $R^8$ is —F. In embodiments, $R^8$ is —Cl. In embodiments, $R^8$ is —Br. In embodiments, $R^8$ is —I. In embodiments, $R^8$ is unsubstituted $C_1$-$C_4$ alkyl. In embodiments, $R^8$ is unsubstituted $C_2$-$C_4$ alkyl. In embodiments, $R^8$ is —$CH_3$. In embodiments, $R^8$ is —$CH_3$. In embodiments, $R^8$ is —$CH_2CH_3$. In embodiments, $R^8$ is —$C(CH_3)_3$. In embodiments, $R^8$ is —$CH_2CH_2CH_3$. In embodiments, $R^8$ is —$CH(CH_3)_2$. In embodiments, $R^{1D}$ is —$CH_3$; $R^6$ and $R^7$ are hydrogen; and $R^8$ is —OH, —$OCH_3$, —COOH, —$COOCH_3$, —Cl, —Br, or —$C(CH_3)_3$.

In embodiments, $R^{1D}$ is —$CH_3$; $R^6$ is hydrogen; and $R^7$ and $R^8$ are halogen. In embodiments, $R^{1D}$ is —$CH_3$; and $R^7$ and $R^8$ are halogen. In embodiments, $R^{1D}$ is —$CH_3$; $R^6$ is hydrogen; and $R^8$ is halogen. In embodiments, $R^{1D}$ is —$CH_3$; $R^6$ is hydrogen; and $R^7$ is halogen. In embodiments, $R^{1D}$ is —$CH_3$. In embodiments, $R^{1D}$ is —$CH_2CH_3$. In embodiments, $R^6$ is hydrogen. In embodiments, $R^7$ and $R^8$ are halogen. In embodiments, $R^7$ is —F. In embodiments, $R^7$ is —Cl. In embodiments, $R^7$ is —Br. In embodiments, $R^7$ is —I. In embodiments, $R^8$ is —F. In embodiments, $R^8$ is —Cl. In embodiments, $R^8$ is —Br. In embodiments, $R^8$ is —I.

In embodiments, $R^{1D}$ is hydrogen or —$CH_3$; $R^6$ is —C(O)—$OR^{6C}$; and $R^7$ and $R^8$ are hydrogen. In embodiments, $R^{1D}$ is hydrogen; $R^6$ is —C(O)—$OR^{6C}$; and $R^7$ and $R^8$ are hydrogen. In embodiments, $R^{1D}$ is-$CH_3$; $R^6$ is —C(O)—$OR^{6C}$; and $R^7$ and $R^8$ are hydrogen. In embodiments, $R^{1D}$ is hydrogen or —$CH_3$; and $R^7$ and $R^8$ are hydrogen. In embodiments, $R^{1D}$ is hydrogen or —$CH_3$ and $R^6$ is —C(O)—$OR^{6C}$. In embodiments, $R^{1D}$ is hydrogen or —$CH_3$; $R^6$ is —C(O)—OH; and $R^7$ and $R^8$ are hydrogen. In embodiments, $R^{1D}$ is hydrogen or —$CH_3$; $R^6$ is —C(O)—$OCH_3$; and $R^7$ and $R^8$ are hydrogen. In embodiments, $R^{1D}$ is hydrogen or —$CH_3$; $R^6$ is —C(O)—$OR^{6C}$; and $R^7$ is hydrogen.

In embodiments, $R^{1D}$ is hydrogen or —$CH_3$; $R^6$ is —C(O)—$OR^{6C}$; and $R^8$ is hydrogen.

In embodiments, $R^{1D}$ is hydrogen. In embodiments, $R^{1D}$ is —$CH_3$. In embodiments, $R^6$ is —C(O)OH. In embodiments, $R^6$ is —C(O)$OCH_3$. In embodiments, $R^7$ and $R^8$ are hydrogen. In embodiments, $R^7$ is hydrogen. In embodiments, $R^8$ is hydrogen.

In embodiments, the compound has a formula (IX),

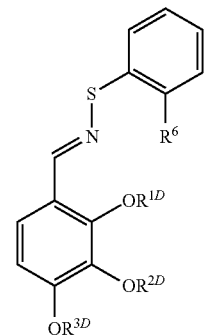

(IX)

In formula (IX), $R^{1D}$, $R^{2D}$, $R^{3D}$, and $R^6$ are as described herein.

In embodiments, $R^{1D}$, $R^{2D}$, and $R^{3D}$ are independently hydrogen or unsubstituted $C_1$-$C_4$ alkyl; and $R^6$ is hydrogen, halogen, —C(O)—$OR^{6C}$, —$OR^{6D}$, or unsubstituted $C_1$-$C_4$ alkyl.

In embodiments, $R^{1D}$, $R^{2D}$, and $R^{3D}$ are independently hydrogen or unsubstituted $C_1$-$C_4$ alkyl. In embodiments, $R^{1D}$ is hydrogen or unsubstituted $C_1$-$C_4$ alkyl. In embodiments, $R^{1D}$ is hydrogen. In embodiments, $R^{1D}$ is unsubstituted $C_1$-$C_4$ alkyl. In embodiments, $R^{1D}$ is unsubstituted methyl. In embodiments, $R^{1D}$ is unsubstituted ethyl. In embodiments, $R^{1D}$ is unsubstituted propyl. In embodiments, $R^{1D}$ is unsubstituted propyl. In embodiments, $R^{1D}$ is unsubstituted butyl. In embodiments, $R^{1D}$ is unsubstituted t-butyl. In embodiments, $R^{2D}$ is hydrogen or unsubstituted $C_1$-$C_4$ alkyl. In embodiments, $R^{2D}$ is hydrogen. In embodiments, $R^{2D}$ is unsubstituted $C_1$-$C_4$ alkyl. In embodiments, $R^{2D}$ is unsubstituted methyl. In embodiments, $R^{2D}$ is unsubstituted ethyl. In embodiments, $R^{2D}$ is unsubstituted propyl. In embodiments, $R^{2D}$ is unsubstituted propyl. In embodiments, $R^{2D}$ is unsubstituted butyl. In embodiments, $R^{2D}$ is unsubstituted t-butyl. In embodiments, $R^{3D}$ is hydrogen or unsubstituted $C_1$-$C_4$ alkyl. In embodiments, $R^{3D}$ is hydrogen. In embodiments, $R^{3D}$ is unsubstituted $C_1$-$C_4$ alkyl. In embodiments, $R^{3D}$ is unsubstituted methyl. In embodiments, $R^{3D}$ is unsubstituted ethyl. In embodiments, $R^{3D}$ is unsubstituted propyl. In embodiments, $R^{3D}$ is unsubstituted propyl. In embodiments, $R^{3D}$ is unsubstituted butyl. In embodiments, $R^{3D}$ is unsubstituted t-butyl.

In embodiments, $R^6$ is hydrogen, halogen, —C(O)—$OR^{6C}$, —$OR^{6D}$, or unsubstituted $C_1$-$C_4$ alkyl. In embodiments, $R^6$ is hydrogen. In embodiments, $R^6$ is halogen. In embodiments, $R^6$ is —F. In embodiments, $R^6$ is —Cl. In embodiments, $R^6$ is —Br. In embodiments, $R^6$ is —I. In embodiments, $R^6$ is —C(O)—$OR^{6C}$. In embodiments, $R^6$ is —C(O)—OH. In embodiments, $R^6$ is —C(O)—$OCH_3$. In embodiments, $R^6$ is —C(O)—$OCH_2CH_3$. In embodiments, $R^6$ is —$OR^{6D}$. In embodiments, $R^6$ is —OH. In embodiments, $R^6$ is —$OCH_3$. In embodiments, $R^6$ is —$OCH_2CH_3$. In embodiments, $R^6$ is —$OC(CH_3)_3$. In embodiments, $R^6$ is unsubstituted $C_1$-$C_4$ alkyl. In embodiments, $R^6$ is unsubstituted methyl. in embodiments, $R^6$ is unsubstituted ethyl. In embodiments, $R^6$ is unsubstituted propyl. In embodiments, $R^6$ is unsubstituted propyl. In embodiments, $R^6$ is unsubstituted butyl. In embodiments, $R^6$ is unsubstituted t-butyl.

In embodiments, $R^{1D}$, $R^{2D}$, and $R^{3D}$ are independently hydrogen or —CH$_3$; and $R^{6C}$ and $R^{6D}$ are independently hydrogen or —CH$_3$. In embodiments, $R^{1D}$, and $R^{3D}$ are independently hydrogen or —CH$_3$; and $R^{6C}$ and $R^{6D}$ are independently hydrogen or —CH$_3$. In embodiments, $R^{1D}$, and $R^{2D}$ are independently hydrogen or —CH$_3$; and $R^{6C}$ and $R^{6D}$ are independently hydrogen or —CH$_3$. In embodiments, $R^{1D}$ is hydrogen or —CH$_3$; and $R^{6C}$ and $R^{6D}$ are independently hydrogen or —CH$_3$. In embodiments, $R^{2D}$ is hydrogen or —CH$_3$; and $R^{6C}$ and $R^{6D}$ are independently hydrogen or —CH$_3$. In embodiments, $R^{3D}$ is hydrogen or —CH$_3$; and $R^{6C}$ and $R^{6D}$ are independently hydrogen or —CH$_3$.

In embodiments, $R^{1D}$, $R^{2D}$, and $R^{3D}$ are independently hydrogen or —CH$_3$. In embodiments, $R^{1D}$ is hydrogen or —CH$_3$. In embodiments, $R^{1D}$ is hydrogen. In embodiments, $R^{1D}$ is —CH$_3$. In embodiments, $R^{2D}$ is hydrogen or —CH$_3$. In embodiments, $R^{2D}$ is hydrogen. In embodiments, $R^{2D}$ is —CH$_3$. In embodiments, $R^{3D}$ is hydrogen or —CH$_3$. In embodiments, $R^{3D}$ is hydrogen. In embodiments, $R^{3D}$ is —CH$_3$. In embodiments, $R^{1D}$, and $R^{3D}$ are hydrogen. In embodiments, $R^{2D}$, and $R^{3D}$ are hydrogen. In embodiments, $R^{1D}$, and $R^{2D}$ are hydrogen. In embodiments, $R^{1D}$, $R^{2D}$, and $R^{3D}$ are hydrogen. In embodiments, $R^{1D}$, and $R^{3D}$ are —CH$_3$. In embodiments, $R^{2D}$, and $R^{3D}$ are —CH$_3$. In embodiments, $R^{1D}$, and $R^{2D}$ are —CH$_3$. In embodiments, $R^{1D}$, $R^{2D}$, and $R^{3D}$ are —CH$_3$.

In embodiments, $R^{6C}$ and $R^{6D}$ are independently hydrogen or —CH$_3$. In embodiments, $R^{6C}$ is hydrogen or —CH$_3$. In embodiments, $R^{6C}$ is hydrogen. In embodiments, $R^{6C}$ is —CH$_3$. In embodiments, $R^{6D}$ is hydrogen or —CH$_3$. In embodiments, $R^{6D}$ is hydrogen. In embodiments, $R^{6D}$ is —CH$_3$. In embodiments, $R^{6C}$ and $R^{6D}$ are hydrogen. In embodiments, $R^{6C}$ and $R^{6D}$ are —CH$_3$.

In embodiments, the compound is:

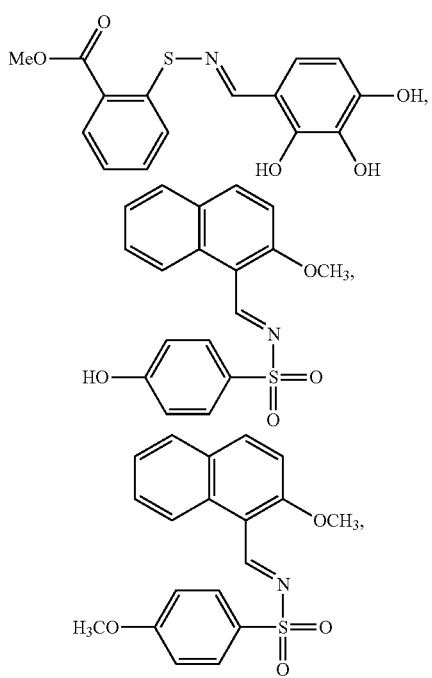

-continued

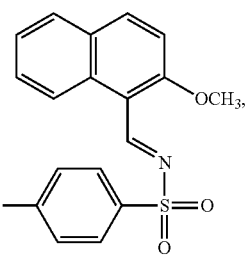

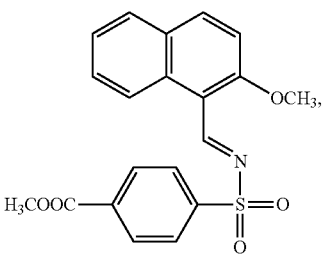

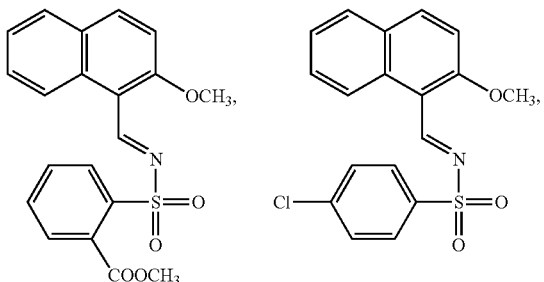

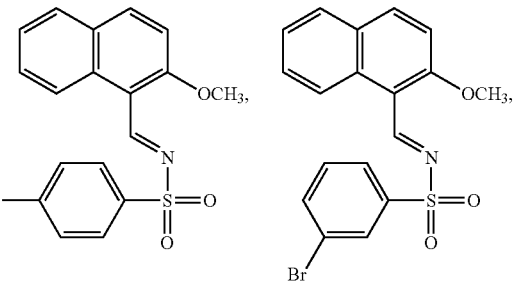

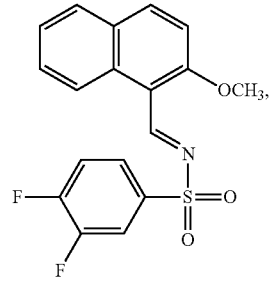

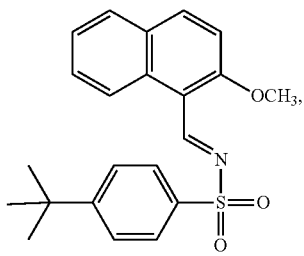

-continued
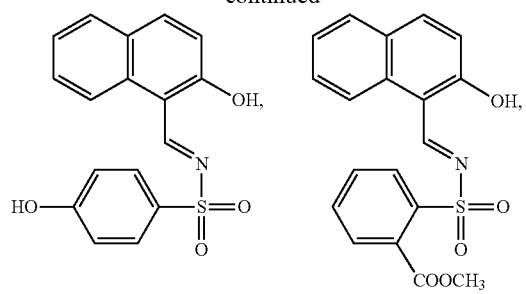
In embodiments, the compound is:
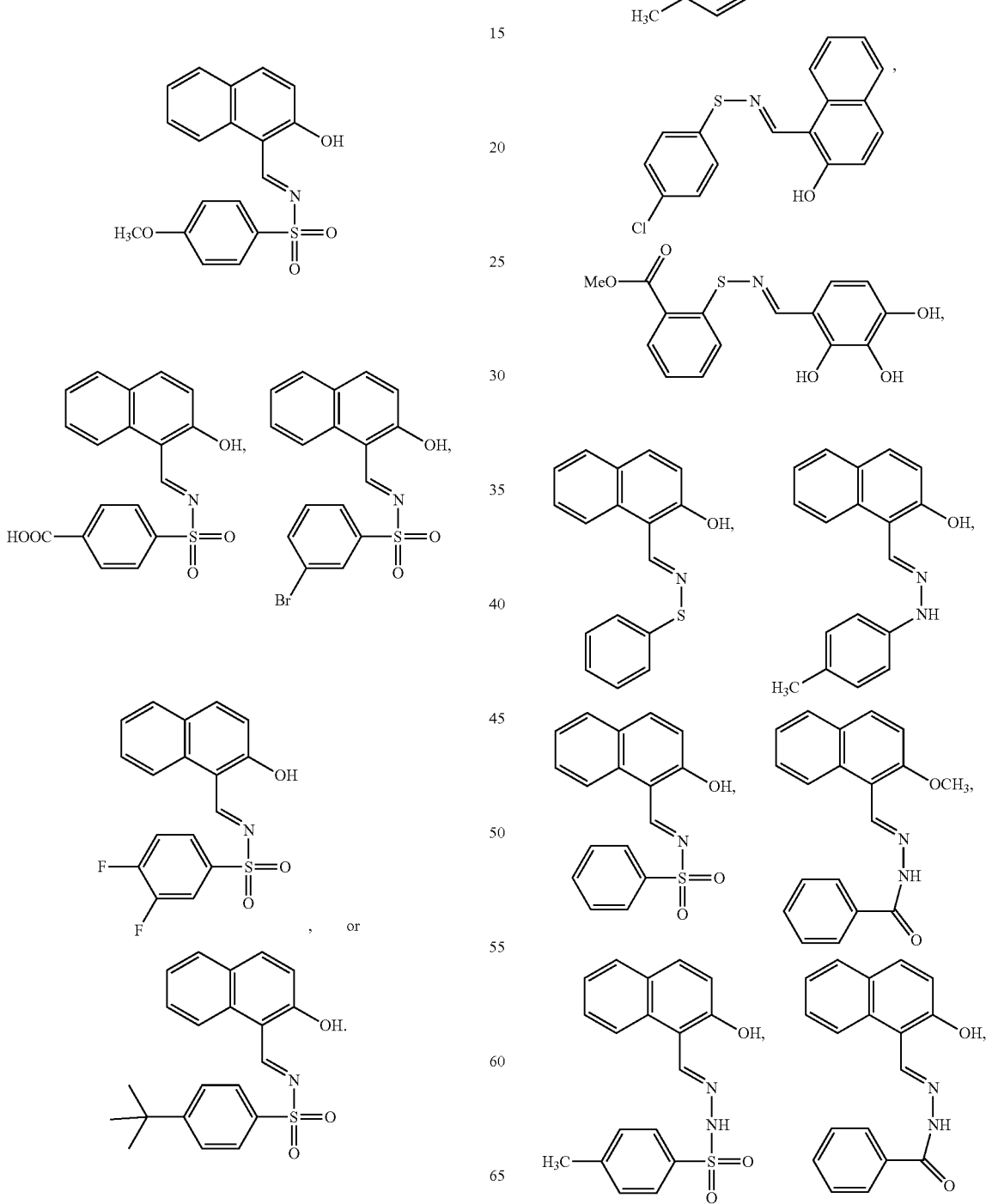

-continued
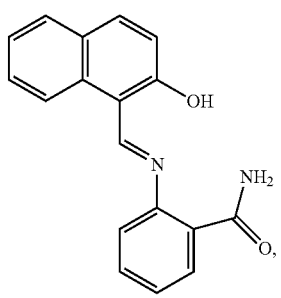
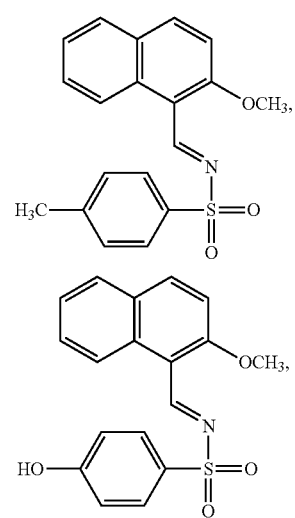
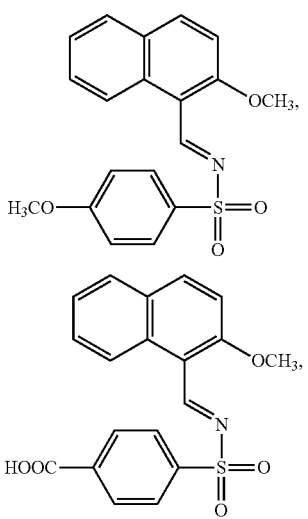
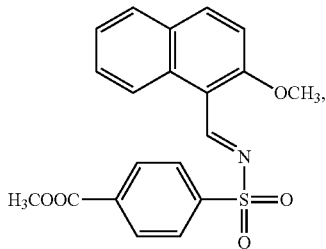
-continued
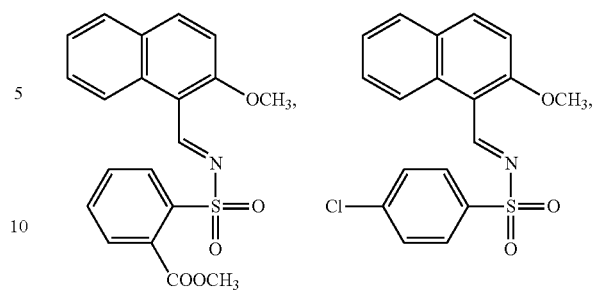
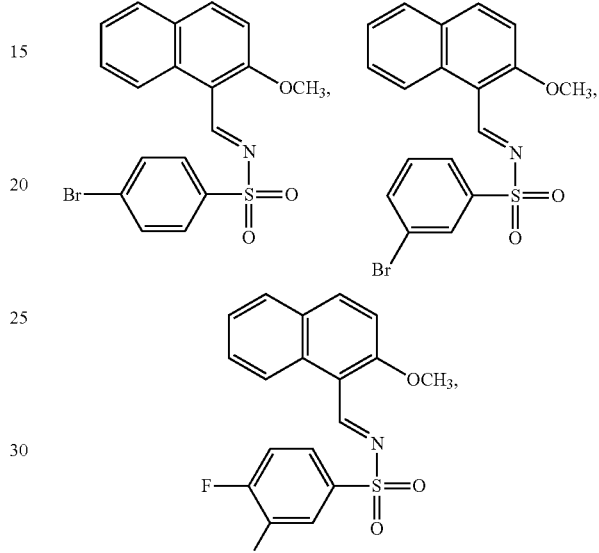
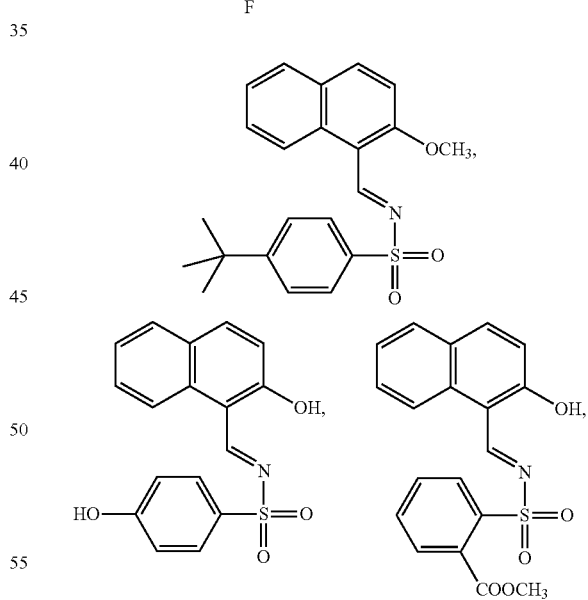
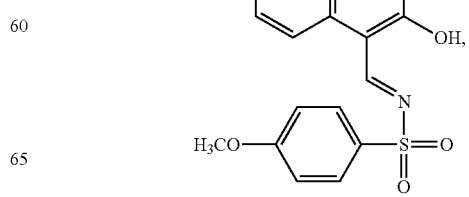

-continued
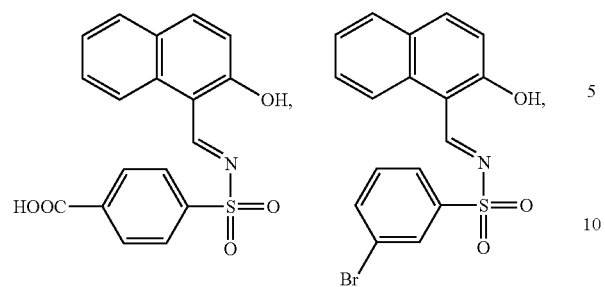
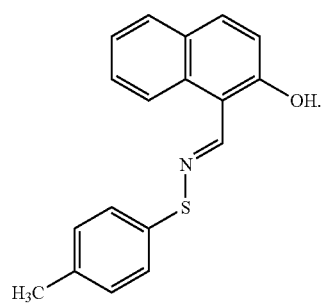 [SMILES: Cc1ccc(S/N=C/c2c(O)ccc3ccccc23)cc1]
In embodiments, the compound is not
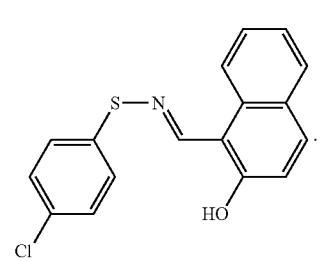 [SMILES: Oc1ccc2ccccc2c1/C=N/Sc1ccc(Cl)cc1]
In embodiments, the compound is not
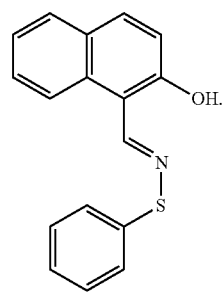 [SMILES: Oc1ccc2ccccc2c1/C=N/Sc1ccccc1]
In embodiments, the compound is not
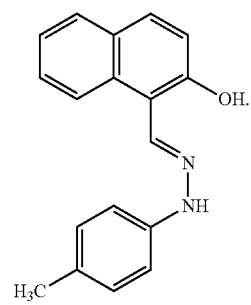 [SMILES: Cc1ccc(N/N=C/c2c(O)ccc3ccccc23)cc1]
In embodiments, the compound is not
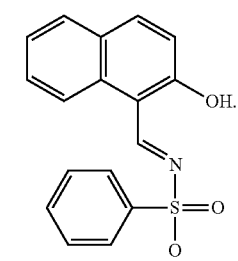
In embodiments, the compound is
not 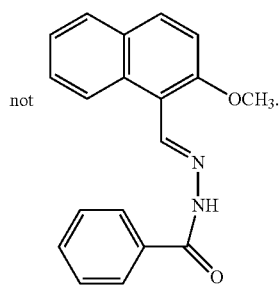 [SMILES: COc1ccc2ccccc2c1/C=N/NC(=O)c1ccccc1]

In embodiments, the compound is not

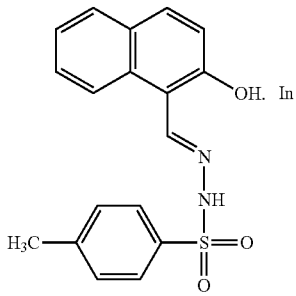

In embodiments, the compound is not

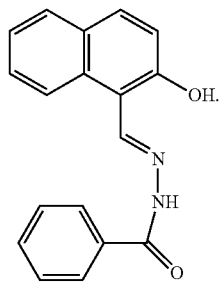 [SMILES: O=C(N/N=C/c1c(O)ccc2ccccc12)c1ccccc1]

In embodiments, the compound is not

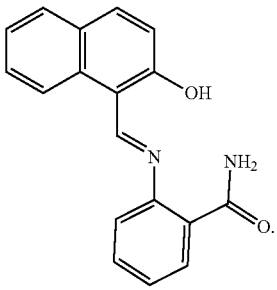 [SMILES: NC(=O)c1ccccc1/N=C/c1c(O)ccc2ccccc12]

In embodiments, the compound is not

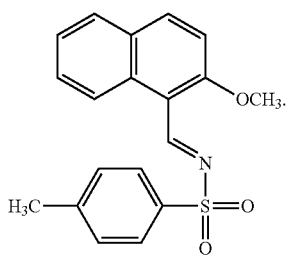

In an aspect is provided a compound, the compound has a formula (X),

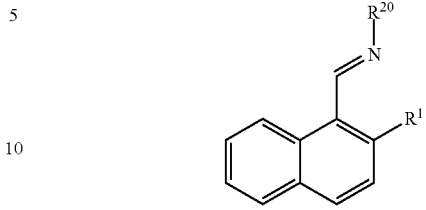

Formula (X). In formula (X), $R^1$ is as described herein. In embodiments, $R^{20}$ is -$L^1$-Ring A. Ring A is substituted or unsubstituted aryl. $L^1$ is a bond, —$CR^{11}R^{12}$—, —$NR^{13}$—, —O—, —S—, —S(O)—, —S(O)_2—, —$NR^{13}$S(O)—, —$NR^{13}$S(O)_2—, or —$NR^{13}$C(O)—.

In embodiments, $L^1$ is a bond. In embodiments, $L^1$ is —$CR^{11}R^{12}$—. In embodiments, $L^1$ is —$CH_2$—. In embodiments, $L^1$ is —$NR^{13}$—. In embodiments, $L^1$ is —NH—. In embodiments, $L^1$ is —$NCH_3$—. In embodiments, $L^1$ is —O—. In embodiments, $L^1$ is —S—. In embodiments, $L^1$ is —$S(O)_2$—. In embodiments, $L^1$ is —$NR^{13}S(O)_2$—. In embodiments, $L^1$ is —$NHS(O)_2$—. In embodiments, $L^1$ is —$NR^{13}C(O)$—. In embodiments, $L^1$ is —NHC(O)—.

Ring A is substituted or unsubstituted aryl (e.g., $C_6$-$C_{12}$, $C_6$-$C_{10}$, or phenyl). In embodiments, Ring A is substituted (e.g., substituted with a substituent group, a size-limited substituent group, or lower substituent group) or unsubstituted aryl (e.g., $C_6$-$C_{12}$, $C_6$-$C_{10}$, or phenyl). In embodiments, Ring A is substituted (e.g., substituted with a substituent group, a size-limited substituent group, or lower substituent group) aryl (e.g., $C_6$-$C_{12}$, $C_6$-$C_{10}$, or phenyl). In embodiments, Ring A is an unsubstituted aryl (e.g., $C_6$-$C_{12}$, $C_6$-$C_{10}$, or phenyl).

Ring A is $R^{19}$-substituted or unsubstituted aryl (e.g., $C_6$-$C_{12}$, $C_6$-$C_{10}$, or phenyl). In embodiments, Ring A is $R^{19}$-substituted aryl (e.g., $C_6$-$C_{12}$, $C_6$-$C_{10}$, or phenyl). Ring A is $R^{19}$-unsubstituted aryl (e.g., $C_6$-$C_{12}$, $C_6$-$C_{10}$, or phenyl). In embodiments, Ring A is $R^{19}$-substituted or unsubstituted phenyl. In embodiments, Ring A is $R^{19}$-substituted phenyl. In embodiments, Ring A is unsubstituted phenyl. In embodiments, Ring A is $R^{19}$-substituted or unsubstituted naphthyl. In embodiments, Ring A is $R^{19}$-substituted naphthyl. In embodiments, Ring A is unsubstituted naphthyl. In embodiments, Ring A is $R^{19}$-substituted or unsubstituted anthracenyl. In embodiments, Ring A is $R^{19}$-substituted anthracenyl. In embodiments, Ring A is unsubstituted anthracenyl. In embodiments, Ring A is $R^{19}$-substituted or unsubstituted phenanthenyl. In embodiments, Ring A is $R^{19}$-substituted phenanthenyl. In embodiments, Ring A is unsubstituted phenanthenyl. In embodiments, Ring A is $R^{19}$-substituted or unsubstituted chrysenyl. In embodiments, Ring A is $R^{19}$-substituted chrysenyl. In embodiments, Ring A is unsubstituted chrysenyl. In embodiments, Ring A is $R^{19}$-substituted or unsubstituted pyrenyl. In embodiments, Ring A is $R^{19}$-substituted pyrenyl. In embodiments, Ring A is unsubstituted pyrenyl.

$R^{19}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{19F}$-substituted or unsubstituted alkyl (e.g., $C_1$-$C_8$, $C_1$-$C_6$, or $C_1$-$C_4$ alkyl), $R^{19F}$-substituted or unsubstituted heteroalkyl (e.g., 2 to 8 membered, 2 to 6 membered, or 2 to 4 membered heteroalkyl), $R^{19F}$-substituted or unsubstituted cycloalkyl(e.g., $C_3$-$C_8$, $C_3$-$C_6$, or $C_5$-$C_6$ cycloalkyl), $R^{19F}$-substituted or unsubstituted heterocycloalkyl (e.g., 3 to 8 membered, 3 to 6 membered, or 5 to 6 membered heterocycloalkyl), $R^{19F}$-substituted or unsubstituted aryl (e.g., $C_6$-$C_{10}$, $C_{10}$ aryl, or phenyl), or $R^{19F}$-substituted or unsubstituted heteroaryl (e.g., 5 to 10 membered, 5 to 9 membered, or 5 to 6 membered heteroaryl). $R^{19}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —COMB, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{19F}$-substituted alkyl (e.g., $C_1$-$C_8$, $C_1$-$C_6$, or $C_1$-$C_4$ alkyl), $R^{19F}$-substituted heteroalkyl (e.g., 2 to 8 membered, 2 to 6 membered, or 2 to 4 membered heteroalkyl), $R^{19F}$-substituted cycloalkyl(e.g., $C_3$-$C_8$, $C_3$-$C_6$, or $C_5$-$C_6$ cycloalkyl), $R^{19F}$-substituted heterocycloalkyl (e.g., 3 to 8 membered, 3 to 6 membered, or 5 to 6 membered heterocycloalkyl), $R^{19F}$-substituted aryl (e.g., $C_6$-$C_{10}$, $C_{10}$ aryl, or phenyl), or $R^{19F}$-substituted heteroaryl (e.g., 5 to 10 membered, 5 to 9 membered, or 5 to 6 membered heteroaryl). $R^{19}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl(e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, in the formula (X), $R^1$ is —$OCH_3$. In embodiments, $R^{20}$ is:

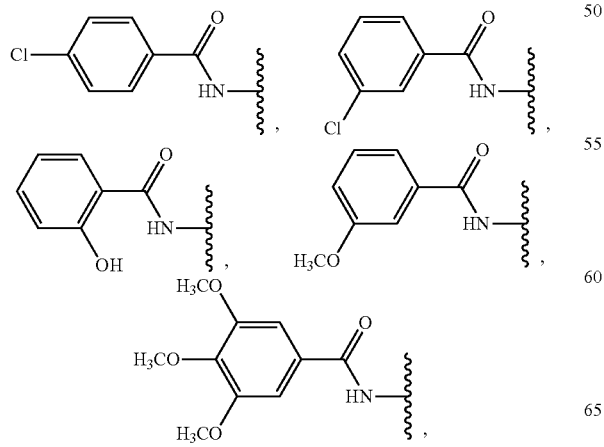

In embodiments, in the formula (X), $R^1$ is —OH. In embodiments, $R^{20}$ is:

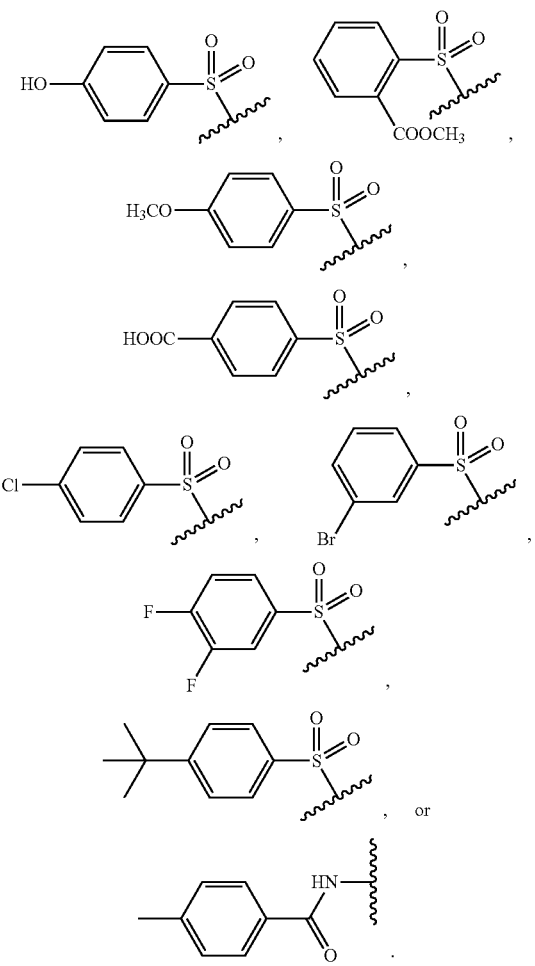

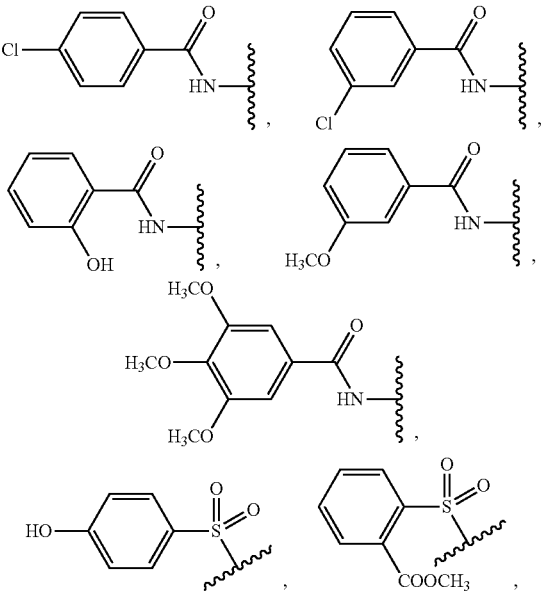

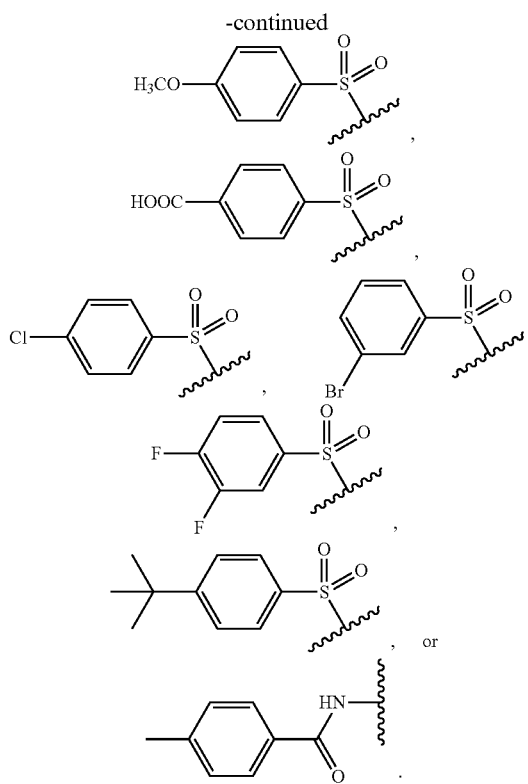

In embodiments, $R^1$ is hydrogen, halogen (e.g., —F, —Cl, Br, —I), —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —NHC(O)$NR^{1A}R^{1B}$, —$N(O)_{m1}$, —$NR^{1A}R^{1B}$, —C(O)$R^{1C}$, —C(O)—$OR^{1C}$, —C(O) $NR^{1A}R^{1B}$, —$OR^{1D}$, —$NR^{1A}SO_2R^{1D}$, —$NR^{1A}C(O) R^{1C}$, —$NR^{1A}C(O)OR^{1C}$, —$NR^{1A}OR^{1C}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$ or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n1 is an integer from 0 to 4 (e.g. 0). m1 and v1 are independently an integer from 1 to 2. $X^1$ is independently —F, —Cl, —Br, or —I. In embodiments, $R^1$ is —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O) $NH_2$, —C(O)$NHCH_3$, —OH, —$OCH_3$, —$NHSO_2H$, —$NHSO_2CH_3$, —NHC(O)H, —$NCH_3C(O)H$, —NHC(O) OH, —$NCH_3C(O)OH$, —NHOH, —$NCH_3OH$, or —$NCH_3OCH_3$.

In embodiments $R^1$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O) $NH_2$, —C(O)$NHCH_3$, —OH, —$OCH_3$, —$NHSO_2H$, —$NHSO_2CH_3$, —NHC(O)H, —$NCH_3C(O)H$, —NHC(O) OH, —$NCH_3C(O)OH$, —NHOH, —$NCH_3OH$, —$NCH_3OCH_3$, $R^{1E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{1E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{1E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{1E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{1E}$-substituted or unsubstituted aryl (e.g., $C_6$-$C_{12}$, $C_6$-$C_{10}$, or phenyl), or $R^{1E}$-substituted or unsubstituted heteroaryl (e.g., 5 to 12 membered, 5 to 10 membered, 5 to 9 membered, or 5 to 6 membered). In embodiments, $R^1$ is hydrogen, —F, —Cl, Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O) $NH_2$, —C(O)$NHCH_3$, —OH, —$OCH_3$, —$NHSO_2H$, —$NHSO_2CH_3$, —NHC(O)H, —$NCH_3C(O)H$, —NHC(O)

OH, —NCH₃C(O)OH, —NHOH, —NCH₃OH, —NCH₃OCH₃, unsubstituted alkyl (e.g, $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{1E}$ is independently oxo, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —OH, —NH₂, —COOH, —CONH₂, —NO₂, —SH, —SCH₃, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, $R^{1F}$-substituted or unsubstituted alkyl (e.g., $C_1$-$C_8$, $C_1$-$C_6$, or $C_1$-$C_4$ alkyl), $R^{1F}$-substituted or unsubstituted heteroalkyl (e.g., 2 to 8 membered, 2 to 6 membered, or 2 to 4 membered heteroalkyl), $R^{1F}$-substituted or unsubstituted cycloalkyl (e.g., $C_3$-$C_8$, $C_3$-$C_6$, or $C_5$-$C_6$ cycloalkyl), $R^{1F}$-substituted or unsubstituted heterocycloalkyl (e.g., 3 to 8 membered, 3 to 6 membered, or 5 to 6 membered heterocycloalkyl), $R^{1F}$-substituted or unsubstituted aryl (e.g., $C_6$-$C_{10}$, $C_{10}$ aryl, or phenyl), or $R^{1F}$-substituted or unsubstituted heteroaryl (e.g., 5 to 10 membered, 5 to 9 membered, or 5 to 6 membered heteroaryl). In embodiments, $R^{1E}$ is independently oxo, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —OH, —NH₂, —COOH, —CONH₂, —NO₂, —SH, —SCH₃, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, $R^{1F}$-substituted alkyl (e.g., $C_1$-$C_8$, $C_1$-$C_6$, or $C_1$-$C_4$ alkyl), $R^{1F}$-substituted heteroalkyl (e.g., 2 to 8 membered, 2 to 6 membered, or 2 to 4 membered heteroalkyl), $R^{1F}$-substituted cycloalkyl (e.g., $C_3$-$C_8$, $C_3$-$C_6$, or $C_5$-$C_6$ cycloalkyl), $R^{1F}$-substituted heterocycloalkyl (e.g., 3 to 8 membered, 3 to 6 membered, or 5 to 6 membered heterocycloalkyl), $R^{1F}$-substituted aryl (e.g., $C_6$-$C_{10}$, $C_{10}$ aryl, or phenyl), or $R^{1F}$-substituted heteroaryl (e.g., 5 to 10 membered, 5 to 9 membered, or 5 to 6 membered heteroaryl). In embodiments, $R^{1E}$ is independently oxo, halogen, —CF₃, —CCl₃, —CBr₃, —CI₃, —CHF₂, —CHCl₂, —CHBr₂, —CHI₂, —CH₂F, —CH₂Cl, —CH₂Br, —CH₂I, —CN, —N₃, —OH, —NH₂, —COOH, —CONH₂, —NO₂, —SH, —SCH₃, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^2$ is hydrogen, halogen (e.g., —F, —Cl, —Br, —I), —CX²₃, —CHX²₂, —CH₂X², —OCX²₃, —OCH₂X², —OCHX²₂, —N₃, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O) R$^{2C}$, —NR$^{2A}$C(O)OR$^{2C}$, —NR$^{2A}$OR$^{2C}$, substituted (e.g., substituted with a substituent group, a size-limited substituent group, or lower substituent group) or unsubstituted alkyl (e.g., $C_1$-$C_{20}$, $C_1$-$C_{12}$. $C_1$-$C_8$. $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n2 is an integer from 0 to 4 (e.g. 0). m2 and v2 are independently an integer from 1 to 2. $X^2$ is independently —F, —Cl, —Br, or —I. In embodiments, $R^2$ is e.g., —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, or —NCH₃OCH₃.

In embodiments, $R^2$ is hydrogen, —F, —Cl, —Br, —I, —CF₃, —CHF₂, —CH₂F, —CCl₃, —CHCl₂, —CH₂Cl, —CBr₃, —CHBr₂, —CH₂Br, —CI₃, —CHI₂, —CH₂I, —OCF₃, —OCCl₃, —OCBr₃, —OCI₃, —OCHF₂, —OCHCl₂, —OCHBr₂, —OCHI₂, —OCH₂F, —OCH₂Cl, —OCH₂Br, —OCH₂I, —N₃, —CN, —SH, —SCH₃, —SO₂H, —SO₂CH₃, —SO₂NH₂, —SO₂NHCH₃, —NHC(O)NH₂, —NHC(O)NHCH₃, —NO₂, —NH₂, —NHCH₃, —C(O)H, —C(O)CH₃, —C(O)OH, —C(O)OCH₃, —C(O)NH₂, —C(O)NHCH₃, —OH, —OCH₃, —NHSO₂H, —NHSO₂CH₃, —NHC(O)H, —NCH₃C(O)H, —NHC(O)OH, —NCH₃C(O)OH, —NHOH, —NCH₃OH, —NCH₃OCH₃, $R^{2E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{2E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{2E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{2E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{2E}$-substituted or unsubstituted aryl (e.g., $C_6$-$C_{12}$, $C_6$-$C_{10}$, or phenyl), or $R^{2E}$-substituted or unsubstituted heteroaryl (e.g., 5 to 12 membered, 5 to 10 membered, 5 to 9 membered, or 5 to 6 membered). In embodiments, $R^2$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{2E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{2E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{2E}$-substituted cycloalkyl (e.g., $C_3$-$C_{10}$, $C_3$-$C_8$, $C_3$-$C_6$, $C_4$-$C_6$, or $C_5$-$C_6$), $R^{2E}$-substituted heterocycloalkyl (e.g., 3 to 10 membered, 3 to 8 membered, 3 to 6 membered, 4 to 6 membered, 4 to 5 membered, or 5 to 6 membered), $R^{2E}$-substituted aryl (e.g., $C_6$-$C_{12}$, $C_6$-$C_{10}$, or phenyl), or $R^{2E}$-substituted heteroaryl (e.g., 5 to 12 membered, 5 to 10 membered, 5 to 9 membered, or 5 to 6 membered). In embodiments, $R^2$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{2E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{2F}$-substituted or unsubstituted alkyl (e.g., $C_1$-$C_8$, $C_1$-$C_6$, or $C_1$-$C_4$ alkyl), $R^{2F}$-substituted or unsubstituted heteroalkyl (e.g., 2 to 8 membered, 2 to 6 membered, or 2 to 4 membered heteroalkyl), $R^{2F}$-substituted or unsubstituted cycloalkyl (e.g., $C_3$-$C_8$, $C_3$-$C_6$, or $C_5$-$C_6$ cycloalkyl), $R^{2F}$-substituted or unsubstituted heterocycloalkyl (e.g., 3 to 8 membered, 3 to 6 membered, or 5 to 6 membered heterocycloalkyl), $R^{2F}$-substituted or unsubstituted aryl (e.g., $C_6$-$C_{10}$, C in aryl, or phenyl), or $R^{2F}$-substituted or unsubstituted heteroaryl (e.g., 5 to 10 membered, 5 to 9 membered, or 5 to 6 membered heteroaryl). In embodiments, $R^{2E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{2F}$-substituted alkyl (e.g., $C_1$-$C_8$, $C_1$-$C_6$, or $C_1$-$C_4$ alkyl), $R^{2F}$-substituted heteroalkyl (e.g., 2 to 8 membered, 2 to 6 membered, or 2 to 4 membered heteroalkyl), $R^{2F}$-substituted cycloalkyl (e.g., $C_3$-$C_8$, $C_3$-$C_6$, or $C_5$-$C_6$ cycloalkyl), $R^{2F}$-substituted heterocycloalkyl (e.g., 3 to 8 membered, 3 to 6 membered, or 5 to 6 membered heterocycloalkyl), $R^{2F}$-substituted aryl (e.g., $C_6$-$C_{10}$, $C_{10}$ aryl, or phenyl), or $R^{2F}$-substituted heteroaryl (e.g., 5 to 10 membered, 5 to 9 membered, or 5 to 6 membered heteroaryl). In embodiments, $R^{2E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —COMB, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^1$ and $R^2$ together with atoms attached thereto are joined to form $R^{1E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{1E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{1E}$-substituted or unsubstituted aryl (e.g., $C_6$-$C_{12}$, $C_6$-$C_{10}$, or phenyl), or $R^{1E}$-substituted or unsubstituted heteroaryl (e.g., 5 to 12 membered, 5 to 10 membered, 5 to 9 membered, or 5 to 6 membered). In embodiments, $R^1$ and $R^2$ together with atoms attached thereto are joined to form $R^{1E}$-substituted or unsubstituted cyclopentyl. In embodiments, $R^1$ and $R^2$ together with atoms attached thereto are joined to form $R^{1E}$-substituted or unsubstituted cyclohexyl. In embodiments, $R^1$ and $R^2$ together with atoms attached thereto are joined to form $R^{1E}$-substituted or unsubstituted pyridyl. In embodiments, $R^1$ and $R^2$ together with atoms attached thereto are joined to form $R^{1E}$-substituted or unsubstituted piperidinyl. In embodiments, $R^1$ and $R^2$ together with atoms attached thereto are joined to form $R^{1E}$-substituted or unsubstituted morpholinyl. In embodiments, $R^1$ and $R^2$ together with atoms attached thereto are joined to form $R^{1E}$-substituted or unsubstituted phenyl. In embodiments, $R^1$ and $R^2$ together with atoms attached thereto are joined to form $R^{1E}$-substituted or unsubstituted pyrrolyl. In embodiments, $R^1$ and $R^2$ together with atoms attached thereto are joined to form $R^{1E}$-substituted or unsubstituted pyrimidinyl. In embodiments, $R^1$ and $R^2$ together with atoms attached thereto are joined to form $R^{1E}$-substituted or unsubstituted thiophenyl.

In embodiments, $R^3$ is hydrogen, halogen (e.g., —F, —Cl, —Br, —I), —CX$^3_3$, —CHX$^3_2$, —CH$_2$X$^3$, —OCX$^3_3$, —OCH$_2$X$^3$, —OCHX$^3_2$, —N$_3$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O) NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O) OR$^{3C}$, —NR$^{3A}$OR$^{3C}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n3 is an integer from 0 to 4 (e.g. 0). m3 and v3 are independently an integer from 1 to 2. $X^3$ is independently —F, —Cl, —Br, or —I. In embodiments, $R^3$ is —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$.

In embodiments, $R^3$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{3E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{3E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{3E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{3E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{3E}$-substituted or unsubstituted aryl (e.g., $C_6$-$C_{12}$, $C_6$-$C_{10}$, or phenyl), or $R^{3E}$-substituted or unsubstituted heteroaryl (e.g., 5 to 12 membered, 5 to 10 membered, 5 to 9 membered, or 5 to 6 membered). In embodiments, $R^3$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{3E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{3E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{3E}$-substituted cycloalkyl (e.g., $C_3$-$C_{10}$, $C_3$-$C_8$, $C_3$-$C_6$, $C_4$-$C_6$, or $C_5$-$C_6$), $R^{3E}$-substituted heterocycloalkyl (e.g., 3 to 10 membered, 3 to 8 membered, 3 to 6 membered, 4 to 6 membered, 4 to 5 membered, or 5 to 6 membered), $R^{3E}$-substituted aryl (e.g., $C_6$-$C_{12}$, $C_6$-$C_{10}$, or phenyl), or $R^{3E}$-substituted heteroaryl (e.g., 5 to 12 membered, 5 to 10 membered, 5 to 9 membered, or 5 to 6 membered). In embodiments, $R^3$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{3E}$ is independently oxo, halogen, —CF$_3$, —CCl$_3$, —CBr$_3$, —CI$_3$, —CHF$_2$, —CH$_2$Cl, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCH$_2$Cl, —OCHBr$_2$, —OCHI$_2$, —OCH$_2$F, —OCH$_2$Cl, —OCH$_2$Br, —OCH$_2$I, $R^{3F}$-substituted or unsubstituted alkyl (e.g., $C_1$-$C_8$, $C_1$-$C_6$, or $C_1$-$C_4$ alkyl), $R^{3F}$-substituted or unsubstituted heteroalkyl (e.g., 2 to 8 membered, 2 to 6 membered, or 2 to 4 membered heteroalkyl), $R^{3F}$-substituted or unsubstituted cycloalkyl (e.g., $C_3$-$C_8$, $C_3$-$C_6$, or $C_5$-$C_6$ cycloalkyl), $R^{3F}$-substituted or unsubstituted heterocycloalkyl (e.g., 3 to 8 membered, 3 to 6 membered, or 5 to 6 membered heterocycloalkyl), $R^{3F}$-substituted or unsubstituted aryl (e.g., $C_6$-$C_{10}$, $C_{10}$ aryl, or phenyl), or $R^{3F}$-substituted or unsubstituted heteroaryl (e.g., 5 to 10 membered, 5 to 9 membered, or 5 to 6 membered heteroaryl). In embodiments, $R^{3E}$ is independently oxo, halogen, —$CF_3$, —$CCl_3$, —$CBr_3$, —$CI_3$, —$CHF_2$, —$CH_2Cl$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCH_2Cl$, —$OCHBr_2$, —$OCHI_2$, —$OCH_2F$, —$OCH_2Cl$, —$OCH_2Br$, —$OCH_2I$, $R^{3F}$-substituted alkyl (e.g, $C_1$-$C_8$, $C_1$-$C_6$, or $C_1$-$C_4$ alkyl), $R^{3F}$-substituted heteroalkyl (e.g., 2 to 8 membered, 2 to 6 membered, or 2 to 4 membered heteroalkyl), $R^{3F}$-substituted cycloalkyl (e.g., $C_3$-$C_8$, $C_3$-$C_6$, or $C_5$-$C_6$ cycloalkyl), $R^{3F}$-substituted heterocycloalkyl (e.g., 3 to 8 membered, 3 to 6 membered, or 5 to 6 membered heterocycloalkyl), $R^{3F}$-substituted aryl (e.g., $C_6$-$C_{10}$, $C_{10}$ aryl, or phenyl), or $R^{3F}$-substituted heteroaryl (e.g., 5 to 10 membered, 5 to 9 membered, or 5 to 6 membered heteroaryl). In embodiments, $R^{3E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^2$ and $R^3$ together with atoms attached thereto are joined to form $R^{2E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{2E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{2E}$-substituted or unsubstituted aryl (e.g., $C_6$-$C_{12}$, $C_6$-$C_{10}$, or phenyl), or $R^{2E}$-substituted or unsubstituted heteroaryl (e.g., 5 to 12 membered, 5 to 10 membered, 5 to 9 membered, or 5 to 6 membered). In embodiments, $R^2$ and $R^3$ together with atoms attached thereto are joined to form $R^{2E}$-substituted or unsubstituted cyclopentyl. In embodiments, $R^2$ and $R^3$ together with atoms attached thereto are joined to form $R^{2E}$-substituted or unsubstituted cyclohexyl. In embodiments, $R^2$ and $R^3$ together with atoms attached thereto are joined to form $R^{2E}$-substituted or unsubstituted pyridyl. In embodiments, $R^2$ and $R^3$ together with atoms attached thereto are joined to form $R^{2E}$-substituted or unsubstituted piperidinyl. In embodiments, $R^2$ and $R^3$ together with atoms attached thereto are joined to form $R^{2E}$-substituted or unsubstituted morpholinyl. In embodiments, $R^2$ and $R^3$ together with atoms attached thereto are joined to form $R^{2E}$-substituted or unsubstituted phenyl. In embodiments, $R^2$ and $R^3$ together with atoms attached thereto are joined to form $R^{2E}$-substituted or unsubstituted pyrrolyl. In embodiments, $R^2$ and $R^3$ together with atoms attached thereto are joined to form $R^{2E}$-substituted or unsubstituted pyrimidinyl. In embodiments, $R^2$ and $R^3$ together with atoms attached thereto are joined to form $R^{2E}$-substituted or unsubstituted thiophenyl.

In embodiments, $R^4$ is hydrogen, halogen (e.g., —F, —Cl, —Br, —I), —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —NHC(O)$NR^{4A}R^{4B}$, —N(O)$_{m4}$, —$NR^{4A}R^{4B}$, —C(O)$R^{4C}$, —C(O)—$OR^{4C}$, —C(O) $NR^{4A}R^{4B}$, —$OR^{4D}$, —$NR^{4A}SO_2R^{4D}$, —$NR^{4A}C(O)$ $R^{4C}$, —$NR^{4A}C(O)OR^{4C}$, —$NR^{4A}OR^{4C}$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_6$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n4 is an integer from 0 to 4 (e.g. 0). m4 and v4 are independently an integer from 1 to 2. $X^4$ is independently —F, —Cl, —Br, or —I. In embodiments, $R^4$ is (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O) $OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$). In embodiments, $R^4$ is hydrogen.

In embodiments, $R^4$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, $R^{4E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{4E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{4E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{4E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{4E}$-substituted or unsubstituted aryl (e.g., $C_6$-$C_{12}$, $C_6$-$C_{10}$, or phenyl), or $R^{4E}$-substituted or unsubstituted heteroaryl (e.g., 5 to 12 membered, 5 to 10 membered, 5 to 9 membered, or 5 to 6 membered). In embodiments, $R^4$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{4E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{4E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{4E}$-substituted cycloalkyl (e.g., $C_3$-$C_{10}$, $C_3$-$C_8$, $C_3$-$C_6$, $C_4$-$C_6$, or $C_5$-$C_6$), $R^{4E}$-substituted heterocycloalkyl (e.g., 3 to 10 membered, 3 to 8 membered, 3 to 6 membered, 4 to 6 membered, 4 to 5 membered, or 5 to 6 membered), $R^{4E}$-substituted aryl (e.g., $C_6$-$C_{12}$, $C_6$-$C_{10}$, or phenyl), or $R^{4E}$-substituted heteroaryl (e.g., 5 to 12 membered, 5 to 10 membered, 5 to 9 membered, or 5 to 6 membered). In embodiments, $R^4$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{4E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{4F}$-substituted or unsubstituted alkyl (e.g., $C_1$-$C_8$, $C_1$-$C_6$, or $C_1$-$C_4$ alkyl), $R^{4F}$-substituted or unsubstituted heteroalkyl (e.g., 2 to 8 membered, 2 to 6 membered, or 2 to 4 membered heteroalkyl), $R^{4F}$-substituted or unsubstituted cycloalkyl (e.g., $C_3$-$C_8$, $C_3$-$C_6$, or $C_5$-$C_6$ cycloalkyl), $R^{4F}$-substituted or unsubstituted heterocycloalkyl (e.g., 3 to 8 membered, 3 to 6 membered, or 5 to 6 membered heterocycloalkyl), $R^{4F}$-substituted or unsubstituted aryl (e.g., $C_6$-$C_{10}$, $C_{10}$ aryl, or phenyl), or $R^{4F}$-substituted or unsubstituted heteroaryl (e.g., 5 to 10 membered, 5 to 9 membered, or 5 to 6 membered heteroaryl). In embodiments, $R^{4E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{4F}$-substituted alkyl (e.g., $C_1$-$C_8$, $C_1$-$C_6$, or $C_1$-$C_4$ alkyl), $R^{4F}$-substituted heteroalkyl (e.g., 2 to 8 membered, 2 to 6 membered, or 2 to 4 membered heteroalkyl), $R^{4F}$-substituted cycloalkyl (e.g., $C_3$-$C_8$, $C_3$-$C_6$, or $C_5$-$C_6$ cycloalkyl), $R^{4F}$-substituted heterocycloalkyl (e.g., 3 to 8 membered, 3 to 6 membered, or 5 to 6 membered heterocycloalkyl), $R^{4F}$-substituted aryl (e.g., $C_6$-$C_{10}$, $C_{10}$ aryl, or phenyl), or $R^{4F}$-substituted heteroaryl (e.g., 5 to 10 membered, 5 to 9 membered, or 5 to 6 membered heteroaryl). In embodiments, $R^{4E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^3$ and $R^4$ together with atoms attached thereto are joined to form $R^{3E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{3E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{3E}$-substituted or unsubstituted aryl (e.g., $C_6$-$C_{12}$, $C_6$-$C_{10}$, or phenyl), or $R^{3E}$-substituted or unsubstituted heteroaryl (e.g., 5 to 12 membered, 5 to 10 membered, 5 to 9 membered, or 5 to 6 membered). In embodiments, $R^3$ and $R^4$ together with atoms attached thereto are joined to form $R^{3E}$-substituted or unsubstituted cyclopentyl. In embodiments, $R^3$ and $R^4$ together with atoms attached thereto are joined to form $R^{3E}$-substituted or unsubstituted cyclohexyl. In embodiments, $R^3$ and $R^4$ together with atoms attached thereto are joined to form $R^{3E}$-substituted or unsubstituted pyridyl. In embodiments, $R^3$ and $R^4$ together with atoms attached thereto are joined to form $R^{3E}$-substituted or unsubstituted piperidinyl. In embodiments, $R^3$ and $R^4$ together with atoms attached thereto are joined to form $R^{3E}$-substituted or unsubstituted morpholinyl. In embodiments, $R^3$ and $R^4$ together with atoms attached thereto are joined to form $R^{3E}$-substituted or unsubstituted phenyl. In embodiments, $R^3$ and $R^4$ together with atoms attached thereto are joined to form $R^{3E}$-substituted or unsubstituted pyrrolyl. In embodiments, $R^3$ and $R^4$ together with atoms attached thereto are joined to form $R^{3E}$-substituted or unsubstituted pyrimidinyl. In embodiments, $R^3$ and $R^4$ together with atoms attached thereto are joined to form $R^{3E}$-substituted or unsubstituted thiophenyl.

In embodiments, $R^5$ is hydrogen, halogen (e.g., —F, —Cl, —Br, —I), —$CX^5_3$, —$CHX^5_2$, —$CH_2X^5$, —$OCX^5_3$, —$OCH_2X^5$, —$OCHX^5_2$, —$N_3$, —CN, —$SO_{n5}R^{5D}$, —$SO_{v5}NR^{5A}R^{5B}$, —NHC(O)$NR^{5A}R^{5B}$, —N(O)$_{m5}$, —$NR^{5A}R^{5B}$, —C(O)$R^{5C}$, —C(O)—O$R^{5C}$, —C(O) $NR^{5A}R^{5B}$, —$OR^{5D}$, —$NR^{5A}SO_2R^{5D}$, —$NR^{5A}$C(O)$R^{5C}$, —$NR^{5A}$C(O) O$R^{5C}$, —$NR^{5A}OR^{5C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n5 is an integer from 0 to 4 (e.g. 0). m5 and v5 are independently an integer from 1 to 2. $X^5$ is independently —F, —Cl, —Br, or —I. In embodiments, $R^5$ is hydrogen.

In embodiments, $R^5$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{5E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{5E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{5E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{5E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{5E}$-substituted or unsubstituted aryl (e.g., $C_6$-$C_{12}$, $C_6$-$C_{10}$, or phenyl), or $R^{5E}$-substituted or unsubstituted heteroaryl (e.g., 5 to 12 membered, 5 to 10 membered, 5 to 9 membered, or 5 to 6 membered). In embodiments, $R^5$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{5E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{5E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{5E}$-substituted cycloalkyl (e.g., $C_3$-$C_{10}$, $C_3$-$C_8$, $C_3$-$C_6$, $C_4$-$C_6$, or $C_5$-$C_6$), $R^{5E}$-substituted heterocycloalkyl (e.g., 3 to 10 membered, 3 to 8 membered, 3 to 6 membered, 4 to 6 membered, 4 to 5 membered, or 5 to 6 membered), $R^{5E}$-substituted aryl (e.g., $C_6$-$C_{12}$, $C_6$-$C_{10}$, or phenyl), or $R^{5E}$-substituted heteroaryl (e.g., 5 to 12 membered, 5 to 10 membered, 5 to 9 membered, or 5 to 6 membered). In embodiments, $R^5$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g, $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{5E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{5F}$-substituted or unsubstituted alkyl (e.g., $C_1$-$C_8$, $C_1$-$C_6$, or $C_1$-$C_4$ alkyl), $R^{5F}$-substituted or unsubstituted heteroalkyl (e.g., 2 to 8 membered, 2 to 6 membered, or 2 to 4 membered heteroalkyl), $R^{5F}$-substituted or unsubstituted cycloalkyl (e.g., $C_3$-$C_8$, $C_3$-$C_6$, or $C_5$-$C_6$ cycloalkyl), $R^{5F}$-substituted or unsubstituted heterocycloalkyl (e.g., 3 to 8 membered, 3 to 6 membered, or 5 to 6 membered heterocycloalkyl), $R^{5F}$-substituted or unsubstituted aryl (e.g., $C_6$-$C_{10}$, $C_{10}$ aryl, or phenyl), or $R^{5F}$-substituted or unsubstituted heteroaryl (e.g., 5 to 10 membered, 5 to 9 membered, or 5 to 6 membered heteroaryl). In embodiments, $R^{5E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{5F}$-substituted alkyl (e.g, $C_1$-$C_8$, $C_1$-$C_6$, or $C_1$-$C_4$ alkyl), $R^{5F}$-substituted heteroalkyl (e.g., 2 to 8 membered, 2 to 6 membered, or 2 to 4 membered heteroalkyl), $R^{5F}$-substituted cycloalkyl (e.g., $C_3$-$C_8$, $C_3$-$C_6$, or $C_5$-$C_6$ cycloalkyl), $R^{5F}$-substituted heterocycloalkyl (e.g., 3 to 8 membered, 3 to 6 membered, or 5 to 6 membered heterocycloalkyl), $R^{5F}$-substituted aryl (e.g., $C_6$-$C_{10}$, $C_{10}$ aryl, or phenyl), or $R^{5F}$-substituted heteroaryl (e.g., 5 to 10 membered, 5 to 9 membered, or 5 to 6 membered heteroaryl). In embodiments, $R^{5E}$ is independently oxo, halogen, —$CF_3$, —$CCl_3$, —$CBr_3$, —$CI_3$, —$CHF_2$, —$CHCl_2$, —$CHBr_2$—$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^4$ and $R^5$ together with atoms attached thereto are joined to form $R^{4E}$-substituted or unsubstituted cycloalkyl (e.g., $C_3$-$C_{10}$, $C_3$-$C_8$, $C_3$-$C_6$, $C_4$-$C_5$, or $C_5$-$C_6$), $R^{4E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{4E}$-substituted or unsubstituted aryl (e.g., $C_6$-$C_{12}$, $C_6$-$C_{10}$, or phenyl), or $R^{4E}$-substituted or unsubstituted heteroaryl (e.g., 5 to 12 membered, 5 to 10 membered, 5 to 9 membered, or 5 to 6 membered). In embodiments, $R^4$ and $R^5$ together with atoms attached thereto are joined to form $R^{4E}$-substituted or unsubstituted cyclopentyl. In embodiments, $R^4$ and $R^5$ together with atoms attached thereto are joined to form $R^{4E}$-substituted or unsubstituted cyclohexyl. In embodiments, $R^4$ and $R^5$ together with atoms attached thereto are joined to form $R^{4E}$-substituted or unsubstituted pyridyl. In embodiments, $R^4$ and $R^5$ together with atoms attached thereto are joined to form $R^{4E}$-substituted or unsubstituted piperidinyl. In embodiments, $R^4$ and $R^5$ together with atoms attached thereto are joined to form $R^{4E}$-substituted or unsubstituted morpholinyl. In embodiments, $R^4$ and $R^5$ together with atoms attached thereto are joined to form $R^{4E}$-substituted or unsubstituted phenyl. In embodiments, $R^4$ and $R^5$ together with atoms attached thereto are joined to form $R^{4E}$-substituted or unsubstituted pyrrolyl. In embodiments, $R^4$ and $R^5$ together with atoms attached thereto are joined to form $R^{4E}$-substituted or unsubstituted pyrimidinyl. In embodiments, $R^4$ and $R^5$ together with atoms attached thereto are joined to form $R^{4E}$-substituted or unsubstituted thiophenyl.

In embodiments, $R^6$ is hydrogen, halogen (e.g., —F, —Cl, —Br, —I), —$CX^6_3$, —$CHX^6_2$, —$CH_2X^6$, —$OCX^6_3$, —$OCH_2X^6$, —$OCHX^6_2$, —$N_3$, —CN, —$SO_{n6}R^{6D}$, —$SO_{v6}NR^{6A}R^{6B}$, —NHC(O)$NR^{6A}R^{6B}$, —N(O)$_{m6}$, —$NR^{6A}R^{6B}$, —C(O)$R^{6C}$, —C(O)—O$R^{6C}$, —C(O)$NR^{6A}R^{6B}$, —O$R^{6D}$, —$NR^{6A}SO_2R^{6D}$, —$NR^{6A}$C(O) $R^{6C}$, —$NR^{6A}$C(O)O$R^{6C}$, —$NR^{6A}$O$R^{6C}$ (e.g, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n6 is an integer from 0 to 4 (e.g. 0). m6 and v6 are independently an integer from 1 to 2. $X^6$ is independently —F, —Cl, —Br, or —I.

In embodiments, $R^6$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{6E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{6E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{6E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{6E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{6E}$-substituted or unsubstituted aryl (e.g., $C_6$-$C_{12}$, $C_6$-$C_{10}$, or phenyl), or $R^{6E}$-substituted or unsubstituted heteroaryl (e.g., 5 to 12 membered, 5 to 10 membered, 5 to 9 membered, or 5 to 6 membered). In embodiments, $R^6$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{6E}$-substituted alkyl (e.g., C$_1$-C$_{20}$, C$_1$-C$_{12}$, C$_1$-C$_8$, C$_1$-C$_6$, C$_1$-C$_4$, or C$_1$-C$_2$), $R^{6E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{6E}$-substituted cycloalkyl (e.g., C$_3$-C$_{10}$, C$_3$-C$_8$, C$_3$-C$_6$, C$_4$-C$_6$, or C$_5$-C$_6$), $R^{6E}$-substituted heterocycloalkyl (e.g., 3 to 10 membered, 3 to 8 membered, 3 to 6 membered, 4 to 6 membered, 4 to 5 membered, or 5 to 6 membered), $R^{6E}$-substituted aryl (e.g., C$_6$-C$_{12}$, C$_6$-C$_{10}$, or phenyl), or $R^{6E}$-substituted heteroaryl (e.g., 5 to 12 membered, 5 to 10 membered, 5 to 9 membered, or 5 to 6 membered). In embodiments, $R^6$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCH$_2$Cl, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g, C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

$R^{6E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —N$_3$, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{6F}$-substituted or unsubstituted alkyl (e.g., C$_1$-C$_8$, C$_1$-C$_6$, or C$_1$-C$_4$ alkyl), $R^{6F}$-substituted or unsubstituted heteroalkyl (e.g., 2 to 8 membered, 2 to 6 membered, or 2 to 4 membered heteroalkyl), $R^{6F}$-substituted or unsubstituted cycloalkyl (e.g., C$_3$-C$_8$, C$_3$-C$_6$, or C$_5$-C$_6$ cycloalkyl), $R^{6F}$-substituted or unsubstituted heterocycloalkyl (e.g., 3 to 8 membered, 3 to 6 membered, or 5 to 6 membered heterocycloalkyl), $R^{6F}$-substituted or unsubstituted aryl (e.g., C$_6$-C$_{10}$, C$_{10}$ aryl, or phenyl), or $R^{6F}$-substituted or unsubstituted heteroaryl (e.g., 5 to 10 membered, 5 to 9 membered, or 5 to 6 membered heteroaryl). In embodiments, $R^{6E}$ is independently oxo, halogen, —CF$_3$, —CCl$_3$, —CBr$_3$, —CI$_3$, —CHF$_2$, —CHCl$_3$, —CHBr$_2$, —CHI$_2$, —CH$_2$F, —CH$_2$Cl, —CH$_2$Br, —CH$_2$I, —CN, —N$_3$, —CN, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_5$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, $R^7$ is hydrogen, halogen (e.g., —F, —Cl, —Br, —I), —CX$^7_3$, —CHX$^7_2$, —CH$_2$X$^7$, —OCX$^7_3$, —OCH$_2$X$^7$, —OCHX$^7_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O) R$^{7C}$, —NR$^{7A}$C(O)OR$^{7C}$, —NR$^{7A}$OR$^{7C}$ (e.g., —CF$_3$, —CHF$_2$, —CH$_2$F, —CCl$_3$, —CHCl$_3$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or tot lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n7 is an integer from 0 to 4 (e.g. 0). m7 and v7 are independently an integer from 1 to 2. $X^7$ is independently —F, —Cl, —Br, or —I.

In embodiments, $R^7$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)NH$CH_3$, —$NO_2$, —$NH_2$, —NH$CH_3$, —C(O)H, —C(O)$CH_3$, —C(O)OH, —C(O)O$CH_3$, —C(O)$NH_2$, —C(O)NH$CH_3$, —OH, —O$CH_3$, —NHSO$_2$H, —NHSO$_2$CH$_3$, —NHC(O)H, —N$CH_3$C(O)H, —NHC(O)OH, —N$CH_3$C(O)OH, —NHOH, —N$CH_3$OH, —N$CH_3$O$CH_3$, $R^{7E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{7E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{7E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{7E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{7E}$-substituted or unsubstituted aryl (e.g., $C_6$-$C_{12}$, $C_6$-$C_{10}$, or phenyl), or $R^{7E}$-substituted or unsubstituted heteroaryl (e.g., 5 to 12 membered, 5 to 10 membered, 5 to 9 membered, or 5 to 6 membered). In embodiments, $R^7$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)NH$CH_3$, —$NO_2$, —$NH_2$, —NH$CH_3$, —C(O)H, —C(O)$CH_3$, —C(O)OH, —C(O)O$CH_3$, —C(O)$NH_2$, —C(O)NH$CH_3$, —OH, —O$CH_3$, —NHSO$_2$H, —NHSO$_2$CH$_3$, —NHC(O)H, —N$CH_3$C(O)H, —NHC(O)OH, —N$CH_3$C(O)OH, —NHOH, —N$CH_3$OH, —N$CH_3$O$CH_3$, $R^{7E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{7E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{7E}$-substituted cycloalkyl (e.g., $C_3$-$C_{10}$, $C_3$-$C_8$, $C_3$-$C_6$, $C_4$-$C_6$, or $C_5$-$C_6$), $R^{7E}$-substituted heterocycloalkyl (e.g., 3 to 10 membered, 3 to 8 membered, 3 to 6 membered, 4 to 6 membered, 4 to 5 membered, or 5 to 6 membered), $R^{7E}$-substituted aryl (e.g., $C_6$-$C_{12}$, $C_6$-$C_{10}$, or phenyl), or $R^{7E}$-substituted heteroaryl (e.g., 5 to 12 membered, 5 to 10 membered, 5 to 9 membered, or 5 to 6 membered). In embodiments, $R^7$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)NH$CH_3$, —$NO_2$, —$NH_2$, —NH$CH_3$, —C(O)H, —C(O)$CH_3$, —C(O)OH, —C(O)O$CH_3$, —C(O)$NH_2$, —C(O)NH$CH_3$, —OH, —O$CH_3$, —NHSO$_2$H, —NHSO$_2$CH$_3$, —NHC(O)H, —N$CH_3$C(O)H, —NHC(O)OH, —N$CH_3$C(O)OH, —NHOH, —N$CH_3$OH, —N$CH_3$O$CH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{7E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —CON$H_2$, —$NO_2$, —SH, —$SCH_3$, —$SO_3H$, —$SO_4H$, —$SO_2NH_2$, —$NHNH_2$, —$ONH_2$, —NHC(O)NH$NH_2$, —NHC(O)N$H_2$, —NHSO$_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{7F}$-substituted or unsubstituted alkyl (e.g., $C_1$-$C_8$, $C_1$-$C_6$, or $C_1$-$C_4$ alkyl), $R^{7F}$-substituted or unsubstituted heteroalkyl (e.g., 2 to 8 membered, 2 to 6 membered, or 2 to 4 membered heteroalkyl), $R^{7F}$-substituted or unsubstituted cycloalkyl (e.g., $C_3$-$C_8$, $C_3$-$C_6$, or $C_5$-$C_6$ cycloalkyl), $R^{7F}$-substituted or unsubstituted heterocycloalkyl (e.g., 3 to 8 membered, 3 to 6 membered, or 5 to 6 membered heterocycloalkyl), $R^{7F}$-substituted or unsubstituted aryl (e.g., $C_6$-$C_{10}$, C in aryl, or phenyl), or $R^{7F}$-substituted or unsubstituted heteroaryl (e.g., 5 to 10 membered, 5 to 9 membered, or 5 to 6 membered heteroaryl). In embodiments, $R^{7E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —CON$H_2$, —$NO_2$, —SH, —$SCH_3$, —$SO_3H$, —$SO_4H$, —$SO_2NH_2$, —$NHNH_2$, —$ONH_2$, —NHC(O)NH$NH_2$, —NHC(O)N$H_2$, —NHSO$_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{7F}$-substituted alkyl (e.g., $C_1$-$C_8$, $C_1$-$C_6$, or $C_1$-$C_4$ alkyl), $R^{7F}$-substituted heteroalkyl (e.g., 2 to 8 membered, 2 to 6 membered, or 2 to 4 membered heteroalkyl), $R^{7F}$-substituted cycloalkyl (e.g., $C_3$-$C_8$, $C_3$-$C_6$, or $C_5$-$C_6$ cycloalkyl), $R^{7F}$-substituted heterocycloalkyl (e.g., 3 to 8 membered, 3 to 6 membered, or 5 to 6 membered heterocycloalkyl), $R^{7F}$-substituted aryl (e.g., $C_6$-$C_{10}$, $C_{10}$ aryl, or phenyl), or $R^{7F}$-substituted heteroaryl (e.g., 5 to 10 membered, 5 to 9 membered, or 5 to 6 membered heteroaryl). In embodiments, $R^{7E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —CON$H_2$, —$NO_2$, —SH, —$SCH_3$, —$SO_3H$, —$SO_4H$, —$SO_2NH_2$, —$NHNH_2$, —$ONH_2$, —NHC(O)NH$NH_2$, —NHC(O)N$H_2$, —NHSO$_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^6$ and $R^7$ together with atoms attached thereto are joined to form $R^{6E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{6E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{6E}$-substituted or unsubstituted aryl (e.g., $C_6$-$C_{12}$, $C_6$-$C_{10}$, or phenyl), or $R^{6E}$-substituted or unsubstituted heteroaryl (e.g., 5 to 12 membered, 5 to 10 membered, 5 to 9 membered, or 5 to 6 membered). In embodiments, $R^6$ and $R^7$ together with atoms attached thereto are joined to form $R^{6E}$-substituted or unsubstituted cyclopentyl. In embodiments, $R^6$ and $R^7$ together with atoms attached thereto are joined to form $R^{6E}$-substituted or unsubstituted cyclohexyl. In embodiments, $R^6$ and $R^7$ together with atoms attached thereto are joined to form $R^{6E}$-substituted or unsubstituted pyridyl. In embodiments, $R^6$ and $R^7$ together with atoms attached thereto are joined to form $R^{6E}$-substituted or unsubstituted piperidinyl. In embodiments, $R^6$ and $R^7$ together with atoms attached thereto are joined to form $R^{6E}$-substituted or unsubstituted morpholinyl. In embodiments, $R^6$ and $R^7$ together with atoms attached thereto are joined to form $R^{6E}$-substituted or unsubstituted phenyl. In embodiments, $R^6$ and $R^7$ together with atoms attached thereto are joined to form $R^{6E}$-substituted or unsubstituted pyrrolyl. In embodiments, $R^6$ and $R^7$ together with atoms attached thereto are joined to form $R^{6E}$-substituted or unsubstituted pyrimidinyl. In embodiments, $R^6$ and $R^7$ together with atoms attached thereto are joined to form $R^{6E}$-substituted or unsubstituted thiophenyl.

In embodiments, $R^8$ is hydrogen, halogen (e.g., —F, —Cl, —Br, —I), —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O) R$^{8C}$, —NR$^{8A}$C(O)OR$^{8C}$, —NR$^{8A}$OR$^{8C}$ (e.g., —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$ substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n8 is an integer from 0 to 4 (e.g. 0). m8 and v8 are independently an integer from 1 to 2. $X^8$ is independently —F, —Cl, —Br, or —I.

In embodiments, $R^8$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, $R^{8E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{8E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{8E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{8E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{8E}$-substituted or unsubstituted aryl (e.g., $C_6$-$C_{12}$, $C_6$-$C_{10}$, or phenyl), or $R^{8E}$-substituted or unsubstituted heteroaryl (e.g., 5 to 12 membered, 5 to 10 membered, 5 to 9 membered, or 5 to 6 membered). In embodiments, $R^8$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{8E}$ is independently oxo, halogen, —CF$_3$, —CCl$_3$, —CBr$_3$, —CI$_3$, —CHF$_2$, —CH$_2$Cl, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{8F}$-substituted or unsubstituted alkyl (e.g., C$_1$-C$_8$, C$_1$-C$_6$, or C$_1$-C$_4$ alkyl), R$^{8F}$-substituted or unsubstituted heteroalkyl (e.g., 2 to 8 membered, 2 to 6 membered, or 2 to 4 membered heteroalkyl), R$^{8F}$-substituted or unsubstituted cycloalkyl (e.g., C$_3$-C$_8$, C$_3$-C$_6$, or C$_5$-C$_6$ cycloalkyl), R$^{8F}$-substituted or unsubstituted heterocycloalkyl (e.g., 3 to 8 membered, 3 to 6 membered, or 5 to 6 membered heterocycloalkyl), R$^{8F}$-substituted or unsubstituted aryl (e.g., C$_6$-C$_{10}$, C$_{10}$ aryl, or phenyl), or R$^{8F}$-substituted or unsubstituted heteroaryl (e.g., 5 to 10 membered, 5 to 9 membered, or 5 to 6 membered heteroaryl). In embodiments, R$^{8E}$ is independently oxo, halogen, —CF$_3$, —CCl$_3$, —CBr$_3$, —CI$_3$, —CHF$_2$, —CH$_2$Cl, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, R$^7$ and R$^8$ together with atoms attached thereto are joined to form R$^{7E}$-substituted or unsubstituted cycloalkyl (e.g., C$_3$-C$_{10}$, C$_3$-C$_8$, C$_3$-C$_6$, C$_4$-C$_6$, or C$_5$-C$_6$), R$^{7E}$-substituted or unsubstituted heterocycloalkyl (e.g., 3 to 10 membered, 3 to 8 membered, 3 to 6 membered, 4 to 6 membered, 4 to 5 membered, or 5 to 6 membered), R$^{7E}$-substituted or unsubstituted aryl (e.g., C$_6$-C$_{12}$, C$_6$-C$_{10}$, or phenyl), or R$^{7E}$-substituted or unsubstituted heteroaryl (e.g., 5 to 12 membered, 5 to 10 membered, 5 to 9 membered, or 5 to 6 membered). In embodiments, R$^7$ and R$^8$ together with atoms attached thereto are joined to form R$^{7E}$-substituted or unsubstituted cyclopentyl. In embodiments, R$^7$ and R$^8$ together with atoms attached thereto are joined to form R$^{7E}$-substituted or unsubstituted cyclohexyl. In embodiments, R$^7$ and R$^8$ together with atoms attached thereto are joined to form R$^{7E}$-substituted or unsubstituted pyridyl. In embodiments, R$^7$ and R$^8$ together with atoms attached thereto are joined to form R$^{7E}$-substituted or unsubstituted piperidinyl. In embodiments, R$^7$ and R$^8$ together with atoms attached thereto are joined to form R$^{7E}$-substituted or unsubstituted morpholinyl. In embodiments, R$^7$ and R$^8$ together with atoms attached thereto are joined to form R$^{7E}$-substituted or unsubstituted phenyl. In embodiments, R$^7$ and R$^8$ together with atoms attached thereto are joined to form R$^{7E}$-substituted or unsubstituted pyrrolyl. In embodiments, R$^7$ and R$^8$ together with atoms attached thereto are joined to form R$^{7E}$-substituted or unsubstituted pyrimidinyl. In embodiments, R$^7$ and R$^8$ together with atoms attached thereto are joined to form R$^{7E}$-substituted or unsubstituted thiophenyl.

In embodiments, R$^9$ is hydrogen, halogen (e.g., —F, —Cl, —Br, —I), —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O) R$^{9C}$, —NR$^{9A}$C(O)OR$^{9C}$, —NR$^{9A}$OR$^{9C}$ (e.g, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n9 is an integer from 0 to 4 (e.g. 0). m9 and v9 are independently an integer from 1 to 2. $X^9$ is independently —F, —Cl, —Br, or —I.

In embodiments, $R^9$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3$$OCH_3$, $R^{9E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{9E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{9E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{9E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{9E}$-substituted or unsubstituted aryl (e.g., $C_6$-$C_{12}$, $C_6$-$C_{10}$, or phenyl), or $R^{9E}$-substituted or unsubstituted heteroaryl (e.g., 5 to 12 membered, 5 to 10 membered, 5 to 9 membered, or 5 to 6 membered). In embodiments, $R^9$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3$$OCH_3$, $R^{9E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{9E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{9E}$-substituted cycloalkyl (e.g., $C_3$-$C_{10}$, $C_3$-$C_8$, $C_3$-$C_6$, $C_4$-$C_6$, or $C_5$-$C_6$), $R^{9E}$-substituted heterocycloalkyl (e.g., 3 to 10 membered, 3 to 8 membered, 3 to 6 membered, 4 to 6 membered, 4 to 5 membered, or 5 to 6 membered), $R^{9E}$-substituted aryl (e.g., $C_6$-$C_{12}$, $C_6$-$C_{10}$, or phenyl), or $R^{9E}$-substituted heteroaryl (e.g., 5 to 12 membered, 5 to 10 membered, 5 to 9 membered, or 5 to 6 membered). In embodiments, $R^9$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3$$OCH_3$, unsubstituted alkyl (e.g, $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{9E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{9F}$-substituted or unsubstituted alkyl (e.g., $C_1$-$C_8$, $C_1$-$C_6$, or $C_1$-$C_4$ alkyl), $R^{9F}$-substituted or unsubstituted heteroalkyl (e.g., 2 to 8 membered, 2 to 6 membered, or 2 to 4 membered heteroalkyl), $R^{9F}$-substituted or unsubstituted cycloalkyl (e.g., $C_3$-$C_8$, $C_3$-$C_6$, or $C_5$-$C_6$ cycloalkyl), $R^{9F}$-substituted or unsubstituted heterocycloalkyl (e.g., 3 to 8 membered, 3 to 6 membered, or 5 to 6 membered heterocycloalkyl), $R^{9F}$-substituted or unsubstituted aryl (e.g., $C_6$-$C_{10}$, C in aryl, or phenyl), or $R^{9F}$-substituted or unsubstituted heteroaryl (e.g., 5 to 10 membered, 5 to 9 membered, or 5 to 6 membered heteroaryl). In embodiments, $R^{9E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{9F}$-substituted alkyl (e.g, $C_1$-$C_8$, $C_1$-$C_6$, or $C_1$-$C_4$ alkyl), $R^{9F}$-substituted heteroalkyl (e.g., 2 to 8 membered, 2 to 6 membered, or 2 to 4 membered heteroalkyl), $R^{9F}$-substituted cycloalkyl (e.g., $C_3$-$C_8$, $C_3$-$C_6$, or $C_5$-$C_6$ cycloalkyl), $R^{9F}$-substituted heterocycloalkyl (e.g., 3 to 8 membered, 3 to 6 membered, or 5 to 6 membered heterocycloalkyl), $R^{9F}$-substituted aryl (e.g., $C_6$-$C_{10}$, $C_{10}$ aryl, or phenyl), or $R^{9F}$-substituted heteroaryl (e.g., 5 to 10 membered, 5 to 9 membered, or 5 to 6 membered heteroaryl). In embodiments, $R^{9E}$ is independently oxo, halogen, —$CF_3$, —$CCl_3$, —$CBr_3$, —$CI_3$, —$CHF_2$, —$CHCl_3$, —$CHBr_2$—$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^8$ and $R^9$ together with atoms attached thereto are joined to form $R^{8E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{8E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{8E}$-substituted or unsubstituted aryl (e.g., $C_6$-$C_{12}$, $C_6$-$C_{10}$, or phenyl), or $R^{8E}$-substituted or unsubstituted heteroaryl (e.g., 5 to 12 membered, 5 to 10 membered, 5 to 9 membered, or 5 to 6 membered). In embodiments, $R^8$ and $R^9$ together with atoms attached thereto are joined to form $R^{8E}$-substituted or unsubstituted cyclopentyl. In embodiments, $R^8$ and $R^9$ together with atoms attached thereto are joined to form $R^{8E}$-substituted or unsubstituted cyclohexyl. In embodiments, $R^8$ and $R^9$ together with atoms attached thereto are joined to form $R^{8E}$-substituted or unsubstituted pyridyl. In embodiments, $R^8$ and $R^9$ together with atoms attached thereto are joined to form $R^{8E}$-substituted or unsubstituted piperidinyl. In embodiments, $R^8$ and $R^9$ together with atoms attached thereto are joined to form $R^{8E}$-substituted or unsubstituted morpholinyl. In embodiments, $R^8$ and $R^9$ together with atoms attached thereto are joined to form $R^{8E}$-substituted or unsubstituted phenyl. In embodiments, $R^8$ and $R^9$ together with atoms attached thereto are joined to form $R^{8E}$-substituted or unsubstituted pyrrolyl. In embodiments, $R^8$ and $R^9$ together with atoms attached thereto are joined to form $R^{8E}$-substituted or unsubstituted pyrimidinyl. In embodiments, $R^8$ and $R^9$ together with atoms attached thereto are joined to form $R^{8E}$-substituted or unsubstituted thiophenyl.

In embodiments, $R^{10}$ is hydrogen, halogen (e.g., —F, —Cl, —Br, —I), —$CX^{10}_3$, —$CHX^{10}_2$, —$CH_2X^{10}$, —$OCX^{10}_3$, —$OCH_2X^{10}$, —$OCHX^{10}_2$, —$N_3$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n10 is an integer from 0 to 4 (e.g. 0). m10 and v10 are independently an integer from 1 to 2. $X^{10}$ is independently —F, —Cl, —Br, or —I.

In embodiments, $R^{10}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, $R^{10E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{10E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{10E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{10E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{10E}$-substituted or unsubstituted aryl (e.g., $C_6$-$C_{12}$, $C_6$-$C_{10}$, or phenyl), or $R^{10E}$-substituted or unsubstituted heteroaryl (e.g., 5 to 12 membered, 5 to 10 membered, 5 to 9 membered, or 5 to 6 membered). In embodiments, $R^{10}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2$H, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{10E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2$F, —$CH_2$Cl, —$CH_2$Br, —$CH_2$I, —CN, —$N_3$, —OH, —$NH_2$, —COOH, —$CONH_2$, —$NO_2$, —SH, —$SCH_3$, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2$F, —$OCH_2$Cl, —$OCH_2$Br, —$OCH_2$I, $R^{10F}$-substituted or unsubstituted alkyl (e.g., $C_1$-$C_8$, $C_1$-$C_6$, or $C_1$-$C_4$ alkyl), $R^{10F}$-substituted or unsubstituted heteroalkyl (e.g., 2 to 8 membered, 2 to 6 membered, or 2 to 4 membered heteroalkyl), $R^{10F}$-substituted or unsubstituted cycloalkyl (e.g., $C_3$-$C_8$, $C_3$-$C_6$, or $C_5$-$C_6$ cycloalkyl), $R^{10F}$-substituted or unsubstituted heterocycloalkyl (e.g., 3 to 8 membered, 3 to 6 membered, or 5 to 6 membered heterocycloalkyl), $R^{10F}$-substituted or unsubstituted aryl (e.g., $C_6$-$C_{10}$, $C_{10}$ aryl, or phenyl), or $R^{10F}$-substituted or unsubstituted heteroaryl (e.g., 5 to 10 membered, 5 to 9 membered, or 5 to 6 membered heteroaryl). In embodiments, $R^{10E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2$F, —$CH_2$Cl, —$CH_2$Br, —$CH_2$I, —CN, —$N_3$, —OH, —$NH_2$, —COOH, —$CONH_2$, —$NO_2$, —SH, —$SCH_3$, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2$F, —$OCH_2$Cl, —$OCH_2$Br, —$OCH_2$I, $R^{10F}$-substituted alkyl (e.g, $C_1$-$C_8$, $C_1$-$C_6$, or $C_1$-$C_4$ alkyl), $R^{10F}$-substituted heteroalkyl (e.g., 2 to 8 membered, 2 to 6 membered, or 2 to 4 membered heteroalkyl), $R^{10F}$-substituted cycloalkyl (e.g., $C_3$-$C_8$, $C_3$-$C_6$, or $C_5$-$C_6$ cycloalkyl), $R^{10F}$-substituted heterocycloalkyl (e.g., 3 to 8 membered, 3 to 6 membered, or 5 to 6 membered heterocycloalkyl), $R^{10F}$-substituted aryl (e.g., $C_6$-$C_{10}$, $C_{10}$ aryl, or phenyl), or $R^{10F}$-substituted heteroaryl (e.g., 5 to 10 membered, 5 to 9 membered, or 5 to 6 membered heteroaryl). In embodiments, $R^{10E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2$F, —$CH_2$Cl, —$CH_2$Br, —$CH_2$I, —CN, —$N_3$, —OH, —$NH_2$, —COOH, —$CONH_2$, —$NO_2$, —SH, —$SCH_3$, —$SO_3$H, —$SO_4$H, —$SO_2NH_2$, —$NHNH_2$, —$ONH_2$, —NHC(O)$NHNH_2$, —NHC(O)$NH_2$, —$NHSO_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2$F, —$OCH_2$Cl, —$OCH_2$Br, —$OCH_2$I, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^9$ and $R^{10}$ together with atoms attached thereto are joined to form $R^{9E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{9E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{9E}$-substituted or unsubstituted aryl (e.g., $C_6$-$C_{12}$, $C_6$-$C_{10}$, or phenyl), or $R^{9E}$-substituted or unsubstituted heteroaryl (e.g., 5 to 12 membered, 5 to 10 membered, 5 to 9 membered, or 5 to 6 membered). In embodiments, $R^9$ and $R^{10}$ together with atoms attached thereto are joined to form $R^{9E}$-substituted or unsubstituted cyclopentyl. In embodiments, $R^9$ and $R^{10}$ together with atoms attached thereto are joined to form $R^{9E}$-substituted or unsubstituted cyclohexyl. In embodiments, $R^9$ and $R^{10}$ together with atoms attached thereto are joined to form $R^{9E}$-substituted or unsubstituted pyridyl. In embodiments, $R^9$ and $R^{10}$ together with atoms attached thereto are joined to form $R^{9E}$-substituted or unsubstituted piperidinyl. In embodiments, $R^9$ and $R^{10}$ together with atoms attached thereto are joined to form $R^{9E}$-substituted or unsubstituted morpholinyl. In embodiments, $R^9$ and $R^{10}$ together with atoms attached thereto are joined to form $R^{9E}$-substituted or unsubstituted phenyl. In embodiments, $R^9$ and $R^{10}$ together with atoms attached thereto are joined to form $R^{9E}$-substituted or unsubstituted pyrrolyl. In embodiments, $R^9$ and $R^{10}$ together with atoms attached thereto are joined to form $R^{9E}$-substituted or unsubstituted pyrimidinyl. In embodiments, $R^9$ and $R^{10}$ together with atoms attached thereto are joined to form $R^{9E}$-substituted or unsubstituted thiophenyl.

In embodiments, $R^{11}$ is hydrogen, halogen (e.g., —F, —Cl, Br, —I), —$CX^{11}_3$, —$CHX^{11}_2$, —$CH_2X^{11}$, —$OCX^{11}_3$, —$OCH_2X^{11}$, —$OCHX^{11}_2$, —$N_3$, —CN, —$SO_{n11}R^{11D}$, —$SO_{v11}NR^{11A}R^{11B}$, —NHC(O)$NR^{11A}R^{11B}$, —N(O)$_{m11}$, —$NR^{11A}R^{11B}$, —C(O)$R^{11C}$, —C(O)—$OR^{11C}$, —C(O)$NR^{11A}R^{11B}$, —$OR^{11D}$, —$NR^{11A}SO_2R^{11D}$, —$NR^{11A}$C(O)$R^{11C}$, —$NR^{11A}$C(O)$OR^{11C}$, —$NR^{11A}OR^{11C}$ (e.g, —$CF_3$, —$CHF_2$, —$CH_2$F, —$CCl_3$, —$CHCl_2$, —$CH_2$Cl, —$CBr_3$, —$CHBr_2$, —$CH_2$Br, —$CI_3$, —$CHI_2$, —$CH_2$I, —$OCF_3$, —$OCCl_3$, —$OCBr_3$, —$OCI_3$, —$OCHF_2$, —$OCHCl_2$, —$OCHBr_2$, —$OCHI_2$, —$OCH_2$F, —$OCH_2$Cl, —$OCH_2$Br, —$OCH_2$I, —$N_3$, —CN, —SH, —$SCH_3$, —$SO_2$H, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2$H, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g, substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g, substituted with a substituent group, a size-limited substituent group, or lower substituent group) or unsubstituted heteroalkyl (e.g, 2 to 20 membered, 2 to 12 membered, 2 to 8 membered, 2 to 6 membered, 4 to 6 membered, 2 to 3 membered, or 4 to 5 membered), substituted (e.g, substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n11 is an integer from 0 to 4 (e.g. 0). m11 and v11 are independently an integer from 1 to 2. $X^{11}$ is independently —F, —Cl, —Br, or —I.

In embodiments, $R^{11}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3$O$CH_3$, $R^{11E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{11E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{11E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{11E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{11E}$-substituted or unsubstituted aryl (e.g., $C_6$-$C_{12}$, $C_6$-$C_{10}$, or phenyl), or $R^{11E}$-substituted or unsubstituted heteroaryl (e.g., 5 to 12 membered, 5 to 10 membered, 5 to 9 membered, or 5 to 6 membered). In embodiments, $R^{11}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3$O$CH_3$, $R^{11E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{11E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{11E}$-substituted cycloalkyl (e.g., $C_3$-$C_{10}$, $C_3$-$C_8$, $C_3$-$C_6$, $C_4$-$C_6$, or $C_5$-$C_6$), $R^{11E}$-substituted heterocycloalkyl (e.g., 3 to 10 membered, 3 to 8 membered, 3 to 6 membered, 4 to 6 membered, 4 to 5 membered, or 5 to 6 membered), $R^{11E}$-substituted aryl (e.g., $C_6$-$C_{12}$, $C_6$-$C_{10}$, or phenyl), or $R^{11E}$-substituted heteroaryl (e.g., 5 to 12 membered, 5 to 10 membered, 5 to 9 membered, or 5 to 6 membered). In embodiments, $R^{11}$ is hydrogen, —F, —Cl, —Br, —I, —$CF_3$, —$CHF_2$, —$CH_2F$, —$CCl_3$, —$CHCl_3$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)O$CH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3$O$CH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{11E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{11F}$-substituted or unsubstituted alkyl (e.g., $C_1$-$C_8$, $C_1$-$C_6$, or $C_1$-$C_4$ alkyl), $R^{11F}$-substituted or unsubstituted heteroalkyl (e.g., 2 to 8 membered, 2 to 6 membered, or 2 to 4 membered heteroalkyl), $R^{11F}$-substituted or unsubstituted cycloalkyl (e.g., $C_3$-$C_8$, $C_3$-$C_6$, or $C_5$-$C_6$ cycloalkyl), $R^{11F}$-substituted or unsubstituted heterocycloalkyl (e.g., 3 to 8 membered, 3 to 6 membered, or 5 to 6 membered heterocycloalkyl), $R^{11F}$-substituted or unsubstituted aryl (e.g., $C_6$-$C_{10}$, $C_{10}$ aryl, or phenyl), or $R^{11F}$-substituted or unsubstituted heteroaryl (e.g., 5 to 10 membered, 5 to 9 membered, or 5 to 6 membered heteroaryl). In embodiments, $R^{11E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{11F}$-substituted alkyl (e.g., $C_1$-$C_8$, $C_1$-$C_6$, or $C_1$-$C_4$ alkyl), $R^{11F}$-substituted heteroalkyl (e.g., 2 to 8 membered, 2 to 6 membered, or 2 to 4 membered heteroalkyl), $R^{11F}$-substituted cycloalkyl (e.g., $C_3$-$C_8$, $C_3$-$C_6$, or $C_5$-$C_6$ cycloalkyl), $R^{11F}$-substituted heterocycloalkyl (e.g., 3 to 8 membered, 3 to 6 membered, or 5 to 6 membered heterocycloalkyl), $R^{11F}$-substituted aryl (e.g., $C_6$-$C_{10}$, $C_{10}$ aryl, or phenyl), or $R^{11F}$-substituted heteroaryl (e.g., 5 to 10 membered, 5 to 9 membered, or 5 to 6 membered heteroaryl). In embodiments, $R^{11E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{12}$ is hydrogen, halogen (e.g., —F, —Cl, —Br, —I), —$CX^{12}_3$, —$CHX^{12}_2$, —$CH_2X^{12}$, —$OCX^{12}_3$, —$OCH_2X^{12}$, —$OCHX^{12}_2$, —$N_3$, —CN, —$SO_{n12}R^{12D}$, —$SO_{v12}NR^{12A}R^{12B}$, —$NHC(O)NR^{12A}R^{12B}$, —$N(O)_{m12}$, —$NR^{12A}R^{12B}$, —$C(O)R^{12C}$, —$C(O)$—$OR^{12C}$, —$C(O)NR^{12A}R^{12B}$, —$OR^{12D}$, —$NR^{12A}SO_2R^{12D}$, —$NR^{12A}C(O)R^{12C}$, —$NR^{12A}C(O)OR^{12C}$, —$NR^{12A}OR^{12C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted or unsubstituted alkyl (e.g., $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n12 is an integer from 0 to 4 (e.g. 0). m12 and v12 are independently an integer from 1 to 2. $X^{12}$ is independently —F, —Cl, —Br, or —I.

In embodiments, $R^{12}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, $R^{12E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{12E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{12E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{12E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{12E}$-substituted or unsubstituted aryl (e.g., $C_6$-$C_{12}$, $C_6$-$C_{10}$, or phenyl), or $R^{12E}$-substituted or unsubstituted heteroaryl (e.g., 5 to 12 membered, 5 to 10 membered, 5 to 9 membered, or 5 to 6 membered). In embodiments, $R^{12}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —$NHC(O)NH_2$, —$NHC(O)NHCH_3$, —$NO_2$, —$NH_2$, —$NHCH_3$, —C(O)H, —$C(O)CH_3$, —C(O)OH, —$C(O)OCH_3$, —$C(O)NH_2$, —$C(O)NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{12E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{12F}$-substituted or unsubstituted alkyl (e.g., $C_1$-$C_8$, $C_1$-$C_6$, or $C_1$-$C_4$ alkyl), $R^{12F}$-substituted or unsubstituted heteroalkyl (e.g., 2 to 8 membered, 2 to 6 membered, or 2 to 4 membered heteroalkyl), $R^{12F}$-substituted or unsubstituted cycloalkyl (e.g., $C_3$-$C_8$, $C_3$-$C_6$, or $C_5$-$C_6$ cycloalkyl), $R^{12F}$-substituted or unsubstituted heterocycloalkyl (e.g., 3 to 8 membered, 3 to 6 membered, or 5 to 6 membered heterocycloalkyl), $R^{12F}$-substituted or unsubstituted aryl (e.g., $C_6$-$C_{10}$, $C_{10}$ aryl, or phenyl), or $R^{12F}$-substituted or unsubstituted heteroaryl (e.g., 5 to 10 membered, 5 to 9 membered, or 5 to 6 membered heteroaryl). In embodiments, $R^{12E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —COMB, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —NHSO$_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{12F}$-substituted alkyl (e.g, $C_1$-$C_8$, $C_1$-$C_6$, or $C_1$-$C_4$ alkyl), $R^{12F}$-substituted heteroalkyl (e.g., 2 to 8 membered, 2 to 6 membered, or 2 to 4 membered heteroalkyl), $R^{12F}$-substituted cycloalkyl (e.g., $C_3$-$C_8$, $C_3$-$C_6$, or $C_5$-$C_6$ cycloalkyl), $R^{12F}$-substituted heterocycloalkyl (e.g., 3 to 8 membered, 3 to 6 membered, or 5 to 6 membered heterocycloalkyl), $R^{12F}$-substituted aryl (e.g., $C_6$-$C_{10}$, $C_{10}$ aryl, or phenyl), or $R^{12F}$-substituted heteroaryl (e.g., 5 to 10 membered, 5 to 9 membered, or 5 to 6 membered heteroaryl). In embodiments, $R^{12E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —NHSO$_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{13}$ is hydrogen, halogen (e.g., —F, —Cl, —Br, —I), —$CX^{13}_3$, —$CHX^{13}_2$, (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, or —$CH_2I$), —C(O)OH, —C(O)$NH_2$, substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). $X^{13}$ is independently —F, —Cl, —Br, or —I.

In embodiments, $R^{13}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —C(O)OH, —C(O)$NH_2$, $R^{13E}$—$R^{13E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{13E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{13E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{13E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{13E}$-substituted or unsubstituted aryl (e.g., $C_6$-$C_{12}$, $C_6$-$C_{10}$, or phenyl), or $R^{13E}$-substituted or unsubstituted heteroaryl (e.g., 5 to 12 membered, 5 to 10 membered, 5 to 9 membered, or 5 to 6 membered). In embodiments, $R^{13}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —C(O)OH, —C(O)$NH_2$, $R^{13E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{13E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{13E}$-substituted cycloalkyl (e.g., $C_3$-$C_{10}$, $C_3$-$C_8$, $C_3$-$C_6$, $C_4$-$C_6$, or $C_5$-$C_6$), $R^{13E}$-substituted heterocycloalkyl (e.g., 3 to 10 membered, 3 to 8 membered, 3 to 6 membered, 4 to 6 membered, 4 to 5 membered, or 5 to 6 membered), $R^{13E}$-substituted aryl (e.g., $C_6$-$C_{12}$, $C_6$-$C_{10}$, or phenyl), or $R^{13E}$-substituted heteroaryl (e.g., 5 to 12 membered, 5 to 10 membered, 5 to 9 membered, or 5 to 6 membered). In embodiments, $R^{13}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —C(O)OH, —C(O)$NH_2$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{13E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —NHSO$_2$H, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{13F}$-substituted or unsubstituted alkyl (e.g., $C_1$-$C_8$, $C_1$-$C_6$, or $C_1$-$C_4$ alkyl), $R^{13F}$-substituted or unsubstituted heteroalkyl (e.g., 2 to 8 membered, 2 to 6 membered, or 2 to 4 membered heteroalkyl), $R^{13F}$-substituted or unsubstituted cycloalkyl (e.g., $C_3$-$C_8$, $C_3$-$C_6$, or $C_5$-$C_6$ cycloalkyl), $R^{13F}$-substituted or unsubstituted heterocycloalkyl (e.g., 3 to 8 membered, 3 to 6 membered, or 5 to 6 membered heterocycloalkyl), $R^{13F}$-substituted or unsubstituted aryl (e.g., $C_6$-$C_{10}$, $C_{10}$ aryl, or phenyl), or $R^{13F}$-substituted or unsubstituted heteroaryl (e.g., 5 to 10 membered, 5 to 9 membered, or 5 to 6 membered heteroaryl). In embodiments, $R^{13E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —COMB, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{13F}$-substituted alkyl (e.g., $C_1$-$C_8$, $C_1$-$C_6$, or $C_1$-$C_4$ alkyl), $R^{13F}$-substituted heteroalkyl (e.g., 2 to 8 membered, 2 to 6 membered, or 2 to 4 membered heteroalkyl), $R^{13F}$-substituted cycloalkyl (e.g., $C_3$-$C_8$, $C_3$-$C_6$, or $C_5$-$C_6$ cycloalkyl), $R^{13F}$-substituted heterocycloalkyl (e.g., 3 to 8 membered, 3 to 6 membered, or 5 to 6 membered heterocycloalkyl), $R^{13F}$-substituted aryl (e.g., $C_6$-$C_{10}$, $C_{10}$ aryl, or phenyl), or $R^{13F}$-substituted heteroaryl (e.g., 5 to 10 membered, 5 to 9 membered, or 5 to 6 membered heteroaryl). In embodiments, $R^{13E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{14}$ is hydrogen, halogen (e.g., —F, —Cl, —Br, —I), —$CX^{14}_3$, —$CHX^{14}_2$, —$CH_2X^{14}$, —$OCX^{14}_3$, —$OCH_2X^{14}$, —$OCHX^{14}_2$, —$N_3$, —CN, —$SO_{n14}R^{14D}$, —$SO_{v14}NR^{14A}R^{14B}$, —NHC(O)$NR^{14A}R^{14B}$, —N(O)$_{m14}$, —$NR^{14A}R^{14B}$, —C(O)$R^{14C}$, —C(O)—$OR^{14C}$, —C(O)$NR^{14A}R^{14B}$, —$OR^{14D}$, —$NR^{14A}SO_2R^{14D}$, —$NR^{14A}C(O)R^{14C}$, —$NR^{14A}C(O)OR^{14C}$, —$NR^{14A}OR^{14C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, or —$NCH_3OCH_3$), substituted (e.g., substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n14 is an integer from 0 to 4 (e.g. 0). m14 and v14 are independently an integer from 1 to 2. $X^{14}$ is independently —F, —Cl, —Br, or —I. In embodiments, $R^{14}$ is hydrogen.

In embodiments, $R^{14}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, $R^{14E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{14E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{14E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{14E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{14E}$-substituted or unsubstituted aryl (e.g., $C_6$-$C_{12}$, $C_6$-$C_{10}$, or phenyl), or $R^{14E}$-substituted or unsubstituted heteroaryl (e.g., 5 to 12 membered, 5 to 10 membered, 5 to 9 membered, or 5 to 6 membered). In embodiments, $R^{14}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3C(O)H$, —NHC(O)OH, —$NCH_3C(O)OH$, —NHOH, —$NCH_3OH$, —$NCH_3OCH_3$, $R^{14E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{14E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{14E}$-substituted cycloalkyl (e.g., $C_3$-$C_{10}$, $C_3$-$C_8$, $C_3$-$C_6$, $C_4$-$C_6$, or $C_5$-$C_6$), $R^{14E}$-substituted heterocycloalkyl (e.g., 3 to 10 membered, 3 to 8 membered, 3 to 6 membered, 4 to 6 membered, 4 to 5 membered, or 5 to 6 membered), $R^{14E}$-substituted aryl (e.g., $C_6$-$C_{12}$, $C_6$-$C_{10}$, or phenyl), or $R^{14E}$-substituted heteroaryl (e.g., 5 to 12 membered, 5 to 10 membered, 5 to 9 membered, or 5 to 6 membered). In embodiments, $R^{14}$ is hydrogen, —F, —Cl, —Br, —I, —CF$_3$, —CHF$_2$, —CH$_2$F, —CCl$_3$, —CHCl$_3$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

$R^{14E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{14F}$-substituted or unsubstituted alkyl (e.g., C$_1$-C$_8$, C$_1$-C$_6$, or C$_1$-C$_4$ alkyl), $R^{14F}$-substituted or unsubstituted heteroalkyl (e.g., 2 to 8 membered, 2 to 6 membered, or 2 to 4 membered heteroalkyl), $R^{14F}$-substituted or unsubstituted cycloalkyl (e.g., C$_3$-C$_8$, C$_3$-C$_6$, or C$_5$-C$_6$ cycloalkyl), $R^{14F}$-substituted or unsubstituted heterocycloalkyl (e.g., 3 to 8 membered, 3 to 6 membered, or 5 to 6 membered heterocycloalkyl), $R^{14F}$-substituted or unsubstituted aryl (e.g., C$_6$-C$_{10}$, C$_{10}$ aryl, or phenyl), or $R^{14F}$-substituted or unsubstituted heteroaryl (e.g., 5 to 10 membered, 5 to 9 membered, or 5 to 6 membered heteroaryl). In embodiments, $R^{14E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, $R^{14F}$-substituted alkyl (e.g, C$_1$-C$_8$, C$_1$-C$_6$, or C$_1$-C$_4$ alkyl), $R^{14F}$-substituted heteroalkyl (e.g., 2 to 8 membered, 2 to 6 membered, or 2 to 4 membered heteroalkyl), $R^{14F}$-substituted cycloalkyl (e.g., C$_3$-C$_8$, C$_3$-C$_6$, or C$_5$-C$_6$ cycloalkyl), $R^{14F}$-substituted heterocycloalkyl (e.g., 3 to 8 membered, 3 to 6 membered, or 5 to 6 membered heterocycloalkyl), $R^{14F}$-substituted aryl (e.g., C$_6$-C$_{10}$, C$_{10}$ aryl, or phenyl), or $R^{14F}$-substituted heteroaryl (e.g., 5 to 10 membered, 5 to 9 membered, or 5 to 6 membered heteroaryl). In embodiments, $R^{14E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, unsubstituted alkyl (e.g., C$_1$-C$_8$, C$_1$-C$_6$, or C$_1$-C$_4$ alkyl), unsubstituted heteroalkyl (e.g., 2 to 8 membered, 2 to 6 membered, or 2 to 4 membered heteroalkyl), unsubstituted cycloalkyl (e.g., C$_3$-C$_8$, C$_3$-C$_6$, or C$_5$-C$_6$ cycloalkyl), unsubstituted heterocycloalkyl (e.g., 3 to 8 membered, 3 to 6 membered, or 5 to 6 membered heterocycloalkyl), unsubstituted aryl (e.g., C$_6$-C$_{10}$, C$_{10}$ aryl, or phenyl), or unsubstituted heteroaryl (e.g., 5 to 10 membered, 5 to 9 membered, or 5 to 6 membered heteroaryl).

In embodiments, $R^{15}$ is hydrogen, halogen (e.g., —F, —Cl, —Br, —I), —CX$^{15}_3$, —CHX$^{15}_2$, —CH$_2$X$^{15}$, —OCX$^{15}_3$, —OCH$_2$X$^{15}$, —OCHX$^{15}_2$, —N$_3$, —CN, —SO$_{n15}$R$^{15D}$, —SO$_{v15}$NR$^{15A}$R$^{15B}$, —NHC(O)NR$^{15A}$R$^{15B}$, —N(O)$_{m1}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$ (e.g, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n15 is an integer from 0 to 4 (e.g. 0). m15 and v15 are independently an integer from 1 to 2. X$^{15}$ is independently —F, —Cl, —Br, or —I. In embodiments, $R^{15}$ is hydrogen.

In embodiments, $R^{15}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)

$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{15E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{15E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{15E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{15E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{15E}$-substituted or unsubstituted aryl (e.g., $C_6$-$C_{12}$, $C_6$-$C_{10}$, or phenyl), or $R^{15E}$-substituted or unsubstituted heteroaryl (e.g., 5 to 12 membered, 5 to 10 membered, 5 to 9 membered, or 5 to 6 membered). In embodiments, $R^{15}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{15E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{15E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{15E}$-substituted cycloalkyl (e.g., $C_3$-$C_{10}$, $C_3$-$C_8$, $C_3$-$C_6$, $C_4$-$C_6$, or $C_5$-$C_6$), $R^{15E}$-substituted heterocycloalkyl (e.g., 3 to 10 membered, 3 to 8 membered, 3 to 6 membered, 4 to 6 membered, 4 to 5 membered, or 5 to 6 membered), $R^{15E}$-substituted aryl (e.g., $C_6$-$C_{12}$, $C_6$-$C_{10}$, or phenyl), or $R^{15E}$-substituted heteroaryl (e.g., 5 to 12 membered, 5 to 10 membered, 5 to 9 membered, or 5 to 6 membered). In embodiments, $R^{15}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{15E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{15F}$-substituted or unsubstituted alkyl (e.g., $C_1$-$C_8$, $C_1$-$C_6$, or $C_1$-$C_4$ alkyl), $R^{15F}$-substituted or unsubstituted heteroalkyl (e.g., 2 to 8 membered, 2 to 6 membered, or 2 to 4 membered heteroalkyl), $R^{15F}$-substituted or unsubstituted cycloalkyl (e.g., $C_3$-$C_8$, $C_3$-$C_6$, or $C_5$-$C_6$ cycloalkyl), $R^{15F}$-substituted or unsubstituted heterocycloalkyl (e.g., 3 to 8 membered, 3 to 6 membered, or 5 to 6 membered heterocycloalkyl), $R^{15F}$-substituted or unsubstituted aryl (e.g., $C_6$-$C_{10}$, $C_{10}$ aryl, or phenyl), or $R^{15F}$-substituted or unsubstituted heteroaryl (e.g., 5 to 10 membered, 5 to 9 membered, or 5 to 6 membered heteroaryl). In embodiments, $R^{15E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{15F}$-substituted alkyl (e.g, $C_1$-$C_8$, $C_1$-$C_6$, or $C_1$-$C_4$ alkyl), $R^{15F}$-substituted heteroalkyl (e.g., 2 to 8 membered, 2 to 6 membered, or 2 to 4 membered heteroalkyl), $R^{15F}$-substituted cycloalkyl (e.g., $C_3$-$C_8$, $C_3$-$C_6$, or $C_5$-$C_6$ cycloalkyl), $R^{15F}$-substituted heterocycloalkyl (e.g., 3 to 8 membered, 3 to 6 membered, or 5 to 6 membered heterocycloalkyl), $R^{15F}$-substituted aryl (e.g., $C_6$-$C_{10}$, $C_{10}$ aryl, or phenyl), or $R^{15F}$-substituted heteroaryl (e.g., 5 to 10 membered, 5 to 9 membered, or 5 to 6 membered heteroaryl). In embodiments, $R^{15E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{16}$ is hydrogen, halogen (e.g., —F, —Cl, —Br, —I), —$CX^{16}_3$, —$CHX^{16}_2$, —$CH_2X^{16}$, —$OCX^{16}_3$, —$OCH_2X^{16}$, —$OCHX^{16}_2$, —$N_3$, —CN, —$SO_{n16}R^{16D}$, —$SO_{v16}NR^{16A}R^{16B}$, —NHC(O)$NR^{16A}R^{16B}$, —$N(O)_{m16}$, —$NR^{16A}R^{16B}$, —C(O)$R^{16C}$, —C(O)—$OR^{16C}$, —C(O)$NR^{16A}R^{16B}$, —$OR^{16D}$, —$NR^{16A}SO_2R^{16D}$, —$NR^{16A}$C(O)$R^{16C}$, —$NR^{16A}$C(O)$OR^{16C}$, —$NR^{16A}OR^{16C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)

NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, or —NCH$_3$OCH$_3$), substituted (e.g., substituted with a substituent group, a size-limited substituent group, or lower substituent group) or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., C$_3$-C$_{10}$, C$_3$-C$_8$, C$_3$-C$_6$, C$_4$-C$_6$, or C$_5$-C$_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., C$_6$-C$_{12}$, C$_6$-C$_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n16 is an integer from 0 to 4 (e.g. 0). m16 and v16 are independently an integer from 1 to 2. X$^{16}$ is independently —F, —Cl, —Br, or —I. In embodiments, R$^{16}$ is hydrogen.

In embodiments, R$^{16}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$), R$^{16E}$-substituted or unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{16E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), R$^{16E}$-substituted or unsubstituted cycloalkyl (e.g., C$_3$-C$_{10}$, C$_3$-C$_8$, C$_3$-C$_6$, C$_4$-C$_6$, or C$_5$-C$_6$), R$^{16E}$-substituted or unsubstituted heterocycloalkyl (e.g., 3 to 10 membered, 3 to 8 membered, 3 to 6 membered, 4 to 6 membered, 4 to 5 membered, or 5 to 6 membered), R$^{16E}$-substituted or unsubstituted aryl (e.g., C$_6$-C$_{12}$, C$_6$-C$_{10}$, or phenyl), or R$^{16E}$-substituted or unsubstituted heteroaryl (e.g., 5 to 12 membered, 5 to 10 membered, 5 to 9 membered, or 5 to 6 membered). In embodiments, R$^{16}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, R$^{16E}$-substituted alkyl (e.g., C$_1$-C$_{20}$, C$_1$-C$_{12}$, C$_1$-C$_8$, C$_1$-C$_6$, C$_1$-C$_4$, or C$_1$-C$_2$), R$^{16E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), R$^{16E}$-substituted cycloalkyl (e.g., C$_3$-C$_{10}$, C$_3$-C$_8$, C$_3$-C$_6$, C$_4$-C$_6$, or C$_5$-C$_6$), R$^{16E}$-substituted heterocycloalkyl (e.g., 3 to 10 membered, 3 to 8 membered, 3 to 6 membered, 4 to 6 membered, 4 to 5 membered, or 5 to 6 membered), R$^{16E}$-substituted aryl (e.g., C$_6$-C$_{12}$, C$_6$-C$_{10}$, or phenyl), or R$^{16E}$-substituted heteroaryl (e.g., 5 to 12 membered, 5 to 10 membered, 5 to 9 membered, or 5 to 6 membered). In embodiments, R$^{16}$ is hydrogen, —F, —Cl, —Br, —I, —CF$_3$, —CHF$_2$, —CH$_2$F, —CCl$_3$, —CHCl$_2$, —CH$_2$Cl, —CBr$_3$, —CHBr$_2$, —CH$_2$Br, —CI$_3$, —CHI$_2$, —CH$_2$I, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, —N$_3$, —CN, —SH, —SCH$_3$, —SO$_2$H, —SO$_2$CH$_3$, —SO$_2$NH$_2$, —SO$_2$NHCH$_3$, —NHC(O)NH$_2$, —NHC(O)NHCH$_3$, —NO$_2$, —NH$_2$, —NHCH$_3$, —C(O)H, —C(O)CH$_3$, —C(O)OH, —C(O)OCH$_3$, —C(O)NH$_2$, —C(O)NHCH$_3$, —OH, —OCH$_3$, —NHSO$_2$H, —NHSO$_2$CH$_3$, —NHC(O)H, —NCH$_3$C(O)H, —NHC(O)OH, —NCH$_3$C(O)OH, —NHOH, —NCH$_3$OH, —NCH$_3$OCH$_3$, unsubstituted alkyl (e.g., C$_1$-C$_{20}$, C$_1$-C$_{12}$, C$_1$-C$_8$, C$_1$-C$_6$, C$_1$-C$_4$, or C$_1$-C$_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., C$_3$-C$_{10}$, C$_3$-C$_8$, C$_3$-C$_6$, C$_4$-C$_6$, or C$_5$-C$_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., C$_6$-C$_{12}$, C$_6$-C$_{10}$, or phenyl), or unsubstituted heteroaryl (e.g., 5 to 12 membered, 5 to 10 membered, 5 to 9 membered, or 5 to 6 membered).

R$^{16E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{16F}$-substituted or unsubstituted alkyl (e.g., C$_1$-C$_8$, C$_1$-C$_6$, or C$_1$-C$_4$ alkyl), R$^{16F}$-substituted or unsubstituted heteroalkyl (e.g., 2 to 8 membered, 2 to 6 membered, or 2 to 4 membered heteroalkyl), R$^{16F}$-substituted or unsubstituted cycloalkyl (e.g., C$_3$-C$_8$, C$_3$-C$_6$, or C$_5$-C$_6$ cycloalkyl), R$^{16F}$-substituted or unsubstituted heterocycloalkyl (e.g., 3 to 8 membered, 3 to 6 membered, or 5 to 6 membered heterocycloalkyl), R$^{16F}$-substituted or unsubstituted aryl (e.g., C$_6$-C$_{10}$, C$_{10}$ aryl, or phenyl), or R$^{16F}$-substituted or unsubstituted heteroaryl (e.g., 5 to 10 membered, 5 to 9 membered, or 5 to 6 membered heteroaryl). In embodiments, R$^{16E}$ is independently oxo, halogen, —CF$_3$, —CCl$_3$, —CBr$_3$, —CI$_3$, —CHF$_2$, —CHCl$_2$, —CHBr$_2$, —CHI$_2$, —CH$_2$F, —CH$_2$Cl, —CH$_2$Br, —CH$_2$I, —CN, —N$_3$, —OH, —NH$_2$, —COOH, —CONH$_2$, —NO$_2$, —SH, —SCH$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCF$_3$, —OCCl$_3$, —OCBr$_3$, —OCI$_3$, —OCHF$_2$, —OCHCl$_2$, —OCHBr$_2$, —OCHI$_2$, —OCH$_2$F, —OCH$_2$Cl, —OCH$_2$Br, —OCH$_2$I, R$^{16F}$-substituted alkyl (e.g., C$_1$-C$_8$, C$_1$-C$_6$, or C$_1$-C$_4$ alkyl), R$^{16F}$-substituted heteroalkyl (e.g., 2 to 8 membered, 2 to 6 membered, or 2 to 4 membered heteroalkyl), R$^{16F}$-substituted cycloalkyl (e.g., $C_3$-$C_8$, $C_3$-$C_6$, or $C_5$-$C_6$ cycloalkyl), $R^{16F}$-substituted heterocycloalkyl (e.g., 3 to 8 membered, 3 to 6 membered, or 5 to 6 membered heterocycloalkyl), $R^{16F}$-substituted aryl (e.g., $C_6$-$C_{10}$, $C_{10}$ aryl, or phenyl), or $R^{16F}$-substituted heteroaryl (e.g., 5 to 10 membered, 5 to 9 membered, or 5 to 6 membered heteroaryl). In embodiments, $R^{16E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

In embodiments, $R^{17}$ is hydrogen, halogen (e.g., —F, —Cl, —Br, —I), —$CX^{17}_3$, —$CHX^{17}_2$, —$CH_2X^{17}$, —$OCX^{17}_3$, —$OCH_2X^{17}$, —$OCHX^{17}_2$, —$N_3$, —CN, —$SO_{n17}R^{17D}$, —$SO_{v17}NR^{17A}R^{17B}$, —NHC(O)$NR^{17A}R^{17B}$, —N(O)$_{m17}$, —$NR^{17A}R^{17B}$, —C(O)$R^{17C}$, —C(O)—$OR^{17C}$, —C(O)$NR^{17A}R^{17B}$, —$OR^{17D}$, —$NR^{17A}SO_2R^{17D}$, —$NR^{17A}$C(O)$R^{17C}$, —$NR^{17A}$C(O)$OR^{17C}$, —$NR^{17A}OR^{17C}$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, or —$NCH_3OCH_3$), substituted (e.g, substituted with a substituent group, a size-limited substituent group, or lower substituent group) or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). n17 is an integer from 0 to 4 (e.g. 0). m17 and v17 are independently an integer from 1 to 2. $X^{17}$ is independently —F, —Cl, —Br, or —I. In embodiments, $R^{17}$ is hydrogen.

In embodiments, $R^{17}$ is hydrogen, —F, —Cl, —Br, —I, —$CF_3$, —$CHF_2$, —$CH_2F$, —$CCl_3$, —$CH_2Cl$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{17E}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{17E}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{17E}$-substituted or unsubstituted cycloalkyl (e.g., $C_3$-$C_{10}$, $C_3$-$C_8$, $C_3$-$C_6$, $C_4$-$C_6$, or $C_5$-$C_6$), $R^{17E}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{17E}$-substituted or unsubstituted aryl (e.g., $C_6$-$C_{12}$, $C_6$-$C_{10}$, or phenyl), or $R^{17E}$-substituted or unsubstituted heteroaryl (e.g., 5 to 12 membered, 5 to 10 membered, 5 to 9 membered, or 5 to 6 membered). In embodiments, $R^{17}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, $R^{17E}$-substituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{17E}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{17E}$-substituted cycloalkyl (e.g., $C_3$-$C_{10}$, $C_3$-$C_8$, $C_3$-$C_6$, $C_4$-$C_6$, or $C_5$-$C_6$), $R^{17E}$-substituted heterocycloalkyl (e.g., 3 to 10 membered, 3 to 8 membered, 3 to 6 membered, 4 to 6 membered, 4 to 5 membered, or 5 to 6 membered), $R^{17E}$-substituted aryl (e.g., $C_6$-$C_{12}$, $C_6$-$C_{10}$, or phenyl), or $R^{17E}$-substituted heteroaryl (e.g., 5 to 12 membered, 5 to 10 membered, 5 to 9 membered, or 5 to 6 membered). In embodiments, $R^{17}$ is hydrogen, —F, —Cl, —Br, —I, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, —$N_3$, —CN, —SH, —$SCH_3$, —$SO_2H$, —$SO_2CH_3$, —$SO_2NH_2$, —$SO_2NHCH_3$, —NHC(O)$NH_2$, —NHC(O)$NHCH_3$, —$NO_2$, —$NH_2$, —$NHCH_3$, —C(O)H, —C(O)$CH_3$, —C(O)OH, —C(O)$OCH_3$, —C(O)$NH_2$, —C(O)$NHCH_3$, —OH, —$OCH_3$, —$NHSO_2H$, —$NHSO_2CH_3$, —NHC(O)H, —$NCH_3$C(O)H, —NHC(O)OH, —$NCH_3$C(O)OH, —NHOH, —$NCH_3$OH, —$NCH_3OCH_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

$R^{17E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{17F}$-substituted or unsubstituted alkyl (e.g., $C_1$-$C_8$, $C_1$-$C_6$, or $C_1$-$C_4$ alkyl), $R^{17F}$-substituted or unsubstituted heteroalkyl (e.g., 2 to 8 membered, 2 to 6 membered, or 2 to 4 membered heteroalkyl), $R^{17F}$-substituted or unsubstituted cycloalkyl (e.g., $C_3$-$C_8$, $C_3$-$C_6$, or $C_5$-$C_6$ cycloalkyl), $R^{17F}$-substituted or unsubstituted heterocycloalkyl (e.g., 3 to 8 membered, 3 to 6 membered, or 5 to 6 membered heterocycloalkyl), $R^{17F}$-substituted or unsubstituted aryl (e.g., $C_6$-$C_{10}$, $C_{10}$ aryl, or phenyl), or $R^{17F}$-substituted or unsubstituted heteroaryl (e.g., 5 to 10 membered, 5 to 9 membered, or 5 to 6 membered heteroaryl). In embodiments, $R^{17E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —COMB, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, $R^{17F}$-substituted alkyl (e.g, $C_1$-$C_8$, $C_1$-$C_6$, or $C_1$-$C_4$ alkyl), $R^{17F}$-substituted heteroalkyl (e.g., 2 to 8 membered, 2 to 6 membered, or 2 to 4 membered heteroalkyl), $R^{17F}$-substituted cycloalkyl (e.g., $C_3$-$C_8$, $C_3$-$C_6$, or $C_5$-$C_6$ cycloalkyl), $R^{17F}$-substituted heterocycloalkyl (e.g., 3 to 8 membered, 3 to 6 membered, or 5 to 6 membered heterocycloalkyl), $R^{17F}$-substituted aryl (e.g., $C_6$-$C_{10}$, $C_{10}$ aryl, or phenyl), or $R^{17F}$-substituted heteroaryl (e.g., 5 to 10 membered, 5 to 9 membered, or 5 to 6 membered heteroaryl). In embodiments, $R^{17E}$ is independently oxo, halogen, —$CF_3$, —$CCl_3$, —$CBr_3$, —$CI_3$, —$CHF_2$, —$CHCl_2$, —$CHBr_2$, —$CHI_2$, —$CH_2F$, —$CH_2Cl$, —$CH_2Br$, —$CH_2I$, —CN, —$N_3$, —OH, —$NH_2$, —COOH, —$CONH_2$, —$NO_2$, —SH, —$SCH_3$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCF_3$, —$OCCl_3$, —$OCBr_3$, —$OCI_3$, —$OCHF_2$, —$OCHCl_2$, —$OCHBr_2$, —$OCHI_2$, —$OCH_2F$, —$OCH_2Cl$, —$OCH_2Br$, —$OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$, $C_{10}$ aryl, or phenyl), or unsubstituted heteroaryl (e.g., 5 to 10 membered, 5 to 9 membered, or 5 to 6 membered heteroaryl).

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ are independently hydrogen, —$CX_3$, —$CHX_2$, —$CH_2X$ (e.g., —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$), —COOH, —$CONH_2$, substituted (e.g, substituted with a substituent group, a size-limited substituent group, or lower substituent group) or unsubstituted alkyl (e.g., $C_1$-$C_{20}$, $C_1$-$C_{20}$, $C_1$-$C_8$, $C_1$-$C_6$, $C_1$-$C_4$, or $C_1$-$C_2$), substituted (e.g., substituted with a substituent group, a size-limited substituent group, or lower substituent group) or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), substituted (e.g., substituted with a substituent group, a size-limited substituent group, or lower substituent group) or unsubstituted cycloalkyl (e.g., $C_3$-$C_{10}$, $C_3$-$C_8$, $C_3$-$C_6$, $C_4$-$C_6$, or $C_5$-$C_6$), substituted (e.g., substituted with a substituent group, a size-limited substituent group, or lower substituent group) or unsubstituted heterocycloalkyl (e.g., 3 to 10 membered, 3 to 8 membered, 3 to 6 membered, 4 to 6 membered, 4 to 5 membered, or 5 to 6 membered), substituted (e.g., substituted with a substituent group, a size-limited substituent group, or lower substituent group) or unsubstituted aryl (e.g., $C_6$-$C_{12}$, $C_6$-$C_{10}$, or phenyl), or substituted (e.g., substituted with a substituent group, a size-limited substituent group, or lower substituent group) or unsubstituted heteroaryl (e.g., 5 to 12 membered, 5 to 10 membered, 5 to 9 membered, or 5 to 6 membered). X is independently —F, —Cl, —Br, or —I. In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ are independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —COOH, —$CONH_2$, $R^{18}$-substituted or unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), $R^{18}$-substituted or unsubstituted heteroalkyl (e.g., 2 to 20 membered, 2 to 12 membered, 2 to 8 membered, 2 to 6 membered, 4 to 6 membered, 2 to 3 membered, or 4 to 5 membered), $R^{18}$-substituted or unsubstituted cycloalkyl (e.g., $C_3$-$C_{10}$, $C_3$-$C_{85}$, $C_3$-$C_6$, $C_4$-$C_6$, or $C_5$-$C_6$), $R^{18}$-substituted or unsubstituted heterocycloalkyl (e.g., 3 to 10 membered, 3 to 8 membered, 3 to 6 membered, 4 to 6 membered, 4 to 5 membered, or 5 to 6 membered), $R^{18}$-substituted or unsubstituted aryl (e.g., $C_6$-$C_{12}$, $C_6$-$C_{10}$, or phenyl), or $R^{18}$-substituted or unsubstituted heteroaryl (e.g., 5 to 12 membered, 5 to 10 membered, 5 to 9 membered, or 5 to 6 membered). In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ are independently hydrogen, —$CF_3$, —$CHF_2$, —$CH_2F$, —$CCl_3$, —$CHCl_2$, —$CH_2Cl$, —$CBr_3$, —$CHBr_2$, —$CH_2Br$, —$CI_3$, —$CHI_2$, —$CH_2I$, —COOH, —$CONH_2$, $R^{18}$-substituted alkyl (e.g, $C_1$-$C_{20}$, $C_1$-$C_{12}$, $C_1$-$C_8$, $C_1$-$C_6$, $C_1$-$C_4$, or $C_1$-$C_2$), $R^{18}$-substituted heteroalkyl (e.g., 2 to 20 membered, 2 to 12 membered, 2 to 8 membered, 2 to 6 membered, 4 to 6 membered, 2 to 3 membered, or 4 to 5 membered), $R^{18}$-substituted cycloalkyl (e.g., $C_3$-$C_{10}$, $C_3$-$C_8$, $C_3$-$C_6$, $C_4$-$C_6$, or $C_5$-$C_6$), $R^{18}$-substituted heterocycloalkyl (e.g., 3 to 10 membered, 3 to 8 membered, 3 to 6 membered, 4 to 6 membered, 4 to 5 membered), $R^{18}$-substituted aryl (e.g., $C_6$-$C_{12}$, $C_6$-$C_{10}$, or phenyl), or $R^{18}$-substituted heteroaryl (e.g., 5 to 12 membered, 5 to 10 membered, 5 to 9 membered, or 5 to 6 membered). In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ are independently hydrogen, $—CF_3$, $—CHF_2$, $—CH_2F$, $—CCl_3$, $—CHCl_2$, $—CH_2Cl$, $—CBr_3$, $—CHBr_2$, $—CH_2Br$, $—CI_3$, $—CHI_2$, $—CH_2I$, $—COOH$, $—CONH_2$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_8$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). In embodiments, each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$, $R^{12D}$, $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ are independently hydrogen.

Each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form $R^{18}$-substituted or unsubstituted heterocycloalkyl (e.g., 3 to 10 membered, 3 to 8 membered, 3 to 6 membered, 4 to 6 membered, 4 to 5 membered, or 5 to 6 membered), or $R^{18}$-substituted or unsubstituted heteroaryl (e.g., 5 to 12 membered, 5 to 10 membered, 5 to 9 membered, or 5 to 6 membered). Each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form $R^{18}$-substituted heterocycloalkyl (e.g., 3 to 10 membered, 3 to 8 membered, 3 to 6 membered, 4 to 6 membered, 4 to 5 membered, or 5 to 6 membered), or $R^{18}$-substituted heteroaryl (e.g., 5 to 12 membered, 5 to 10 membered, 5 to 9 membered, or 5 to 6 membered). Each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form unsubstituted heterocycloalkyl (e.g., 3 to 10 membered, 3 to 8 membered, 3 to 6 membered, 4 to 6 membered, 4 to 5 membered, or 5 to 6 membered), or unsubstituted heteroaryl (e.g., 5 to 12 membered, 5 to 10 membered, 5 to 9 membered, or 5 to 6 membered). In embodiments, each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form $R^{18}$-substituted or unsubstituted pyridyl. In embodiments, each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form $R^{18}$-substituted or unsubstituted piperidinyl. In embodiments, each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form $R^{18}$-substituted or unsubstituted morpholinyl. In embodiments, each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ joined to form $R^{18}$-substituted or unsubstituted pyrrolyl. In embodiments, each $R^{1A}$ and $R^{1B}$, $R^{2A}$ and $R^{2B}$, $R^{3A}$ and $R^{3B}$, $R^{4A}$ and $R^{4B}$, $R^{5A}$ and $R^{5B}$, $R^{6A}$ and $R^{6B}$, $R^{7A}$ and $R^{7B}$, $R^{8A}$ and $R^{8B}$, $R^{9A}$ and $R^{9B}$, $R^{10A}$ and $R^{10B}$, $R^{11A}$ and $R^{11B}$, $R^{12A}$ and $R^{12B}$, $R^{14A}$ and $R^{14B}$, $R^{15A}$ and $R^{15B}$, $R^{16A}$ and $R^{16B}$, and $R^{17A}$ and $R^{17B}$ together with nitrogen attached thereto may be joined to form $R^{18}$-substituted or unsubstituted pyrimidinyl.

$R^{1F}$, $R^{2F}$, $R^{3F}$, $R^{4F}$, $R^{5F}$, $R^{6F}$, $R^{7F}$, $R^{8F}$, $R^{9F}$, $R^{10F}$, $R^{11F}$, $R^{12F}$, $R^{13F}$, $R^{14F}$, $R^{15F}$, $R^{16F}$, $R^{17F}$, $R^{18}$ and $R^{19F}$ are independently oxo, halogen, $—CF_3$, $—CCl_3$, $—CBr_3$, $—CI_3$, $—CHF_2$, $—CHCl_2$, $—CHBr_2$, $—CHI_2$, $—CH_2F$, $—CH_2Cl$, $—CH_2Br$, $—CH_2I$, $—CN$, $—N_3$, $—OH$, $—NH_2$, $—COOH$, $—CONH_2$, $—NO_2$, $—SH$, $—SCH_3$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCF_3$, $—OCCl_3$, $—OCBr_3$, $—OCI_3$, $—OCHF_2$, $—OCHCl_2$, $—OCHBr_2$, $—OCHI_2$, $—OCH_2F$, $—OCH_2Cl$, $—OCH_2Br$, $—OCH_2I$, unsubstituted alkyl (e.g., $C_1$-$C_8$, $C_1$-$C_6$, or $C_1$-$C_4$ alkyl), unsubstituted heteroalkyl (e.g., 2 to 8 membered, 2 to 6 membered, or 2 to 4 membered heteroalkyl), unsubstituted cycloalkyl (e.g., $C_3$-$C_8$, $C_3$-$C_6$, or $C_5$-$C_6$ cycloalkyl), unsubstituted heterocycloalkyl (e.g., 3 to 8 membered, 3 to 6 membered, or 5 to 6 membered heterocycloalkyl), unsubstituted aryl (e.g., $C_6$-$C_{10}$ aryl, $C_{10}$ aryl or phenyl), or unsubstituted heteroaryl (e.g., 5 to 10 membered, 5 to 9 membered, or 5 to 6 membered heteroaryl).

X, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, and $X^{17}$ are independently $—F$, $—Cl$, $—Br$, or $—I$. In embodiments, X is $—F$. In embodiments, X is $—Cl$. In embodiments, X is $—Br$. In embodiments, X is $—I$. In embodiments, $X^1$ is $—F$. In embodiments, $X^1$ is $—Cl$. In embodiments, $X^1$ is $—Br$. In embodiments, $X^1$ is $—I$. In embodiments, $X^1$ is $—F$. In embodiments, $X^1$ is $—Cl$. In embodiments, $X^1$ is $—Br$. In embodiments, $X^1$ is $—I$. In embodiments, $X^2$ is $—F$. In embodiments, $X^2$ is $—Cl$. In embodiments, $X^2$ is $—Br$. In embodiments, $X^2$ is $—I$. In embodiments, $X^3$ is $—F$. In embodiments, $X^3$ is $—Cl$. In embodiments, $X^3$ is $—Br$. In embodiments, $X^3$ is $—I$. In embodiments, $X^4$ is $—F$. In embodiments, $X^4$ is $—Cl$. In embodiments, $X^4$ is $—Br$. In embodiments, $X^4$ is $—I$. In embodiments, $X^5$ is $—F$. In embodiments, $X^5$ is $—Cl$. In embodiments, $X^5$ is $—Br$. In embodiments, $X^5$ is $—I$. In embodiments, $X^6$ is $—F$. In embodiments, $X^6$ is $—Cl$. In embodiments, $X^6$ is $—Br$. In embodiments, $X^6$ is $—I$. In embodiments, $X^7$ is $—F$. In embodiments, $X^7$ is $—Cl$. In embodiments, $X^7$ is $—Br$. In embodiments, $X^7$ is $—I$. In embodiments, $X^8$ is $—F$. In embodiments, $X^8$ is $—Cl$. In embodiments, $X^8$ is $—Br$. In embodiments, $X^8$ is $—I$. In embodiments, $X^9$ is —F. In embodiments, $X^9$ is —Cl. In embodiments, $X^9$ is —Br. In embodiments, $X^9$ is —I. In embodiments, $X^{10}$ is —F. In embodiments, $X^{10}$ is —Cl. In embodiments, $X^{10}$ is —Br. In embodiments, $X^{10}$ is —I. In embodiments, $X^{11}$ is —F. In embodiments, $X^{11}$ is —Cl. In embodiments, $X^{11}$ is —Br. In embodiments, $X^{11}$ is —I. In embodiments, $X^{12}$ is —F. In embodiments, $X^{12}$ is —Cl. In embodiments, $X^{12}$ is —Br. In embodiments, $X^{12}$ is —I. In embodiments, $X^{13}$ is —F. In embodiments, $X^{13}$ is —Cl. In embodiments, $X^{13}$ is —Br. In embodiments, $X^{13}$ is —I. In embodiments, $X^{14}$ is —F. In embodiments, $X^{14}$ is —Cl. In embodiments, $X^{14}$ is —Br. In embodiments, $X^{14}$ is —I. In embodiments, $X^{15}$ is —F. In embodiments, $X^{15}$ is —Cl. In embodiments, $X^{15}$ is —Br. In embodiments, $X^{15}$ is —I. In embodiments, $X^{16}$ is —F. In embodiments, $X^{16}$ is —Cl. In embodiments, $X^{16}$ is —Br. In embodiments, $X^{16}$ is —I. In embodiments, $X^{17}$ is —F. In embodiments, $X^{17}$ is —Cl. In embodiments, $X^{17}$ is —Br. In embodiments, $X^{17}$ is —I.

$n1, n2, n3, n4, n5, n6, n7, n8, n9, n10, n12, n14, n15, n16$ and $n17$ are independently an integer from 0 to 4 (e.g. 0). In embodiments, n1 is 0. In embodiments, n1 is 1. In embodiment, n1 is 2. In embodiments, n1 is 3. In embodiment, n1 is 4. In embodiments, n2 is 0. In embodiments, n2 is 1. In embodiment, n2 is 2. In embodiments, n2 is 3. In embodiment, n2 is 4. In embodiments, n3 is 0. In embodiments, n3 is 1. In embodiment, n3 is 2. In embodiments, n3 is 3. In embodiment, n3 is 4. In embodiments, n4 is 0. In embodiments, n4 is 1. In embodiment, n4 is 2. In embodiments, n4 is 3. In embodiment, n4 is 4. In embodiments, n5 is 0. In embodiments, n5 is 1. In embodiment, n5 is 2. In embodiments, n5 is 3. In embodiments, n5 is 4. In embodiments, n6 is 0. In embodiments, n6 is 1. In embodiment, n6 is 2. In embodiments, n6 is 3. In embodiment, n6 is 4. In embodiments, n7 is 0. In embodiments, n7 is 1. In embodiment, n7 is 2. In embodiments, n7 is 3. In embodiments, n7 is 4. In embodiments, n8 is 0. In embodiments, n8 is 1. In embodiment, n8 is 2. In embodiments, n8 is 3. In embodiment, n8 is 4. In embodiments, n9 is 0. In embodiments, n9 is 1. In embodiment, n9 is 2. In embodiments, n9 is 3. In embodiment, n9 is 4. In embodiments, n10 is 0. In embodiments, n10 is 1. In embodiment, n10 is 2. In embodiments, n10 is 3. In embodiment, n10 is 4. In embodiments, n11 is 0. In embodiments, n11 is 1. In embodiment, n11 is 2. In embodiments, n11 is 3. In embodiments, n11 is 4. In embodiments, n12 is 0. In embodiments, n12 is 1. In embodiments, n12 is 2. In embodiments, n12 is 3. In embodiment, n12 is 4. In embodiments, n14 is 0. In embodiments, n14 is 1. In embodiment, n14 is 2. In embodiments, n14 is 3. In embodiment, n14 is 4. In embodiments, n15 is 0. In embodiments, n15 is 1. In embodiment, n15 is 2. In embodiments, n15 is 3. In embodiment, n15 is 4. In embodiments, n16 is 0. In embodiments, n16 is 1. In embodiment, n16 is 2. In embodiments, n16 is 3. In embodiment, n16 is 4. In embodiments, n17 is 0. In embodiments, n17 is 1. In embodiment, n17 is 2. In embodiments, n17 is 3. In embodiment, n17 is 4.

$m1, m2, m3, m4, m5, m6, m7, m8, m9, m10, m11, m12, m14, m15, m16,$ and $m17$ are independently an integer from 1 to 2. In embodiments, m1 is 1. In embodiment, m1 is 2. In embodiments, m2 is 1. In embodiment, m2 is 2. In embodiments, m3 is 1. In embodiment, m3 is 2. In embodiments, m4 is 1. In embodiment, m4 is 2. In embodiments, m5 is 1. In embodiment, m5 is 2. In embodiments, m6 is 1. In embodiment, m6 is 2. In embodiments, m7 is 1. In embodiment, m7 is 2. In embodiments, m8 is 1. In embodiment, m8 is 2. In embodiments, m9 is 1. In embodiment, m9 is 2. In embodiments, m10 is 1. In embodiment, m10 is 2. In embodiments, m11 is 1. In embodiment, m11 is 2. In embodiments, m12 is 1. In embodiment, m12 is 2. In embodiments, m14 is 1. In embodiment, m14 is 2. In embodiments, m15 is 1. In embodiment, m15 is 2. In embodiments, m16 is 1. In embodiment, m16 is 2. In embodiments, m17 is 1. In embodiment, m17 is 2.

$v1, v2, v3, v4, v5, v6, v7, v8, v9, v10, v11, v12, v14, v15, v16$ and $v17$ are independently an integer from 1 to 2. In embodiments, v1 is 1. In embodiment, v1 is 2. In embodiments, v2 is 1. In embodiment, v2 is 2. In embodiments, v3 is 1. In embodiment, v3 is 2. In embodiments, v4 is 1. In embodiment, v4 is 2. In embodiments, v5 is 1. In embodiment, v5 is 2. In embodiments, v6 is 1. In embodiment, v6 is 2. In embodiments, v7 is 1. In embodiment, v7 is 2. In embodiments, v8 is 1. In embodiment, v8 is 2. In embodiments, v9 is 1. In embodiment, v9 is 2. In embodiments, v10 is 1. In embodiment, v10 is 2. In embodiments, v11 is 1. In embodiment, v11 is 2. In embodiments, v12 is 1. In embodiment, v12 is 2. In embodiments, v14 is 1. In embodiment, v14 is 2. In embodiments, v15 is 1. In embodiment, v15 is 2. In embodiments, v16 is 1. In embodiment, v16 is 2. In embodiments, v17 is 1. In embodiment, v17 is 2.

In embodiments, when $L^1$ is —S—, $R^1$ is —OH, and $R^4$ and $R^5$ together with atoms attached thereto are joined to form unsubstituted phenyl, then $R^6$ is not —$CH_3$. In embodiments, when $L^1$ is —S—, $R^1$ is —OH, and $R^4$ and $R^5$ together with atoms attached thereto are joined to form unsubstituted phenyl, then $R^6$ is not —$CH_2CH_3$. In embodiments, when $L^1$ is —S—, $R^1$ is —OH, and $R^4$ and $R^5$ together with atoms attached thereto are joined to form unsubstituted phenyl, then $R^6$ is not —$CH_3$. In embodiments, when $L^1$ is —S—, $R^1$ is —OH, and $R^4$ and $R^5$ together with atoms attached thereto are joined to form unsubstituted phenyl, then $R^6$ is not —$CH_2CH_3$. In embodiments, when $L^1$ is —S— and $R^4$ and $R^5$ together with atoms attached thereto are joined to form unsubstituted phenyl, then $R^6$ is not —$CH_3$. In embodiments, when $L^1$ is —S—, and $R^4$ and $R^5$ together with atoms attached thereto are joined to form unsubstituted phenyl, then $R^6$ is not —$CH_2CH_3$. In embodiments, when $L^1$ is —S— and $R^1$ is —OH, then $R^6$ is not —$CH_3$. In embodiments, when $L^1$ is —S— and $R^1$ is —OH, then $R^6$ is not —$CH_2CH_3$. In embodiments, when $L^1$ is —S— or —O—, $R^1$ is —OH, and $R^4$ and $R^5$ together with atoms attached thereto are joined to form unsubstituted phenyl, then $R^6$ is not —$CH_3$. In embodiments, when $L^1$ is —S— or —O, $R^1$ is —OH, and $R^4$ and $R^5$ together with atoms attached thereto are joined to form unsubstituted phenyl, then $R^6$ is not —$CH_2CH_3$. In embodiments, $R^6$ is not —$CH_3$. In embodiments, $R^6$ is not —$CH_2CH_3$. In embodiments, $R^6$ is not —$CH_3$. In embodiments, $R^6$ is not substituted or unsubstituted $C_1$-$C_3$ alkyl. In embodiments, $R^6$ is not unsubstituted $C_1$-$C_3$ alkyl.

In embodiments, when $L^1$ is —S—, $R^1$ is —OH, and $R^4$ and $R^5$ together with atoms attached thereto are joined to form unsubstituted phenyl, then $R^8$ is not —$CH_3$. In embodiments, when $L^1$ is —S—, $R^1$ is —OH, and $R^4$ and $R^5$ together with atoms attached thereto are joined to form unsubstituted phenyl, then $R^8$ is not —$CH_2CH_3$. In embodiments, when $L^1$ is —S—, $R^1$ is —OH, and $R^4$ and $R^5$ together with atoms attached thereto are joined to form unsubstituted phenyl, then $R^8$ is not —$CH_3$. In embodiments, when $L^1$ is —S—, $R^1$ is —OH, and $R^4$ and $R^5$ together with atoms attached thereto are joined to form unsubstituted phenyl, then $R^8$ is not —$CH_2CH_3$. In embodiments, when $L^1$ is —S— and $R^4$ and $R^5$ together with atoms attached thereto are joined to form unsubstituted phenyl, then $R^8$ is not —$CH_3$. In embodiments, when $L^1$ is —S—, and $R^4$ and $R^5$ together with atoms attached thereto are joined to form unsubstituted phenyl, then $R^8$ is not —$CH_2CH_3$. In embodiments, when $L^1$ is —S— and $R^1$ is —OH, then $R^8$ is not —$CH_3$. In embodiments, when $L^1$ is —S— and $R^1$ is —OH, then $R^8$ is not —$CH_2CH_3$. In embodiments, when $L^1$ is —S— or —O—, $R^1$ is —OH, and $R^4$ and $R^5$ together with atoms attached thereto are joined to form unsubstituted phenyl, then $R^8$ is not —$CH_3$. In embodiments, when $L^1$ is —S— or —O, $R^1$ is —OH, and $R^4$ and $R^5$ together with atoms attached thereto are joined to form unsubstituted phenyl, then $R^8$ is not —$CH_2CH_3$. In embodiments, $R^8$ is not —$CH_3$. In embodiments, $R^8$ is not —$CH_2CH_3$. In embodiments, $R^8$ is not —$CH_3$. In embodiments, $R^8$ is not substituted or unsubstituted $C_1$-$C_3$ alkyl. In embodiments, $R^8$ is not unsubstituted $C_1$-$C_3$ alkyl.

In embodiments, when $L^1$ is —S—, $R^1$ is —OH, and $R^4$ and $R^5$ together with atoms attached thereto are joined to form unsubstituted phenyl, then $R^{10}$ is not —$CH_3$. In embodiments, when $L^1$ is —S—, $R^1$ is —OH, and $R^4$ and $R^5$ together with atoms attached thereto are joined to form unsubstituted phenyl, then $R^{10}$ is not —$CH_2CH_3$. In embodiments, when $L^1$ is —S—, $R^1$ is —OH, and $R^4$ and $R^5$ together with atoms attached thereto are joined to form unsubstituted phenyl, then $R^{10}$ is not —$CH_3$. In embodiments, when $L^1$ is —S—, $R^1$ is —OH, and $R^4$ and $R^5$ together with atoms attached thereto are joined to form unsubstituted phenyl, then $R^{10}$ is not —$CH_2CH_3$. In embodiments, when $L^1$ is —S— and $R^4$ and $R^5$ together with atoms attached thereto are joined to form unsubstituted phenyl, then $R^{10}$ is not —$CH_3$. In embodiments, when $L^1$ is —S— and $R^4$ and $R^5$ together with atoms attached thereto are joined to form unsubstituted phenyl, then $R^{10}$ is not —$CH_2CH_3$. In embodiments, when $L^1$ is —S— and $R^1$ is —OH, then $R^{10}$ is not —$CH_3$. In embodiments, when $L^1$ is —S— and $R^1$ is —OH, then $R^{10}$ is not —$CH_2CH_3$. In embodiments, when $L^1$ is —S— or —O—, $R^1$ is —OH, and $R^4$ and $R^5$ together with atoms attached thereto are joined to form unsubstituted phenyl, then $R^{10}$ is not —$CH_3$. In embodiments, when $L^1$ is —S— or —O, $R^1$ is —OH, and $R^4$ and $R^5$ together with atoms attached thereto are joined to form unsubstituted phenyl, then $R^{10}$ is not —$CH_2CH_3$. In embodiments, $R^{10}$ is not —$CH_3$. In embodiments, $R^{10}$ is not —$CH_2CH_3$. In embodiments, $R^{10}$ is not —$CH_3$. In embodiments, $R^{10}$ is not substituted or unsubstituted $C_1$-$C_3$ alkyl. In embodiments, $R^{10}$ is not unsubstituted $C_1$-$C_3$ alkyl.

In embodiments, when $L^1$ is —S—, $R^5$ is —OH, and $R^1$ and $R^2$ together with atoms attached thereto are joined to form unsubstituted phenyl, then $R^6$ is not —$CH_3$. In embodiments, when $L^1$ is —S—, $R^5$ is —OH, and $R^1$ and $R^2$ together with atoms attached thereto are joined to form unsubstituted phenyl, then $R^6$ is not —$CH_2CH_3$. In embodiments, when $L^1$ is —S—, $R^5$ is —OH, and $R^1$ and $R^2$ together with atoms attached thereto are joined to form unsubstituted phenyl, then $R^6$ is not —$CH_3$. In embodiments, when $L^1$ is —S—, $R^5$ is —OH, and $R^1$ and $R^2$ together with atoms attached thereto are joined to form unsubstituted phenyl, then $R^6$ is not —$CH_2CH_3$. In embodiments, when $L^1$ is —S—, and $R^1$ and $R^2$ together with atoms attached thereto are joined to form unsubstituted phenyl, then $R^6$ is not —$CH_3$. In embodiments, when $L^1$ is —S— and $R^1$ and $R^2$ together with atoms attached thereto are joined to form unsubstituted phenyl, then $R^6$ is not —$CH_2CH_3$. In embodiments, when $L^1$ is —S— and $R^5$ is —OH, then $R^6$ is not —$CH_3$. In embodiments, when $L^1$ is —S— and $R^5$ is —OH, then $R^6$ is not —$CH_2CH_3$. In embodiments, when $L^1$ is —S— or —O—, $R^5$ is —OH, and $R^1$ and $R^2$ together with atoms attached thereto are joined to form unsubstituted phenyl, then $R^6$ is not —$CH_3$. In embodiments, when $L^1$ is —S— or —O, $R^5$ is —OH, and $R^1$ and $R^2$ together with atoms attached thereto are joined to form unsubstituted phenyl, then $R^6$ is not —$CH_2CH_3$. In embodiments, $R^6$ is not —$CH_3$. In embodiments, $R^6$ is not —$CH_2CH_3$. In embodiments, $R^6$ is not —$CH_3$. In embodiments, $R^6$ is not substituted or unsubstituted $C_1$-$C_3$ alkyl. In embodiments, $R^6$ is not unsubstituted $C_1$-$C_3$ alkyl.

In embodiments, when $L^1$ is —S—, $R^5$ is —OH, and $R^1$ and $R^2$ together with atoms attached thereto are joined to form unsubstituted phenyl, then $R^8$ is not —$CH_3$. In embodiments, when $L^1$ is —S—, $R^5$ is —OH, and $R^1$ and $R^2$ together with atoms attached thereto are joined to form unsubstituted phenyl, then $R^8$ is not —$CH_2CH_3$. In embodiments, when $L^1$ is —S—, $R^5$ is —OH, and $R^1$ and $R^2$ together with atoms attached thereto are joined to form unsubstituted phenyl, then $R^8$ is not —$CH_3$. In embodiments, when $L^1$ is —S—, $R^5$ is —OH, and $R^1$ and $R^2$ together with atoms attached thereto are joined to form unsubstituted phenyl, then $R^8$ is not —$CH_2CH_3$. In embodiments, when $L^1$ is —S—, and $R^1$ and $R^2$ together with atoms attached thereto are joined to form unsubstituted phenyl, then $R^8$ is not —$CH_3$. In embodiments, when $L^1$ is —S— and $R^1$ and $R^2$ together with atoms attached thereto are joined to form unsubstituted phenyl, then $R^8$ is not —$CH_2CH_3$. In embodiments, when $L^1$ is —S— and $R^5$ is —OH, then $R^8$ is not —$CH_3$. In embodiments, when $L^1$ is —S— and $R^5$ is —OH, then $R^8$ is not —$CH_2CH_3$. In embodiments, when $L^1$ is —S— or —O—, $R^5$ is —OH, and $R^1$ and $R^2$ together with atoms attached thereto are joined to form unsubstituted phenyl, then $R^8$ is not —$CH_3$. In embodiments, when $L^1$ is —S— or —O, $R^5$ is —OH, and $R^1$ and $R^2$ together with atoms attached thereto are joined to form unsubstituted phenyl, then $R^8$ is not —$CH_2CH_3$. In embodiments, $R^8$ is not —$CH_3$. In embodiments, $R^8$ is not —$CH_2CH_3$. In embodiments, $R^8$ is not —$CH_3$. In embodiments, $R^8$ is not substituted or unsubstituted $C_1$-$C_3$ alkyl. In embodiments, $R^8$ is not unsubstituted $C_1$-$C_3$ alkyl.

In embodiments, when $L^1$ is —S—, $R^5$ is —OH, and $R^1$ and $R^2$ together with atoms attached thereto are joined to form unsubstituted phenyl, then $R^{10}$ is not —$CH_3$. In embodiments, when $L^1$ is —S—, $R^5$ is —OH, and $R^1$ and $R^2$ together with atoms attached thereto are joined to form unsubstituted phenyl, then $R^{10}$ is not —$CH_2CH_3$. In embodiments, when $L^1$ is —S—, $R^5$ is —OH, and $R^1$ and $R^2$ together with atoms attached thereto are joined to form unsubstituted phenyl, then $R^{10}$ is not —$CH_3$. In embodiments, when $L^1$ is —S—, $R^5$ is —OH, and $R^1$ and $R^2$ together with atoms attached thereto are joined to form unsubstituted phenyl, then $R^{10}$ is not —$CH_2CH_3$. In embodiments, when $L^1$ is —S— and $R^1$ and $R^2$ together with atoms attached thereto are joined to form unsubstituted phenyl, then $R^{10}$ is not —$CH_3$. In embodiments, when $L^1$ is —S—, and $R^1$ and $R^2$ together with atoms attached thereto are joined to form unsubstituted phenyl, then $R^{10}$ is not —$CH_2CH_3$. In embodiments, when $L^1$ is —S— and $R^5$ is —OH, then $R^{10}$ is not —$CH_3$. In embodiments, when $L^1$ is —S— and $R^5$ is —OH, then $R^{10}$ is not —$CH_2CH_3$. In embodiments, when $L^1$ is —S— or —O—, $R^5$ is —OH, and $R^1$ and $R^2$ together with atoms attached thereto are joined to form unsubstituted phenyl, then $R^{10}$ is not —$CH_3$. In embodiments, when $L^1$ is —S— or —O—, $R^5$ is —OH, and $R^1$ and $R^2$ together with atoms attached thereto are joined to form unsubstituted phenyl, then $R^{10}$ is not —$CH_2CH_3$. In embodiments, $R^{10}$ is not —$CH_3$. In embodiments, $R^{10}$ is not —$CH_2CH_3$. In embodiments, $R^{10}$ is not —$CH_3$. In embodiments, $R^{10}$ is not substituted or unsubstituted $C_1$-$C_3$ alkyl. In embodiments, $R^{10}$ is not unsubstituted $C_1$-$C_3$ alkyl.

In embodiments, when $R^4$ and $R^5$ together with atoms attached thereto are joined to form unsubstituted phenyl, $L^1$ is a bond, $R^1$ is —OH or —OCH$_3$, and $R^7$, $R^8$ and $R^9$ are hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^7$, $R^8$ and $R^9$ are hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^7$, $R^8$ and $R^9$ are hydrogen, then $R^6$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^7$, $R^8$ and $R^9$ are hydrogen, then $R^{10}$ is not —C(O)NH$_2$. In embodiments, when $R^4$ and $R^5$ together with atoms attached thereto are joined to form unsubstituted phenyl, $L^1$ is a bond, $R^1$ is —OH, and $R^7$, $R^8$ and $R^9$ are hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OCH$_3$, and $R^7$, $R^8$ and $R^9$ are hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^7$ and $R^9$ are hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^7$ and $R^8$ are hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^8$ and $R^9$ are hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^7$ is hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^8$ is hydrogen, then $R^6$ or $R^{10}$ is not —C(O)NH$_2$. In embodiments, when $R^4$ and $R^5$ together with atoms attached thereto are joined to form unsubstituted phenyl, $L^1$ is a bond, $R^1$ is —OH or —OCH$_3$, and $R^9$ is hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^7$ and $R^9$ are hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^7$ and $R^8$ are hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^8$ and $R^9$ are hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^7$ is hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^8$ is hydrogen, then $R^6$ or $R^{10}$ is not —C(O)NH$_2$. In embodiments, when $R^4$ and $R^5$ together with atoms attached thereto are joined to form substituted or unsubstituted phenyl, $L^1$ is a bond, $R^1$ is —OH or —OCH$_3$, and $R^9$ is hydrogen, then $R^6$ or $R^{10}$ is not —C(O)NH$_2$.

In embodiments, when $R^1$ and $R^2$ together with atoms attached thereto are joined to form unsubstituted phenyl, $L^1$ is a bond, $R^5$ is —OH or —OCH$_3$, and $R^7$, $R^8$ and $R^9$ are hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^7$, $R^8$ and $R^9$ are hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^7$, $R^8$ and $R^9$ are hydrogen, then $R^6$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^7$, $R^8$ and $R^9$ are hydrogen, then $R^{10}$ is not —C(O)NH$_2$. In embodiments, when $R^1$ and $R^2$ together with atoms attached thereto are joined to form unsubstituted phenyl, $L^1$ is a bond, $R^5$ is —OH, and $R^7$, $R^8$ and $R^9$ are hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OCH$_3$, and $R^7$, $R^8$ and $R^9$ are hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^7$ and $R^9$ are hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^7$ and $R^8$ are hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^8$ and $R^9$ are hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^7$ is hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^8$ is hydrogen, then $R^6$ or $R^{10}$ is not —C(O)NH$_2$. In embodiments, when $R^1$ and $R^2$ together with atoms attached thereto are joined to form unsubstituted phenyl, $L^1$ is a bond, $R^5$ is —OH or —OCH$_3$, and $R^9$ is hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^7$ and $R^9$ are hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^7$ and $R^8$ are hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^8$ and $R^9$ are hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^7$ is hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^8$ is hydrogen, then $R^6$ or $R^{10}$ is not —C(O)NH$_2$. In embodiments, when $R^1$ and $R^2$ together with atoms attached thereto are joined to form substituted or unsubstituted phenyl, $L^1$ is a bond, $R^5$ is —OH or —OCH$_3$, and $R^9$ is hydrogen, then $R^6$ or $R^{10}$ is not —C(O)NH$_2$.

In embodiments, when $R^4$ and $R^5$ together with atoms attached thereto are joined to form unsubstituted phenyl, $L^1$ is —S— or —S(O)$_2$—, $R^1$ is —OH, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form substituted or unsubstituted phenyl, $L^1$ is —S— or —S(O)$_2$—, $R^1$ is —OH, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^6$, $R^7$, $R^9$ and $R^{10}$ are hydrogen, then $R^8$ is not hydrogen. In embodiments, when $R^4$ and $R^5$ together with atoms attached thereto are joined to form unsubstituted phenyl, $L^1$ is —S— or —S(O)$_2$—, $R^1$ is —OH, and $R^6$, $R^7$, $R^9$ and $R^{10}$ are hydrogen, then $R^8$ is not —Cl. In embodiments, when $R^4$ and $R^5$ together with atoms attached thereto are joined to form unsubstituted phenyl, $L^1$ is —S— or —S(O)$_2$—, $R^1$ is —OH, and $R^6$, $R^7$, $R^9$ and $R^{10}$ are hydrogen, then $R^8$ is not-CH$_3$. In embodiments, when $R^4$ and $R^5$ together with atoms attached thereto are joined to form unsubstituted phenyl, $L^1$ is —S—, $R^1$ is —OH, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S—, $R^1$ is —OH, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^6$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^7$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^6$ and $R^7$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^7$ and $R^9$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^6$, $R^7$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —S— or —S(O)$_2$—, $R^1$ is —OH, and $R^6$, $R^7$ and $R^9$ are hydrogen, then $R^8$ is not hydrogen, —Cl or —CH$_3$.

In embodiments, when $R^1$ and $R^2$ together with atoms attached thereto are joined to form unsubstituted phenyl, $L^1$ is —S— or —S(O)$_2$—, $R^5$ is —OH, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form substituted or unsubstituted phenyl, $L^1$ is —S— or —S(O)$_2$—, $R^5$ is —OH, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^6$, $R^7$, $R^9$ and $R^{10}$ are hydrogen, then $R^8$ is not hydrogen. In embodiments, when $R^1$ and $R^2$ together with atoms attached thereto are joined to form unsubstituted phenyl, $L^1$ is —S— or —S(O)$_2$—, $R^5$ is —OH, and $R^6$, $R^7$, $R^9$ and $R^{10}$ are hydrogen, then $R^8$ is not —Cl. In embodiments, when $R^1$ and $R^2$ together with atoms attached thereto are joined to form unsubstituted phenyl, $L^1$ is —S— or —S(O)$_2$—, $R^5$ is —OH, and $R^6$, $R^7$, $R^9$ and $R^{10}$ are hydrogen, then $R^8$ is not-CH$_3$. In embodiments, when $R^1$ and $R^2$ together with atoms attached thereto are joined to form unsubstituted phenyl, $L^1$ is —S—, $R^5$ is —OH, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S—, $R^5$ is —OH, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^6$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^7$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^6$ and $R^7$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^7$ and $R^9$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^6$, $R^7$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —S— or —S(O)$_2$—, $R^5$ is —OH, and $R^6$, $R^7$ and $R^9$ are hydrogen, then $R^8$ is not hydrogen, —Cl or —CH$_3$.

In embodiments, when $R^4$ and $R^5$ together with atoms attached thereto are joined to form unsubstituted phenyl, $L^1$ is —S(O)$_2$—, $R^1$ is —OCH$_3$, and $R^6$, $R^7$, $R^9$ and $R^{10}$ are hydrogen, then $R^8$ is not hydrogen or —CH$_3$. In embodiments, when $R^4$ and $R^5$ together with atoms attached thereto are joined to form substituted or unsubstituted phenyl, $L^1$ is —S(O)$_2$—, $R^1$ is —OCH$_3$, and $R^6$, $R^7$, $R^9$ and $R^{10}$ are hydrogen, then $R^8$ is not hydrogen or —CH$_3$. In embodiments, when $R^4$ and $R^5$ together with atoms attached thereto are joined to form unsubstituted phenyl, $L^1$ is —S(O)$_2$—, $R^1$ is —OCH$_3$, and $R^6$, $R^7$, $R^9$ and $R^{10}$ are hydrogen, then $R^8$ is not hydrogen. In embodiments, when $R^4$ and $R^5$ together with atoms attached thereto are joined to form unsubstituted phenyl, $L^1$ is —S(O)$_2$—, $R^1$ is —OCH$_3$, and $R^6$, $R^7$, $R^9$ and $R^{10}$ are hydrogen, then $R^8$ is not —CH$_3$. In embodiments, when $R^4$ and $R^5$ together with atoms attached thereto are joined to form unsubstituted phenyl, $L^1$ is —S(O)$_2$—, $R^1$ is —OCH$_3$, and $R^6$, $R^7$, $R^9$ and $R^{10}$ are hydrogen, then $R^8$ is not unsubstituted $C_1$-$C_3$ alkyl. In embodiments, when $R^4$ and $R^5$ together with atoms attached thereto are joined to form unsubstituted phenyl, $L^1$ is —S(O)$_2$—, $R^1$ is —OCH$_3$, and $R^6$, $R^7$, $R^9$ and $R^{10}$ are hydrogen, then $R^8$ is not substituted or unsubstituted $C_1$-$C_3$ alkyl. In embodiments, when $R^4$ and $R^5$ together with atoms attached thereto are joined to form unsubstituted phenyl, $L^1$ is —S(O)$_2$—, $R^1$ is —OCH$_3$, and $R^6$ and $R^{10}$ are hydrogen, then $R^8$ is not hydrogen or —CH$_3$. In embodiments, when $R^4$ and $R^5$ together with atoms attached thereto are joined to form unsubstituted phenyl, $L^1$ is —S(O)$_2$—, $R^1$ is —OCH$_3$, and $R^6$, and $R^7$ are hydrogen, then $R^8$ is not hydrogen or —CH$_3$. In embodiments, when $R^4$ and $R^5$ together with atoms attached thereto are joined to form unsubstituted phenyl, $L^1$ is —S(O)$_2$—, $R^1$ is —OCH$_3$, and $R^6$ and $R^9$ are hydrogen, then $R^8$ is not hydrogen or —CH$_3$. In embodiments, when $R^4$ and $R^5$ together with atoms attached thereto are joined to form unsubstituted phenyl, $L^1$ is —S(O)$_2$—, $R^1$ is —OCH$_3$, and $R^7$ and $R^9$ are hydrogen, then $R^8$ is not hydrogen or —CH$_3$. In embodiments, when $R^4$ and $R^5$ together with atoms attached thereto are joined to form unsubstituted phenyl, $L^1$ is —S(O)$_2$—, $R^1$ is —OCH$_3$, and $R^9$ and $R^{10}$ are hydrogen, then $R^8$ is not hydrogen or —CH$_3$.

In embodiments, when $R^1$ and $R^2$ together with atoms attached thereto are joined to form unsubstituted phenyl, $L^1$ is —S(O)$_2$—, $R^5$ is —OCH$_3$, and $R^6$, $R^7$, $R^9$ and $R^{10}$ are hydrogen, then $R^8$ is not hydrogen or —CH$_3$. In embodiments, when $R^1$ and $R^2$ together with atoms attached thereto are joined to form substituted or unsubstituted phenyl, $L^1$ is —S(O)$_2$—, $R^5$ is —OCH$_3$, and $R^6$, $R^7$, $R^9$ and $R^{10}$ are hydrogen, then $R^8$ is not hydrogen or —CH$_3$. In embodiments, when $R^1$ and $R^2$ together with atoms attached thereto are joined to form unsubstituted phenyl, $L^1$ is —S(O)$_2$—, $R^5$ is —OCH$_3$, and $R^6$, $R^7$, $R^9$ and $R^{10}$ are hydrogen, then $R^8$ is not hydrogen. In embodiments, when $R^1$ and $R^2$ together with atoms attached thereto are joined to form unsubstituted phenyl, $L^1$ is —S(O)$_2$—, $R^5$ is —OCH$_3$, and $R^6$, $R^7$, $R^9$ and $R^{10}$ are hydrogen, then $R^8$ is not —CH$_3$. In embodiments, when $R^1$ and $R^2$ together with atoms attached thereto are joined to form unsubstituted phenyl, $L^1$ is —S(O)$_2$—, $R^5$ is —OCH$_3$, and $R^6$, $R^7$, $R^9$ and $R^{10}$ are hydrogen, then $R^8$ is not unsubstituted C$_1$-C$_3$ alkyl. In embodiments, when $R^1$ and $R^2$ together with atoms attached thereto are joined to form unsubstituted phenyl, $L^1$ is —S(O)$_2$—, $R^5$ is —OCH$_3$, and $R^6$, $R^7$, $R^9$ and $R^{10}$ are hydrogen, then $R^8$ is not substituted or unsubstituted C$_1$-C$_3$ alkyl. In embodiments, when $R^1$ and $R^2$ together with atoms attached thereto are joined to form unsubstituted phenyl, $L^1$ is —S(O)$_2$—, $R^5$ is —OCH$_3$, and $R^6$ and $R^{10}$ are hydrogen, then $R^8$ is not hydrogen or —CH$_3$. In embodiments, when $R^1$ and $R^2$ together with atoms attached thereto are joined to form unsubstituted phenyl, $L^1$ is —S(O)$_2$—, $R^5$ is —OCH$_3$, and $R^6$, and $R^7$ are hydrogen, then $R^8$ is not hydrogen or —CH$_3$. In embodiments, when $R^1$ and $R^2$ together with atoms attached thereto are joined to form unsubstituted phenyl, $L^1$ is —S(O)$_2$—, $R^5$ is —OCH$_3$, and $R^6$ and $R^9$ are hydrogen, then $R^8$ is not hydrogen or —CH$_3$. In embodiments, when $R^1$ and $R^2$ together with atoms attached thereto are joined to form unsubstituted phenyl, $L^1$ is —S(O)$_2$—, $R^5$ is —OCH$_3$, and $R^7$ and $R^9$ are hydrogen, then $R^8$ is not hydrogen or —CH$_3$. In embodiments, when $R^1$ and $R^2$ together with atoms attached thereto are joined to form unsubstituted phenyl, $L^1$ is —S(O)$_2$—, $R^5$ is —OCH$_3$, and $R^9$ and $R^{10}$ are hydrogen, then $R^8$ is not hydrogen or —CH$_3$.

In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form substituted or unsubstituted phenyl, $L^1$ is —NHS(O)$_2$—, $R^1$ is —OH or —OCH$_3$, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$—, $R^1$ is —OH or —OCH$_3$, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not hydrogen. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not —Cl. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not halogen. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not unsubstituted C$_1$-C$_3$ alkyl. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not substituted or unsubstituted C$_1$-C$_3$ alkyl. In embodiments, when $R^4$ and $R^5$ together with atoms attached thereto are joined to form unsubstituted phenyl, $L^1$ is —NH—, $R^1$ is —OH or —OCH$_3$, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OCH$_3$, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$ and $R^7$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$ and $R^9$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^7$ and $R^9$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^7$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^7$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^9$ and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, and $R^{10}$ are hydrogen, then $R^8$ is not hydrogen, —Cl or —CH$_3$. In embodiments, when $R^4$ and $R^5$ together with atoms attached thereto are joined to form unsubstituted phenyl, $L^1$ is —NHS(O)$_2$— or —NH—, $R^1$ is —OH or —OCH$_3$, and $R^6$, $R^7$, and $R^9$ are hydrogen, then $R^8$ is not hydrogen, —Cl or —CH$_3$.

In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form substituted or unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$—, $R^5$ is —OH or —OCH$_3$, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not hydrogen. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not —Cl. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not halogen. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not unsubstituted C$_1$-C$_3$ alkyl. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not substituted or unsubstituted C$_1$-C$_3$ alkyl. In embodiments, when $R^1$ and $R^2$ together with atoms attached thereto are joined to form unsubstituted phenyl, $L^1$ is —NH—, $R^5$ is —OH or —OCH$_3$, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OCH$_3$, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$ and $R^7$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$ and $R^9$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^7$ and $R^9$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^7$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^7$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^9$ and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, and $R^{10}$ are hydrogen, then $R^8$ is not hydrogen, —Cl or —CH$_3$. In embodiments, when $R^1$ and $R^2$ together with atoms attached thereto are joined to form unsubstituted phenyl, $L^1$ is —NHS(O)$_2$— or —NH—, $R^5$ is —OH or —OCH$_3$, and $R^6$, $R^7$, and $R^9$ are hydrogen, then $R^8$ is not hydrogen, —Cl or —CH$_3$.

In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form substituted or unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$ and $R^7$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$ and $R^9$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$ and $R^9$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not hydrogen. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not halogen. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not unsubstituted $C_1$-$C_4$ alkyl. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not substituted or unsubstituted $C_1$-$C_4$ alkyl. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$ and $R^9$ are hydrogen, then $R^8$ is not —OH, or —OCH$_3$.

In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form substituted or unsubstituted phenyl, $L^1$ is —NHC(O)—, $R^5$ is —OH or —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$ and $R^7$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$ and $R^9$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$ and $R^{10}$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$ and $R^9$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$ and $R^9$ are hydrogen, then $R^8$ is not hydrogen, —Cl, —Br, —CH$_3$, —C(CH$_3$)$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$ and $R^{10}$ are hydrogen, then $R^8$ is not hydrogen. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$, $R^9$ and $R^{10}$ are hydrogen, then $R^8$ is not halogen. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$, $R^9$ and $R^{10}$ are hydrogen, then $R^8$ is not unsubstituted $C_1$-$C_4$ alkyl. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$, $R^9$ and $R^{10}$ are hydrogen, then $R^8$ is not substituted or unsubstituted $C_1$-$C_4$ alkyl. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^7$ and $R^9$ are hydrogen, then $R^8$ is not —OH, or —OCH$_3$.

In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form substituted or unsubstituted phenyl, $L^1$ is —NHC(O)—, $R^1$ is —OH or —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OCH$_3$, and $R^6$, $R^7$, $R^9$ and $R^{10}$ are hydrogen, then $R^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^7$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$ and R$^7$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^7$ and R$^9$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$ and R$^{10}$ are hydrogen, then R$^8$ is not hydrogen, —Cl, —Br, —CH$_3$, —C(CH$_3$)$_3$, —OH, or —OCH$_3$. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not hydrogen. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not halogen. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not unsubstituted C$_1$-C$_4$ alkyl. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not substituted or unsubstituted C$_1$-C$_4$ alkyl. In embodiments, when R$^4$ and R$^5$ together with atoms attached thereto are joined to form unsubstituted phenyl, L$^1$ is —NHC(O)—, R$^1$ is —OH or —OCH$_3$, and R$^6$, R$^7$, R$^9$ and R$^{10}$ are hydrogen, then R$^8$ is not —OH, or —OCH$_3$.

In embodiments, when R$^1$ and R$^2$ together with atoms attached thereto are joined to form unsubstituted phenyl, L$^1$ is —NHC(O)—, R$^5$ is —OH or —OCH$_3$, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form substituted or unsubstituted phenyl, L$^1$ is —NHC(O)—, R$^5$ is —OH or —OCH$_3$, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OCH$_3$, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH, and R$^6$, R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^6$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^7$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^6$ and R$^7$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^7$ and R$^9$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^7$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^6$, R$^9$ and R$^{10}$ are hydrogen, then R$^8$ is not hydrogen, —Cl, —Br, —CH$_3$, —C(CH$_3$)$_3$, —OH, or —OCH$_3$. In embodiments, when R$^1$ and R$^2$ together with atoms attached thereto are joined to form unsubstituted phenyl, L$^1$ is —NHC(O)—, R$^5$ is —OH or —OCH$_3$, and R$^6$, R$^7$ and R$^{10}$ are hydrogen, then R$^8$ is not hydrogen. In embodiments, when R$^1$ and R$^2$ together with atoms attached thereto are joined to form unsubstituted phenyl, L$^1$ is —NHC(O)—, R$^5$ is —OH or —OCH$_3$, and R$^6$, R$^7$, R$^9$ and R$^{10}$ are hydrogen, then R$^8$ is not halogen. In embodiments, when R$^1$ and R$^2$ together with atoms attached thereto are joined to form unsubstituted phenyl, L$^1$ is —NHC(O)—, R$^5$ is —OH or —OCH$_3$, and R$^6$, R$^7$, R$^9$ and R$^{10}$ are hydrogen, then R$^8$ is not unsubstituted C$_1$-C$_4$ alkyl. In embodiments, when R$^1$ and R$^2$ together with atoms attached thereto are joined to form unsubstituted phenyl, L$^1$ is —NHC(O)—, R$^5$ is —OH or —OCH$_3$, and R$^6$, R$^7$, R$^9$ and R$^{10}$ are hydrogen, then R$^8$ is not substituted or unsubstituted C$_1$-C$_4$ alkyl. In embodiments, when R$^1$ and R$^2$ together with atoms attached thereto are joined to form unsubstituted phenyl, $L^1$ is —NHC(O)—, $R^5$ is —OH or —OCH$_3$, and $R^6$, $R^7$, $R^9$ and $R^{10}$ are hydrogen, then $R^8$ is not —OH, or —OCH$_3$.

In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form substituted or unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OCH$_3$, and $R^6$, $R^8$ and $R^{10}$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH, and $R^6$, $R^8$ and $R^{10}$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not halogen. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not unsubstituted C$_1$-C$_4$ alkyl. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not substituted or unsubstituted C$_1$-C$_4$ alkyl. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^8$ and $R^{10}$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$ and $R^{10}$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$ and $R^8$ are hydrogen, then $R^7$ or $R^9$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^6$, $R^8$ and $R^{10}$ are hydrogen, then $R^7$ or $R^9$ is not —Cl, —Br, —CH$_3$, —OH, or —OCH$_3$.

In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not —Cl, —Br, —CH$_3$, —OH, or —OCH$_3$. In embodiments, when $R^1$ and $R^2$ together with atoms attached thereto are joined to form substituted or unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OCH$_3$, and $R^6$, $R^8$ and $R^{10}$ are hydrogen, then $R^7$ or $R^9$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH, and $R^6$, $R^8$ and $R^{10}$ are hydrogen, then $R^7$ or $R^9$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^9$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not halogen. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not unsubstituted C$_1$-C$_4$ alkyl. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not substituted or unsubstituted C$_1$-C$_4$ alkyl. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^8$ and $R^{10}$ are hydrogen, then $R^7$ or $R^9$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$ and $R^8$ are hydrogen, then $R^7$ or $R^9$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^6$, $R^8$ and $R^{10}$ are hydrogen, then $R^7$ or $R^9$ is not —Cl, —Br, —CH$_3$, —OH, or —OCH$_3$.

In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form substituted or unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH, and $R^7$, $R^8$ and $R^9$ are hydrogen, then $R^6$ or $R^{10}$ is not —Cl, —Br, —CH$_3$, —OH, or —OCH$_3$.

In embodiments, when $R^4$ and $R^5$ together with atoms attached thereto are joined to form unsubstituted phenyl, $L^1$ is —NHC(O)—, $R^1$ is —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^8$ and $R^9$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$ and $R^9$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$ and $R^8$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not halogen. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not —OH, or —OCH$_3$. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not unsubstituted C$_1$-C$_4$ alkyl. In embodiments, when $R^4$ and $R^5$ together with atoms attached thereto are joined to form unsubstituted phenyl, $L^1$ is —NHC(O)—, $R^1$ is —OH or —OCH$_3$, and $R^7$, $R^8$ and $R^9$ are hydrogen, then $R^6$ or $R^{10}$ is not substituted or unsubstituted C$_1$-C$_4$ alkyl.

In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form substituted or unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH, and $R^7$, $R^8$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^8$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$ and $R^8$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not —Cl, —Br, —CH$_3$, —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not halogen. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not —OH, or —OCH$_3$. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not unsubstituted C$_1$-C$_4$ alkyl. In embodiments, when $R^1$ and $R^2$ together with atoms attached thereto are joined to form unsubstituted phenyl, $L^1$ is —NHC(O)—, $R^5$ is —OH or —OCH$_3$, and $R^7$, $R^8$ and $R^9$ are hydrogen, then $R^6$ or $R^{10}$ is not substituted or unsubstituted C$_1$-C$_4$ alkyl.

In embodiments, when $R^4$ and $R^5$ together with atoms attached thereto are joined to form unsubstituted phenyl, $L^1$ is —NHC(O)—, and $R^1$ is —OH or —OCH$_3$, then at least one of $R^6$, $R^7$ and $R^8$ are not —OCH$_3$, or at least one of $R^8$, $R^9$ and $R^{10}$ are not —OCH$_3$. In embodiments, when $R^4$ and $R^5$ together with atoms attached thereto are joined to form substituted or unsubstituted phenyl, $L^1$ is —NHC(O)—, and $R^1$ is —OH or —OCH$_3$, then at least one of $R^6$, $R^7$ and $R^8$ are not —OCH$_3$, or at least one of $R^8$, $R^9$ and $R^{10}$ are not —OCH$_3$. In embodiments, when $R^4$ and $R^5$ together with atoms attached thereto are joined to form unsubstituted phenyl, $L^1$ is —NHC(O)—, and $R^1$ is —OCH$_3$, then at least one of $R^6$, $R^7$ and $R^8$ are not —OCH$_3$. In embodiments, when $R^4$ and $R^5$ together with atoms attached thereto are joined to form unsubstituted phenyl, $L^1$ is —NHC(O)—, and $R^1$ is —OH, then at least one of $R^7$ and $R^8$ are not —OCH$_3$. In embodiments, when $R^4$ and $R^5$ together with atoms attached thereto are joined to form unsubstituted phenyl, $L^1$ is —NHC(O)—, and $R^1$ is —OH or —OCH$_3$, then at least one of $R^6$ and $R^8$ are not —OCH$_3$. In embodiments, when $R^4$ and $R^5$ together with atoms attached thereto are joined to form unsubstituted phenyl, $L^1$ is —NHC(O)—, and $R^1$ is —OH or —OCH$_3$, then at least one of $R^6$ and $R^7$ are not —OCH$_3$. In embodiments, when $R^4$ and $R^5$ together with atoms attached thereto are joined to form unsubstituted phenyl, $L^1$ is —NHC(O)—, and $R^1$ is —OH or —OCH$_3$, then at least one of $R^9$ and $R^{10}$ are not —OCH$_3$. In embodiments, when $R^4$ and $R^5$ together with atoms attached thereto are joined to form unsubstituted phenyl, $L^1$ is —NHC(O)—, and $R^1$ is —OH or —OCH$_3$, then at least one of $R^8$ and $R^{10}$ are not —OCH$_3$. In embodiments, when $R^4$ and $R^5$ together with atoms attached thereto are joined to form unsubstituted phenyl, $L^1$ is —NHC(O)—, and $R^1$ is —OH or —OCH$_3$, then at least one of $R^8$ and $R^9$ are not —OCH$_3$.

In embodiments, when $R^1$ and $R^2$ together with atoms attached thereto are joined to form unsubstituted phenyl, $L^1$ is —NHC(O)—, and $R^5$ is —OH or —OCH$_3$, then at least one of $R^6$, $R^7$ and $R^8$ are not —OCH$_3$, or at least one of $R^8$, $R^9$ and $R^{10}$ are not —OCH$_3$. In embodiments, when $R^1$ and $R^2$ together with atoms attached thereto are joined to form substituted or unsubstituted phenyl, $L^1$ is —NHC(O)—, and $R^5$ is —OH or —OCH$_3$, then at least one of $R^6$, $R^7$ and $R^8$ are not —OCH$_3$, or at least one of $R^8$, $R^9$ and $R^{10}$ are not —OCH$_3$. In embodiments, when $R^1$ and $R^2$ together with atoms attached thereto are joined to form unsubstituted phenyl, $L^1$ is —NHC(O)—, and $R^5$ is —OCH$_3$, then at least one of $R^6$, $R^7$ and $R^8$ are not —OCH$_3$. In embodiments, when $R^1$ and $R^2$ together with atoms attached thereto are joined to form unsubstituted phenyl, $L^1$ is —NHC(O)—, and $R^5$ is —OH, then at least one of $R^7$ and $R^8$ are not —OCH$_3$. In embodiments, when $R^1$ and $R^2$ together with atoms attached thereto are joined to form unsubstituted phenyl, $L^1$ is —NHC(O)—, and $R^5$ is —OH or —OCH$_3$, then at least one of $R^6$ and $R^8$ are not —OCH$_3$. In embodiments, when $R^1$ and $R^2$ together with atoms attached thereto are joined to form unsubstituted phenyl, $L^1$ is —NHC(O)—, and $R^5$ is —OH or —OCH$_3$, then at least one of $R^6$ and $R^7$ are not —OCH$_3$. In embodiments, when $R^1$ and $R^2$ together with atoms attached thereto are joined to form unsubstituted phenyl, $L^1$ is —NHC(O)—, and $R^5$ is —OH or —OCH$_3$, then at least one of $R^9$ and $R^{10}$ are not —OCH$_3$. In embodiments, when $R^1$ and $R^2$ together with atoms attached thereto are joined to form unsubstituted phenyl, $L^1$ is —NHC(O)—, and $R^5$ is —OH or —OCH$_3$, then at least one of $R^8$ and $R^{10}$ are not —OCH$_3$. In embodiments, when $R^1$ and $R^2$ together with atoms attached thereto are joined to form unsubstituted phenyl, $L^1$ is —NHC(O)—, and $R^5$ is —OH or —OCH$_3$, then at least one of $R^8$ and $R^9$ are not —OCH$_3$.

In embodiments, the compound is:

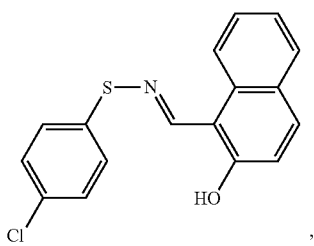

,

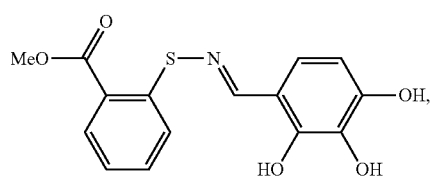

,

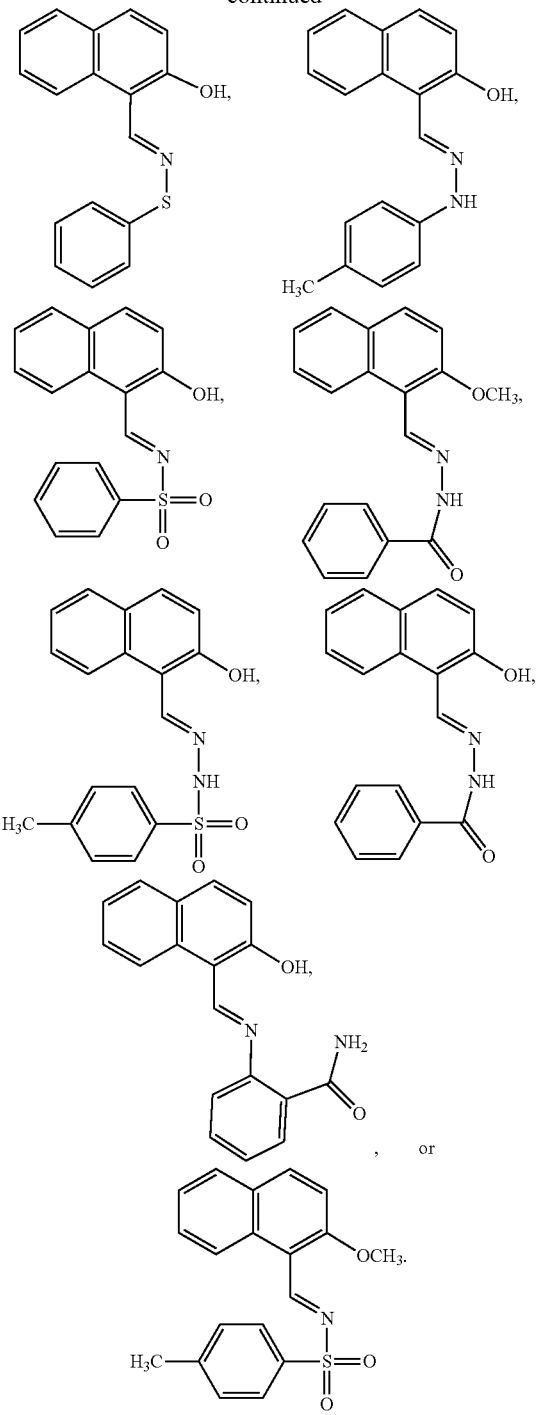

or

In embodiments, the compound is a compound described herein (e.g., in an aspect, embodiment, example, table, figure, scheme, appendix, or claim).

III. Pharmaceutical Compositions

Also provided herein are pharmaceutical formulations. In embodiments, the pharmaceutical formulation includes a compound (e.g. formula (I), (IIA), (IIB), (III), (IV), (V), (VI), (VII), or (VIII)) described above (including all embodiments thereof) and a pharmaceutically acceptable excipient.

In embodiments, the pharmaceutical composition includes a compound (e.g. formula (I), (IIA), (IIB), (III), (IV), (V), (VI), (VII), or (VIII)) described above that inhibits poly(ADP-ribose) Glycohydrolase (PARG) in a cancer cell. In embodiments, the compound has a half maximal inhibitory concentration (IC$_{50}$) against PARG less than about 100 μM. In embodiments, the compound has IC$_{50}$ against PARG less than about 10 μM. In embodiments, the compound has IC$_{50}$ against PARG less than about 1 μM. In embodiments, the compound has IC$_{50}$ against PARG less than about 500 nM. In embodiments, the compound has IC$_{50}$ against PARG less than about 400 nM. In embodiments, the compound has IC$_{50}$ against PARG less than about 300 nM. In embodiments, the compound has IC$_{50}$ against PARG less than about 200 nM. In embodiments, the compound has IC$_{50}$ against PARG less than about 100 nM. In embodiments, the compound has IC$_{50}$ against PARG less than about 90 nM. In embodiments, the compound has IC$_{50}$ against PARG less than about 80 nM. In embodiments, the compound has IC$_{50}$ against PARG less than about 70 nM. In embodiments, the compound has IC$_{50}$ against PARG less than about 60 nM. In embodiments, the compound has IC$_{50}$ against PARG less than about 50 nM. In embodiments, the compound has IC$_{50}$ against PARG less than about 40 nM. In embodiments, the compound has IC$_{50}$ against PARG less than about 30 nM. In embodiments, the compound has IC$_{50}$ against PARG less than about 20 nM. In embodiments, the compound has an inhibitory concentration against PARG less than about 10 nM.

In embodiments, the pharmaceutical composition includes a compound of:

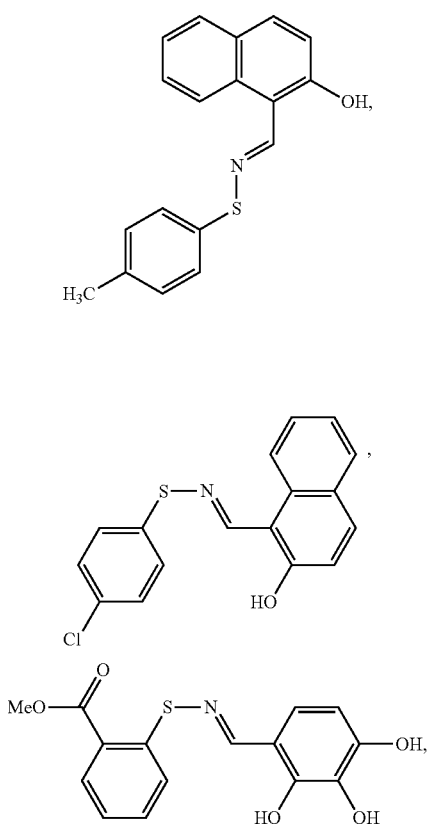

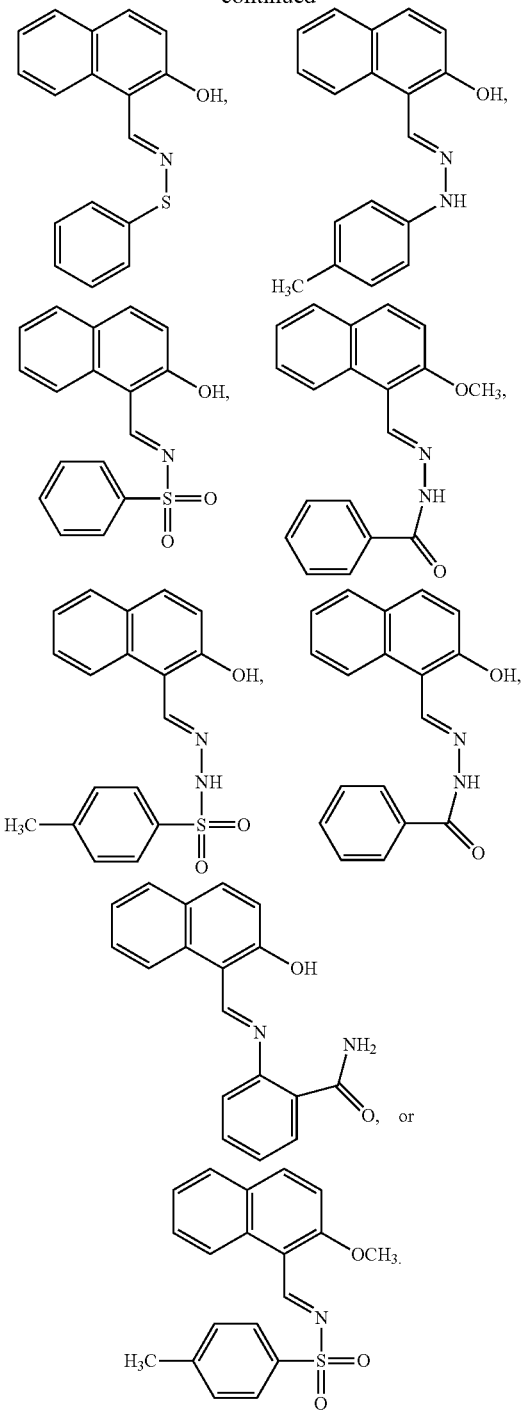

The pharmaceutical compositions described herein, including embodiments thereof may be used in the treatment of cancers. In embodiments, the pharmaceutical compositions described herein, including embodiments thereof may be used in the treatment of solid and blood tumors, including ovarian cancer, breast cancer (e.g. triple-negative breast cancer), lung cancer (e.g. small cell or non-small cell lung cancer), leukemia (e.g. AML or CML), lymphoma, pancreatic cancer, kidney cancer, uterine cancer, colon cancer (e.g. colon carcinoma), fallopian tube cancer, melanoma, liver cancer, sarcoma, multiple myeloma, brain cancer (e.g. glioblastoma), bladder cancer, esophagus cancer, gastric cancer, head and neck cancer, cholangiocarcinoma, mesothelioma and prostate cancer. In embodiments, the pharmaceutical compositions described herein, including embodiments thereof may be used in the treatment of breast cancer, e.g. triple-negative breast cancer. In embodiments, the pharmaceutical compositions described herein, including embodiments thereof may be used in the treatment of ovarian cancer. In embodiments, the pharmaceutical compositions described herein, including embodiments thereof may be used in the treatment of non-small cell lung cancer. In embodiments, the pharmaceutical compositions described herein, including embodiments thereof may be used in the treatment of pancreatic cancer. In embodiments, the pharmaceutical compositions described herein, including embodiments thereof may be used in the treatment of glioblastoma. In embodiments, the pharmaceutical compositions described herein, including embodiments thereof may be used in the treatment of uterine cancer. In embodiments, the pharmaceutical compositions described herein, including embodiments thereof may be used in the treatment of prostate cancer. In embodiments, the pharmaceutical compositions described herein, including embodiments thereof may be used in the treatment of colon carcinoma. In embodiments, the pharmaceutical compositions described herein, including embodiments thereof may be used in the treatment of fallopian tube cancer. In embodiments, the pharmaceutical compositions described herein, including embodiments thereof may be used in the treatment of acute leukemia.

In embodiments, the pharmaceutical composition includes a compound described herein (e.g., in an aspect, embodiment, example, table, figure, scheme, appendix, or claim) and a pharmaceutically acceptable excipient.

1. Formulations

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al. In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, PA) and WO 96/05309, the teachings of both of which are hereby incorporated by reference.

IV. Methods of Treatments

Provided herein are methods of treating a cancer in a subject in need thereof, the method comprising administering an effective amount a compound (e.g. formula (I), (IIA), (IIB), (III), (IV), (V), (VI), (VII), or (VIII)) described herein. In embodiments, the cancer is ovarian cancer, breast cancer (e.g. triple-negative breast cancer), lung cancer (e.g. small cell or non-small cell lung cancer), leukemia (e.g. AML or CML), lymphoma, pancreatic cancer, kidney cancer, uterine cancer, colon cancer (e.g. colon carcinoma), fallopian tube cancer, melanoma, liver cancer, sarcoma, multiple myeloma, brain cancer (e.g. glioblastoma), bladder cancer, esophagus cancer, gastric cancer, head and neck cancer, cholangiocarcinoma, mesothelioma or prostate cancer. In embodiments, the cancer is breast cancer, e.g. triple-negative breast cancer. In embodiments, the cancer is ovarian cancer. In embodiments, the cancer is non-small cell lung cancer. In embodiments, the cancer is pancreatic cancer. In embodiments, the cancer is glioblastoma. In embodiments, the cancer is uterine cancer. In embodiments, the cancer is prostate cancer. In embodiments, the cancer is colon carcinoma. In embodiments, the cancer is fallopian tube cancer. In embodiments, the cancer is acute leukemia. In embodiments, the cancer is bladder cancer. In embodiments, the cancer is esophagus cancer. In embodiments, the cancer is gastric cancer. In embodiments, the cancer is head and neck cancer. In embodiments, the cancer is cholangiocarcinoma. In embodiments, the cancer is mesothelioma. In embodiments, the cancer is prostate cancer. In embodiments, the cancer is BRCA1-mutant TNBC. In embodiments, the cancer is BRCA2-mutant TNBC. In embodiments, the cancer is BRCA1-deficient TNBC. In embodiments, the cancer is BRCA2-deficient TNBC. In embodiments, the cancer is PARPi-resistance ovarian cancer (e.g., UWB1.289). In embodiments, the cancer is osteosarcoma.

In embodiments, the method of treating cancer includes suppression or inhibition of PARylation and/or dePARylation in the tumor cells with defective DNA repair system. In embodiments, the method of treating cancer includes suppression or inhibition of dePARylation in the tumor cells by inhibiting dePARylation enzyme (PARG). In embodiments, the method of treating cancer includes inhibiting dePARylation enzyme (PARG) by using an effective amount of the PARG inhibitor (e.g., a compound described herein). In embodiments, the method of treating cancer includes suppression or reduction of dePARylation in the tumor cells by contacting the cancer or tumor cell with an effective amount of the PARG inhibitor. In embodiments, the method of treating cancer includes inhibiting dePARylation enzyme (PARG) by using effective amount of a compound (e.g. formula (I), (IIA), (IIB), (III), (IV), (V), (VI), (VII), or (VIII)) described herein (including all embodiments thereof). In embodiments, the method of treating cancer includes inhibiting dePARylation enzyme (PARG) in a cancer or tumor cell by contacting the cancer or tumor cell with the effective amount of a compound (e.g. formula (I), (IIA), (IIB), (III), (IV), (V), (VI), (VII), or (VIII)) described above (including all embodiments thereof). In embodiments, the tumor cell is a breast cancer cell, e.g., triple-negative breast cancer cell.

In embodiments, the compound is:

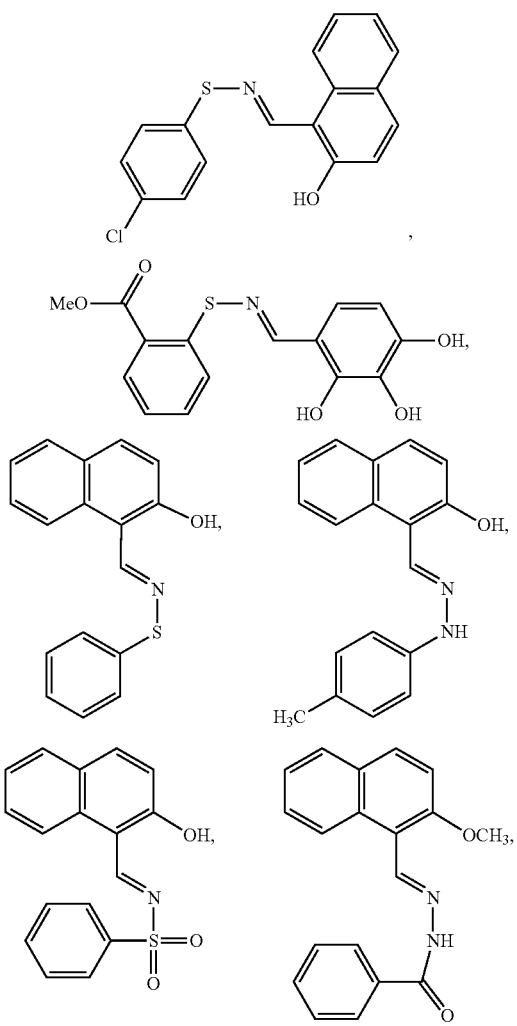

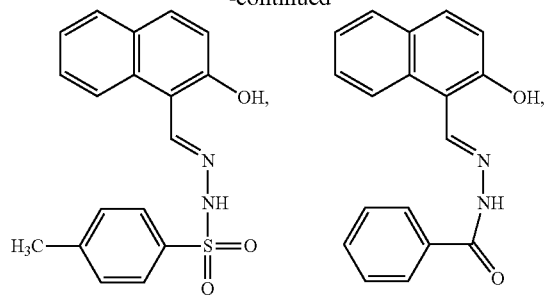

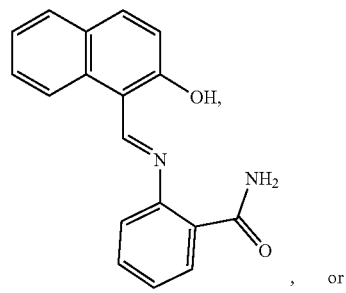

, or

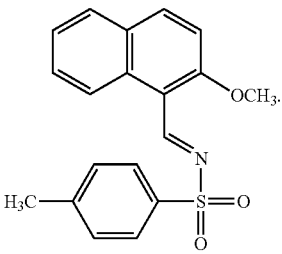 [SMILES: COc1ccc2ccccc2c1/C=N/S(=O)(=O)c1ccc(C)cc1]

In embodiments, the methods of treating cancer described herein yield a suppression of tumor growth. The suppressed tumor growth may indicate the absence of toxicity symptoms (e.g. body weight loss). Those skilled in the art understand that body weight loss observed during cancer treatments is a result of toxicity associated with the treatment (e.g. killing of healthy tissue). Accordingly, the compounds described herein may provide effective therapeutic value without toxicity issues normally associated with cancer treatments.

V. Other Aspects

Embodiments P

Embodiment P1. A method of treating cancer in a subject in need thereof, the method comprising administering to the subject an effective amount of a compound having a formula (I),

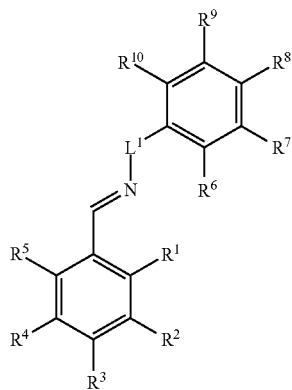

(I)

wherein:
L¹ is —CR¹¹R¹²—, —NR¹³—, —O—, or —S—;
R¹ is hydrogen, halogen, —CX¹₃, —CHX¹₂, —CH₂X¹, —OCX¹ᶜ, —OCH₂X¹, —OCHX¹₂, —N₃, —CN, —SO$_{n1}$R¹ᴰ, —SO$_{v1}$NR¹ᴬR¹ᴮ, —NHC(O)NR¹ᴬR¹ᴮ, —N(O)$_{m1}$, —NR¹ᴬR¹ᴮ, —C(O)R¹ᶜ, C(O)—OR¹ᶜ, —C(O)NR¹ᴬR¹ᴮ, —OR¹ᴰ, —NR¹ᴬSO₂R¹ᴰ, —NR¹ᴬC(O)R¹ᶜ, —NR¹ᴬC(O)OR¹ᶜ, —NR¹ᴬOR¹ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R² is hydrogen, halogen, —CX²₃, —CHX²₂, —CH₂X², —OCX²₃, —OCH₂X², —OCHX²₂, —N₃, —CN, —SO$_{n2}$R²ᴰ, —SO$_{v2}$NR²ᴬR²ᴮ, —NHC(O)NR²ᴬR²ᴮ, —N(O)$_{m2}$, —NR²ᴬR²ᴮ, —C(O)R²ᶜ, C(O)—OR²ᶜ, —C(O)NR²ᴬR²ᴮ, —OR²ᴰ, —NR²ᴬSO₂R²ᴰ, —NR²ᴬC(O)R²ᶜ, —NR²ᴬC(O)OR²ᶜ, —NR²ᴬOR²ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R³ is hydrogen, halogen, —CX³₃, —CHX³₂, —CH₂X³, —OCX³₃, —OCH₂X³, —OCHX³₂, —N₃, —CN, —SO$_{n3}$R³ᴰ, —SO$_{v3}$NR³ᴬR³ᴮ, —NHC(O)NR³ᴬR³ᴮ, —N(O)$_{m3}$, —NR³ᴬR³ᴮ, —C(O)R³ᶜ, C(O)—OR³ᶜ, —C(O)NR³ᴬR³ᴮ, —OR³ᴰ, —NR³ᴬSO₂R³ᴰ, —NR³ᴬC(O)R³ᶜ, —NR³ᴬC(O)OR³ᶜ, —NR³ᴬOR³ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R⁴ is hydrogen, halogen, —CX⁴₃, —CHX⁴₂, —CH₂X⁴, —OCX⁴₃, —OCH₂X⁴, —OCHX⁴₂, —N₃, —CN, —SO$_{n4}$R⁴ᴰ, —SO$_{v4}$NR⁴ᴬR⁴ᴮ, —NHC(O)NR⁴ᴬR⁴ᴮ, —N(O)$_{m4}$, —NR⁴ᴬR⁴ᴮ, —C(O)R⁴ᶜ, C(O)—OR⁴ᶜ, —C(O)NR⁴ᴬR⁴ᴮ, —OR⁴ᴰ, —NR⁴ᴬSO₂R⁴ᴰ, —NR⁴ᴬC(O)R⁴ᶜ, —NR⁴ᴬC(O)OR⁴ᶜ, —NR⁴ᴬOR⁴ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R⁵ is hydrogen, halogen, —CX⁵₃, —CHX⁵₂, —CH₂X⁵, —OCX⁵₃, —OCH₂X⁵, —OCHX⁵₂, —N₃, —CN, —SO$_{n5}$R⁵ᴰ, —SO$_{v5}$NR⁵ᴬR⁵ᴮ, —NHC(O)NR⁵ᴬR⁵ᴮ, —N(O)$_{m5}$, —NR⁵ᴬR⁵ᴮ, —C(O)R⁵ᶜ, C(O)—OR⁵ᶜ, —C(O)NR⁵ᴬR⁵ᴮ, —OR⁵ᴰ, —NR⁵ᴬSO₂R⁵ᴰ, —NR⁵ᴬC(O)R⁵ᶜ, —NR⁵ᴬC(O)OR⁵ᶜ, —NR⁵ᴬOR⁵ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R⁶ is hydrogen, halogen, —CX⁶₃, —CHX⁶₂, —CH₂X⁶, —OCX⁶₃, —OCH₂X⁶, —OCHX⁶₂, —N₃, —CN, —SO$_{n6}$R⁶ᴰ, —SO$_{v6}$NR⁶ᴬR⁶ᴮ, —NHC(O)NR⁶ᴬR⁶ᴮ, —N(O)$_{m6}$, —NR⁶ᴬR⁶ᴮ, —C(O)R⁶ᶜ, C(O)—OR⁶ᶜ, —C(O)NR⁶ᴬR⁶ᴮ, —OR⁶ᴰ, —NR⁶ᴬSO₂R⁶ᴰ, —NR⁶ᴬC(O)R⁶ᶜ, —NR⁶ᴬC(O)OR⁶ᶜ, —NR⁶ᴬOR⁶ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R⁷ is hydrogen, halogen, —CX⁷₃, —CHX⁷₂, —CH₂X⁷, —OCX⁷₃, —OCH₂X⁷, —OCHX⁷₂, —N₃, —CN, —SO$_{n7}$R⁷ᴰ, —SO$_{v7}$NR⁷ᴬR⁷ᴮ, —NHC(O)NR⁷ᴬR⁷ᴮ, —N(O)$_{m7}$, —NR⁷ᴬR⁷ᴮ, —C(O)R⁷ᶜ, C(O)—OR⁷ᶜ, —C(O)NR⁷ᴬR⁷ᴮ, —OR⁷ᴰ, —NR⁷ᴬSO₂R⁷ᴰ, —NR⁷ᴬC(O)R⁷ᶜ, —NR⁷ᴬC(O)OR⁷ᶜ, —NR⁷ᴬOR⁷ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R⁸ is hydrogen, halogen, —CX⁸₃, —CHX⁸₂, —CH₂X⁸, —OCX⁸₃, —OCH₂X⁸, —OCHX⁸₂, —N₃, —CN, —SO$_{n8}$R⁸ᴰ, —SO$_{v8}$NR⁸ᴬR⁸ᴮ, —NHC(O)NR⁸ᴬR⁸ᴮ, —N(O)$_{m8}$, —NR⁸ᴬR⁸ᴮ, —C(O)R⁸ᶜ, C(O)—OR⁸ᶜ, —C(O)NR⁸ᴬR⁸ᴮ, —OR⁸ᴰ, —NR⁸ᴬSO₂R⁸ᴰ, —NR⁸ᴬC(O)R⁸ᶜ, —NR⁸ᴬC(O)OR⁸ᶜ, —NR⁸ᴬOR⁸ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R⁹ is hydrogen, halogen, —CX⁹₃, —CHX⁹₂, —CH₂X⁹, —OCX⁹₃, —OCH₂X⁹, —OCHX⁹₂, —N₃, —CN, —SO$_{n9}$R⁹ᴰ, —SO$_{v9}$NR⁹ᴬR⁹ᴮ, —NHC(O)NR⁹ᴬR⁹ᴮ, —N(O)$_{m9}$, —NR⁹ᴬR⁹ᴮ, —C(O)R⁹ᶜ, C(O)—OR⁹ᶜ, —C(O)NR⁹ᴬR⁹ᴮ, —OR⁹ᴰ, —NR⁹ᴬSO₂R⁹ᴰ, —NR⁹ᴬC(O)R⁹ᶜ, —NR⁹ᴬC(O)OR⁹ᶜ, —NR⁹ᴬOR⁹ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R¹⁰ is hydrogen, halogen, —CX¹⁰₃, —CHX¹⁰₂, —CH₂X¹⁰, —OCX¹⁰₃, —OCH₂X¹⁰, —OCHX¹⁰₂, —N₃, —CN, —SO$_{n10}$R¹⁰ᴰ, —SO$_{v10}$NR¹⁰ᴬR¹⁰ᴮ, —NHC(O)NR¹⁰ᴬR¹⁰ᴮ, —N(O)$_{m10}$, —NR¹⁰ᴬR¹⁰ᴮ, —C(O)R¹⁰ᶜ, —C(O)—OR¹⁰ᶜ, —C(O)NR¹⁰ᴬR¹⁰ᴮ, —OR¹⁰ᴰ, —NR¹⁰ᴬSO₂R¹⁰ᴰ, —NR¹⁰ᴬC(O)R¹⁰ᶜ, —NR¹⁰ᴬC(O)OR¹⁰ᶜ, —NR¹⁰ᴬOR¹⁰ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
R¹¹ is hydrogen, halogen, —CX¹¹₃, —CHX¹¹₂, —CH₂X¹¹, —OCX¹¹₃, —OCH₂X¹¹, —OCHX¹¹₂, —N₃, —CN, —SO$_{n11}$R¹¹ᴰ, —SO$_{v11}$NR¹¹ᴬR¹¹ᴮ,

151

—NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O) R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, X$^1$, X$^2$, X$^3$, X$^4$, X$^5$, X$^6$, X$^7$, X$^8$, X$^9$, X$^{10}$, X$^{11}$, X$^{12}$, and X$^{13}$ are independently —F, —Cl, —Br, or —I, or a salt thereof.

152

Embodiment P2. The method of Embodiment P1, wherein the compound has a formula (II):

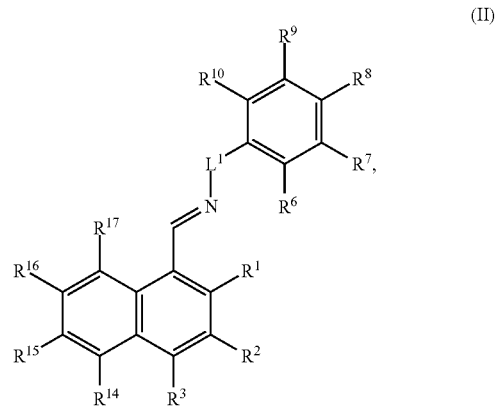

(II)

wherein:

R$^{14}$ is hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —N$_3$, —CN, —SO$_{n14}$R$^{14D}$, —SO$_{v14}$NR$^{14A}$R$^{14B}$, —NHC(O)NR$^{14A}$R$^{14B}$, —N(O)$_{m14}$, —NR$^{14A}$R$^{14B}$, —C(O)R$^{14C}$, —C(O)—OR$^{14C}$, —C(O)NR$^{14A}$R$^{14B}$, —OR$^{14D}$, —NR$^{14A}$SO$_2$R$^{14D}$, —NR$^{14A}$C(O) R$^{14C}$, —NR$^{14A}$C(O)OR$^{14C}$, —NR$^{14A}$OR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —N$_3$, —CN, —SO$_{n15}$R$^{15D}$, —SO$_{v15}$NR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O) R$^{15C}$, —NR$^{15A}$C(O)OR$^{15C}$, —NR$^{15A}$OR$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —N$_3$, —CN, —SO$_{n16}$R$^{16D}$, —SO$_{v16}$NR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O) R$^{16C}$, —NR$^{16A}$C(O)OR$^{16C}$, —NR$^{16A}$OR$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ is hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —N$_3$, —CN, —SO$_{n17}$R$^{17D}$, —SO$_{v17}$NR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O) R$^{17C}$, —NR$^{17A}$C(O)OR$^{17C}$, —NR$^{17A}$OR$^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{14A}$, $R^{14B}$, $R^{14C}$, $R^{14D}$, $R^{15A}$, $R^{15B}$ $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}$, $X^{15}$, $X^{16}$, and $X^{17}$ are independently —F, —Cl, —Br, or —I.

Embodiment P3. The method of any one of Embodiments P1-P2, wherein $L^1$ is —O— or —S—.

Embodiment P4. The method of any one of Embodiments P1-P3, wherein at least one of $R^1$, $R^2$ and $R^3$ are —OH.

Embodiment P5. The method of any one of Embodiments P1-P4, wherein $R^7$ and $R^9$ are hydrogen.

Embodiment P6. The method of any one of Embodiments P1-P5, wherein each $R^6$, $R^8$, and $R^{10}$ is independently hydrogen, halogen, —$N_3$, —CN, —$NO_2$, —$NH_2$, —C(O)H, —C(O)CH$_3$, —C(O)OH, —C(O)OCH$_3$, —C(O)NH$_2$, —OH, —OCH$_3$, or substituted or unsubstituted $C_1$-$C_3$ alkyl.

Embodiment P7. The method of any one of Embodiments P1-P6, wherein the compound has a formula (III),

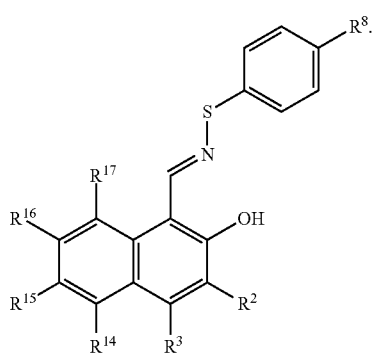

(III)

Embodiment P8. The method of any one of Embodiments P1-P6, wherein the compound has a formula (III),

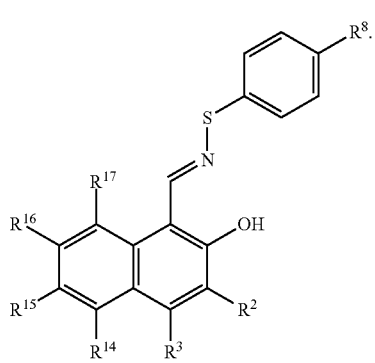

(III)

Embodiment P9. The method of any one of Embodiments P1-P8, wherein the compound is

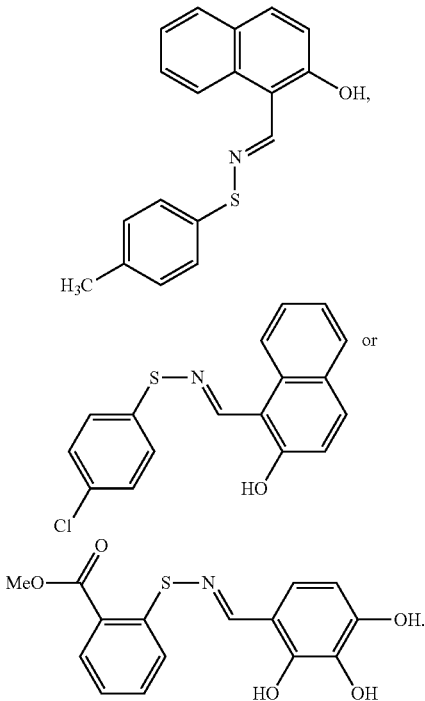

Embodiment P10. The method of any one of Embodiments P1-P9, wherein the compound inhibits poly(ADP-ribose) glycohydrolase (PARG) in a cancer cell.

Embodiment P11. The method of any one of Embodiments P1-P10, wherein the cancer is selected from: breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

Embodiment P12. The method of Embodiment P11, wherein the cancer is lymphoma.

Embodiment P13. A method of inhibiting a poly(ADP-ribose) glycohydrolase (PARG), the method comprising contacting the PARG with a compound having a formula (I),

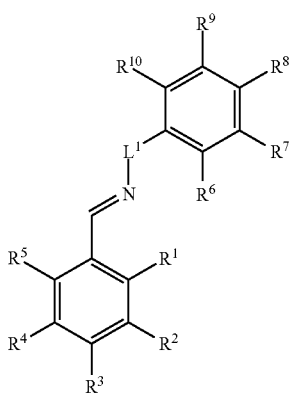

(I)

wherein:

$L^1$ is $-CR^{11}R^{12}-$, $-NR^{13}-$, $-O-$, or $-S-$;

$R^1$ is hydrogen, halogen, $-CX^1_3$, $-CHX^1_2$, $-CH_2X^1$, $-OCX^1_3$, $-OCH_2X^1$, $-OCHX^1_2$, $-N_3$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-CX^2_3$, $-CHX^2_2$, $-CH_2X^2$, $-OCX^2_3$, $-OCH_2X^2$, $-OCHX^2_2$, $-N_3$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CX^3_3$, $-CHX^3_2$, $-CH_2X^3$, $-OCX^3_3$, $-OCH_2X^3$, $-OCHX^3_2$, $-N_3$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-CX^4_3$, $-CHX^4_2$, $-CH_2X^4$, $-OCX^4_3$, $-OCH_2X^4$, $-OCHX^4_2$, $-N_3$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-CX^5_3$, $-CHX^5_2$, $-CH_2X^5$, $-OCX^5_3$, $-OCH_2X^5$, $-OCHX^5_2$, $-N_3$, $-CN$, $-SO_{n5}R^{5D}$, $-SO_{v5}NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl, substituted or unsubstituted heteroalkyl, substituted or unsubstituted heterocycloalkyl, substituted or unsubstituted aryl, or substituted or unsubstituted heteroaryl;

$R^6$ is hydrogen, halogen, $-CX^6_3$, $-CHX^6_2$, $-CH_2X^6$, $-OCX^6_3$, $-OCH_2X^6$, $-OCHX^6_2$, $-N_3$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-CX^7_3$, $-CHX^7_2$, $-CH_2X^7$, $-OCX^7_3$, $-OCH_2X^7$, $-OCHX^7_2$, $-N_3$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $-CX^8_3$, $-CHX^8_2$, $-CH_2X^8$, $-OCX^8_3$, $-OCH_2X^8$, $-OCHX^8_2$, $-N_3$, $-CN$, $-SO_{n8}R^{8D}$, $-SO_{v8}NR^{8A}R^{8B}$, $-NHC(O)NR^{8A}R^{8B}$, $-N(O)_{m8}$, $-NR^{8A}R^{8B}$, $-C(O)R^{8C}$, $-C(O)-OR^{8C}$, $-C(O)NR^{8A}R^{8B}$, $-OR^{8D}$, $-NR^{8A}SO_2R^{8D}$, $-NR^{8A}C(O)R^{8C}$, $-NR^{8A}C(O)OR^{8C}$, $-NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^9_3$, $-CHX^9_2$, $-CH_2X^9$, $-OCX^9_3$, $-OCH_2X^9$, $-OCHX^9_2$, $-N_3$, $-CN$, $-SO_{n9}R^{9D}$, $-SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-N_3$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-N_3$, $-CN$, $-SO_{n11}R^{11D}$, $-SO_{v11}NR^{11A}R^{11B}$, $-NHC(O)NR^{11A}R^{11B}$, $-N(O)_{m11}$, $-NR^{11A}R^{11B}$, $-C(O)R^{11C}$, $-C(O)-OR^{11C}$, $-C(O)NR^{11A}R^{11B}$, $-OR^{11D}$, $-NR^{11A}SO_2R^{11D}$, $-NR^{11A}C(O)R^{11C}$, $-NR^{11A}C(O)OR^{11C}$, $-NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)O R^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, $-CX^{13}{}_3$, $-CHX^{13}{}_2$, $-CH_2X^{13}$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently $-F$, $-Cl$, $-Br$, or $-I$, or a salt thereof.

Embodiment P14. The method of Embodiment P13, wherein the compound has a formula (II):

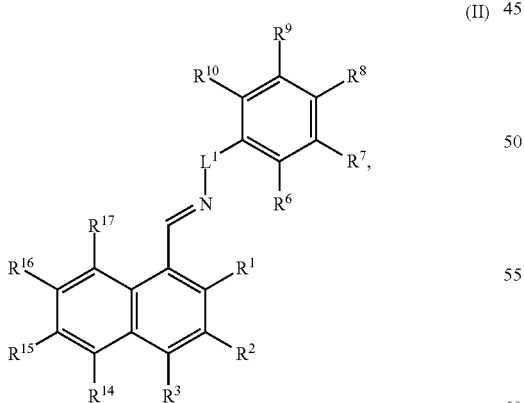

(II)

wherein:

$R^{14}$ is hydrogen, halogen, $-CX^{14}{}_3$, $-CHX^{14}{}_2$, $-CH_2X^{14}$, $-OCX^{14}{}_3$, $-OCH_2X^{14}$, $-OCHX^{14}{}_2$, $-N_3$, $-CN$, $-SO_{n14}R^{14D}$, $-SO_{v14}NR^{14A}R^{14B}$, $-NHC(O)NR^{14A}R^{14B}$, $-N(O)_{m14}$, $-NR^{14A}R^{14B}$, $-C(O)R^{14C}$, $-C(O)-OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)O\ R^{14C}$, $-NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $-CX^{15}{}_3$, $-CHX^{15}{}_2$, $-CH_2X^{15}$, $-OCX^{15}{}_3$, $-OCH_2X^{15}$, $-OCHX^{15}{}_2$, $-N_3$, $-CN$, $-SO_{n15}R^{15D}$, $-SO_{v15}NR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)O\ R^{15C}$, $-NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, $-CX^{16}{}_3$, $-CHX^{16}{}_2$, $-CH_2X^{16}$, $-OCX^{16}{}_3$, $-OCH_2X^{16}$, $-OCHX^{16}{}_2$, $-N_3$, $-CN$, $-SO_{n16}R^{16D}$, $-SO_{v16}NR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)O\ R^{16C}$, $-NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, $-CX^{17}{}_3$, $-CHX^{17}{}_2$, $-CH_2X^{17}$, $-OCX^{17}{}_3$, $-OCH_2X^{17}$, $-OCHX^{17}{}_2$, $-N_3$, $-CN$, $-SO_{n17}R^{17D}$, $-SO_{v17}NR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}$, $X^{15}$, $X^{16}$, and $X^{17}$ are independently $-F$, $-Cl$, $-Br$, or $-I$.

Embodiment P15. The method of any one of Embodiments P13-P14, wherein $L^1$ is $-O-$ or $-S-$.

Embodiment P16. The method of any one of Embodiments P13-P15, wherein at least one of $R^1$, $R^2$ and $R^3$ are $-OH$.

Embodiment P17. The method of any one of Embodiments P13-P16, wherein $R^7$ and $R^9$ are hydrogen.

Embodiment P18. The method of any one of Embodiments P13-P17, wherein each $R^6$, $R^8$, and $R^{10}$ is independently hydrogen, halogen, $-N_3$, $-CN$, $-NO_2$, $-NH_2$, —C(O)H, —C(O)CH₃, —C(O)OH, —C(O)OCH₃, —C(O)NH₂, —OH, —OCH₃, or substituted or unsubstituted $C_1$-$C_3$ alkyl.

Embodiment P19. The method of any one of Embodiments P13-P18, wherein the compound has a formula (III),

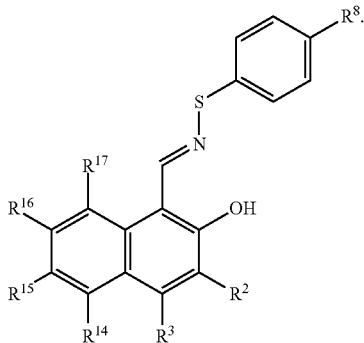

(III)

Embodiment P20. The method of any one of Embodiments P13-P18, wherein the compound has a formula (IV).

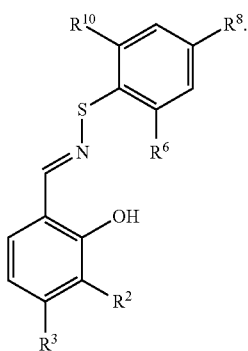

(IV)

Embodiment P21. The method of any one of Embodiments P13-P20, wherein the compound is

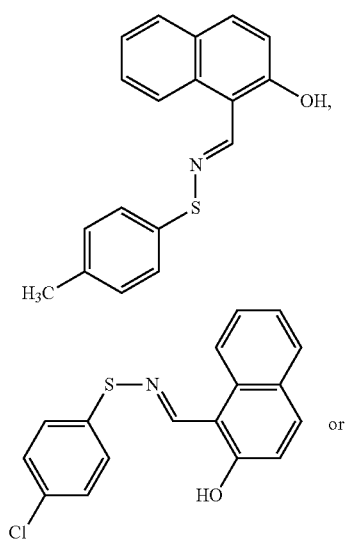

or

-continued

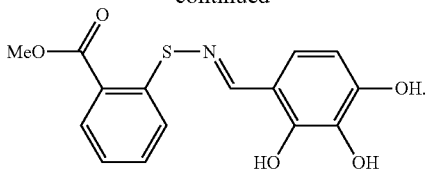

Embodiment P22. The method of any one of Embodiments P13-P21, wherein the compound inhibits the poly (ADP-ribose) glycohydrolase (PARG) in a cancer cell.

Embodiment P23. The method of Embodiment P22, wherein the cancer cell is from breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

Embodiment P24. A compound having a formula (I),

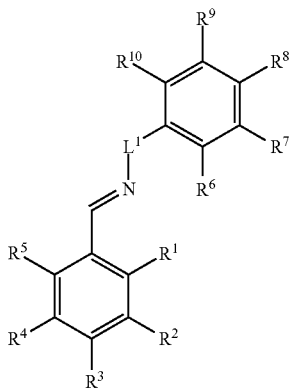

(I)

wherein, $L^1$ is —$CR^{11}R^{12}$—, —$NR^{13}$—, —O—, or —S—;

$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}$ $OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}$ $OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —CX$^4_3$, —CHX$^4_2$, —CH$_2$X$^4$, —OCX$^4_3$, —OCH$_2$X$^4$, —OCHX$^4_2$, —N$_3$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —CX$^5_3$, —CHX$^5_2$, —CH$_2$X$^5$, —OCX$^5_3$, —OCH$_2$X$^5$, —OCHX$^5_2$, —N$_3$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —CX$^6_3$, —CHX$^6_2$, —CH$_2$X$^6$, —OCX$^6_3$, —OCH$_2$X$^6$, —OCHX$^6_2$, —N$_3$, —CN, —SO$_{n6}$R$^{6D}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O) R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O) R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently —F, —Cl, —Br, or —I, or a salt thereof, provided that when $L^1$ is —S—, $R^1$ is —OH, and $R^4$ and $R^5$ together with atoms attached thereto are joined to form unsubstituted phenyl, then $R^6$ is not —$CH_3$; and when $L^1$ is —S—, $R^1$ is —OH, and $R^4$ and $R^5$ together with atoms attached thereto are joined to form unsubstituted phenyl, then $R^{10}$ is not —$CH_3$.

Embodiment P25. A compound having a formula (I),

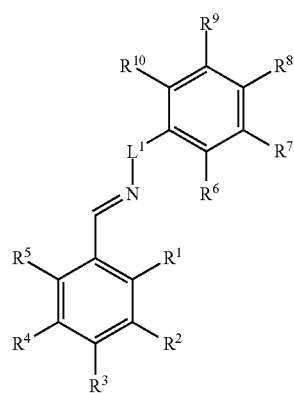

(I)

wherein, $L^1$ is —$CR^{11}R^{12}$—, —$NR^{13}$—, —O—, or —S—;

$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —$N_3$, —CN, —$SO_{n5}R^{5D}$, —$SO_{v5}NR^{5A}R^{5B}$, —$NHC(O)NR^{5A}R^{5B}$, —$N(O)_{m5}$, —$NR^{5A}R^{5B}$, —$C(O)R^{5C}$, —$C(O)$—$OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^6_3$, —$CHX^6_2$, —$CH_2X^6$, —$OCX^6_3$, —$OCH_2X^6$, —$OCHX^6_2$, —$N_3$, —CN, —$SO_{n6}R^{6D}$, —$SO_{v6}NR^{6A}R^{6B}$, —$NHC(O)NR^{6A}R^{6B}$, —$N(O)_{m6}$, —$NR^{6A}R^{6B}$, —$C(O)R^{6C}$, —$C(O)$—$OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^7_3$, —$CHX^7_2$, —$CH_2X^7$, —$OCX^7_3$, —$OCH_2X^7$, —$OCHX^7_2$, —$N_3$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^8_3$, —$CHX^8_2$, —$CH_2X^8$, —$OCX^8_3$, —$OCH_2X^8$, —$OCHX^8_2$, —$N_3$, —CN, —$SO_{n8}R^{8D}$, —$SO_{v8}NR^{8A}R^{8B}$, —$NHC(O)NR^{8A}R^{8B}$, —$N(O)_{m8}$, —$NR^{8A}R^{8B}$, —$C(O)R^{8C}$, —$C(O)$—$OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^9_3$, —$CHX^9_2$, —$CH_2X^9$, —$OCX^9_3$, —$OCH_2X^9$, —$OCHX^9_2$, —$N_3$, —CN, —$SO_{n9}R^{9D}$, —$SO_{v9}NR^{9A}R^{9B}$, —$NHC(O)NR^{9A}R^{9B}$, —$N(O)_{m9}$, —$NR^{9A}R^{9B}$, —$C(O)R^{9C}$, —$C(O)$—$OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-N_3$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)$ $R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-N_3$, $-CN$, $-SO_{n11}R^{11D}$, $-SO_{v11}NR^{11A}R^{11B}$, $-NHC(O)NR^{11A}R^{11B}$, $-N(O)_{m11}$, $-NR^{11A}R^{11B}$, $-C(O)R^{11C}$, $-C(O)-OR^{11C}$, $-C(O)NR^{11A}R^{11B}$, $-OR^{11D}$, $-NR^{11A}SO_2R^{11D}$, $-NR^{11A}C(O)$ $R^{11C}$, $-NR^{11A}C(O)OR^{11C}$, $-NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)$ $R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, $-CX^{13}_3$, $-CHX^{13}_2$, $-CH_2X^{13}$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently $-F$, $-Cl$, $-Br$, or $-I$, or a salt thereof, provided that when $L^1$ is $-S-$, $R^1$ is $-OH$, and $R^4$ and $R^5$ together with atoms attached thereto are joined to form unsubstituted phenyl, then $R^6$ is not $-CH_3$; and when $L^1$ is $-S-$, $R^1$ is $-OH$, and $R^4$ and $R^5$ together with atoms attached thereto are joined to form unsubstituted phenyl, then $R^{10}$ is not $-CH_3$.

Embodiment P26. The compound of any one of Embodiments P24-P25, wherein $L^1$ is $-O-$ or $-S-$.

Embodiment P27. The compound of any one of Embodiments P24-P26, wherein at least one of $R^1$, $R^2$ and $R^3$ are $-OH$.

Embodiment P28. The compound of any one of Embodiments P24-P27, wherein $R^7$ and $R^9$ are hydrogen.

Embodiment P29. The compound of any one of Embodiments P24-P28, wherein each $R^6$, $R^8$, and $R^{10}$ is independently hydrogen, halogen, $-N_3$, $-CN$, $-NO_2$, $-NH_2$, $-C(O)H$, $-C(O)CH_3$, $-C(O)OH$, $-C(O)OCH_3$, $-C(O)NH_2$, $-OH$, $-OCH_3$, or substituted or unsubstituted $C_1$-$C_3$ alkyl.

Embodiment P30. The compound of any one of Embodiments P24-P29, wherein the compound has a formula (III),

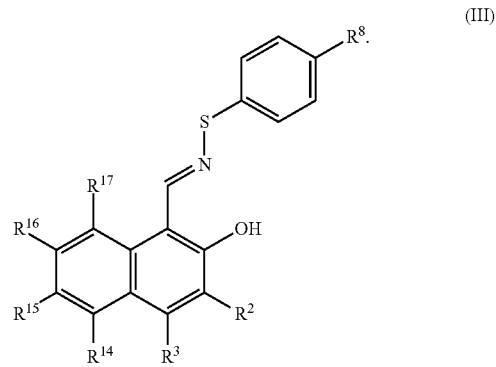

(III)

Embodiment P31. The compound of any one of Embodiments P24-P29, wherein the compound has a formula (IV),

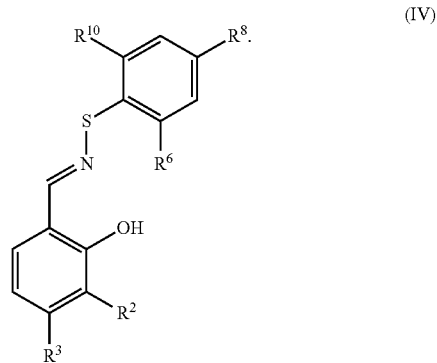

(IV)

Embodiment P32. The compound of any one of Embodiments P24-P31, wherein the compound is

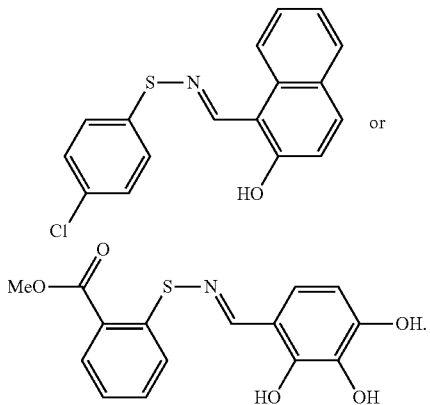

or

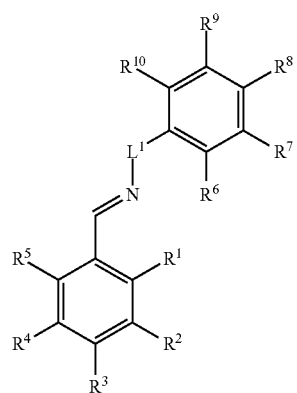

Embodiment P33. A pharmaceutical composition comprising a compound having a formula (I), $$\text{(I)}$$

wherein,
$L^1$ is $-CR^{11}R^{12}-$, $-NR^{13}-$, $-O-$, or $-S-$;
$R^1$ is hydrogen, halogen, $-CX^1_3$, $-CHX^1_2$, $-CH_2X^1$, $-OCX^1_3$, $-OCH_2X^1$, $-OCHX^1_2$, $-N_3$, $-CN$, $-SO_{n1}R^{1D}$, $-SO_{v1}NR^{1A}R^{1B}$, $-NHC(O)NR^{1A}R^{1B}$, $-N(O)_{m1}$, $-NR^{1A}R^{1B}$, $-C(O)R^{1C}$, $C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is hydrogen, halogen, $-CX^2_3$, $-CHX^2_2$, $-CH_2X^2$, $-OCX^2_3$, $-OCH_2X^2$, $-OCHX^2_2$, $-N_3$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, halogen, $-CX^3_3$, $-CHX^3_2$, $-CH_2X^3$, $-OCX^3_3$, $-OCH_2X^3$, $-OCHX^3_2$, $-N_3$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^4$ is hydrogen, halogen, $-CX^4_3$, $-CHX^4_2$, $-CH_2X^4$, $-OCX^4_3$, $-OCH_2X^4$, $-OCHX^4_2$, $-N_3$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^5$ is hydrogen, halogen, $-CX^5_3$, $-CHX^5_2$, $-CH_2X^5$, $-OCX^5_3$, $-OCH_2X^5$, $-OCHX^5_2$, $-N_3$, $-CN$, $-SO_{n5}R^{5D}$, $-SO_{v5}NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^6$ is hydrogen, halogen, $-CX^6_3$, $-CHX^6_2$, $-CH_2X^6$, $-OCX^6_3$, $-OCH_2X^6$, $-OCHX^6_2$, $-N_3$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$ is hydrogen, halogen, $-CX^7_3$, $-CHX^7_2$, $-CH_2X^7$, $-OCX^7_3$, $-OCH_2X^7$, $-OCHX^7_2$, $-N_3$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^8$ is hydrogen, halogen, $-CX^8_3$, $-CHX^8_2$, $-CH_2X^8$, $-OCX^8_3$, $-OCH_2X^8$, $-OCHX^8_2$, $-N_3$, $-CN$, $-SO_{n8}R^{8D}$, $-SO_{v8}NR^{8A}R^{8B}$, $-NHC(O)NR^{8A}R^{8B}$, $-N(O)_{m8}$, $-NR^{8A}R^{8B}$, $-C(O)R^{8C}$, $-C(O)-OR^{8C}$, $-C(O)NR^{8A}R^{8B}$, $-OR^{8D}$, $-NR^{8A}SO_2R^{8D}$, $-NR^{8A}C(O)R^{8C}$, $-NR^{8A}C(O)OR^{8C}$, $-NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^9$ is hydrogen, halogen, $-CX^9_3$, $-CHX^9_2$, $-CH_2X^9$, $-OCX^9_3$, $-OCH_2X^9$, $-OCHX^9_2$, $-N_3$, $-CN$, $-SO_{n9}R^{9D}$, $-SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, X$^1$, X$^2$, X$^3$, X$^4$, X$^5$, X$^6$, X$^7$, X$^8$, X$^9$, X$^{10}$, X$^{11}$, X$^{12}$, and X$^{13}$ are independently —F, —Cl, —Br, or —I, or a salt thereof, and a pharmaceutically acceptable carrier.

Embodiment P34. The pharmaceutical composition of Embodiment P33, wherein the compound has a formula (II):

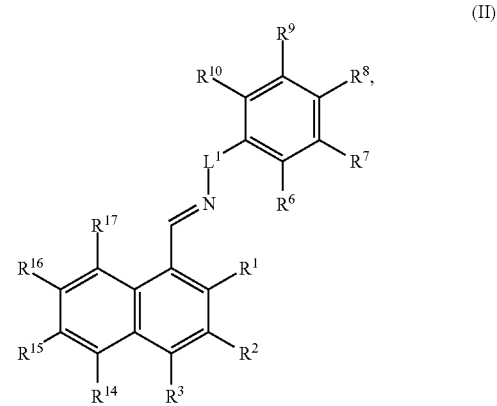

(II)

wherein:

R$^{14}$ is hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —N$_3$, —CN, —SO$_{n14}$R$^{14D}$, —SO$_{v14}$NR$^{14A}$R$^{14B}$, —NHC(O)NR$^{14A}$R$^{14B}$, —N(O)$_{m14}$, —NR$^{14A}$R$^{14B}$, C(O)R$^{14C}$, —C(O)—OR$^{14C}$, —C(O)NR$^{14A}$R$^{14B}$, —OR$^{14D}$, —NR$^{14A}$SO$_2$R$^{14D}$, —NR$^{14A}$C(O)R$^{14C}$, —NR$^{14A}$C(O)OR$^{14C}$, —NR$^{14A}$OR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —N$_3$, —CN, —SO$_{n15}$R$^{15D}$, —SO$_{v15}$NR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)O R$^{15C}$, —NR$^{15A}$OR$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —N$_3$, —CN, —SO$_{n16}$R$^{16D}$, —SO$_{v16}$NR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-N_3$, $-CN$, $-N_3$, $-SO_{n17}R^{17B}$, $-SO_{v17}NR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}, X^{15}, X^{16}$, and $X^{17}$ are independently —F, —Cl, —Br, or —I.

Embodiment P35. The pharmaceutical composition of any one of Embodiments P33-P34, wherein $L^1$ is —O— or —S—.

Embodiment P36. The pharmaceutical composition pound of any one of Embodiments P33-P35, wherein at least one of $R^1$, $R^2$ and $R^3$ are —OH.

Embodiment P37. The pharmaceutical composition of any one of Embodiments P33-P36, wherein $R^7$ and $R^9$ are hydrogen.

Embodiment P38. The pharmaceutical composition of any one of Embodiments P33-P37, wherein each $R^6$, $R^8$, and $R^{10}$ is independently hydrogen, halogen, $-N_3$, $-CN$, $-NO_2$, $-NH_2$, $-C(O)H$, $-C(O)CH_3$, $-C(O)OH$, $-C(O)OCH_3$, $-C(O)NH_2$, $-OH$, $-OCH_3$, or substituted or unsubstituted $C_1$-$C_3$ alkyl.

Embodiment P39. The pharmaceutical composition of any one of Embodiments P33-P38, wherein the compound has a formula (III),

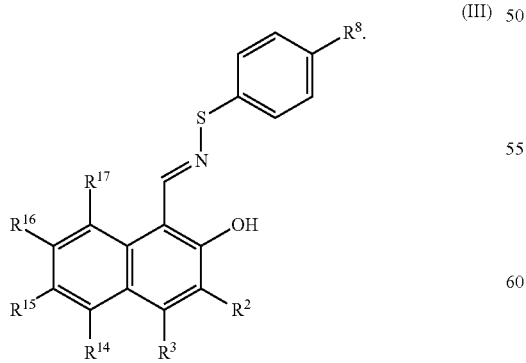

(III)

Embodiment P40. The pharmaceutical composition of any one of Embodiments P33-P38, wherein the compound has a formula (IV).

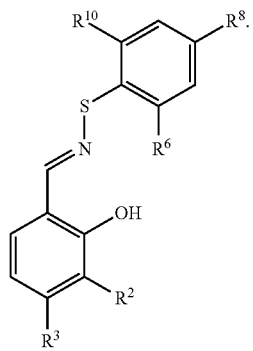

(IV)

Embodiment P41. The pharmaceutical composition of any one of Embodiments P33-P40, wherein the compound is

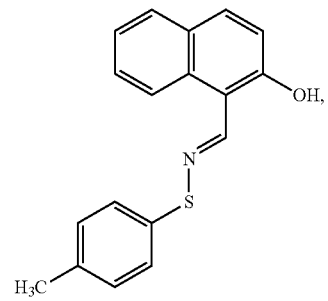

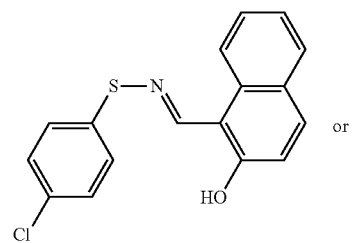 or

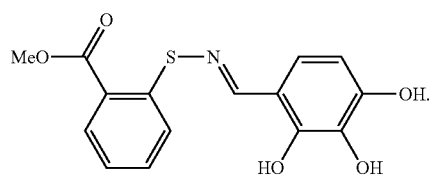

Embodiments Q

Embodiment Q1. A method of treating cancer in a subject in need thereof, the method comprising administering to the subject an effective amount of a compound having a formula (I),

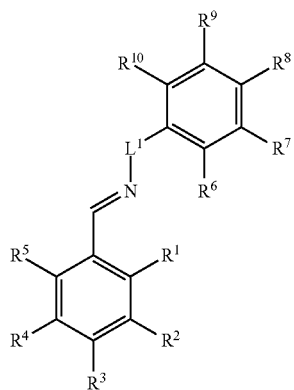

(I)

wherein:
L¹ is a bond, —CR¹¹R¹²—, —NR¹³—, —O—, —S—, —S(O)₂—, —NR¹³S(O)₂—, or —NR¹³C(O)—;

R¹ is hydrogen, halogen, —CX¹₃, —CHX¹₂, —CH₂X¹, —OCX¹₃, —OCH₂X¹, —OCHX¹₂, —N₃, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is hydrogen, halogen, —CX²₃, —CHX²₂, —CH₂X², —OCX²₃, —OCH₂X², —OCHX²₂, —N₃, —CN, —SO$_{n2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is hydrogen, halogen, —CX³₃, —CHX³₂, —CH₂X³, —OCX³₃, —OCH₂X³, —OCHX³₂, —N₃, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, C(O)—OR$^{3C}$, —C(O)NR$^{3A}$R$^{3B}$, —OR$^{3D}$, —NR$^{3A}$SO₂R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁴ is hydrogen, halogen, —CX⁴₃, —CHX⁴₂, —CH₂X⁴, —OCX⁴₃, —OCH₂X⁴, —OCHX⁴₂, —N₃, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, C(O)—OR$^{4C}$, —C(O)NR$^{4A}$R$^{4B}$, —OR$^{4D}$, —NR$^{4A}$SO₂R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is hydrogen, halogen, —CX⁵₃, —CHX⁵₂, —CH₂X⁵, —OCX⁵₃, —OCH₂X⁵, —OCHX⁵₂, —N₃, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, C(O)—OR$^{5C}$, —C(O)NR$^{5A}$R$^{5B}$, —OR$^{5D}$, —NR$^{5A}$SO₂R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁶ is hydrogen, halogen, —CX⁶₃, —CHX⁶₂, —CH₂X⁶, —OCX⁶₃, —OCH₂X⁶, —OCHX⁶₂, —N₃, —CN, —SO$_{n6}$R$^{6D}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, C(O)—OR$^{6C}$, —C(O)NR$^{6A}$R$^{6B}$, —OR$^{6D}$, —NR$^{6A}$SO₂R$^{6D}$, —NR$^{6A}$C(O)R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁷ is hydrogen, halogen, —CX⁷₃, —CHX⁷₂, —CH₂X⁷, —OCX⁷₃, —OCH₂X⁷, —OCHX⁷₂, —N₃, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, C(O)—OR$^{7C}$, —C(O)NR$^{7A}$R$^{7B}$, —OR$^{7D}$, —NR$^{7A}$SO₂R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁸ is hydrogen, halogen, —CX⁸₃, —CHX⁸₂, —CH₂X⁸, —OCX⁸₃, —OCH₂X⁸, —OCHX⁸₂, —N₃, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, C(O)—OR$^{8C}$, —C(O)NR$^{8A}$R$^{8B}$, —OR$^{8D}$, —NR$^{8A}$SO₂R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ is hydrogen, halogen, —CX⁹₃, —CHX⁹₂, —CH₂X⁹, —OCX⁹₃, —OCH₂X⁹, —OCHX⁹₂, —N₃, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, C(O)—OR$^{9C}$, —C(O)NR$^{9A}$R$^{9B}$, —OR$^{9D}$, —NR$^{9A}$SO₂R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹⁰ is hydrogen, halogen, —CX¹⁰₃, —CHX¹⁰₂, —CH₂X¹⁰, —OCX¹⁰₃, —OCH₂X¹⁰, —OCHX¹⁰₂, —N₃, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO₂R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹¹ is hydrogen, halogen, —CX¹¹₃, —CHX¹¹₂, —CH₂X¹¹, —OCX¹¹₃, —OCH₂X¹¹, —OCHX¹¹₂, —$N_3$, —CN, —$SO_{n11}R^{11D}$, —$SO_{v11}NR^{11A}R^{11B}$, —$NHC(O)NR^{11A}R^{11B}$, —$N(O)_{m11}$, —$NR^{11A}R^{11B}$, —$C(O)R^{11C}$, —C(O)—$OR^{11C}$, —$C(O)NR^{11A}R^{11B}$, —$OR^{11D}$, —$NR^{11A}SO_2R^{11D}$, —$NR^{11A}C(O)R^{11C}$, —$NR^{11A}C(O)OR^{11C}$, —$NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, —$CX^{12}_3$, —$CHX^{12}_2$, —$CH_2X^{12}$, —$OCX^{12}_3$, —$OCH_2X^{12}$, —$OCHX^{12}_2$, —$N_3$, —CN, —$SO_{n12}R^{12D}$, —$SO_{v12}NR^{12A}R^{12B}$, —$NHC(O)NR^{12A}R^{12B}$, —$N(O)_{m12}$, —$NR^{12A}R^{12B}$, —$C(O)R^{12C}$, —C(O)—$OR^{12C}$, —$C(O)NR^{12A}R^{12B}$, —$OR^{12D}$, —$NR^{12A}SO_2R^{12D}$, —$NR^{12A}C(O)$ $R^{12C}$, —$NR^{12A}C(O)OR^{12C}$, —$NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, —$CX^{13}_3$, —$CHX^{13}_2$, —$CH_2X^{13}$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently —F, —Cl, —Br, or —I, or a salt thereof.

Embodiment Q2. The method of Embodiment Q1, wherein the compound has a formula (II):

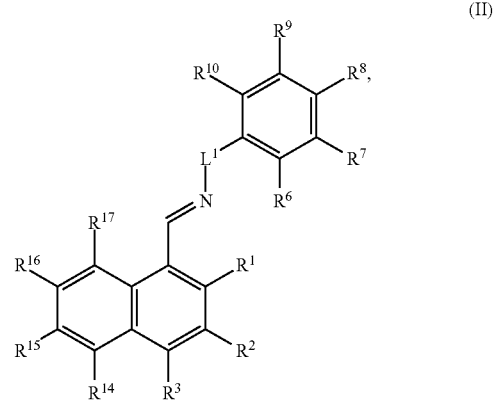

(II)

wherein:

$R^{14}$ is hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —$N_3$, —CN, —$SO_{n14}R^{14D}$, —$SO_{v14}NR^{14A}R^{14B}$, —$NHC(O)NR^{14A}R^{14B}$, —$N(O)_{m14}$, —$NR^{14A}R^{14B}$, —$C(O)R^{14C}$, —C(O)—$OR^{14C}$, —$C(O)NR^{14A}R^{14B}$, —$OR^{14D}$, —$NR^{14A}SO_2R^{14D}$, —$NR^{14A}C(O)$ $R^{14C}$, —$NR^{14A}C(O)OR^{14C}$, —$NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —$N_3$, —CN, —$SO_{n15}R^{15D}$, —$SO_{v15}NR^{15A}R^{15B}$, —$NHC(O)NR^{15A}R^{15B}$, —$N(O)_{m14}$, —$NR^{15A}R^{15B}$, —$C(O)R^{15C}$, —C(O)—$OR^{15C}$, —$C(O)NR^{15A}R^{15B}$, —$OR^{15D}$, —$NR^{15A}SO_2R^{15D}$, —$NR^{15A}C(O)$ $R^{15C}$, —$NR^{15A}C(O)OR^{15C}$, —$NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —$N_3$, —CN, —$SO_{n16}R^{16D}$, —$SO_{v16}NR^{16A}R^{16B}$, —$NHC(O)NR^{16A}R^{16B}$, —$N(O)_{m16}$, —$NR^{16A}R^{16B}$, —$C(O)R^{16C}$, —C(O)—$OR^{16C}$, —$C(O)NR^{16A}R^{16B}$, —$OR^{16D}$, —$NR^{16A}SO_2R^{16D}$, —$NR^{16A}C(O)$ $R^{16C}$, —$NR^{16A}C(O)OR^{16C}$, —$NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —$N_3$, —CN, —$SO_{n17}R^{17D}$, —$SO_{v17}NR^{17A}R^{17B}$, —$NHC(O)NR^{17A}R^{17B}$, —$N(O)_{m17}$, —$NR^{17A}R^{17B}$, —$C(O)R^{17C}$, —C(O)—$OR^{17C}$, —$C(O)NR^{17A}R^{17B}$, —$OR^{17D}$, —$NR^{17A}SO_2R^{17D}$, —$NR^{17A}C(O)$ $R^{17C}$, —$NR^{17A}C(O)OR^{17C}$, —$NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}$, $X^{15}$, $X^{16}$, and $X^{17}$ are independently $-F$, $-Cl$, $-Br$, or $-I$.

Embodiment Q3. The method of any one of Embodiments Q1-Q2, wherein $L^1$ is $-O-$ or $-S-$.

Embodiment Q4. The method of any one of Embodiments Q1-Q2, wherein $L^1$ is a bond.

Embodiment Q5. The method of any one of Embodiments Q1-Q2, wherein $L^1$ is $-S(O)_2-$, $-NR^{13}S(O)_2-$ or $-NR^{13}C(O)-$.

Embodiment Q6. The method of any one of Embodiments Q1-Q5, wherein at least one of $R^1$, $R^2$ and $R^3$ are $-OH$ or $-OCH_3$.

Embodiment Q7. The method of any one of Embodiments Q1-Q6, wherein $R^7$ and $R^9$ are hydrogen.

Embodiment Q8. The method of any one of Embodiments Q1-Q7, wherein each $R^6$, $R^8$, and $R^{10}$ is independently hydrogen, halogen, $-N_3$, $-CN$, $-NO_2$, $-NH_2$, $-C(O)H$, $-C(O)CH_3$, $-C(O)OH$, $-C(O)OCH_3$, $-C(O)NH_2$, $-OH$, $-OCH_3$, or substituted or unsubstituted $C_1$-$C_3$ alkyl.

Embodiment Q9 The method of any one of Embodiments Q1-Q8, wherein the compound has a formula (III),

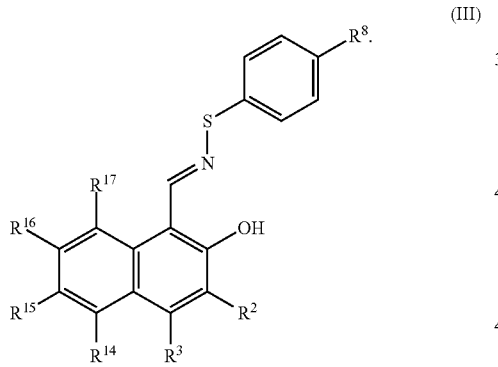

(III)

Embodiment Q10. The method of any one of Embodiments Q1-Q8, wherein the compound has a formula (IV),

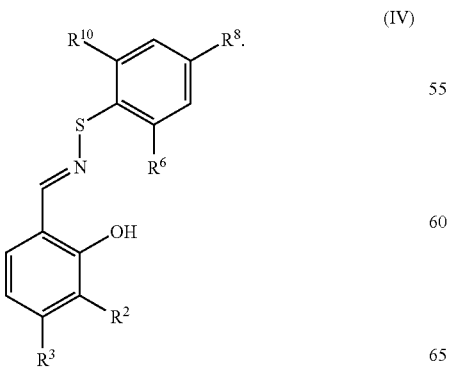

(IV)

Embodiment Q11. The method of any one of Embodiments Q1-Q8, wherein the compound has a formula (V),

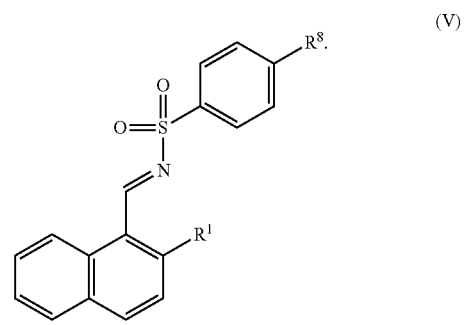

(V)

Embodiment Q12. The method of any one of Embodiments Q1-Q8, wherein the compound has a formula (VI),

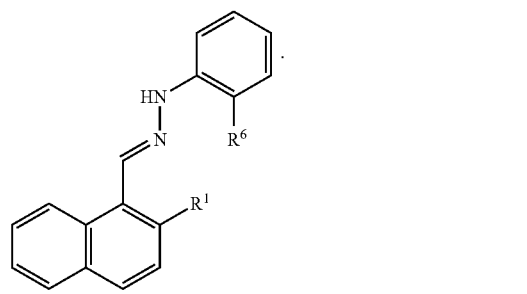

(VI)

Embodiment Q13. The method of any one of Embodiments Q1-Q8, wherein the compound has a formula (VII),

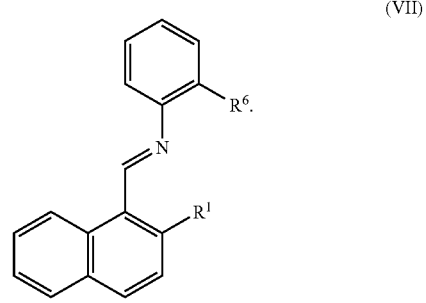

(VII)

Embodiment Q14. The method of any one of Embodiments Q1-Q13, wherein the compound is

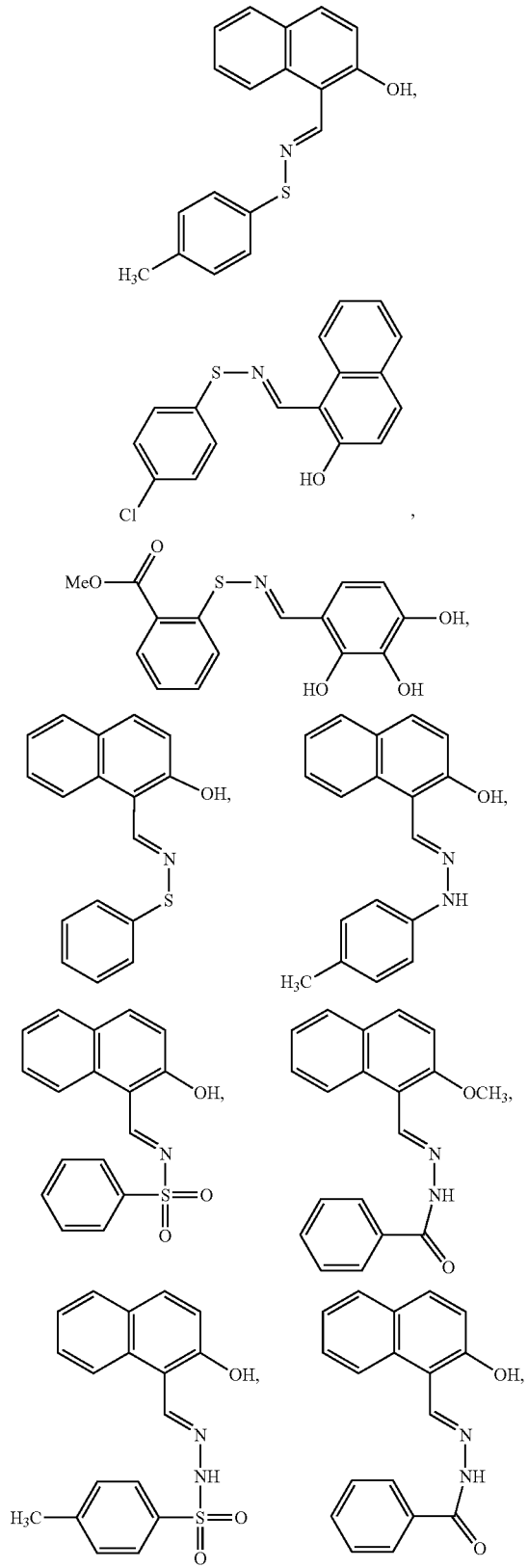

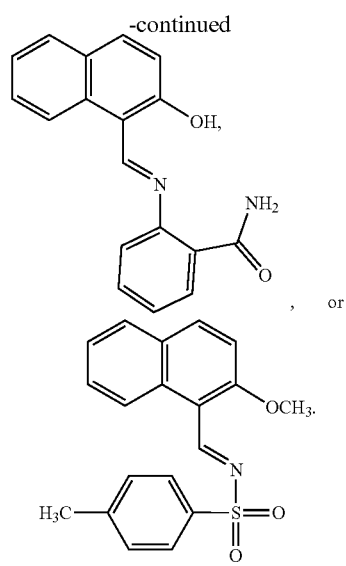

, or

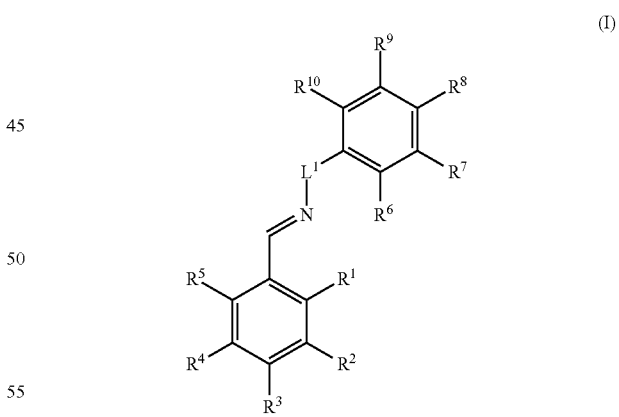

Embodiment Q15. The method of any one of Embodiments Q1-Q14, wherein the compound inhibits poly(ADP-ribose) glycohydrolase (PARG) in a cancer cell.

Embodiment Q16. The method of any one of Embodiments Q1-Q15, wherein the cancer is selected from: breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

Embodiment Q17. The method of Embodiment Q16, wherein the cancer is lymphoma.

Embodiment Q18. A method of inhibiting a poly(ADP-ribose) glycohydrolase (PARG), the method comprising contacting the PARG with a compound having a formula (I), (I)

wherein:
$L^1$ is a bond, —$CR^{11}R^{12}$—, —$NR^{13}$—, —O—, —S—, —$S(O)_2$—, —$NR^{13}S(O)_2$—, or —$NR^{13}C(O)$—;
$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted het- $R^2$ is hydrogen, halogen, $-CX^2{}_3$, $-CHX^2{}_2$, $-CH_2X^2$, $-OCX^2{}_3$, $-OCH_2X^2$, $-OCHX^2{}_2$, $-N_3$, $-CN$, $-SO_{n2}R^{2D}$, $-SO_{v2}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-CX^3{}_3$, $-CHX^3{}_2$, $-CH_2X^3$, $-OCX^3{}_3$, $-OCH_2X^3$, $-OCHX^3{}_2$, $-N_3$, $-CN$, $-SO_{n3}R^{3D}$, $-SO_{v3}NR^{3A}R^{3B}$, $-NHC(O)NR^{3A}R^{3B}$, $-N(O)_{m3}$, $-NR^{3A}R^{3B}$, $-C(O)R^{3C}$, $-C(O)-OR^{3C}$, $-C(O)NR^{3A}R^{3B}$, $-OR^{3D}$, $-NR^{3A}SO_2R^{3D}$, $-NR^{3A}C(O)R^{3C}$, $-NR^{3A}C(O)OR^{3C}$, $-NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-CX^4{}_3$, $-CHX^4{}_2$, $-CH_2X^4$, $-OCX^4{}_3$, $-OCH_2X^4$, $-OCHX^4{}_2$, $-N_3$, $-CN$, $-SO_{n4}R^{4D}$, $-SO_{v4}NR^{4A}R^{4B}$, $-NHC(O)NR^{4A}R^{4B}$, $-N(O)_{m4}$, $-NR^{4A}R^{4B}$, $-C(O)R^{4C}$, $-C(O)-OR^{4C}$, $-C(O)NR^{4A}R^{4B}$, $-OR^{4D}$, $-NR^{4A}SO_2R^{4D}$, $-NR^{4A}C(O)R^{4C}$, $-NR^{4A}C(O)OR^{4C}$, $-NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-CX^5{}_3$, $-CHX^5{}_2$, $-CH_2X^5$, $-OCX^5{}_3$, $-OCH_2X^5$, $-OCHX^5{}_2$, $-N_3$, $-CN$, $-SO_{n5}R^{5D}$, $-SO_{v5}NR^{5A}R^{5B}$, $-NHC(O)NR^{5A}R^{5B}$, $-N(O)_{m5}$, $-NR^{5A}R^{5B}$, $-C(O)R^{5C}$, $-C(O)-OR^{5C}$, $-C(O)NR^{5A}R^{5B}$, $-OR^{5D}$, $-NR^{5A}SO_2R^{5D}$, $-NR^{5A}C(O)R^{5C}$, $-NR^{5A}C(O)OR^{5C}$, $-NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, $-CX^6{}_3$, $-CHX^6{}_2$, $-CH_2X^6$, $-OCX^6{}_3$, $-OCH_2X^6$, $-OCHX^6{}_2$, $-N_3$, $-CN$, $-SO_{n6}R^{6D}$, $-SO_{v6}NR^{6A}R^{6B}$, $-NHC(O)NR^{6A}R^{6B}$, $-N(O)_{m6}$, $-NR^{6A}R^{6B}$, $-C(O)R^{6C}$, $-C(O)-OR^{6C}$, $-C(O)NR^{6A}R^{6B}$, $-OR^{6D}$, $-NR^{6A}SO_2R^{6D}$, $-NR^{6A}C(O)R^{6C}$, $-NR^{6A}C(O)OR^{6C}$, $-NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, $-CX^7{}_3$, $-CHX^7{}_2$, $-CH_2X^7$, $-OCX^7{}_3$, $-OCH_2X^7$, $-OCHX^7{}_2$, $-N_3$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)OR^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $-CX^8{}_3$, $-CHX^8{}_2$, $-CH_2X^8$, $-OCX^8{}_3$, $-OCH_2X^8$, $-OCHX^8{}_2$, $-N_3$, $-CN$, $-SO_{n8}R^{8D}$, $-SO_{v8}NR^{8A}R^{8B}$, $-NHC(O)NR^{8A}R^{8B}$, $-N(O)_{m8}$, $-NR^{8A}R^{8B}$, $-C(O)R^{8C}$, $-C(O)-OR^{8C}$, $-C(O)NR^{8A}R^{8B}$, $-OR^{8D}$, $-NR^{8A}SO_2R^{8D}$, $-NR^{8A}C(O)R^{8C}$, $-NR^{8A}C(O)OR^{8C}$, $-NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^9{}_3$, $-CHX^9{}_2$, $-CH_2X^9$, $-OCX^9{}_3$, $-OCH_2X^9$, $-OCHX^9{}_2$, $-N_3$, $-CN$, $-SO_{n9}R^{9D}$, $-SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10}{}_3$, $-CHX^{10}{}_2$, $-CH_2X^{10}$, $-OCX^{10}{}_3$, $-OCH_2X^{10}$, $-OCHX^{10}{}_2$, $-N_3$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11}{}_3$, $-CHX^{11}{}_2$, $-CH_2X^{11}$, $-OCX^{11}{}_3$, $-OCH_2X^{11}$, $-OCHX^{11}{}_2$, $-N_3$, $-CN$, $-SO_{n11}R^{11D}$, $-SO_{v11}NR^{11A}R^{11B}$, $-NHC(O)NR^{11A}R^{11B}$, $-N(O)_{m11}$, $-NR^{11A}R^{11B}$, $-C(O)R^{11C}$, $-C(O)-OR^{11C}$, $-C(O)NR^{11A}R^{11B}$, $-OR^{11D}$, $-NR^{11A}SO_2R^{11D}$, $-NR^{11A}C(O)R^{11C}$, $-NR^{11A}C(O)OR^{11C}$, $-NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12}{}_3$, $-CHX^{12}{}_2$, $-CH_2X^{12}$, $-OCX^{12}{}_3$, $-OCH_2X^{12}$, $-OCHX^{12}{}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, $-CX^{13}{}_3$, $-CHX^{13}{}_2$, $-CH_2X^{13}$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently —F, —Cl, —Br, or —I, or a salt thereof.

Embodiment Q19. The method of Embodiment Q18, wherein the compound has a formula (II):

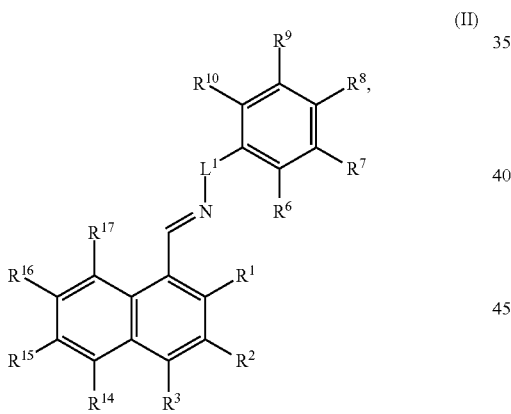

(II)

wherein:

$R^{14}$ is hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —$N_3$, —CN, —$SO_{n14}R^{14D}$, —$SO_{v14}NR^{14A}R^{14B}$, —$NHC(O)NR^{14A}R^{14B}$, —$N(O)_{m14}$, —$NR^{14A}R^{14B}$, —$C(O)R^{14C}$, —$C(O)$—$OR^{14C}$, —$C(O)NR^{14A}R^{14B}$, —$OR^{14D}$, —$NR^{14A}SO_2R^{14D}$, —$NR^{14A}C(O)R^{14C}$, —$NR^{14A}C(O)OR^{14C}$, —$NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —$CX^{15}_3$, —$CHX^{15}_2$, —$CH_2X^{15}$, —$OCX^{15}_3$, —$OCH_2X^{15}$, —$OCHX^{15}_2$, —$N_3$, —CN, —$SO_{n15}R^{15D}$, —$SO_{v15}NR^{15A}R^{15B}$, —$NHC(O)NR^{15A}R^{15B}$, —$N(O)_{m15}$, —$NR^{15A}R^{15B}$, —$C(O)R^{15C}$, —$C(O)$—$OR^{15C}$, —$C(O)NR^{15A}R^{15B}$, —$OR^{15D}$, —$NR^{15A}SO_2R^{15D}$, —$NR^{15A}C(O)R^{15C}$, —$NR^{15A}C(O)OR^{15C}$, —$NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —$N_3$, —CN, —$SO_{n16}R^{16D}$, —$SO_{v16}NR^{16A}R^{16B}$, —$NHC(O)NR^{16A}R^{16B}$, —$N(O)_{m16}$, —$NR^{16A}R^{16B}$, —$C(O)R^{16C}$, —$C(O)$—$OR^{16C}$, —$C(O)NR^{16A}R^{16B}$, —$OR^{16D}$, —$NR^{16A}SO_2R^{16D}$, —$NR^{16A}C(O)R^{16C}$, —$NR^{16A}C(O)OR^{16C}$, —$NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —$N_3$, —CN, —$SO_{n17}R^{17D}$, —$SO_{v17}NR^{17A}R^{17B}$, —$NHC(O)NR^{17A}R^{17B}$, —$N(O)_{m17}$, —$NR^{17A}R^{17B}$, —$C(O)R^{17C}$, —$C(O)$—$OR^{17C}$, —$C(O)NR^{17A}R^{17B}$, —$OR^{17D}$, —$NR^{17A}SO_2R^{17D}$, —$NR^{17A}C(O)R^{17C}$, —$NR^{17A}C(O)OR^{17C}$, —$NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}$, $X^{15}$, $X^{16}$, and $X^{17}$ are independently —F, —Cl, —Br, or —I.

Embodiment Q20. The method of any one of Embodiments Q18-Q19, wherein $L^1$ is —O— or —S—.

Embodiment Q21. The method of any one of Embodiments Q18-Q19, wherein $L^1$ is a bond.

Embodiment Q22. The method of any one of Embodiments Q18-Q19, wherein $L^1$ is —$S(O)_2$—, —$NR^{13}S(O)_2$— or —$NR^{13}C(O)$—.

Embodiment Q23. The method of any one of Embodiments Q18-Q22, wherein at least one of $R^1$, $R^2$ and $R^3$ are —OH or —$OCH_3$.

Embodiment Q24. The method of any one of Embodiments Q18-Q23, wherein $R^7$ and $R^9$ are hydrogen.

Embodiment Q25. The method of any one of Embodiments Q18-Q24, wherein each $R^6$, $R^8$, and $R^{10}$ is independently hydrogen, halogen, —$N_3$, —CN, —$NO_2$, —$NH_2$, —C(O)H, —$C(O)CH_3$, —C(O)OH, —$C(O)OCH_3$, —$C(O)NH_2$, —OH, —$OCH_3$, or substituted or unsubstituted $C_1$-$C_3$ alkyl.

Embodiment Q26. The method of any one of Embodiments Q18-Q25, wherein the compound has a formula (III),

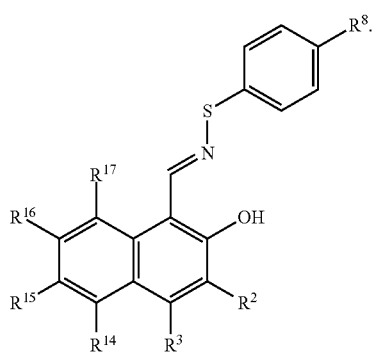

(III)

Embodiment Q27. The method of any one of Embodiments Q18-Q25, wherein the compound has a formula (IV),

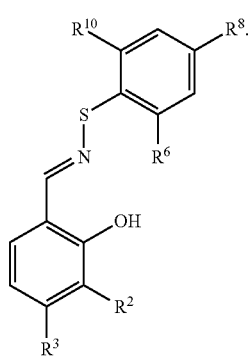

(IV)

Embodiment Q28. The method of any one of Embodiments Q18-Q25, wherein the compound has a formula (V),

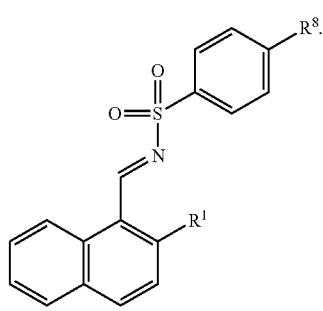

(V)

Embodiment Q29. The method of any one of Embodiments Q18-Q25, wherein the compound has a formula (VI).

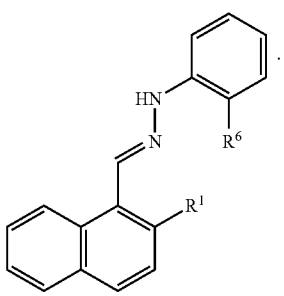

(VI)

Embodiment Q30. The method of any one of Embodiments Q18-Q25, wherein the compound has a formula (VII),

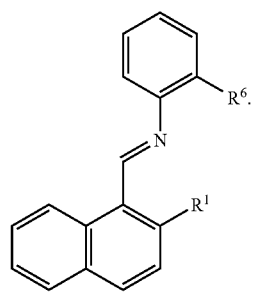

(VII)

Embodiment Q31. he method of any one of Embodiments Q18-Q30, wherein the compound is

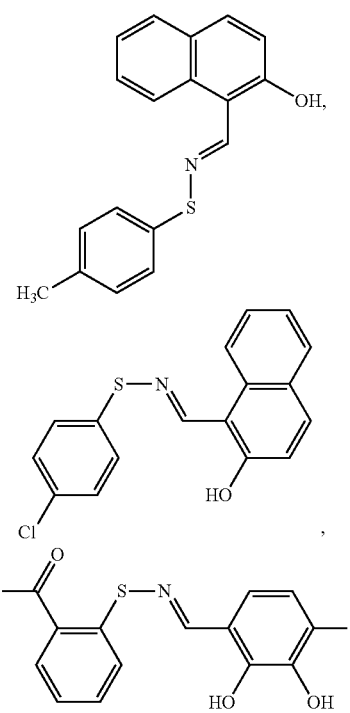

-continued

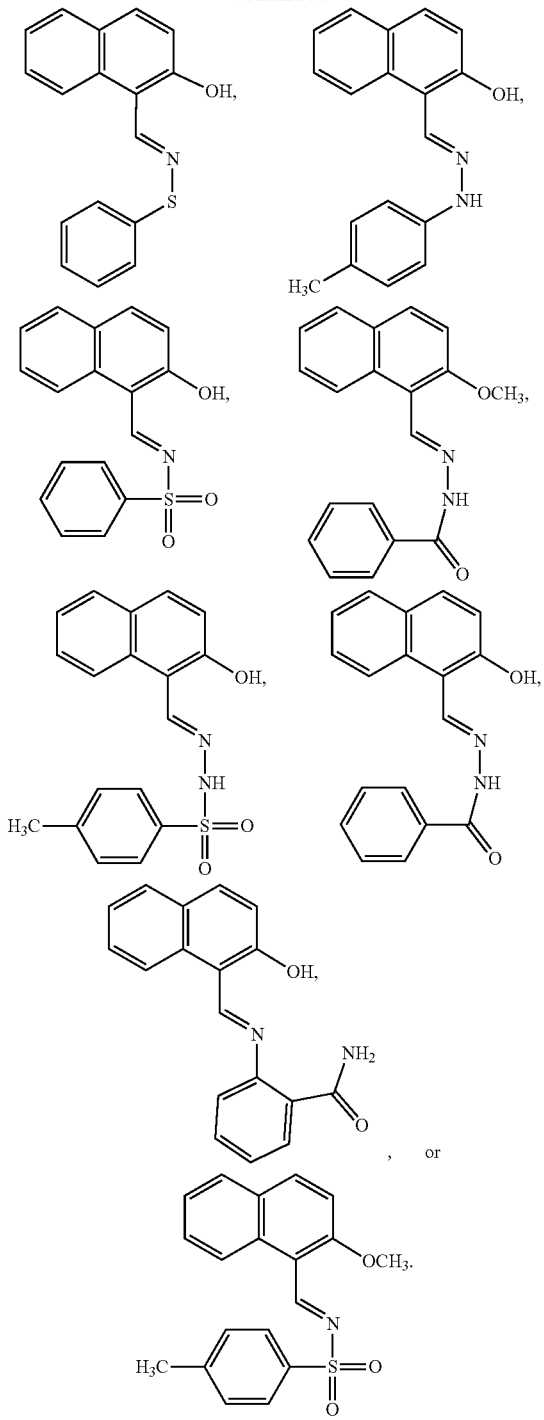

, or

Embodiment Q32. The method of any one of Embodiments Q18-Q31, wherein the compound inhibits the poly (ADP-ribose) glycohydrolase (PARG) in a cancer cell.

Embodiment Q33. The method of Embodiment Q32, wherein the cancer cell is from breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

Embodiment Q34. A compound having a formula (I),

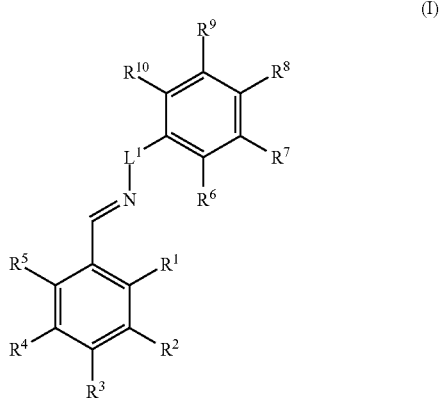

(I)

wherein, $L^1$ is a bond, —$CR^{11}R^{12}$—, —$NR^{13}$—, —O—, —S—, —$S(O)_2$—, —$NR^{13}S(O)_2$—, or —$NR^{13}C(O)$—;

$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —$N_3$, —CN, —SO$_{n6}$R$^{6D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —CX$^6_3$, —CHX$^6_2$, —CH$_2$X$^6$, —OCX$^6_3$, —OCH$_2$X$^6$, —OCHX$^6_2$, —N$_3$, —CN, —SO$_{n6}$R$^{®}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CX$^7_3$, —CHX$^7_2$, —CH$_2$X$^7$, —OCX$^7_3$, —OCH$_2$X$^7$, —OCHX$^7_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —CX$^8_3$, —CHX$^8_2$, —CH$_2$X$^8$, —OCX$^8_3$, —OCH$_2$X$^8$, —OCHX$^8_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^9_3$, —CHX$^9_2$, —CH$_2$X$^9$, —OCX$^9_3$, —OCH$_2$X$^9$, —OCHX$^9_2$, —N$_3$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, X$^1$, X$^2$, X$^3$, X$^4$, X$^5$, X$^6$, X$^7$, X$^8$, X$^9$, X$^{10}$, X$^{11}$, X$^{12}$, and X$^{13}$ are independently —F, —Cl, —Br, or —I, or a salt thereof, provided that when L$^1$ is —S—, R$^1$ is —OH, and R$^4$ and R$^5$ together with atoms attached thereto are joined to form unsubstituted phenyl, then R$^6$ is not —CH$_3$; when L$^1$ is —S—, R$^1$ is —OH, and R$^4$ and R$^5$ together with atoms attached thereto are joined to form unsubstituted phenyl, then R$^8$ is not —CH$_3$; and when L$^1$ is —S—, R$^1$ is —OH, and R$^4$ and R$^5$ together with atoms attached thereto are joined to form unsubstituted phenyl, then R$^{10}$ is not —CH$_3$.

Embodiment Q35. The compound of Embodiment Q34, wherein the compound has a formula (II):

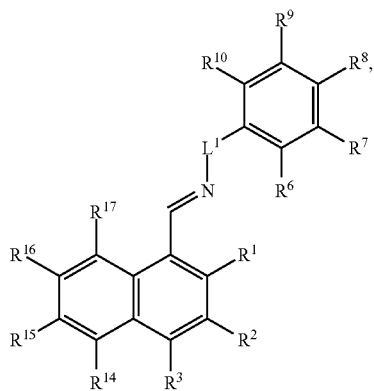

(II)

wherein:
R$^{14}$ is hydrogen, halogen, —CX$^{14}_3$, —CHX$^{14}_2$, —CH$_2$X$^{14}$, —OCX$^{14}_3$, —OCH$_2$X$^{14}$, OCHX$^{14}_2$, —N$_3$, —CN, —SO$_{n14}$R$^{14D}$, —SO$_{v14}$NR$^{14A}$R$^{14B}$, —NHC(O)NR$^{14A}$R$^{14B}$, —N(O)$_{m14}$, —NR$^{14A}$R$^{14B}$, —C(O)R$^{14C}$, —C(O)—OR$^{14C}$, —C(O)NR$^{14A}$R$^{14B}$, —OR$^{14D}$, —NR$^{14A}$SO$_2$R$^{14D}$, —NR$^{14A}$C(O)R$^{14C}$, —NR$^{14A}$C(O)OR$^{14C}$, —NR$^{14A}$OR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —N$_3$, —CN, —SO$_{n15}$R$^{15D}$, —SO$_{v15}$NR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)OR$^{15C}$, —NR$^{15A}$OR$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —N$_3$, —CN, —SO$_{n16}$R$^{16D}$, —SO$_{v16}$NR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ is hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —N$_3$, —CN, —SO$_{n17}$R$^{17D}$, —SO$_{v17}$NR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, and R$^{17D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and X$^{14}$, X$^{15}$, X$^{16}$, and X$^{17}$ are independently —F, —Cl, —Br, or —I.

Embodiment Q36. The compound of any one of claims 1-2, wherein L$^1$ is —O— or —S—.

Embodiment Q37. The compound of any one of Embodiments Q34-Q35, wherein L$^1$ is a bond.

Embodiment Q38. The compound of any one of Embodiments Q34-Q35, wherein L$^1$ is —S(O)$_2$—, —NR$^{13}$S(O)$_2$— or —NR$^{13}$C(O)—.

Embodiment Q39. The compound of any one of Embodiments Q34-Q38, wherein at least one of R$^1$, R$^2$ and R$^3$ are —OH or —OCH$_3$.

Embodiment Q40. The compound of any one of Embodiments Q34-Q39, wherein R$^7$ and R$^9$ are hydrogen.

Embodiment Q41. The compound of any one of Embodiments Q34-Q40, wherein each R$^6$, R$^8$, and R$^{10}$ is independently hydrogen, halogen, —N$_3$, —CN, —NO$_2$, —NH$_2$, —C(O)H, —C(O)CH$_3$, —C(O)OH, —C(O)OCH$_3$, —C(O)NH$_2$, —OH, —OCH$_3$, or substituted or unsubstituted C$_1$-C$_3$ alkyl.

Embodiment Q42. The compound of any one of Embodiments Q34-Q41, wherein the compound has a formula (III),

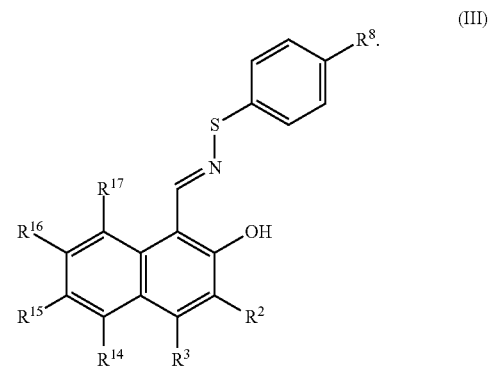

(III)

Embodiment Q43. The compound of any one of Embodiments Q34-Q41, wherein the compound has a formula (IV),

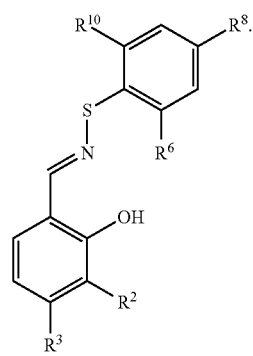
(IV)

Embodiment Q44. The compound of any one of Embodiments Q34-Q41, wherein the compound has a formula (V),

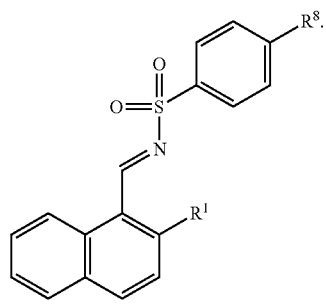
(V)

Embodiment Q45. The compound of any one of Embodiments Q34-Q41, wherein the compound has a formula (VI),

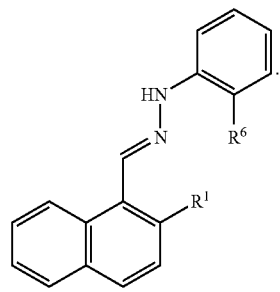
(VI)

Embodiment Q46. The compound of any one of Embodiments Q34-Q41, wherein the compound has a formula (VII),

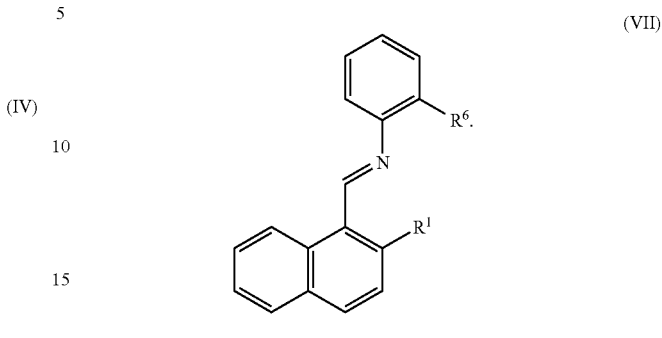
(VII)

Embodiment Q46. The compound of any one of Embodiments Q34-Q46, wherein the compound is

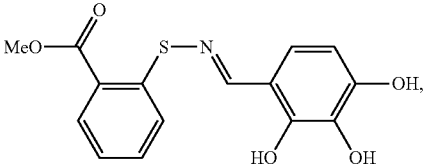

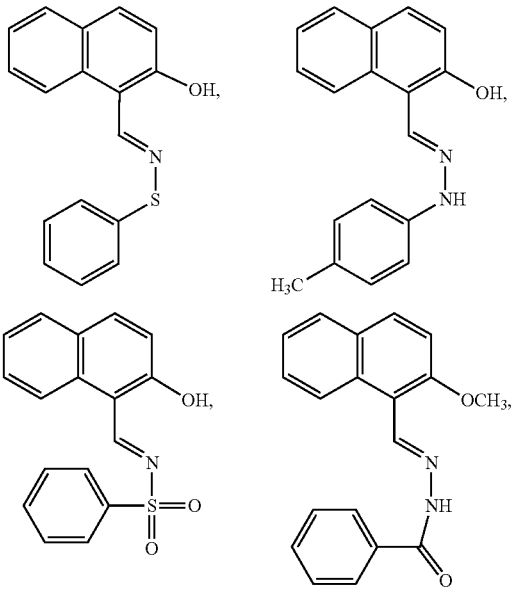

-continued

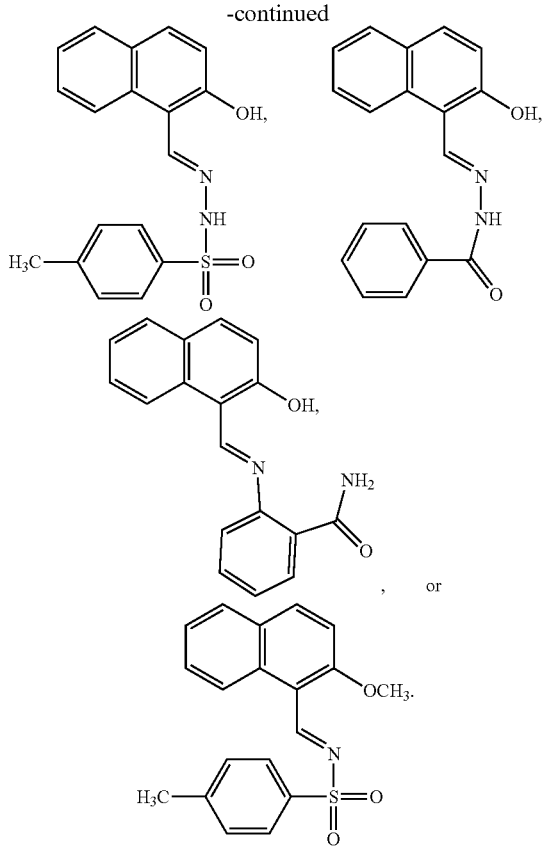

, or

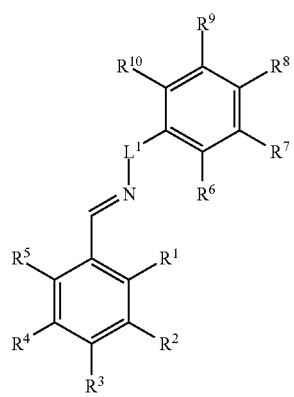

Embodiment Q48. A pharmaceutical composition comprising a compound having a formula (I), (I)

wherein, $L^1$ is a bond, —$CR^{11}R^{12}$—, —$NR^{13}$—, —O—, —S—, —$S(O)_2$—, —$NR^{13}S(O)_2$—, or —$NR^{13}C(O)$—;

$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, $C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, $C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —$N_3$, —CN, —$SO_{n5}R^{5D}$, —$SO_{v5}NR^{5A}R^{5B}$, —$NHC(O)NR^{5A}R^{5B}$, —$N(O)_{m5}$, —$NR^{5A}R^{5B}$, —$C(O)R^{5C}$, —$C(O)$—$OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^6_3$, —$CHX^6_2$, —$CH_2X^6$, —$OCX^6_3$, —$OCH_2X^6$, —$OCHX^6_2$, —$N_3$, —CN, —$SO_{n6}R^{6D}$, —$SO_{v6}NR^{6A}R^{6B}$, —$NHC(O)NR^{6A}R^{6B}$, —$N(O)_{m6}$, —$NR^{6A}R^{6B}$, —$C(O)R^{6C}$, —$C(O)$—$OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^7_3$, —$CHX^7_2$, —$CH_2X^7$, —$OCX^7_3$, —$OCH_2X^7$, —$OCHX^7_2$, —$N_3$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, $-CX^8_3$, $-CHX^8_2$, $-CH_2X^8$, $-OCX^8_3$, $-OCH_2X^8$, $-OCHX^8_2$, $-N_3$, $-CN$, $-SO_{n8}R^{8D}$, $-SO_{v8}NR^{8A}R^{8B}$, $-NHC(O)NR^{8A}R^{8B}$, $-N(O)_{m8}$, $-NR^{8A}R^{8B}$, $-C(O)R^{8C}$, $-C(O)-OR^{8C}$, $-C(O)NR^{8A}R^{8B}$, $-OR^{8D}$, $-NR^{8A}SO_2R^{8D}$, $-NR^{8A}C(O)R^{8C}$, $-NR^{8A}C(O)OR^{8C}$, $-NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, $-CX^9_3$, $-CHX^9_2$, $-CH_2X^9$, $-OCX^9_3$, $-OCH_2X^9$, $-OCHX^9_2$, $-N_3$, $-CN$, $-SO_{n9}R^{9D}$, $-SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-N_3$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-N_3$, $-CN$, $-SO_{n11}R^{11D}$, $-SO_{v11}NR^{11A}R^{11B}$, $-NHC(O)NR^{11A}R^{11B}$, $-N(O)_{m11}$, $-NR^{11A}R^{11B}$, $-C(O)R^{11C}$, $-C(O)-OR^{11C}$, $-C(O)NR^{11A}R^{11B}$, $-OR^{11D}$, $-NR^{11A}SO_2R^{11D}$, $-NR^{11A}C(O)R^{11C}$, $-NR^{11A}C(O)OR^{11C}$, $-NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, $-CX^{13}_3$, $-CHX^{13}_2$, $-CH_2X^{13}$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently $-F$, $-Cl$, $-Br$, or $-I$, or a salt thereof, and a pharmaceutically acceptable carrier.

Embodiment Q49. The pharmaceutical composition of Embodiment Q48, wherein the compound has a formula (II):

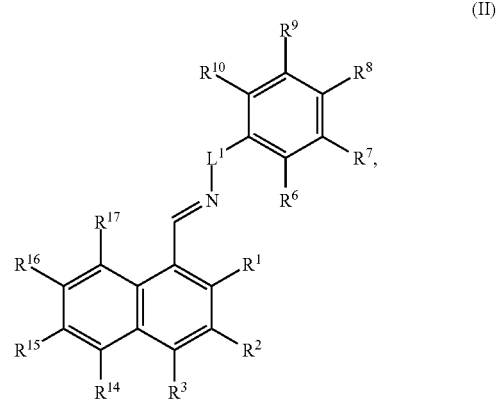

(II)

wherein:

$R^{14}$ is hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-N_3$, $-CN$, $-SO_{n14}R^{14D}$, $-SO_{v14}NR^{14A}R^{14B}$, $-NHC(O)NR^{14A}R^{14B}$, $-N(O)_{m14}$, $-NR^{14A}R^{14B}$, $C(O)R^{14C}$, $-C(O)-OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)OR^{14C}$, $-NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $-CX^{15}_3$, $-CHX^{15}_2$, $-CH_2X^{15}$, $-OCX^{15}_3$, $-OCH_2X^{15}$, $-OCHX^{15}_2$, $-N_3$, $-CN$, $-SO_{n15}R^{15D}$, $-SO_{v15}NR^{15A}R^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O)R$^{15C}$, —NR$^{15A}$C(O)O R$^{15C}$, —NR$^{15A}$OR$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{16}$ is hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —N$_3$, —CN, —SO$_{n16}$R$^{16D}$, —SO$_{v16}$NR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{17}$ is hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —N$_3$, —CN, —N$_3$, —SO$_{n17}$R$^{17D}$, —SO$_{v17}$NR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O) R$^{17C}$, —NR$^{17A}$C(O)OR$^{17C}$, —NR$^{17A}$OR$^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, and R$^{17D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and X$^{14}$, X$^{15}$, X$^{16}$, and X$^{17}$ are independently —F, —Cl, —Br, or —I.

Embodiment Q50. The pharmaceutical composition of any one of Embodiments Q48-Q49, wherein L$^1$ is —O— or —S—.

Embodiment Q51. The pharmaceutical composition of any one of Embodiments Q48-Q49, wherein L$^1$ is a bond.

Embodiment Q52. The pharmaceutical composition of any one of Embodiments Q48-Q49, wherein L$^1$ is —S(O)$_2$—, —NR$^{13}$S(O)$_2$— or —NR$^{13}$C(O)—.

Embodiment Q53. The pharmaceutical composition of any one of Embodiments Q48-Q52, wherein at least one of R$^1$, R$^2$ and R$^3$ are —OH or —OCH$_3$.

Embodiment Q54. The pharmaceutical composition of any one of Embodiments Q48-Q53, wherein R$^7$ and R$^9$ are hydrogen.

Embodiment Q55. The pharmaceutical composition of any one of Embodiments Q48-Q54, wherein each R$^6$, R$^8$, and R$^{10}$ is independently hydrogen, halogen, —N$_3$, —CN, —NO$_2$, —NH$_2$, —C(O)H, —C(O)CH$_3$, —C(O)OH, —C(O)OCH$_3$, —C(O)NH$_2$, —OH, —OCH$_3$, or substituted or unsubstituted C$_1$-C$_3$ alkyl.

Embodiment Q56. The pharmaceutical composition of any one of Embodiments Q48-Q55, wherein the compound has a formula (III)

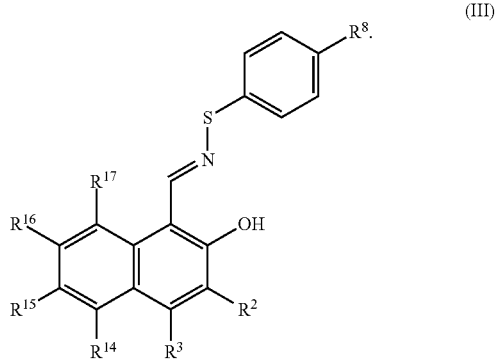

Embodiment Q57. The pharmaceutical composition of any one of Embodiments Q48-Q55, wherein the compound has a formula (IV),

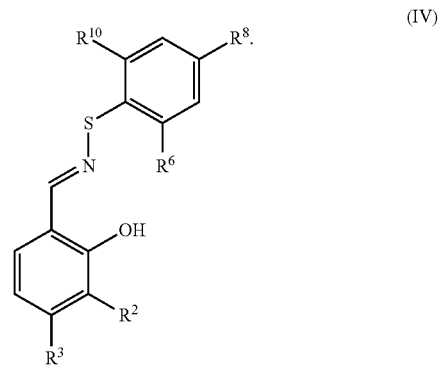

Embodiment Q58. The pharmaceutical composition of any one of Embodiments Q48-Q55, wherein the compound has a formula (V),

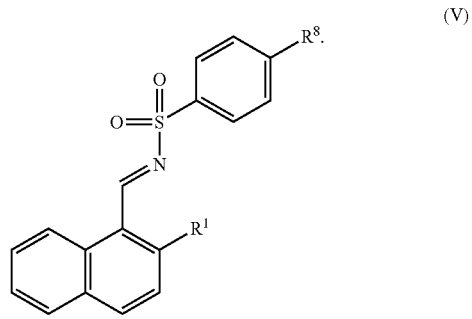

Embodiment Q59. The pharmaceutical composition of any one of Embodiments Q48-Q55, wherein the compound has a formula (VI),

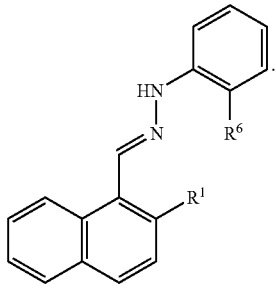
(VI)
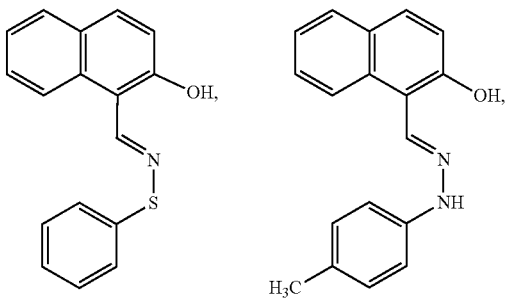
Embodiment Q60. The pharmaceutical composition of any one of Embodiments Q48-Q55, wherein the compound has a formula (VII),
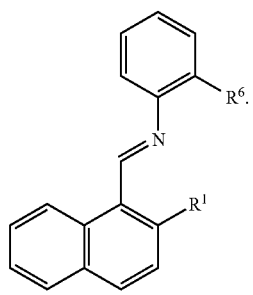
(VII)
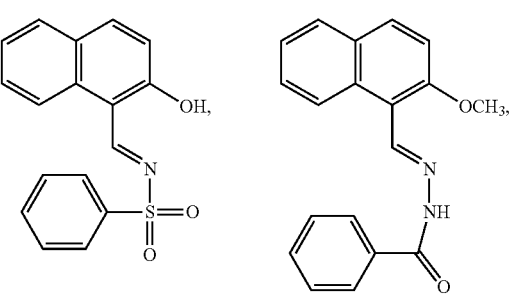
Embodiment Q61. The pharmaceutical composition of any one of Embodiments Q48-Q60, wherein the compound is
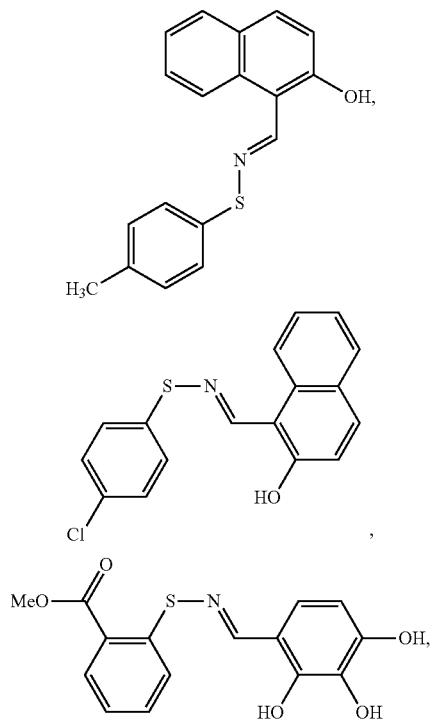
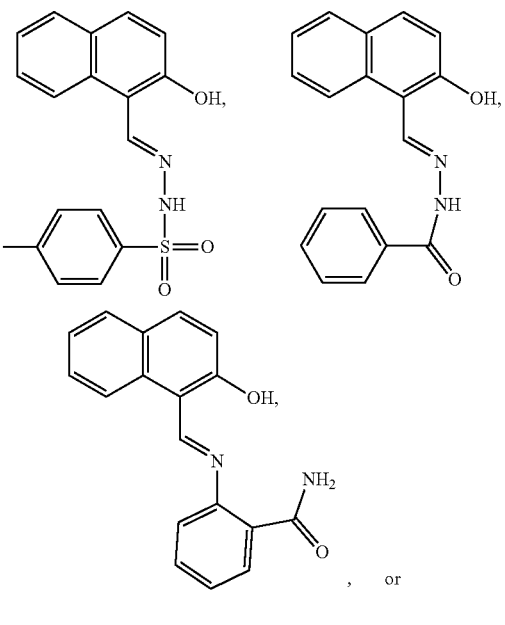
, or
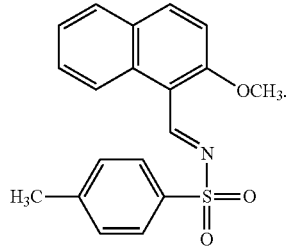

EMBODIMENTS

Embodiment 1. A compound having a formula (I),

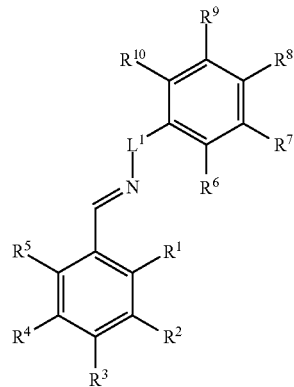

wherein, $L^1$ is a bond, —$CR^{11}R^{12}$—, —$NR^{13}$—, —O—, —S—, —S(O)—, —S(O)$_2$—, —$NR^{13}$S(O)—, —$NR^{13}$S(O)$_2$—, or —$NR^{13}$C(O)—;

$R^1$ is hydrogen, halogen, —$CX^1_3$, —$CHX^1_2$, —$CH_2X^1$, —$OCX^1_3$, —$OCH_2X^1$, —$OCHX^1_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}$ $OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$. —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}$ $OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$. —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}$ $OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}$ $OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —$N_3$, —CN, —$SO_{n5}R^{5D}$, —$SO_{v5}NR^{5A}R^{5B}$, —$NHC(O)NR^{5A}R^{5B}$, —$N(O)_{m5}$, —$NR^{5A}R^{5B}$, —$C(O)R^{5C}$, —$C(O)$—$OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}$ $OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^6_3$, —$CHX^6_2$, —$CH_2X^6$, —$OCX^6_3$, —$OCH_2X^6$, —$OCHX^6_2$, —$N_3$, —CN, —$SO_{n6}R^{6D}$, —$SO_{v6}NR^{6A}R^{6B}$, —$NHC(O)NR^{6A}R^{6B}$, —$N(O)_{m6}$, —$NR^{6A}R^{6B}$, —$C(O)R^{6C}$, —$C(O)$—$OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}$ $OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^7_3$, —$CHX^7_2$, —$CH_2X^7$, —$OCX^7_3$, —$OCH_2X^7$, —$OCHX^7_2$, —$N_3$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}$ $OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^8_3$, —$CHX^8_2$, —$CH_2X^8$, —$OCX^8_3$, —$OCH_2X^8$, —$OCHX^8_2$, —$N_3$, —CN, —$SO_{n8}R^{8D}$, —$SO_{v8}NR^{8A}R^{8B}$, —$NHC(O)NR^{8A}R^{8B}$, —$N(O)_{m8}$, —$NR^{8A}R^{8B}$, —$C(O)R^{8C}$, —$C(O)$—$OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}$ $OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^9_3$, —$CHX^9_2$, —$CH_2X^9$, —$OCX^9_3$, —$OCH_2X^9$, —$OCHX^9_2$, —$N_3$, —CN, —$SO_{n9}R^{9D}$, —$SO_{v9}NR^{9A}R^{9B}$, —$NHC(O)NR^{9A}R^{9B}$, —$N(O)_{m9}$, —$NR^{9A}R^{9B}$, —$C(O)R^{9C}$, —$C(O)$—$OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}$ $OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, —$CX^{10}_3$, —$CHX^{10}_2$, —$CH_2X^{10}$, —$OCX^{10}_3$, —$OCH_2X^{10}$, —$OCHX^{10}_2$, —$N_3$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-N_3$, $-CN$, $-SO_{n11}R^{11D}$, $-SO_{v11}NR^{11A}R^{11B}$, $-NHC(O)NR^{11A}R^{11B}$, $-N(O)_{m11}$, $-NR^{11A}R^{11B}$, $-C(O)R^{11C}$, $-C(O)-OR^{11C}$, $-C(O)NR^{11A}R^{11B}$, $-OR^{11D}$, $-NR^{11A}SO_2R^{11D}$, $-NR^{11A}C(O)R^{11C}$, $-NR^{11A}C(O)OR^{11C}$, $-NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, $-CX^{13}_3$, $-CHX^{13}_2$, $-CH_2X^{13}$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently $-F$, $-Cl$, $-Br$, or $-I$, or a salt thereof, provided that:

when $R^4$ and $R^5$ together with atoms attached thereto are joined to form unsubstituted phenyl, $L^1$ is a bond, $R^1$ is $-OH$ or $-OCH_3$, and $R^7$, $R^8$ and $R^9$ are hydrogen, then $R^6$ or $R^{10}$ is not $-C(O)NH_2$;

when $R^4$ and $R^5$ together with atoms attached thereto are joined to form unsubstituted phenyl, $L^1$ is $-S-$ or $-S(O)_2-$, $R^1$ is $-OH$, and $R^6$, $R^7$, $R^9$ and $R^{10}$ are hydrogen, then $R^8$ is not hydrogen, $-Cl$ or $-CH_3$;

when $R^4$ and $R^5$ together with atoms attached thereto are joined to form unsubstituted phenyl, $L^1$ is $-S(O)_2-$, $R^1$ is $-OCH_3$, and $R^6$, $R^7$, $R^9$ and $R^{10}$ are hydrogen, then $R^8$ is not hydrogen or $-CH_3$;

when $R^4$ and $R^5$ together with atoms attached thereto are joined to form unsubstituted phenyl, $L^1$ is $-NHS(O)_2-$ or $-NH-$, $R^1$ is $-OH$ or $-OCH_3$, and $R^6$, $R^7$, $R^9$ and $R^{10}$ are hydrogen, then $R^8$ is not hydrogen, $-Cl$ or $-CH_3$;

when $R^4$ and $R^5$ together with atoms attached thereto are joined to form unsubstituted phenyl, $L^1$ is $-NHC(O)-$, $R^1$ is $-OH$ or $-OCH_3$, and $R^6$, $R^7$, $R^9$ and $R^{10}$ are hydrogen, then $R^8$ is not hydrogen, $-Cl$, $-Br$, $-CH_3$, $-C(CH_3)_3$, $-OH$, or $-OCH_3$;

when $R^4$ and $R^5$ together with atoms attached thereto are joined to form unsubstituted phenyl, $L^1$ is $-NHC(O)-$, $R^1$ is $-OH$ or $-OCH_3$, and $R^6$, $R^7$, $R^9$ and $R^{10}$ are hydrogen, then $R^8$ is not hydrogen, $-Cl$, $-Br$, $-CH_3$, $-C(CH_3)_3$, $-OH$, or $-OCH_3$;

when $R^4$ and $R^5$ together with atoms attached thereto are joined to form unsubstituted phenyl, $L^1$ is $-NHC(O)-$, $R^1$ is $-OH$ or $-OCH_3$, and $R^6$, $R^8$ and $R^{10}$ are hydrogen, then $R^7$ or $R^9$ is not $-Cl$, $-Br$, $-CH_3$, $-OH$, or $-OCH_3$;

when $R^4$ and $R^5$ together with atoms attached thereto are joined to form unsubstituted phenyl, $L^1$ is $-NHC(O)-$, $R^1$ is $-OH$ or $-OCH_3$, and $R^7$, $R^8$ and $R^9$ are hydrogen, then $R^6$ or $R^{10}$ is not $-Cl$, $-Br$, $-CH_3$, $-OH$, or $-OCH_3$;

when $R^4$ and $R^5$ together with atoms attached thereto are joined to form unsubstituted phenyl, $L^1$ is $-NHC(O)-$, and $R^1$ is $-OH$ or $-OCH_3$, then at least one of $R^6$, $R^7$ and $R^8$ are not $-OCH_3$, or at least one of $R^8$, $R^9$ and $R^{10}$ are not $-OCH_3$.

Embodiment 2. The compound of Embodiment 1, wherein the compound has a formula (IIA):

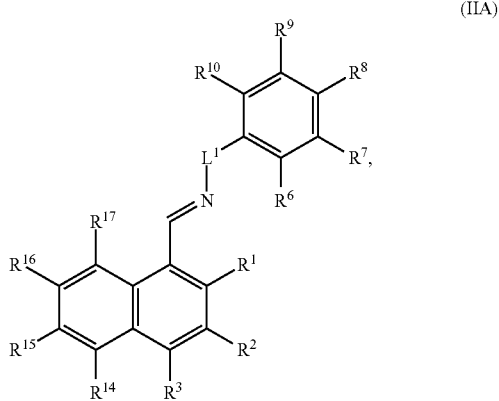

(IIA)

wherein:

$R^{14}$ is hydrogen, halogen, $-CX^{14}_3$, $-CHX^{14}_2$, $-CH_2X^{14}$, $-OCX^{14}_3$, $-OCH_2X^{14}$, $OCHX^{14}_2$, $-N_3$, $-CN$, $-SO_{n14}R^{14D}$, $-SO_{v14}NR^{14A}R^{14B}$, $-NHC(O)NR^{14A}R^{14B}$, $-N(O)_{m14}$, $-NR^{14A}R^{14B}$, $-C(O)R^{14C}$, $-C(O)-OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)OR^{14C}$, $-NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $-CX^{15}_3$, $-CHX^{15}_2$, $-CH_2X^{15}$, $-OCX^{15}_3$, $-OCH_2X^{15}$, $-OCHX^{15}_2$, $-N_3$, $-CN$, $-SO_{n15}R^{15D}$, $-SO_{v15}NR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, $-CX^{16}_3$, $-CHX^{16}_2$, $-CH_2X^{16}$, $-OCX^{16}_3$, $-OCH_2X^{16}$, $-OCHX^{16}_2$, $-N_3$, $-CN$, $-SO_{n16}R^{16D}$, $-SO_{v16}NR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-N_3$, $-CN$, $-SO_{n17}R^{17D}$, $-SO_{v17}NR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}$, $X^{15}$, $X^{16}$, and $X^{17}$ are independently $-F$, $-Cl$, $-Br$, or $-I$.

Embodiment 3. The compound of any one of Embodiments 1-2, wherein $L^1$ is $-O-$ or $-S-$.

Embodiments 4. The compound of any one of Embodiments 1-2, wherein $L^1$ is a bond.

Embodiment 5. The compound of any one of Embodiments 1-2, wherein $L^1$ is $-S(O)-$, $-S(O)_2-$, $-NR^{13}S(O)-$, $-NR^{13}S(O)_2-$ or $-NR^{13}C(O)-$.

Embodiment 6. The compound of any one of Embodiments 1-5, wherein at least one of $R^1$, $R^2$ and $R^3$ are $-OH$ or $-OCH_3$.

Embodiment 7. The compound of any one of Embodiments 1-6, wherein $R^7$ and $R^9$ are hydrogen.

Embodiment 8. The compound of any one of Embodiments 1-7, wherein each $R^6$, $R^8$, and $R^{10}$ is independently hydrogen, halogen, $-N_3$, $-CN$, $-NO_2$, $-NH_2$, $-C(O)H$, $-C(O)CH_3$, $-C(O)OH$, $-C(O)OCH_3$, $-C(O)NH_2$, $-OH$, $-OCH_3$, or substituted or unsubstituted $C_1-C_3$ alkyl.

Embodiment 9. The compound of any one of Embodiments 1-8, wherein the compound has a formula (III),

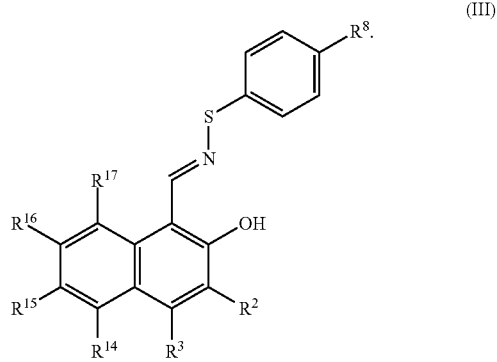

(III)

Embodiment 10. The compound of any one of Embodiments 1-8, wherein the compound has a formula (IV),

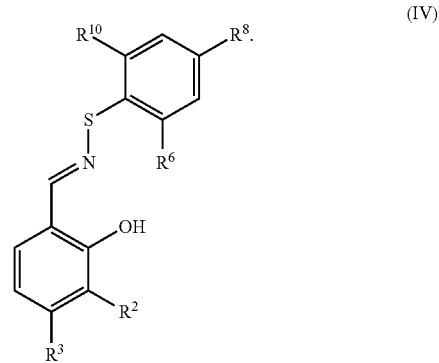

(IV)

Embodiment 11. The compound of any one of Embodiments 1-8, wherein the compound has a formula (V),

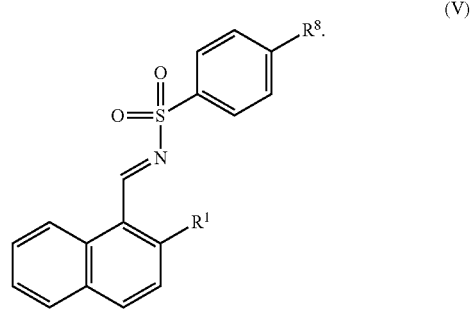

(V)

Embodiment 12. The compound of any one of Embodiments 1-8, wherein the compound has a formula (VI), (VI)

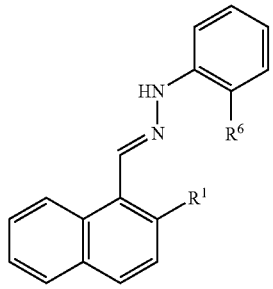

Embodiment 13. The compound of any one of Embodiments 1-8, wherein the compound has a formula (VII), (VII)

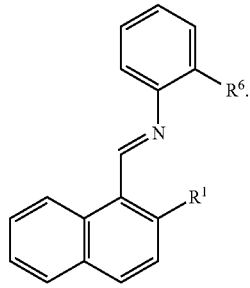

Embodiment 14. The compound of Embodiment 1, wherein the compound has a formula (VIII), (VIII)

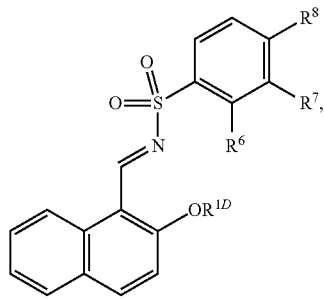

wherein:
$R^{1D}$ is hydrogen or unsubstituted $C_1$-$C_4$ alkyl;
$R^6$ is hydrogen or —C(O)—$OR^{6C}$;
$R^7$ is hydrogen or halogen; and
$R^8$ is halogen, —$OR^{8D}$, —C(O)—$OR^{8C}$, or unsubstituted $C_2$-$C_4$ alkyl.

Embodiment 15. The compound of Embodiment 14, wherein $R^{1D}$, $R^{6C}$, $R^{8C}$, and $R^{8D}$ are independently hydrogen or —$CH_3$.

Embodiment 16. The compound of Embodiment 15, wherein:
$R^{1D}$ is hydrogen;
$R^6$ and $R^7$ are hydrogen; and
$R^8$ is —OH, —$OCH_3$, —COOH, —Br, or —$C(CH_3)_3$.

Embodiment 17. The compound of Embodiment 15, wherein:
$R^{1D}$ is —$CH_3$;
$R^6$ and $R^7$ are hydrogen; and
$R^8$ is —OH, —$OCH_3$, —COOH, —$COOCH_3$, —Cl, —Br, or —$C(CH_3)_3$.

Embodiment 18. The compound of Embodiment 15, wherein:
$R^{1D}$ is hydrogen or —$CH_3$;
$R^6$ is hydrogen; and
$R^7$ and $R^8$ are halogen.

Embodiment 19. The compound of Embodiment 15, wherein:
$R^{1D}$ is hydrogen or —$CH_3$;
$R^7$ is halogen; and
$R^7$ and $R^8$ are hydrogen.

Embodiment 20. The compound of Embodiment 15, wherein:
$R^{1D}$ is hydrogen or —$CH_3$;
$R^6$ is —C(O)—$OR^{6C}$; and
$R^7$ and $R^8$ are hydrogen.

Embodiment 21. The compound of Embodiment 1, wherein the compound has a formula (IX), (IX)

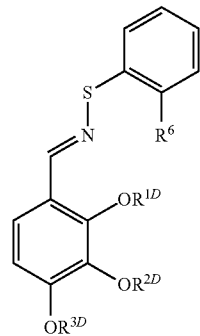

wherein:
$R^{1D}$, $R^{2D}$, and $R^{3D}$ are independently hydrogen or unsubstituted $C_1$-$C_4$ alkyl; and
$R^6$ is hydrogen, halogen, —C(O)—$OR^{6C}$, —$OR^{6D}$, or unsubstituted $C_1$-$C_4$ alkyl.

Embodiment 22. The compound of Embodiment 21, wherein:
$R^{1D}$, $R^{2D}$, and $R^{3D}$ are independently hydrogen or —$CH_3$; and
$R^{6C}$ and $R^{6D}$ are independently hydrogen or —$CH_3$.

Embodiment 23. The compound of any one of Embodiments 1-22, wherein the compound is:

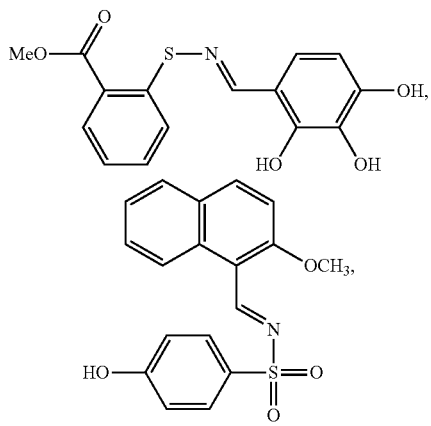

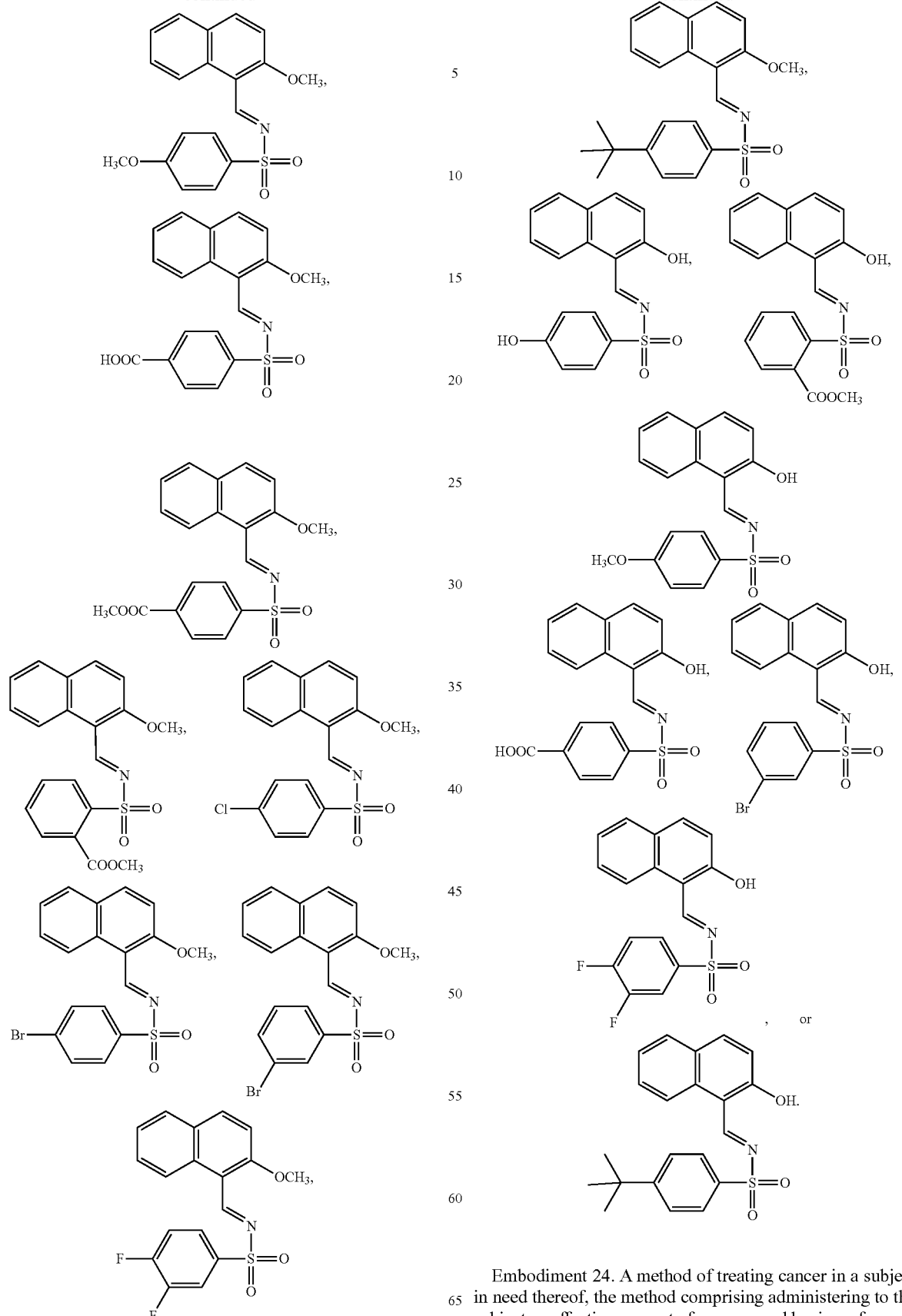
Embodiment 24. A method of treating cancer in a subject in need thereof, the method comprising administering to the subject an effective amount of a compound having a formula (I),

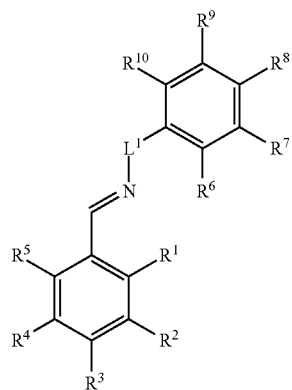

(I)

wherein:
L¹ is a bond, —CR¹¹R¹²—, —NR¹³—, —O—, —S—, —S(O)—, —S(O)₂—, —NR¹³S(O)—, —NR¹³S(O)₂—, or —NR¹³C(O)—;

R¹ is hydrogen, halogen, —CX¹₃, —CHX¹₂, —CH₂X¹, —OCX¹₃, —OCH₂X¹, —OCHX¹₂, —N₃, —CN, —SO$_{n1}$R¹ᴰ, —SO$_{v1}$NR¹ᴬR¹ᴮ, —NHC(O)NR¹ᴬR¹ᴮ, —N(O)$_{m1}$, —NR¹ᴬR¹ᴮ, —C(O)R¹ᶜ, C(O)—OR¹ᶜ, —C(O)NR¹ᴬR¹ᴮ, —OR¹ᴰ, —NR¹ᴬSO₂R¹ᴰ, —NR¹ᴬC(O)R¹ᶜ, —NR¹ᴬC(O)OR¹ᶜ, —NR¹ᴬOR¹ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R² is hydrogen, halogen, —CX²₃, —CHX²₂, —CH₂X², —OCX²₃, —OCH₂X², —OCHX²₂, —N₃, —CN, —SO$_{n2}$R²ᴰ, —SO$_{v2}$NR²ᴬR²ᴮ, —NHC(O)NR²ᴬR²ᴮ, —N(O)$_{m2}$, —NR²ᴬR²ᴮ, —C(O)R²ᶜ, C(O)—OR²ᶜ, —C(O)NR²ᴬR²ᴮ, —OR²ᴰ, —NR²ᴬSO₂R²ᴰ, —NR²ᴬC(O)R²ᶜ, —NR²ᴬC(O)OR²ᶜ, —NR²ᴬOR²ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R³ is hydrogen, halogen, —CX³₃, —CHX³₂, —CH₂X³, —OCX³₃, —OCH₂X³, —OCHX³₂, —N₃, —CN, —SO$_{n3}$R³ᴰ, —SO$_{v3}$NR³ᴬR³ᴮ, —NHC(O)NR³ᴬR³ᴮ, —N(O)$_{m3}$, —NR³ᴬR³ᴮ, —C(O)R³ᶜ, C(O)—OR³ᶜ, —C(O)NR³ᴬR³ᴮ, —OR³ᴰ, —NR³ᴬSO₂R³ᴰ, —NR³ᴬC(O)R³ᶜ, —NR³ᴬC(O)OR³ᶜ, —NR³ᴬOR³ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁴ is hydrogen, halogen, —CX⁴₃, —CHX⁴₂, —CH₂X⁴, —OCX⁴₃, —OCH₂X⁴, —OCHX⁴₂, —N₃, —CN, —SO$_{n4}$R⁴ᴰ, —SO$_{v4}$NR⁴ᴬR⁴ᴮ, —NHC(O)NR⁴ᴬR⁴ᴮ, —N(O)$_{m4}$, —NR⁴ᴬR⁴ᴮ, —C(O)R⁴ᶜ, C(O)—OR⁴ᶜ, —C(O)NR⁴ᴬR⁴ᴮ, —OR⁴ᴰ, —NR⁴ᴬSO₂R⁴ᴰ, —NR⁴ᴬC(O)R⁴ᶜ, —NR⁴ᴬC(O)OR⁴ᶜ, —NR⁴ᴬOR⁴ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁵ is hydrogen, halogen, —CX⁵₃, —CHX⁵₂, —CH₂X⁵, —OCX⁵₃, —OCH₂X⁵, —OCHX⁵₂, —N₃, —CN, —SO$_{n5}$R⁵ᴰ, —SO$_{v5}$NR⁵ᴬR⁵ᴮ, —NHC(O)NR⁵ᴬR⁵ᴮ, —N(O)$_{m5}$, —NR⁵ᴬR⁵ᴮ, —C(O)R⁵ᶜ, C(O)—OR⁵ᶜ, —C(O)NR⁵ᴬR⁵ᴮ, —OR⁵ᴰ, —NR⁵ᴬSO₂R⁵ᴰ, —NR⁵ᴬC(O)R⁵ᶜ, —NR⁵ᴬC(O)OR⁵ᶜ, —NR⁵ᴬOR⁵ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁶ is hydrogen, halogen, —CX⁶₃, —CHX⁶₂, —CH₂X⁶, —OCX⁶₃, —OCH₂X⁶, —OCHX⁶₂, —N₃, —CN, —SO$_{n6}$R⁶ᴰ, —SO$_{v6}$NR⁶ᴬR⁶ᴮ, —NHC(O)NR⁶ᴬR⁶ᴮ, —N(O)$_{m6}$, —NR⁶ᴬR⁶ᴮ, —C(O)R⁶ᶜ, C(O)—OR⁶ᶜ, —C(O)NR⁶ᴬR⁶ᴮ, —OR⁶ᴰ, —NR⁶ᴬSO₂R⁶ᴰ, —NR⁶ᴬC(O)R⁶ᶜ, —NR⁶ᴬC(O)OR⁶ᶜ, —NR⁶ᴬOR⁶ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁷ is hydrogen, halogen, —CX⁷₃, —CHX⁷₂, —CH₂X⁷, —OCX⁷₃, —OCH₂X⁷, —OCHX⁷₂, —N₃, —CN, —SO$_{n7}$R⁷ᴰ, —SO$_{v7}$NR⁷ᴬR⁷ᴮ, —NHC(O)NR⁷ᴬR⁷ᴮ, —N(O)$_{m7}$, —NR⁷ᴬR⁷ᴮ, —C(O)R⁷ᶜ, C(O)—OR⁷ᶜ, —C(O)NR⁷ᴬR⁷ᴮ, —OR⁷ᴰ, —NR⁷ᴬSO₂R⁷ᴰ, —NR⁷ᴬC(O)R⁷ᶜ, —NR⁷ᴬC(O)OR⁷ᶜ, —NR⁷ᴬOR⁷ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁸ is hydrogen, halogen, —CX⁸₃, —CHX⁸₂, —CH₂X⁸, —OCX⁸₃, —OCH₂X⁸, —OCHX⁸₂, —N₃, —CN, —SO$_{n8}$R⁸ᴰ, —SO$_{v8}$NR⁸ᴬR⁸ᴮ, —NHC(O)NR⁸ᴬR⁸ᴮ, —N(O)$_{m8}$, —NR⁸ᴬR⁸ᴮ, —C(O)R⁸ᶜ, C(O)—OR⁸ᶜ, —C(O)NR⁸ᴬR⁸ᴮ, —OR⁸ᴰ, —NR⁸ᴬSO₂R⁸ᴰ, —NR⁸ᴬC(O)R⁸ᶜ, —NR⁸ᴬC(O)OR⁸ᶜ, —NR⁸ᴬOR⁸ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R⁹ is hydrogen, halogen, —CX⁹₃, —CHX⁹₂, —CH₂X⁹, —OCX⁹₃, —OCH₂X⁹, —OCHX⁹₂, —N₃, —CN, —SO$_{n9}$R⁹ᴰ, —SO$_{v9}$NR⁹ᴬR⁹ᴮ, —NHC(O)NR⁹ᴬR⁹ᴮ, —N(O)$_{m9}$, —NR⁹ᴬR⁹ᴮ, —C(O)R⁹ᶜ, C(O)—OR⁹ᶜ, —C(O)NR⁹ᴬR⁹ᴮ, —OR⁹ᴰ, —NR⁹ᴬSO₂R⁹ᴰ, —NR⁹ᴬC(O)R⁹ᶜ, —NR⁹ᴬC(O)OR⁹ᶜ, —NR⁹ᴬOR⁹ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R¹⁰ is hydrogen, halogen, —CX¹⁰₃, —CHX¹⁰₂, —CH₂X¹⁰, —OCX¹⁰₃, —OCH₂X¹⁰, —OCHX¹⁰₂, —N₃, —CN, —SO$_{n10}$R¹⁰ᴰ, —SO$_{v10}$NR¹⁰ᴬR¹⁰ᴮ, —NHC(O)NR¹⁰ᴬR¹⁰ᴮ, —N(O)$_{m10}$, —NR¹⁰ᴬR¹⁰ᴮ, —C(O)R¹⁰ᶜ, —C(O)—OR¹⁰ᶜ, —C(O)NR¹⁰ᴬR¹⁰ᴮ, —OR¹⁰ᴰ, —NR¹⁰ᴬSO₂R¹⁰ᴰ, —NR¹⁰ᴬC(O)R¹⁰ᶜ, —NR¹⁰ᴬC(O)OR¹⁰ᶜ, —NR¹⁰ᴬOR¹⁰ᶜ, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

215

$R^{11}$ is hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O) R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, —CX$^{13}_3$, —CHX$^{13}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, X$^1$, X$^2$, X$^3$, X$^4$, X$^5$, X$^6$, X$^7$, X$^8$, X$^9$, X$^{10}$, X$^{11}$, X$^{12}$, and X$^{13}$ are independently —F, —Cl, —Br, or —I, or a salt thereof.

216

Embodiment 25. The method of Embodiment 24, wherein the compound has a formula (II):

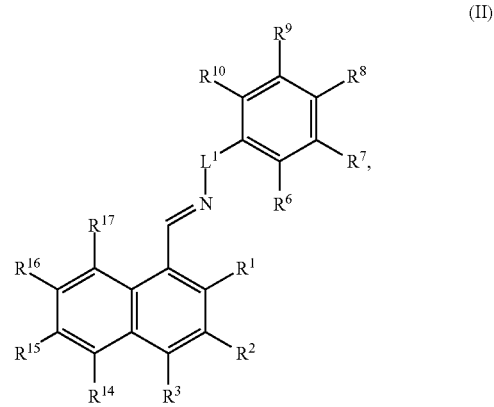

(II)

wherein:

$R^{14}$ is hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —N$_3$, —CN, —SO$_{n14}$R$^{14D}$, —SO$_{v14}$NR$^{14A}$R$^{14B}$, —NHC(O)NR$^{14A}$R$^{14B}$, —N(O)$_{m14}$, —NR$^{14A}$R$^{14B}$, —C(O)R$^{14C}$, —C(O)—OR$^{14C}$, —C(O)NR$^{14A}$R$^{14B}$, —OR$^{14D}$, —NR$^{14A}$SO$_2$R$^{14D}$, —NR$^{14A}$C(O) R$^{14C}$, —NR$^{14A}$C(O)OR$^{14C}$, —NR$^{14A}$OR$^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —N$_3$, —CN, —SO$_{n15}$R$^{15D}$, —SO$_{v15}$NR$^{15A}$R$^{15B}$, —NHC(O)NR$^{15A}$R$^{15B}$, —N(O)$_{m15}$, —NR$^{15A}$R$^{15B}$, —C(O)R$^{15C}$, —C(O)—OR$^{15C}$, —C(O)NR$^{15A}$R$^{15B}$, —OR$^{15D}$, —NR$^{15A}$SO$_2$R$^{15D}$, —NR$^{15A}$C(O) R$^{15C}$, —NR$^{15A}$C(O)OR$^{15C}$, —NR$^{15A}$OR$^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —N$_3$, —CN, —SO$_{n16}$R$^{16D}$, —SO$_{v16}$NR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O) R$^{16C}$, —NR$^{16A}$C(O)OR$^{16C}$, —NR$^{16A}$OR$^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —N$_3$, —CN, —SO$_{n17}$R$^{17D}$, —SO$_{v17}$NR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O) R$^{17C}$, —NR$^{17A}$C(O)OR$^{17C}$, —NR$^{17A}$OR$^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, —$CX_3$, —$CHX_2$, —$CH_2X$, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and $X^{14}$, $X^{15}$, $X^{16}$, and $X^{17}$ are independently —F, —Cl, —Br, or —I.

Embodiment 26. The method of any one of Embodiments 24-25, wherein $L^1$ is —O— or —S—.

Embodiment 27. The method of any one of Embodiments 24-25, wherein $L^1$ is a bond.

Embodiment 28. The method of any one of Embodiments 24-25, wherein $L^1$ is —$S(O)_2$—, —$NR^{13}S(O)_2$— or —$NR^{13}C(O)$—.

Embodiment 29. The method of any one of Embodiments 24-28, wherein at least one of $R^1$, $R^2$ and $R^3$ are —OH or —$OCH_3$.

Embodiment 30. The method of any one of Embodiments 24-29, wherein $R^7$ and $R^9$ are hydrogen.

Embodiment 31. The method of any one of Embodiments 24-30, wherein each $R^6$, $R^8$, and $R^{10}$ is independently hydrogen, halogen, —$N_3$, —CN, —$NO_2$, —$NH_2$, —C(O)H, —$C(O)CH_3$, —C(O)OH, —$C(O)OCH_3$, —$C(O)NH_2$, —OH, —$OCH_3$, or substituted or unsubstituted $C_1$-$C_3$ alkyl.

Embodiment 32. The method of any one of Embodiments 24-31, wherein the compound has a formula (III),

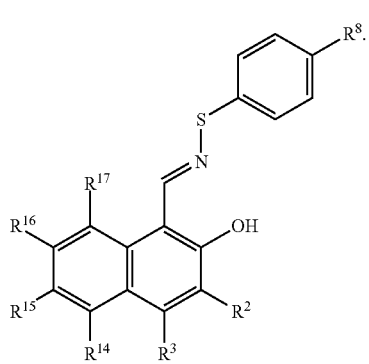
(III)

Embodiment 33. The method of any one of Embodiments 24-31, wherein the compound has a formula (IV),

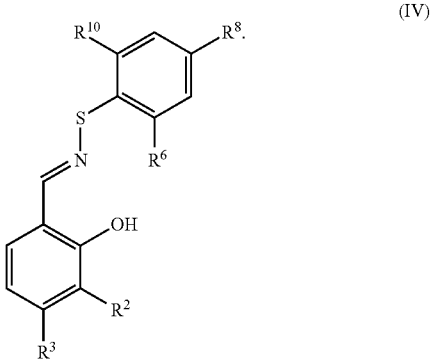
(IV)

Embodiment 34. The method of any one of Embodiments 24-31, wherein the compound has a formula (V),

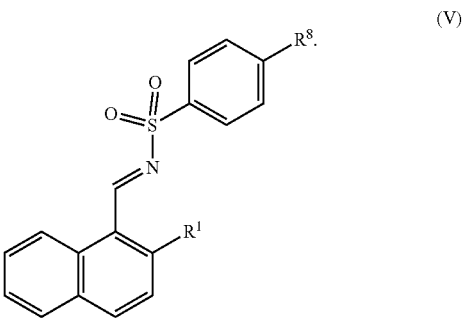
(V)

Embodiment 35. The method of any one of Embodiments 24-31, wherein the compound has a formula (VI),

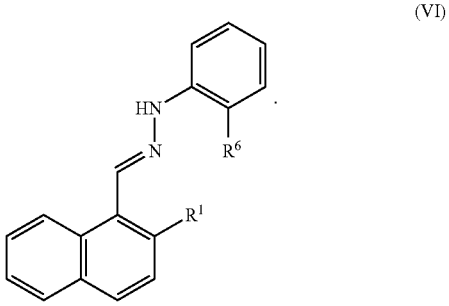
(VI)

Embodiment 36. The method of any one of Embodiments 24-31, wherein the compound has a formula (VII),

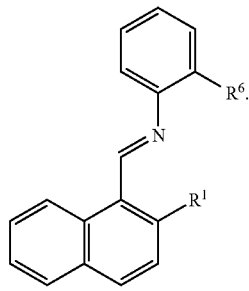

(VII)

Embodiment 37. The method of Embodiment 24, wherein the compound has a formula (VIII),

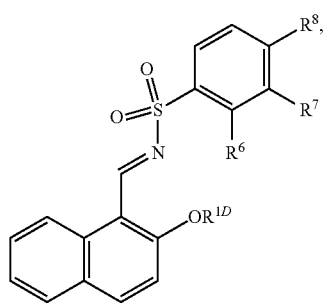

(VIII)

wherein:
$R^{1D}$ is hydrogen or unsubstituted $C_1$-$C_4$ alkyl;
$R^6$ is hydrogen or —C(O)—$OR^{6C}$;
$R^7$ is hydrogen or halogen; and
$R_8$ is halogen, —$OR^{8D}$, —C(O)—$OR^{8C}$, or unsubstituted $C_2$-$C_4$ alkyl.

Embodiment 38. The method of Embodiment 37, wherein $R^{1D}$, $R^{6C}$, $R^{8C}$, and $R^{8D}$ are independently hydrogen or —$CH_3$.

Embodiment 39. The method of Embodiment 38, wherein:
$R^{1D}$ is hydrogen;
$R^6$ and $R^7$ are hydrogen; and
$R^8$ is —OH, —$OCH_3$, —COOH, —Br, or —$C(CH_3)_3$.

Embodiment 40. The method of Embodiment 38, wherein:
$R^{1D}$ is —$CH_3$;
$R^6$ and $R^7$ are hydrogen; and
$R^8$ is —OH, —$OCH_3$, —COOH, —$COOCH_3$, —Cl, —Br, or —$C(CH_3)_3$.

Embodiment 41. The method of Embodiment 38, wherein:
$R^{1D}$ is hydrogen or —$CH_3$;
$R^6$ is hydrogen; and
$R^7$ and $R^8$ are halogen.

Embodiment 42. The method of Embodiment 38, wherein:
$R^{1D}$ is hydrogen or —$CH_3$;
$R^7$ is halogen; and
$R^7$ and $R^8$ are hydrogen.

Embodiment 43. The method of Embodiment 38, wherein:
$R^{1D}$ is hydrogen or —$CH_3$;
$R^6$ is —C(O)—$OR^{6C}$; and
$R^7$ and $R^8$ are hydrogen.

Embodiment 44. The method of Embodiment 24, wherein the compound has a formula (IX).

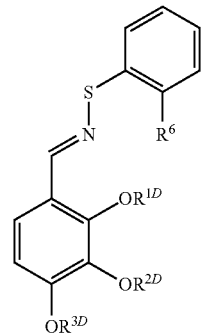

(IX)

wherein:
$R^{1D}$, $R^{2D}$, and $R^{3D}$ are independently hydrogen or unsubstituted $C_1$-$C_4$ alkyl; and
$R^6$ is hydrogen, halogen, —C(O)—$OR^{6C}$, —$OR^{6D}$, or unsubstituted $C_1$-$C_4$ alkyl.

Embodiment 45. The method of Embodiment 44, wherein:
$R^{1D}$, $R^{2D}$, and $R^{3D}$ are independently hydrogen or —$CH_3$; and
$R^{6C}$ and $R^{6D}$ are independently hydrogen or —$CH_3$.

Embodiment 46. The method of any one of Embodiments 24-45, wherein the compound is

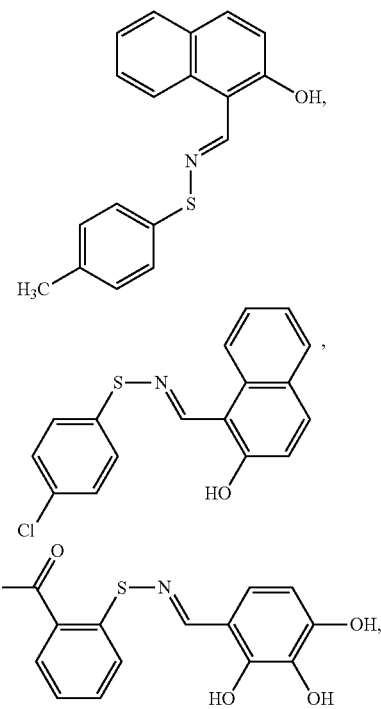

221
-continued
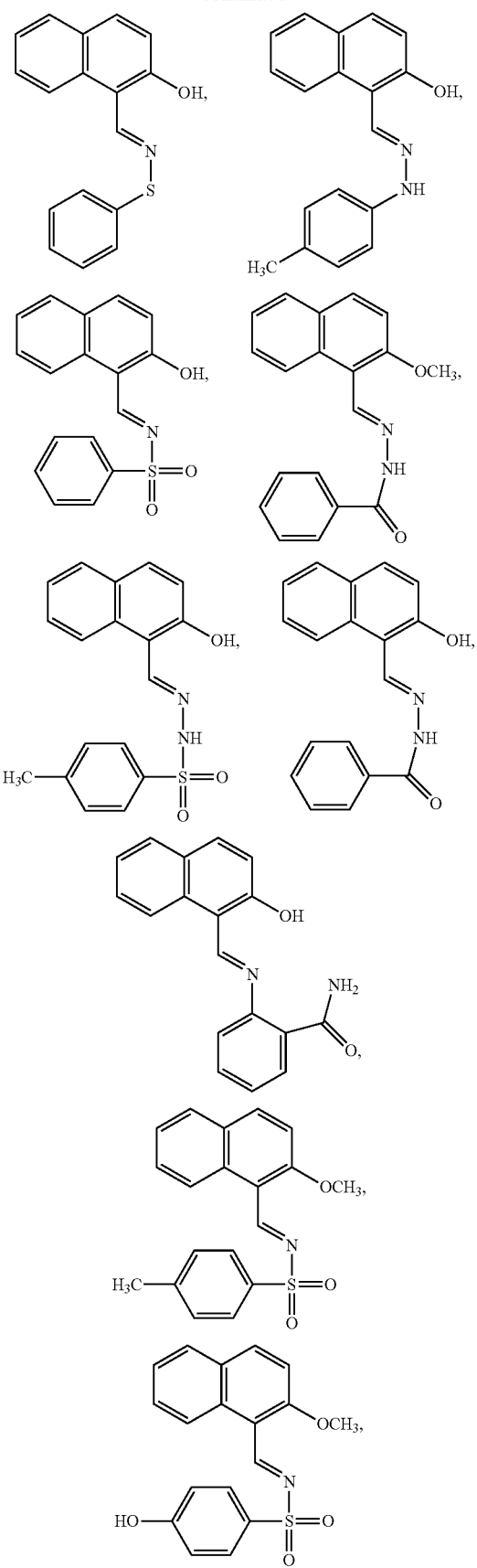
222
-continued
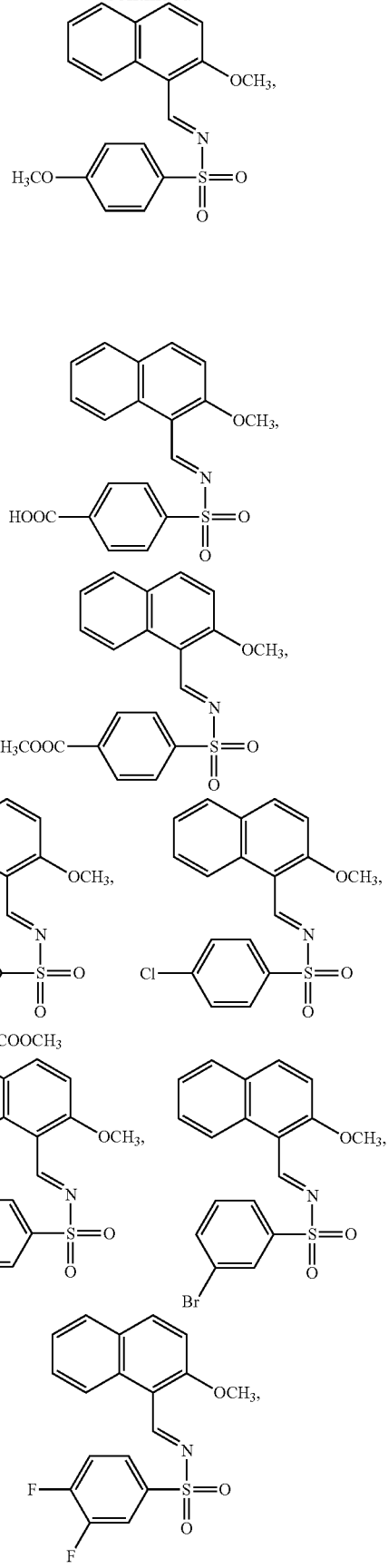

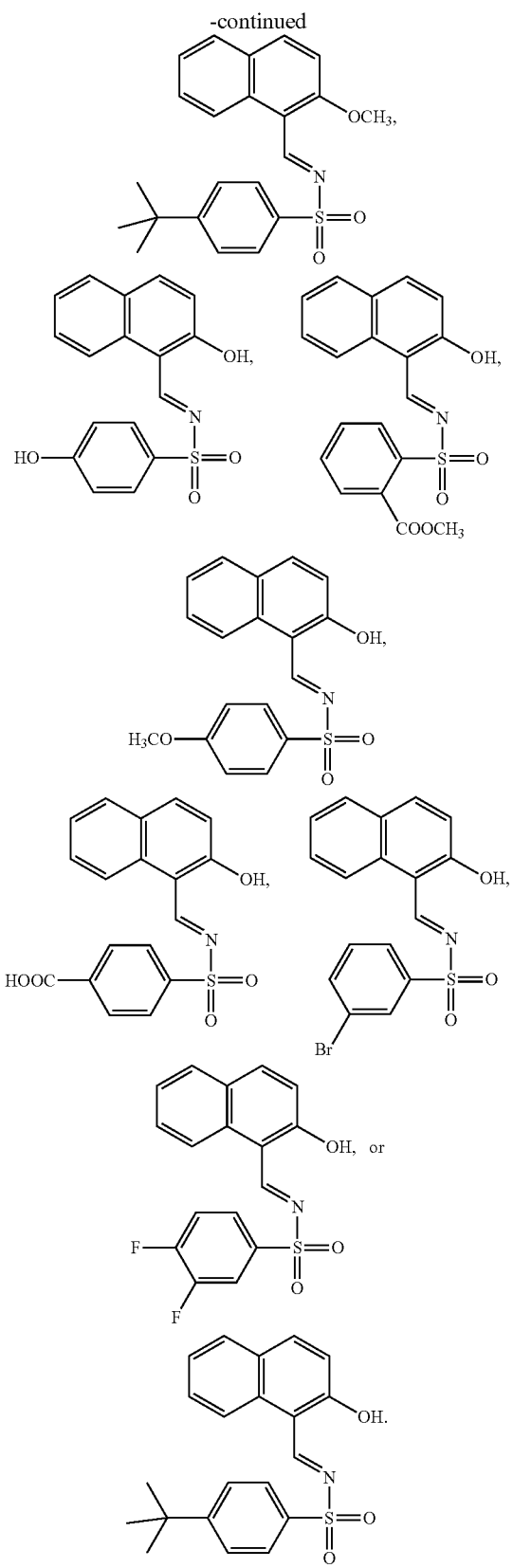

Embodiment 47. The method of any one of Embodiments 24-46, wherein the compound inhibits poly(ADP-ribose) glycohydrolase (PARG) in a cancer cell.

Embodiment 48. The method of any one of Embodiments 24-47, wherein the cancer is selected from: breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

Embodiment 49. The method of Embodiment 48, wherein the cancer is lymphoma.

Embodiment 50. A method of inhibiting a poly(ADP-ribose) glycohydrolase (PARG), the method comprising contacting the PARG with a compound having a formula (I),

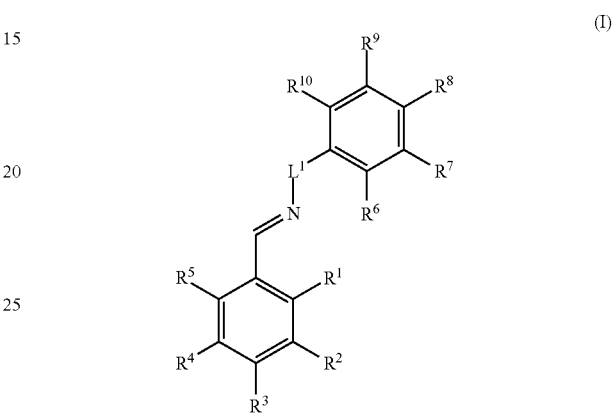

(I)

wherein:
L$^1$ is a bond, —CR$^{11}$R$^{12}$—, —NR$^{13}$—, —O—, —S—, —S(O)—, —S(O)$_2$—, —NR$^{13}$S(O)—, —NR$^{13}$S(O)$_2$—, or —NR$^{13}$C(O)—;

R$^1$ is hydrogen, halogen, —CX$^3_3$, —CHX$^1_2$, —CH$_2$X$^1$, —OCX$^1_3$, —OCH$_2$X$^1$, —OCHX$^1_2$, —N$_3$, —CN, —SO$_{n1}$R$^{1D}$, —SO$_{v1}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is hydrogen, halogen, —CX$^2_3$, —CHX$^2_2$, —CH$_2$X$^2$, —OCX$^2_3$, —OCH$_2$X$^2$, —OCHX$^2_2$, —N$_3$, —CN, —SO$_{v2}$R$^{2D}$, —SO$_{v2}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen, halogen, —CX$^3_3$, —CHX$^3_2$, —CH$_2$X$^3$, —OCX$^3_3$, —OCH$_2$X$^3$, —OCHX$^3_2$, —N$_3$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —CX$^4{}_3$, —CHX$^4{}_2$, —CH$_2$X$^4$, —OCX$^4{}_3$, —OCH$_2$X$^4$, —OCHX$^4{}_2$, —N$_3$, —CN, —SO$_{n4}$R$^{4D}$, —SO$_{v4}$NR$^{4A}$R$^{4B}$, —NHC(O)NR$^{4A}$R$^{4B}$, —N(O)$_{m4}$, —NR$^{4A}$R$^{4B}$, —C(O)R$^{4C}$, —C(O)—OR$^{4C}$, —C(O)NR$^{4A}$R$^{4B}$, —OR$^{4D}$, —NR$^{4A}$SO$_2$R$^{4D}$, —NR$^{4A}$C(O)R$^{4C}$, —NR$^{4A}$C(O)OR$^{4C}$, —NR$^{4A}$OR$^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —CX$^5{}_3$, —CHX$^5{}_2$, —CH$_2$X$^5$, —OCX$^5{}_3$, —OCH$_2$X$^5$, —OCHX$^5{}_2$, —N$_3$, —CN, —SO$_{n5}$R$^{5D}$, —SO$_{v5}$NR$^{5A}$R$^{5B}$, —NHC(O)NR$^{5A}$R$^{5B}$, —N(O)$_{m5}$, —NR$^{5A}$R$^{5B}$, —C(O)R$^{5C}$, —C(O)—OR$^{5C}$, —C(O)NR$^{5A}$R$^{5B}$, —OR$^{5D}$, —NR$^{5A}$SO$_2$R$^{5D}$, —NR$^{5A}$C(O)R$^{5C}$, —NR$^{5A}$C(O)OR$^{5C}$, —NR$^{5A}$OR$^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is hydrogen, halogen, —CX$^6{}_3$, —CHX$^6{}_2$, —CH$_2$X$^6$, —OCX$^6{}_3$, —OCH$_2$X$^6$, —OCHX$^6{}_2$, —N$_3$, —CN, —SO$_{n6}$R$^{6D}$, —SO$_{v6}$NR$^{6A}$R$^{6B}$, —NHC(O)NR$^{6A}$R$^{6B}$, —N(O)$_{m6}$, —NR$^{6A}$R$^{6B}$, —C(O)R$^{6C}$, —C(O)—OR$^{6C}$, —C(O)NR$^{6A}$R$^{6B}$, —OR$^{6D}$, —NR$^{6A}$SO$_2$R$^{6D}$, —NR$^{6A}$C(O)R$^{6C}$, —NR$^{6A}$C(O)OR$^{6C}$, —NR$^{6A}$OR$^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$ is hydrogen, halogen, —CX$^7{}_3$, —CHX$^7{}_2$, —CH$_2$X$^7$, —OCX$^7{}_3$, —OCH$_2$X$^7$, —OCHX$^7{}_2$, —N$_3$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, —NR$^{7A}$SO$_2$R$^{7D}$, —NR$^{7A}$C(O)R$^{7C}$, —NR$^{7A}$C(O)OR$^{7C}$, —NR$^{7A}$OR$^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^8$ is hydrogen, halogen, —CX$^8{}_3$, —CHX$^8{}_2$, —CH$_2$X$^8$, —OCX$^8{}_3$, —OCH$_2$X$^8$, —OCHX$^8{}_2$, —N$_3$, —CN, —SO$_{n8}$R$^{8D}$, —SO$_{v8}$NR$^{8A}$R$^{8B}$, —NHC(O)NR$^{8A}$R$^{8B}$, —N(O)$_{m8}$, —NR$^{8A}$R$^{8B}$, —C(O)R$^{8C}$, —C(O)—OR$^{8C}$, —C(O)NR$^{8A}$R$^{8B}$, —OR$^{8D}$, —NR$^{8A}$SO$_2$R$^{8D}$, —NR$^{8A}$C(O)R$^{8C}$, —NR$^{8A}$C(O)OR$^{8C}$, —NR$^{8A}$OR$^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^9$ is hydrogen, halogen, —CX$^9{}_3$, —CHX$^9{}_2$, —CH$_2$X$^9$, —OCX$^9{}_3$, —OCH$_2$X$^9$, —OCHX$^9{}_2$, —N$_3$, —CN, —SO$_{v9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O)R$^{9C}$, —NR$^{9A}$C(O)OR$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10}$ is hydrogen, halogen, —CX$^{10}{}_3$, —CHX$^{10}{}_2$, —CH$_2$X$^{10}$, —OCX$^{10}{}_3$, —OCH$_2$X$^{10}$, —OCHX$^{10}{}_2$, —N$_3$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{11}$ is hydrogen, halogen, —CX$^{11}{}_3$, —CHX$^{11}{}_2$, —CH$_2$X$^{11}$, —OCX$^{11}{}_3$, —OCH$_2$X$^{11}$, —OCHX$^{11}{}_2$, —N$_3$, —CN, —SO$_{n11}$R$^{11D}$, —SO$_{v11}$NR$^{11A}$R$^{11B}$, —NHC(O)NR$^{11A}$R$^{11B}$, —N(O)$_{m11}$, —NR$^{11A}$R$^{11B}$, —C(O)R$^{11C}$, —C(O)—OR$^{11C}$, —C(O)NR$^{11A}$R$^{11B}$, —OR$^{11D}$, —NR$^{11A}$SO$_2$R$^{11D}$, —NR$^{11A}$C(O)R$^{11C}$, —NR$^{11A}$C(O)OR$^{11C}$, —NR$^{11A}$OR$^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{12}$ is hydrogen, halogen, —CX$^{12}{}_3$, —CHX$^{12}{}_2$, —CH$_2$X$^{12}$, —OCX$^{12}{}_3$, —OCH$_2$X$^{12}$, —OCHX$^{12}{}_2$, —N$_3$, —CN, —SO$_{n12}$R$^{12D}$, —SO$_{v12}$NR$^{12A}$R$^{12B}$, —NHC(O)NR$^{12A}$R$^{12B}$, —N(O)$_{m12}$, —NR$^{12A}$R$^{12B}$, —C(O)R$^{12C}$, —C(O)—OR$^{12C}$, —C(O)NR$^{12A}$R$^{12B}$, —OR$^{12D}$, —NR$^{12A}$SO$_2$R$^{12D}$, —NR$^{12A}$C(O)R$^{12C}$, —NR$^{12A}$C(O)OR$^{12C}$, —NR$^{12A}$OR$^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{13}$ is hydrogen, —CX$^{13}{}_3$, —CHX$^{13}{}_2$, —CH$_2$X$^{13}$, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{1C}$, R$^{1D}$, R$^{2A}$, R$^{2B}$, R$^{2C}$, R$^{2D}$, R$^{3A}$, R$^{3B}$, R$^{3C}$, R$^{3D}$, R$^{4A}$, R$^{4B}$, R$^{4C}$, R$^{4D}$, R$^{5A}$, R$^{5B}$, R$^{5C}$, R$^{5D}$, R$^{6A}$, R$^{6B}$, R$^{6C}$, R$^{6D}$, R$^{7A}$, R$^{7B}$, R$^{7C}$, R$^{7D}$, R$^{8A}$, R$^{8B}$, R$^{8C}$, R$^{8D}$, R$^{9A}$, R$^{9B}$, R$^{9C}$, R$^{9D}$, R$^{10A}$, R$^{10B}$, R$^{10C}$, R$^{10D}$, R$^{11A}$, R$^{11B}$, R$^{11C}$, R$^{11D}$, R$^{12A}$, R$^{12B}$, R$^{12C}$ and R$^{12D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^1$ and R$^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

R$^4$ and R$^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and X, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently —F, —Cl, —Br, or —I, or a salt thereof.

Embodiment 51. The method of Embodiment 50, wherein the compound has a formula (II):

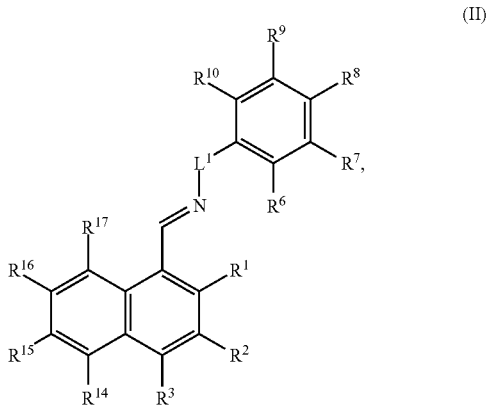

(II)

wherein:
- $R^{14}$ is hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-N_3$, $-CN$, $-SO_{n14}R^{14D}$, $-SO_{v14}NR^{14A}R^{14B}$, $-NHC(O)NR^{14A}R^{14B}$, $-N(O)_{m14}$, $-NR^{14A}R^{14B}$, $-C(O)R^{14C}$, $-C(O)-OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)OR^{14C}$, $-NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{15}$ is hydrogen, halogen, $-CX^{15}_3$, $-CHX^{15}_2$, $-CH_2X^{15}$, $-OCX^{15}_3$, $-OCH_2X^{15}$, $-OCHX^{15}_2$, $-N_3$, $-CN$, $-SO_{n15}R^{15D}$, $-SO_{v15}NR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)OR^{15C}$, $-NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{16}$ is hydrogen, halogen, $-CX^{16}_3$, $-CHX^{16}_2$, $-CH_2X^{16}$, $-OCX^{16}_3$, $-OCH_2X^{16}$, $-OCHX^{16}_2$, $-N_3$, $-CN$, $-SO_{n16}R^{16D}$, $-SO_{v16}NR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^{17}$ is hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-N_3$, $-CN$, $-SO_{n17}R^{17D}$, $-SO_{v17}NR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- Each $R^{14A}$, $R^{14B}$, $R^{14C}$, $R^{14D}$, $R^{15A}$, $R^{15B}$, $R^{15C}$, $R^{15D}$, $R^{16A}$, $R^{16B}$, $R^{16C}$, $R^{16D}$, $R^{17A}$, $R^{17B}$, $R^{17C}$, and $R^{17D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- n14, n15, n16, and n17 are independently an integer from 0 to 4;
- m14, m15, m16, m17, v14, v15, v16, and v17 are independently an integer from 1 to 2; and
- $X^{14}$, $X^{15}$, $X^{16}$, and $X^{17}$ are independently —F, —Cl, —Br, or —I.

Embodiment 52. The method of any one of Embodiments 50-51, wherein $L^1$ is —O— or —S—.

Embodiment 53. The method of any one of Embodiments 50-51, wherein $L^1$ is a bond.

Embodiment 54. The method of any one of Embodiments 50-51, wherein $L^1$ is $-S(O)_2-$, $-NR^{13}S(O)_2-$ or $-NR^{13}C(O)-$ Embodiment 55. The method of any one of Embodiments 50-51, wherein $L^1$ is $-S(O)_2-$, $-NR^{13}S(O)_2-$ or $-NR^{13}C(O)-$.

Embodiment 56. The method of any one of Embodiments 50-55, wherein $R^7$ and $R^9$ are hydrogen.

Embodiment 57. The method of any one of Embodiments 50-56, wherein each $R^6$, $R^8$, and $R^{10}$ is independently hydrogen, halogen, $-N_3$, $-CN$, $-NO_2$, $-NEB$, $-C(O)H$, $-C(O)CH_3$, $-C(O)OH$, $-C(O)OCH_3$, $-C(O)NH_2$, $-OH$, $-OCH_3$, or substituted or unsubstituted $C_1$-$C_3$ alkyl.

Embodiment 58. The method of any one of Embodiments 50-57, wherein the compound has a formula (III),

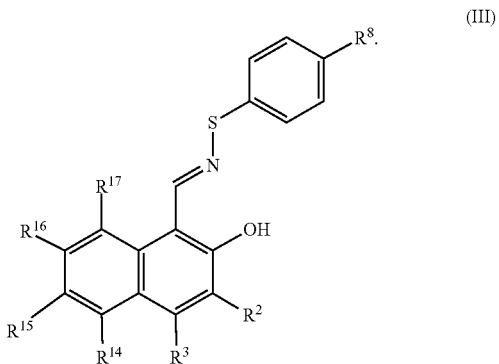

(III)

Embodiment 59. The method of any one of Embodiments 50-57, wherein the compound has a formula (IV),

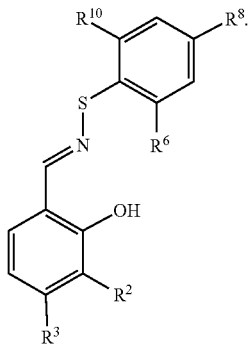
(IV)

Embodiment 60. The method of any one of Embodiments 50-57, wherein the compound has a formula (V), (V)

Embodiment 61. The method of any one of Embodiments 50-57, wherein the compound has a formula (VI), (VI)

Embodiment 62. The method of any one of Embodiments 50-57, wherein the compound has a formula (VII).

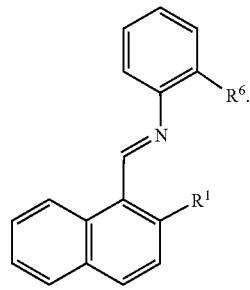
(VII)

Embodiment 63. The method of Embodiment 50, wherein the compound has a formula (VIII),

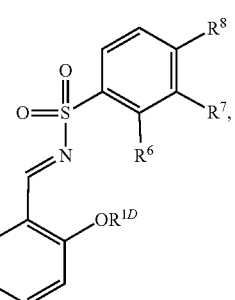
(VIII)

wherein:
$R^{1D}$ is hydrogen or unsubstituted $C_1$-$C_4$ alkyl;
$R^6$ is hydrogen or —C(O)—OR$^{6C}$;
$R^7$ is hydrogen or halogen; and
$R_8$ is halogen, —OR$^{8D}$, —C(O)—OR$^{8C}$, or unsubstituted $C_2$-$C_4$ alkyl.

Embodiment 64. The method of Embodiment 63, wherein $R^{1D}$, $R^{6C}$, $R^{8C}$, and $R^{8D}$ are independently hydrogen or —CH$_3$.

Embodiment 65. The method of Embodiment 64, wherein:
$R^{1D}$ is hydrogen;
$R^6$ and $R^7$ are hydrogen; and
$R^8$ is —OH, —OCH$_3$, —COOH, —Br, or —C(CH$_3$)$_3$.

Embodiment 66. The method of Embodiment 64, wherein:
$R^{1D}$ is —CH$_3$;
$R^6$ and $R^7$ are hydrogen; and
$R^8$ is —OH, —OCH$_3$, —COOH, —COOCH$_3$, —Cl, —Br, or —C(CH$_3$)$_3$.

Embodiment 67. The compound of Embodiment 64, wherein:
$R^{1D}$ is hydrogen or —CH$_3$;
$R^6$ is hydrogen; and
$R^7$ and $R^8$ are halogen.

Embodiment 68. The method of Embodiment 64, wherein:
$R^{1D}$ is hydrogen or —CH$_3$;
$R^7$ is halogen; and
$R^7$ and $R^8$ are hydrogen.

Embodiment 69. The method of Embodiment 64, wherein:
$R^{1D}$ is hydrogen or —CH$_3$;
$R^6$ is —C(O)—OR$^{6C}$; and
$R^7$ and $R^8$ are hydrogen.

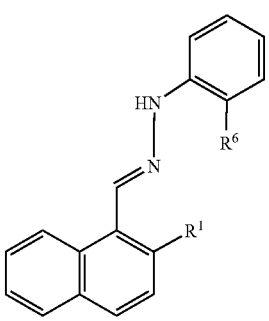

Embodiment 70. The method of Embodiment 50, wherein the compound has a formula (IX),

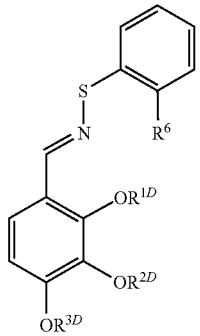

(IX)

wherein:
R$^{1D}$, R$^{2D}$, and R$^{3D}$ are independently hydrogen or unsubstituted C$_1$-C$_4$ alkyl; and
R$^6$ is hydrogen, halogen, —C(O)—OR$^{6C}$, —OR$^{6D}$, or unsubstituted C$_1$-C$_4$ alkyl.

Embodiment 71. The method of Embodiment 70, wherein:
R$^{1D}$, R$^{2D}$, and R$^{3D}$ are independently hydrogen or —CH$_3$; and
R$^{6C}$ and R$^{6D}$ are independently hydrogen or —CH$_3$.

Embodiment 72. The method of any one of Embodiments 50-71, wherein the compound is

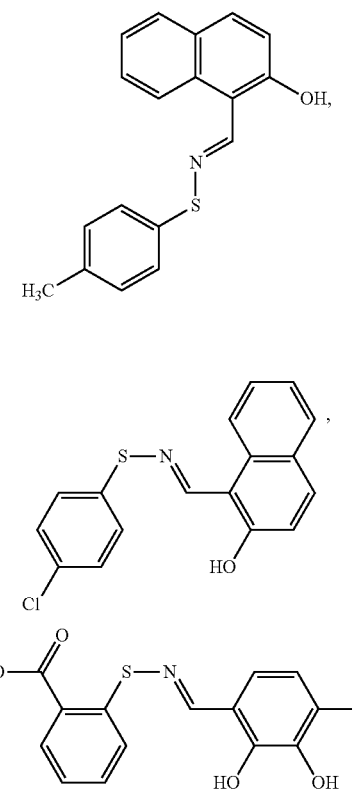

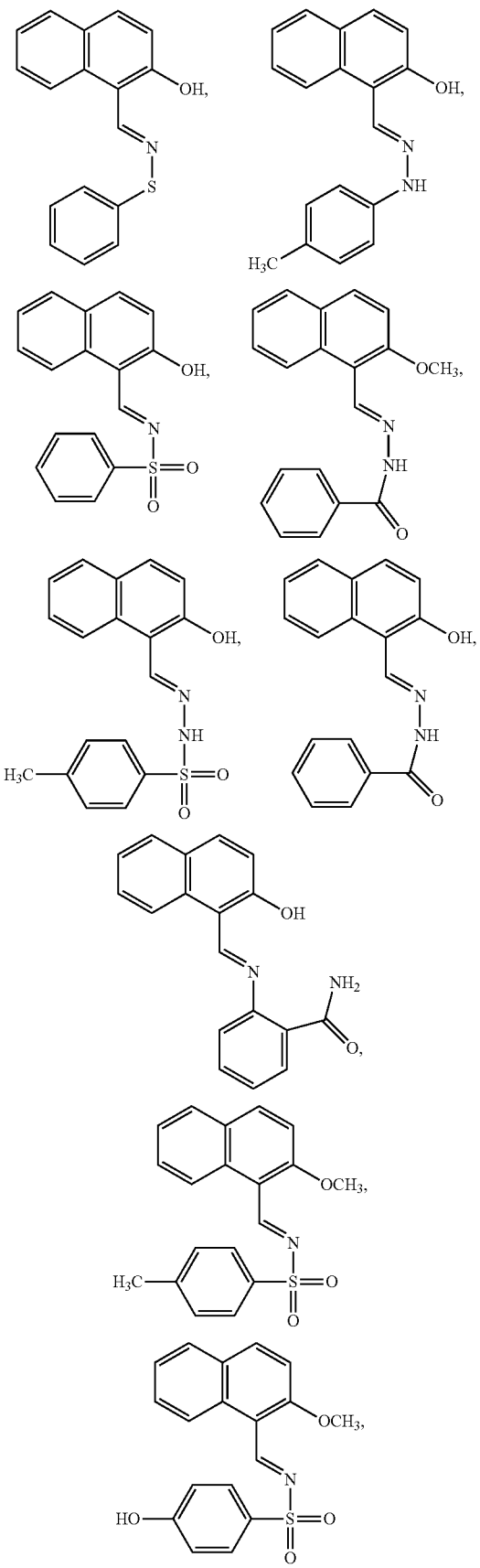

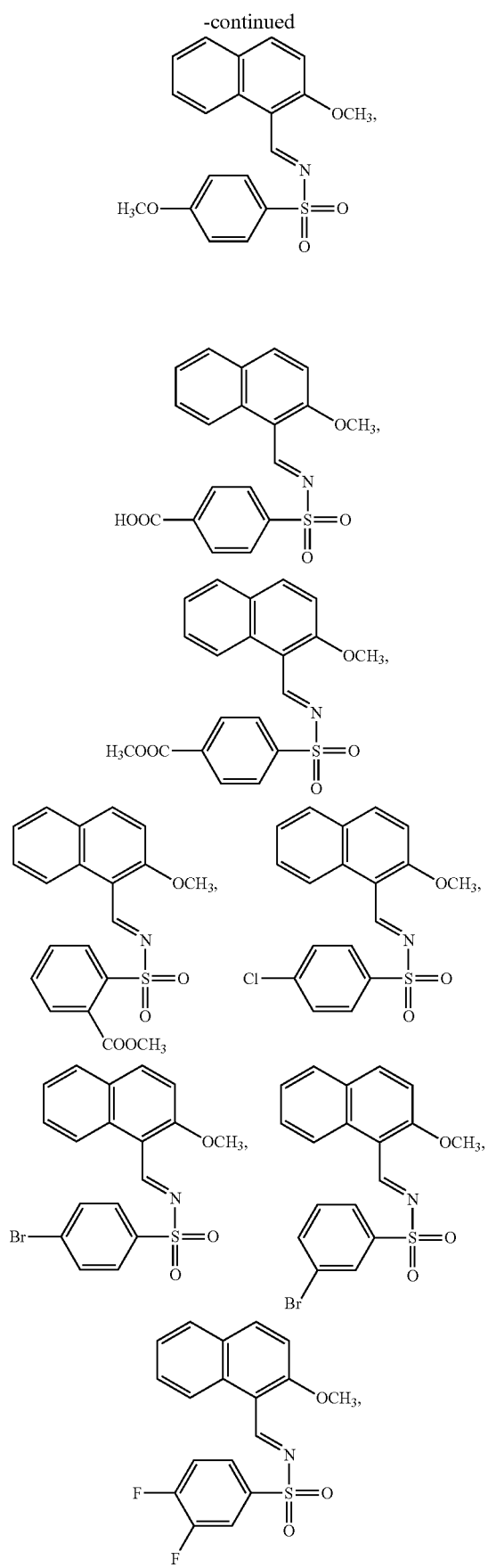
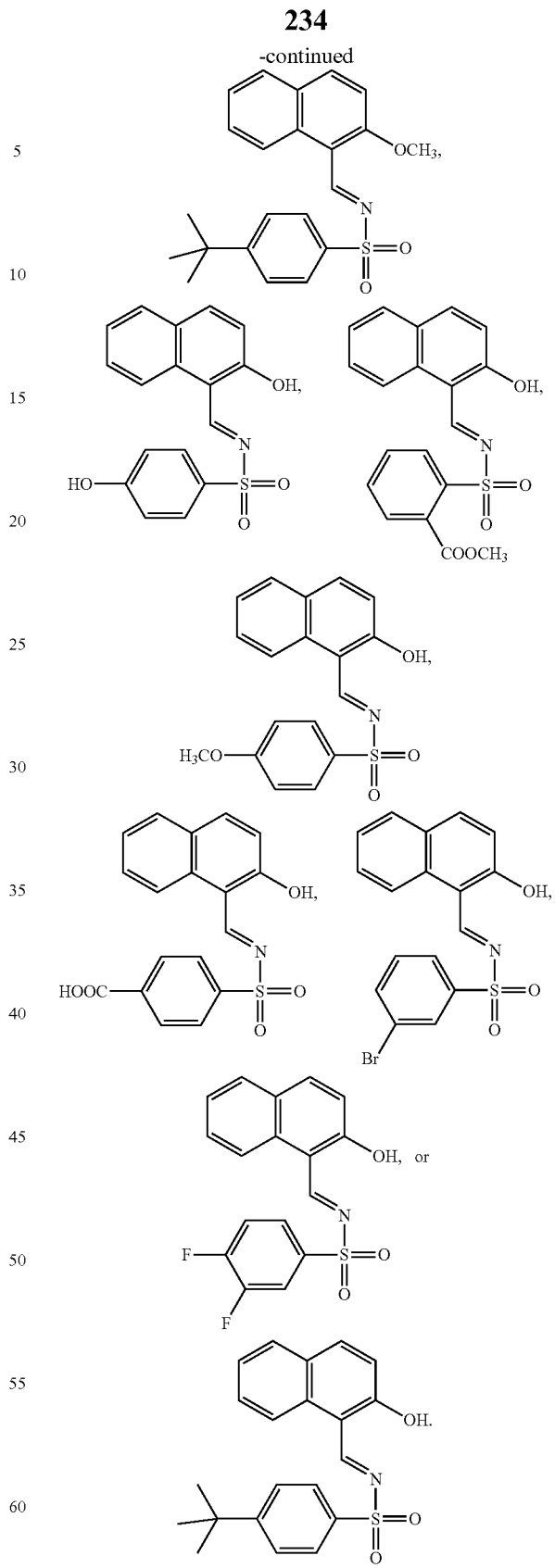
Embodiment 73. The method of any one of Embodiments 52-72, wherein the compound inhibits the poly(ADP-ribose) glycohydrolase (PARG) in a cancer cell.

Embodiment 74. The method of Embodiment 73, wherein the cancer cell is from breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

Embodiment 75. A pharmaceutical composition comprising a pharmaceutically acceptable excipient and compound having a formula (I),

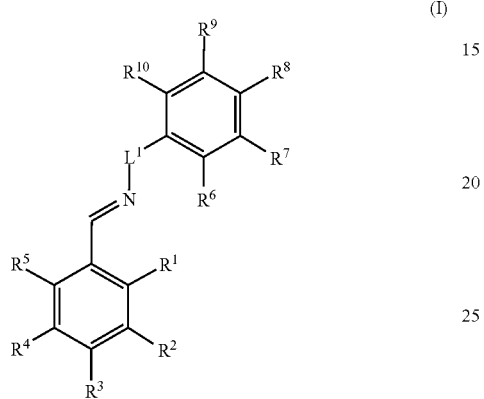

(I)

wherein, $L^1$ is a bond, —$CR^{11}R^{12}$—, —$NR^{13}$—, —O—, —S—, —S(O)—, —S(O)$_2$—, —$NR^{13}$S(O)—, —$NR^{13}$S(O)$_2$—, or —$NR^{13}$C(O)—;

$R^1$ is hydrogen, halogen, —$CX^1_3$, —$CHX^1_2$, —$CH_2X^1$, —$OCX^1_3$, —$OCH_2X^1$, —$OCHX^2_2$, —$N_3$, —CN, —$SO_{n1}R^{1D}$, —$SO_{v1}NR^{1A}R^{1B}$, —$NHC(O)NR^{1A}R^{1B}$, —$N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, —$CX^2_3$, —$CHX^2_2$, —$CH_2X^2$, —$OCX^2_3$, —$OCH_2X^2$, —$OCHX^2_2$, —$N_3$, —CN, —$SO_{n2}R^{2D}$, —$SO_{v2}NR^{2A}R^{2B}$, —$NHC(O)NR^{2A}R^{2B}$, —$N(O)_{m2}$, —$NR^{2A}R^{2B}$, —$C(O)R^{2C}$, C(O)—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, —$CX^3_3$, —$CHX^3_2$, —$CH_2X^3$, —$OCX^3_3$, —$OCH_2X^3$, —$OCHX^3_2$, —$N_3$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, —$CX^4_3$, —$CHX^4_2$, —$CH_2X^4$, —$OCX^4_3$, —$OCH_2X^4$, —$OCHX^4_2$, —$N_3$, —CN, —$SO_{n4}R^{4D}$, —$SO_{v4}NR^{4A}R^{4B}$, —$NHC(O)NR^{4A}R^{4B}$, —$N(O)_{m4}$, —$NR^{4A}R^{4B}$, —$C(O)R^{4C}$, —$C(O)$—$OR^{4C}$, —$C(O)NR^{4A}R^{4B}$, —$OR^{4D}$, —$NR^{4A}SO_2R^{4D}$, —$NR^{4A}C(O)R^{4C}$, —$NR^{4A}C(O)OR^{4C}$, —$NR^{4A}OR^{4C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, —$CX^5_3$, —$CHX^5_2$, —$CH_2X^5$, —$OCX^5_3$, —$OCH_2X^5$, —$OCHX^5_2$, —$N_3$, —CN, —$SO_{n5}R^{5D}$, —$SO_{v5}NR^{5A}R^{5B}$, —$NHC(O)NR^{5A}R^{5B}$, —$N(O)_{m5}$, —$NR^{5A}R^{5B}$, —$C(O)R^{5C}$, —$C(O)$—$OR^{5C}$, —$C(O)NR^{5A}R^{5B}$, —$OR^{5D}$, —$NR^{5A}SO_2R^{5D}$, —$NR^{5A}C(O)R^{5C}$, —$NR^{5A}C(O)OR^{5C}$, —$NR^{5A}OR^{5C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is hydrogen, halogen, —$CX^6_3$, —$CHX^6_2$, —$CH_2X^6$, —$OCX^6_3$, —$OCH_2X^6$, —$OCHX^6_2$, —$N_3$, —CN, —$SO_{n6}R^{6D}$, —$SO_{v6}NR^{6A}R^{6B}$, —$NHC(O)NR^{6A}R^{6B}$, —$N(O)_{m6}$, —$NR^{6A}R^{6B}$, —$C(O)R^{6C}$, —$C(O)$—$OR^{6C}$, —$C(O)NR^{6A}R^{6B}$, —$OR^{6D}$, —$NR^{6A}SO_2R^{6D}$, —$NR^{6A}C(O)R^{6C}$, —$NR^{6A}C(O)OR^{6C}$, —$NR^{6A}OR^{6C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is hydrogen, halogen, —$CX^7_3$, —$CHX^7_2$, —$CH_2X^7$, —$OCX^7_3$, —$OCH_2X^7$, —$OCHX^7_2$, —$N_3$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^8$ is hydrogen, halogen, —$CX^8_3$, —$CHX^8_2$, —$CH_2X^8$, —$OCX^8_3$, —$OCH_2X^8$, —$OCHX^8_2$, —$N_3$, —CN, —$SO_{n8}R^{8D}$, —$SO_{v8}NR^{8A}R^{8B}$, —$NHC(O)NR^{8A}R^{8B}$, —$N(O)_{m8}$, —$NR^{8A}R^{8B}$, —$C(O)R^{8C}$, —$C(O)$—$OR^{8C}$, —$C(O)NR^{8A}R^{8B}$, —$OR^{8D}$, —$NR^{8A}SO_2R^{8D}$, —$NR^{8A}C(O)R^{8C}$, —$NR^{8A}C(O)OR^{8C}$, —$NR^{8A}OR^{8C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^9$ is hydrogen, halogen, —$CX^9_3$, —$CHX^9_2$, —$CH_2X^9$, —$OCX^9_3$, —$OCH_2X^9$, —$OCHX^9_2$, —$N_3$, —CN, —$SO_{n9}R^{9D}$, —$SO_{v9}NR^{9A}R^{9B}$, —$NHC(O)NR^{9A}R^{9B}$, —$N(O)_{m9}$, —$NR^{9A}R^{9B}$, —$C(O)R^{9C}$, —$C(O)$—$OR^{9C}$, —$C(O)NR^{9A}R^{9B}$, —$OR^{9D}$, —$NR^{9A}SO_2R^{9D}$, —$NR^{9A}C(O)R^{9C}$, —$NR^{9A}C(O)OR^{9C}$, —$NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10}$ is hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-N_3$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{11}$ is hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-N_3$, $-CN$, $-SO_{n11}R^{11D}$, $-SO_{v11}NR^{11A}R^{11B}$, $-NHC(O)NR^{11A}R^{11B}$, $-N(O)_{m11}$, $-NR^{11A}R^{11B}$, $-C(O)R^{11C}$, $-C(O)-OR^{11C}$, $-C(O)NR^{11A}R^{11B}$, $-OR^{11D}$, $-NR^{11A}SO_2R^{11D}$, $-NR^{11A}C(O)R^{11C}$, $-NR^{11A}C(O)OR^{11C}$, $-NR^{11A}OR^{11C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{12}$ is hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-N_3$, $-CN$, $-SO_{n12}R^{12D}$, $-SO_{v12}NR^{12A}R^{12B}$, $-NHC(O)NR^{12A}R^{12B}$, $-N(O)_{m12}$, $-NR^{12A}R^{12B}$, $-C(O)R^{12C}$, $-C(O)-OR^{12C}$, $-C(O)NR^{12A}R^{12B}$, $-OR^{12D}$, $-NR^{12A}SO_2R^{12D}$, $-NR^{12A}C(O)R^{12C}$, $-NR^{12A}C(O)OR^{12C}$, $-NR^{12A}OR^{12C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$ is hydrogen, $-CX^{13}_3$, $-CHX^{13}_2$, $-CH_2X^{13}$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each $R^{1A}$, $R^{1B}$, $R^{1C}$, $R^{1D}$, $R^{2A}$, $R^{2B}$, $R^{2C}$, $R^{2D}$, $R^{3A}$, $R^{3B}$, $R^{3C}$, $R^{3D}$, $R^{4A}$, $R^{4B}$, $R^{4C}$, $R^{4D}$, $R^{5A}$, $R^{5B}$, $R^{5C}$, $R^{5D}$, $R^{6A}$, $R^{6B}$, $R^{6C}$, $R^{6D}$, $R^{7A}$, $R^{7B}$, $R^{7C}$, $R^{7D}$, $R^{8A}$, $R^{8B}$, $R^{8C}$, $R^{8D}$, $R^{9A}$, $R^{9B}$, $R^{9C}$, $R^{9D}$, $R^{10A}$, $R^{10B}$, $R^{10C}$, $R^{10D}$, $R^{11A}$, $R^{11B}$, $R^{11C}$, $R^{11D}$, $R^{12A}$, $R^{12B}$, $R^{12C}$ and $R^{12D}$ is independently hydrogen, $-CX_3$, $-CHX_2$, $-CH_2X$, $-COOH$, $-CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^1$ and $R^2$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

$R^4$ and $R^5$ together with atoms attached thereto are optionally joined to form a substituted or unsubstituted cycloalkyl, substituted or unsubstituted heterocycloalkyl, substituted or unsubstituted aryl, or substituted or unsubstituted heteroaryl;

n1, n2, n3, n4, n5, n6, n7, n8, n9, n10, n11 and n12 are independently an integer from 0 to 4;

m1, m2, m3, m4, m5, m6, m7, m8, m9, m10, m11, m12, v1, v2, v3, v4, v5, v6, v7, v8, v9, v10, v11 and v12 are independently an integer from 1 to 2; and $X$, $X^1$, $X^2$, $X^3$, $X^4$, $X^5$, $X^6$, $X^7$, $X^8$, $X^9$, $X^{10}$, $X^{11}$, $X^{12}$, and $X^{13}$ are independently $-F$, $-Cl$, $-Br$, or $-I$, or a salt thereof, and a pharmaceutically acceptable carrier.

Embodiment 76. The pharmaceutical composition of Embodiment 75, wherein the compound has a formula (II):

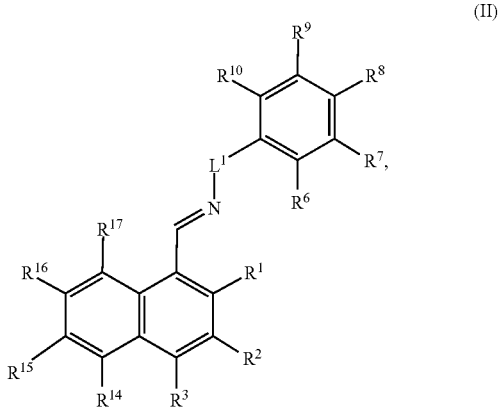

(II)

wherein:

$R^{14}$ is hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-N_3$, $-CN$, $-SO_{n14}R^{14D}$, $-SO_{v14}NR^{14A}R^{14B}$, $-NHC(O)NR^{14A}R^{14B}$, $-N(O)_{m14}$, $-NR^{14A}R^{14B}$, $C(O)R^{14C}$, $-C(O)-OR^{14C}$, $-C(O)NR^{14A}R^{14B}$, $-OR^{14D}$, $-NR^{14A}SO_2R^{14D}$, $-NR^{14A}C(O)R^{14C}$, $-NR^{14A}C(O)OR^{14C}$, $-NR^{14A}OR^{14C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{15}$ is hydrogen, halogen, $-CX^{15}_3$, $-CHX^{15}_2$, $-CH_2X^{15}$, $-OCX^{15}_3$, $-OCH_2X^{15}$, $-OCHX^{15}_2$, $-N_3$, $-CN$, $-SO_{n15}R^{15D}$, $-SO_{v15}NR^{15A}R^{15B}$, $-NHC(O)NR^{15A}R^{15B}$, $-N(O)_{m15}$, $-NR^{15A}R^{15B}$, $-C(O)R^{15C}$, $-C(O)-OR^{15C}$, $-C(O)NR^{15A}R^{15B}$, $-OR^{15D}$, $-NR^{15A}SO_2R^{15D}$, $-NR^{15A}C(O)R^{15C}$, $-NR^{15A}C(O)O R^{15C}$, $-NR^{15A}OR^{15C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{16}$ is hydrogen, halogen, $-CX^{16}_3$, $-CHX^{16}_2$, $-CH_2X^{16}$, $-OCX^{16}_3$, $-OCH_2X^{16}$, $-OCHX^{16}_2$, $-N_3$, $-CN$, $-SO_{n16}R^{16D}$, $-SO_{v16}NR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{17}$ is hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-N_3$, $-CN$, $-N_3$, $-SO_{n17}R^{17D}$, $-SO_{v17}NR^{17A}R^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O) R$^{17C}$, —NR$^{17A}$C(O)OR$^{17C}$, —NR$^{17A}$OR$^{17C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{14A}$, R$^{14B}$, R$^{14C}$, R$^{14D}$, R$^{15A}$, R$^{15B}$, R$^{15C}$, R$^{15D}$, R$^{16A}$, R$^{16B}$, R$^{16C}$, R$^{16D}$, R$^{17A}$, R$^{17B}$, R$^{17C}$, and R$^{17D}$ is independently hydrogen, —CX$_3$, —CHX$_2$, —CH$_2$X, —COOH, —CONH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

n14, n15, n16, and n17 are independently an integer from 0 to 4;

m14, m15, m16, m17, v14, v15, v16, and v17 are independently an integer from 1 to 2; and X$^{14}$, X$^{15}$, X$^{16}$, and X$^{17}$ are independently —F, —Cl, —Br, or —I.

Embodiment 77. The pharmaceutical composition of any one of Embodiments 75-76, wherein L$^1$ is —O— or —S—.

Embodiment 78. The pharmaceutical composition of any one of Embodiments 75-76, wherein L$^1$ is a bond.

Embodiment 79. The pharmaceutical composition of any one of Embodiments 75-76, wherein L$^1$ is —S(O)$_2$—, —NR$^{13}$S(O)$_2$— or —NR$^{13}$C(O)—.

Embodiment 80. The pharmaceutical composition of any one of Embodiments 75-79, wherein at least one of R$^1$, R$^2$ and R$^3$ are —OH or —OCH$_3$.

Embodiment 81. The pharmaceutical composition of any one of Embodiments 75-80, wherein R7 and R9 are hydrogen.

Embodiment 82. The pharmaceutical composition of any one of Embodiments 75-81, wherein each R$^6$, R$^8$, and R$^{10}$ is independently hydrogen, halogen, —N$_3$, —CN, —NO$_2$, —NH$_2$, —C(O)H, —C(O)CH$_3$, —C(O)OH, —C(O)OCH$_3$, —C(O)NH$_2$, —OH, —OCH$_3$, or substituted or unsubstituted C$_1$-C$_3$ alkyl.

Embodiment 83. The pharmaceutical composition of any one of Embodiments 75-82, wherein the compound has a formula (III),

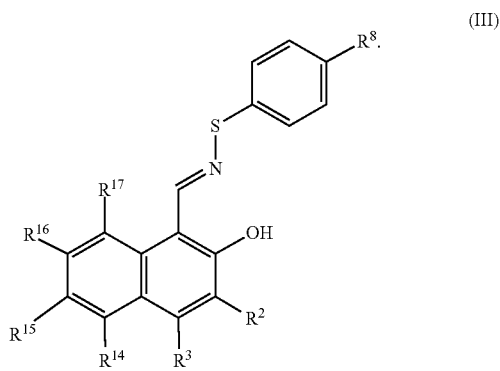

(III)

Embodiment 84. The pharmaceutical composition of any one of Embodiments 75-82, wherein the compound has a formula (IV),

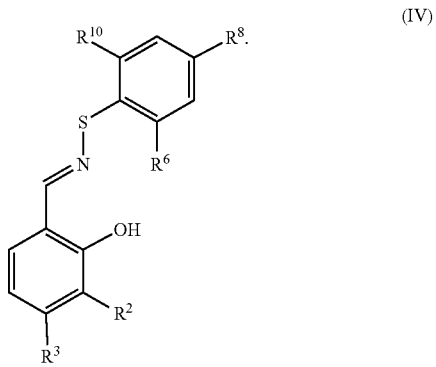

(IV)

Embodiment 85. The pharmaceutical composition of any one of Embodiments 75-82, wherein the compound has a formula (V),

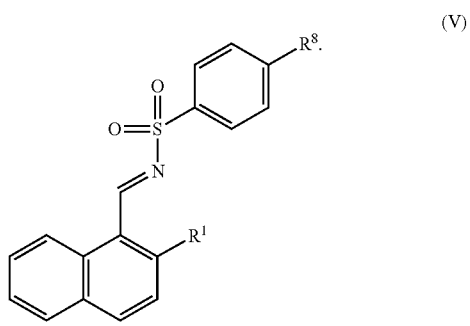

(V)

Embodiment 86. The pharmaceutical composition of any one of Embodiments 75-82, wherein the compound has a formula (VI),

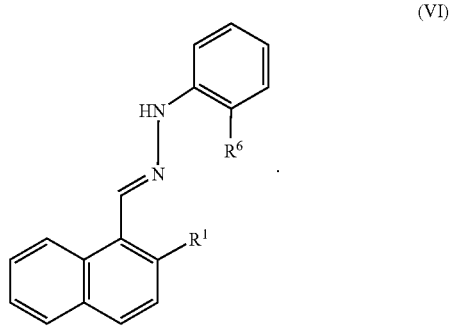

(VI)

Embodiment 87. The pharmaceutical composition of any one of Embodiments 75-82, wherein the compound has a formula (VII),

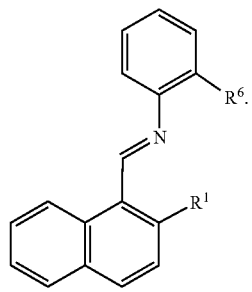

(VII)

Embodiment 88. The pharmaceutical composition of Embodiment 75, wherein the compound has a formula (VIII),

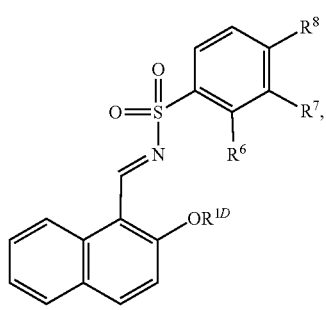

(VIII)

wherein:
R$^{1D}$ is hydrogen or unsubstituted C$_1$-C$_4$ alkyl;
R$^6$ is hydrogen or —C(O)—OR$^{6C}$;
R$^7$ is hydrogen or halogen; and
R$_8$ is halogen, —OR$^{8D}$, —C(O)—OR$^{8C}$, or unsubstituted C$_2$-C$_4$ alkyl.

Embodiment 89. The pharmaceutical composition of Embodiment 88, wherein R$^{1D}$, R$^{6C}$, R$^{8C}$, and R$^{8D}$ are independently hydrogen or —CH$_3$.

Embodiment 90. The pharmaceutical composition of Embodiment 89, wherein:
R$^{1D}$ is hydrogen;
R$^6$ and R$^7$ are hydrogen; and
R$^8$ is —OH, —OCH$_3$, —COOH, —Br, or —C(CH$_3$)$_3$.

Embodiment 91. The pharmaceutical composition of Embodiment 89, wherein:
R$^{1D}$ is —CH$_3$;
R$^6$ and R$^7$ are hydrogen; and
R$^8$ is —OH, —OCH$_3$, —COOH, —COOCH$_3$, —Cl, —Br, or —C(CH$_3$)$_3$.

Embodiment 92. The pharmaceutical composition of Embodiment 89, wherein:
R$^{1D}$ is hydrogen or —CH$_3$;
R$^6$ is hydrogen; and
R$^7$ and R$^8$ are halogen.

Embodiment 93. The pharmaceutical composition of Embodiment 89, wherein:
R$^{1D}$ is hydrogen or —CH$_3$;
R$^7$ is halogen; and
R$^7$ and R$^8$ are hydrogen.

Embodiment 94. The pharmaceutical composition of Embodiment 89, wherein:
R$^{1D}$ is hydrogen or —CH$_3$;
R$^6$ is —C(O)—OR$^{6C}$; and
R$^7$ and R$^8$ are hydrogen.

Embodiment 95. The pharmaceutical composition of Embodiment 75, wherein the compound has a formula (IX),

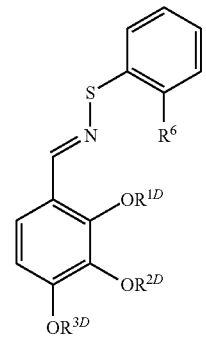

(IX)

wherein:
R$^{1D}$, R$^{2D}$, and R$^{3D}$ are independently hydrogen or unsubstituted C$_1$-C$_4$ alkyl; and
R$^6$ is hydrogen, halogen, —C(O)—OR$^{6C}$, —OR$^{6D}$, or unsubstituted C$_1$-C$_4$ alkyl.

Embodiment 96. The pharmaceutical composition of Embodiment 95, wherein:
R$^{1D}$, R$^{2D}$, and R$^{3D}$ are independently hydrogen or —CH$_3$; and
R$^{6C}$ and R$^{6D}$ are independently hydrogen or —CH$_3$.

Embodiment 97. The pharmaceutical composition of any one of Embodiments 75-96, wherein the compound is

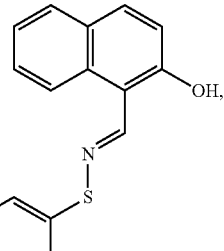

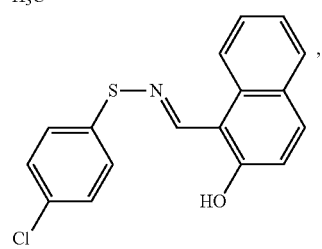

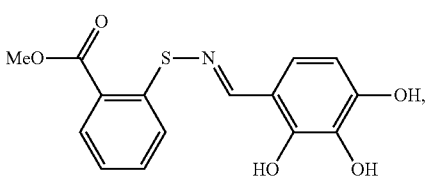

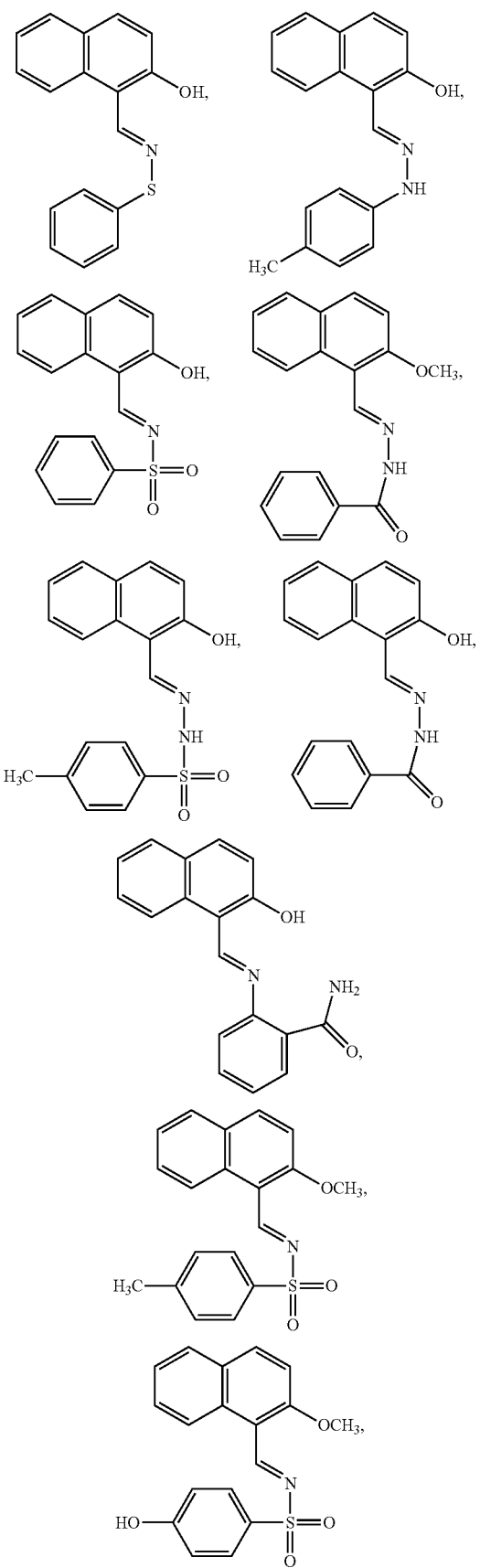
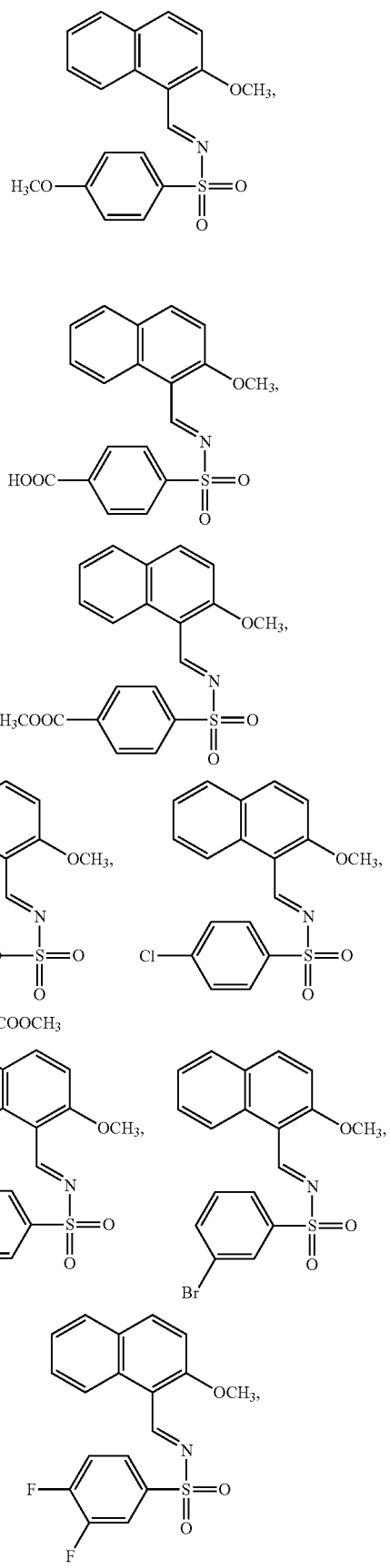

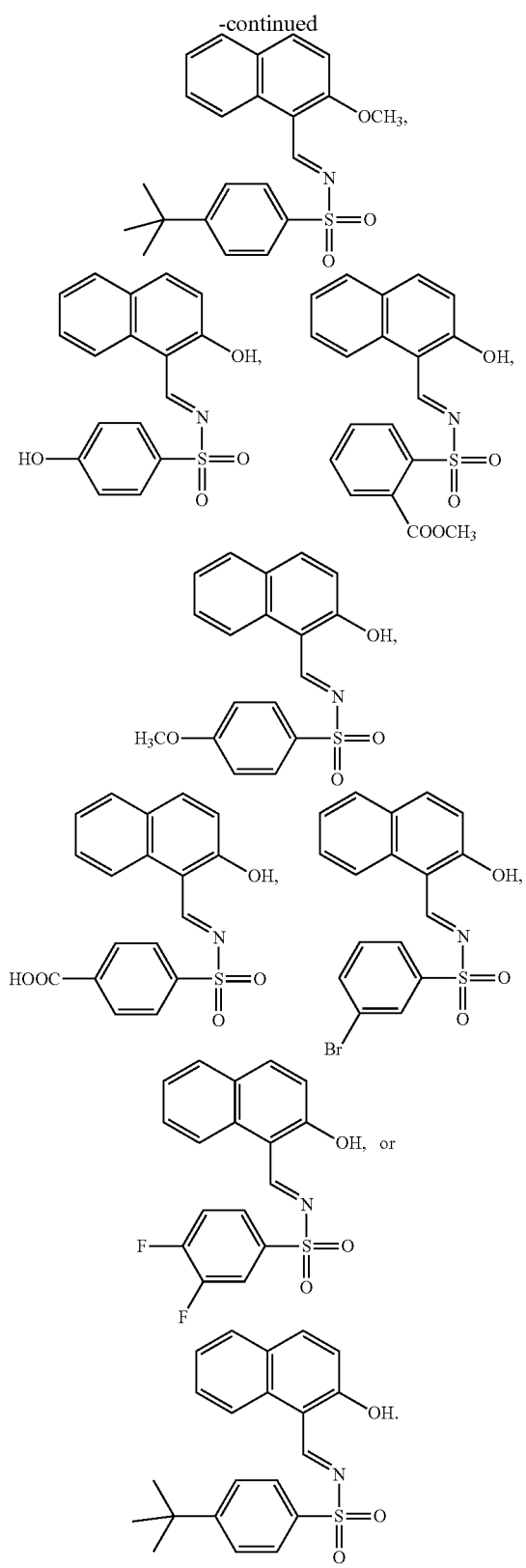

VI. Examples

Although the foregoing section has been described in some detail by way of illustration and example for purposes of clarity of understanding, it is apparent to those skilled in the art that certain minor changes and modifications will be practiced in light of the above teaching. Therefore, the description and examples should not be construed as limiting the scope of any invention described herein.

All references cited herein, including patent applications and publications, are hereby incorporated by reference in their entirety.

Example 1: Cancer Caused by PARylation and/or dePARylation

A cancer can be caused by defective DNA damage repair system in the cancer/tumor cell. Among other things, the cancer can be caused by defective PARP-dependent DNA damage repair system or PARylation. For instance, suppression of PARylation weakens DNA damage repair in the tumor cells with defective DNA repair machinery, and PARP inhibitor treatment further disrupt DNA damage repair in the tumor cells. In addition, the cancer may be related to defective PARG-dependent DNA damage repair system or dePARylation. For instance, suppression of de PARylation weakens DNA damage repair in the tumor cells with defective DNA repair machinery, and PARG inhibitor treatment disrupt downstream of PARylation in DNA damage repair in the tumor cells.

PARylation is a transient posttranslational modification and quickly degraded by PARG, the major dePARylation enzyme. Our recent study suggests that PARylation and dePARylation are not antagonistic processes during DNA damage repair. Instead, transient PARylation and quick dePARylation are sequential events to mediate the recruitment of DNA damage machineries to the sites of DNA damage. We have shown that a number of DNA damage response factors recognize PARylation and is recruited by PARylation to the proximity of DNA lesions. However, PARylation has to be digested so that DNA damage machineries recognize DNA lesions and repair lesions. Thus, dePARylation is an immediate downstream step of PARP-dependent DNA damage repair. And suppression of dePARylation also abolishes PARP-dependent DNA damage repair. Thus, it is very likely that targeting PARG, the dePARylation enzyme, to specifically kill tumor cells.

Example 2: Identification of Novel PARG Inhibitors

Development of potent and cell-permeant PARG inhibitors via multi-step virtual screening and hierarchical selection. Forty candidates from National Cancer Institute (NCI) were selected to examine the efficacy of PARG inhibition by dot blot assay. PARG was incubated with PAR for 20 min at room temperature with or without inhibitors. PAR-digestion results were analyzed using dot blotting with anti-PAR antibody. Two compounds, #5 and #34, showed the good inhibitory activity for PARG. PC and NC mean positive control (PAR only) and negative control (no inhibitor), respectively. $IC_{50}$ value of compound 34 was measured by dot blotting with anti-PAR antibody in a dose course of compound 34.

PAR digestion assay: Recombinant PARG protein were incubated with PAR (10 µM, calculated as the ADP-ribose unit) and DMSO (Negative control, NC) or small molecules for 20 minutes at room temperature. Positive control (PC) only contains PAR in PBS. Samples were spotted onto a nitrocellulose membrane. The membrane was blocked with TBST buffer (0.15 M NaCl, 0.01 M Tris-HCl at pH 7.4, 0.1% Tween 20) supplemented with 5% milk and extensively washed with TBST. The membrane was examined by anti-PAR antibody.

Example 3: Inhibiting De-PARylation Traps Massive PAR-Dependent Factors of DNA Damage Response Recruitment of PAR-dependent CHFR in U2OS cells without or with 100 nM PARG inhibitor (#34) treatment after laser scissor. We used CHRF as a readout for monitoring the level of poly(ADP-ribosyl)ation.

Laser microirradiation and imaging of cells: U2OS cells with transfection of GFP-CHFR were plated on glass-bottomed culture dishes (Mat Tek Corporation) and treated with or without 100 nM PARG inhibitor (#34). Laser microirradiation was performed using an IX 71 microscope (Olympus) coupled with the MicoPoint laser illumination and ablation system (Photonic Instruments, Inc.). A 337.1-nm laser diode (3.4 mW) transmitted through a specific dye cell and then yielded a 365-nm wavelength laser beam that was focused through 603 UPlanSApo/1.35 oil objective to yield a spot size of 0.5-1 mm. The time of cell exposure to the laser beam was ~3.5 nsec. The pulse energy was 170 mJ at 10 Hz. Images were taken by the same microscope with the CellSens software (Olympus). GFP fluorescence at the laser line was converted into a numerical value using Image J. Normalized fluorescent curves from 50 cells from three independent experiments were averaged. The error bars represent the standard deviation.

Example 4: PARG Inhibitor Selectively Kills BRCA-Mutant Cancer Cells

Colony formation assay was performed using HCC1937 (BRCA1-deficient breast cancer cells), HCC1937 BRCA1 (BRCA1-reconstituted HCC1937 cells) cells, PEO-1 (BRCA2-deficient ovarian cancer cells), and PEO-4 (BRCA2-reconstituted PEO-1 cells) with indicated concentrations of PARG inhibitor (#34).

Colony formation assay: HCC1937, HCC1937-BRCA1, PEO-1 or PEO-4 (~1000 cells) were seeded into six-well plates and then treated by various doses of PARG inhibitor (#34). After 14-21 days of culture, the viable cells were fixed by methanol and stained with crystal violet. The number of colonies (>50 cells for each colony) was calculated.

Example 5: Synthesis

Compound 34 can be synthesized as depicted in the following Scheme 1.

Scheme 1

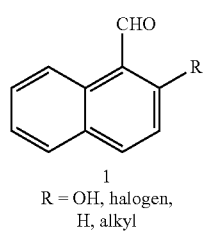

1
R = OH, halogen, H, alkyl

+

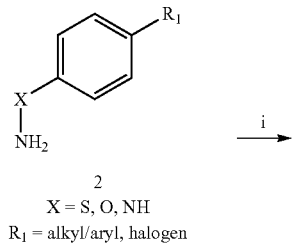

2
X = S, O, NH
$R_1$ = alkyl/aryl, halogen

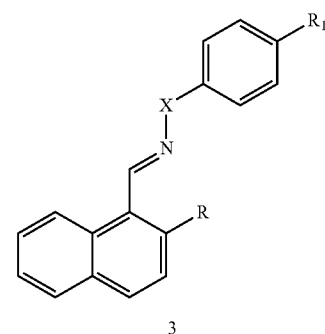

3 i) acetic acid, benzene/ethanol, 80° C.

Compound 1414 can be synthesized as depicted in the following Scheme 2.

Scheme 2

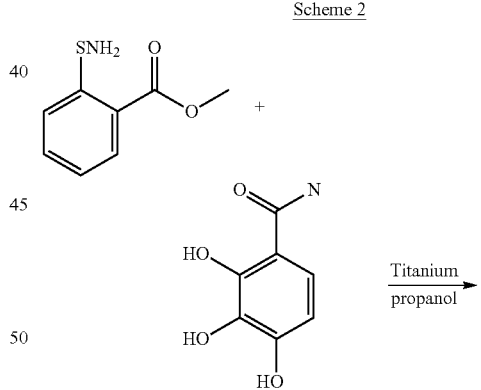

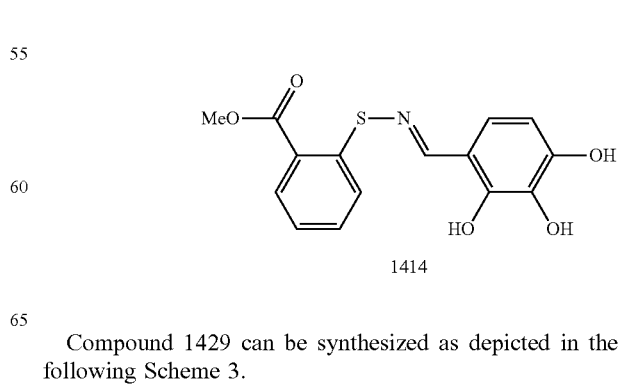

1414

Compound 1429 can be synthesized as depicted in the following Scheme 3.

Scheme 3

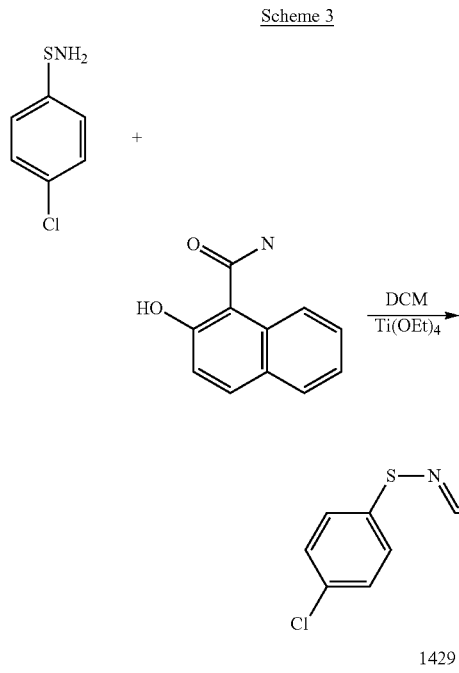

1429

Compound 6 can be synthesized as depicted in the following Scheme 4.

Scheme 4

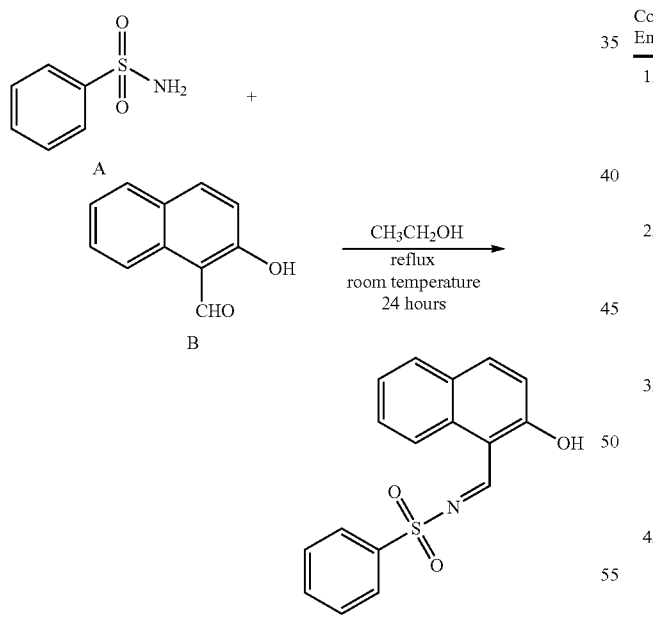

Synthesis of the compounds was verified by NMR spectra and mass spectroscopy (MS).

Example 6: PAR Digestion Assay

Recombinant full length PARG protein is generated from Sf9 insect cells. Recombinant PAR is purified from a biochemical assay using PARP1. PARG is incubated with PAR in the presence of DMSO (Negative control, NC) or small chemical compounds for 20 minutes at room temperature. Positive control (PC) only contains PAR. Samples (1 µl) were spotted onto a nitrocellulose membrane. Then, the membrane was baked for 30 minutes at 60° C. and blocked with TBST buffer (0.15 M NaCl, 0.01 M Tris-HCl at pH 7.4, 0.1% Tween 20) supplemented with 5% milk for 30 minutes at room temperature. After washing with TBST, the membrane was incubated with monoclonal anti-PAR antibody (Trevigen, Inc.) for overnight at 4° C. Following standard western blot method, the signals were visualized by chemiluminescent detection. With the chemical inhibition of the dePARylation activity of PARG, we are able to detect the dot signals of PAR.

Example 7: Compounds

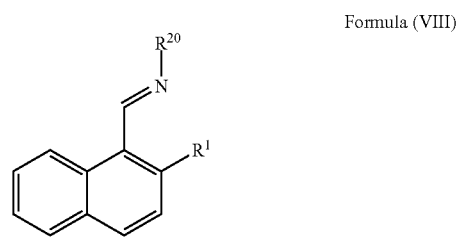

Formula (VIII)

Exemplary compounds having a formula (VIII) are shown in the following Table 1.

TABLE 1

| Compound Entry | $R^1$ | $R^{20}$ |
|---|---|---|
| 1A | —OCH$_3$ | Cl—C$_6$H$_4$—C(O)—NH— |
| 2A |  | 3-Cl—C$_6$H$_4$—C(O)—NH— |
| 3A |  | 2-OH—C$_6$H$_4$—C(O)—NH— |
| 4A |  | 3-H$_3$CO—C$_6$H$_4$—C(O)—NH— |
| 5A |  | 3,4,5-(H$_3$CO)$_3$—C$_6$H$_2$—C(O)—NH— |

TABLE 1-continued

| Compound Entry | R¹ | R²⁰ |
|---|---|---|
| 6A | | 4-hydroxyphenyl sulfonyl |
| 7A | | 2-(methoxycarbonyl)phenyl sulfonyl |
| 8A | | 4-methoxyphenyl sulfonyl |
| 9A | | 4-carboxyphenyl sulfonyl |
| 10A | | 4-chlorophenyl sulfonyl |
| 11A | | 3-bromophenyl sulfonyl |
| 12A | | 3,4-difluorophenyl sulfonyl |
| 13A | | 4-tert-butylphenyl sulfonyl |
| 14A | | 4-methylbenzamido |
| 1B | —OH | 4-chlorobenzamido |
| 2B | | 3-chlorobenzamido |
| 3B | | 2-hydroxybenzamido |
| 4B | | 3-methoxybenzamido |
| 5B (melting point 236.8-237.9° C.) | | 3,4,5-trimethoxybenzamido |
| 6B | | 4-hydroxyphenyl sulfonyl |
| 7B | | 2-(methoxycarbonyl)phenyl sulfonyl |
| 8B | | 4-methoxyphenyl sulfonyl |
| 9B | | 4-carboxyphenyl sulfonyl |
| 10B | | 4-chlorophenyl sulfonyl |
| 11B | | 3-bromophenyl sulfonyl |
| 12B | | 3,4-difluorophenyl sulfonyl |

TABLE 1-continued

| Compound Entry | R¹ | R²⁰ |
|---|---|---|
| 13B | | (tert-butyl-phenyl-sulfonyl group) |
| 14B | | (4-methylbenzamido group) |

Example 8: PARG Inhibition and Cell Viability Assays

Figures 6A, 6B:
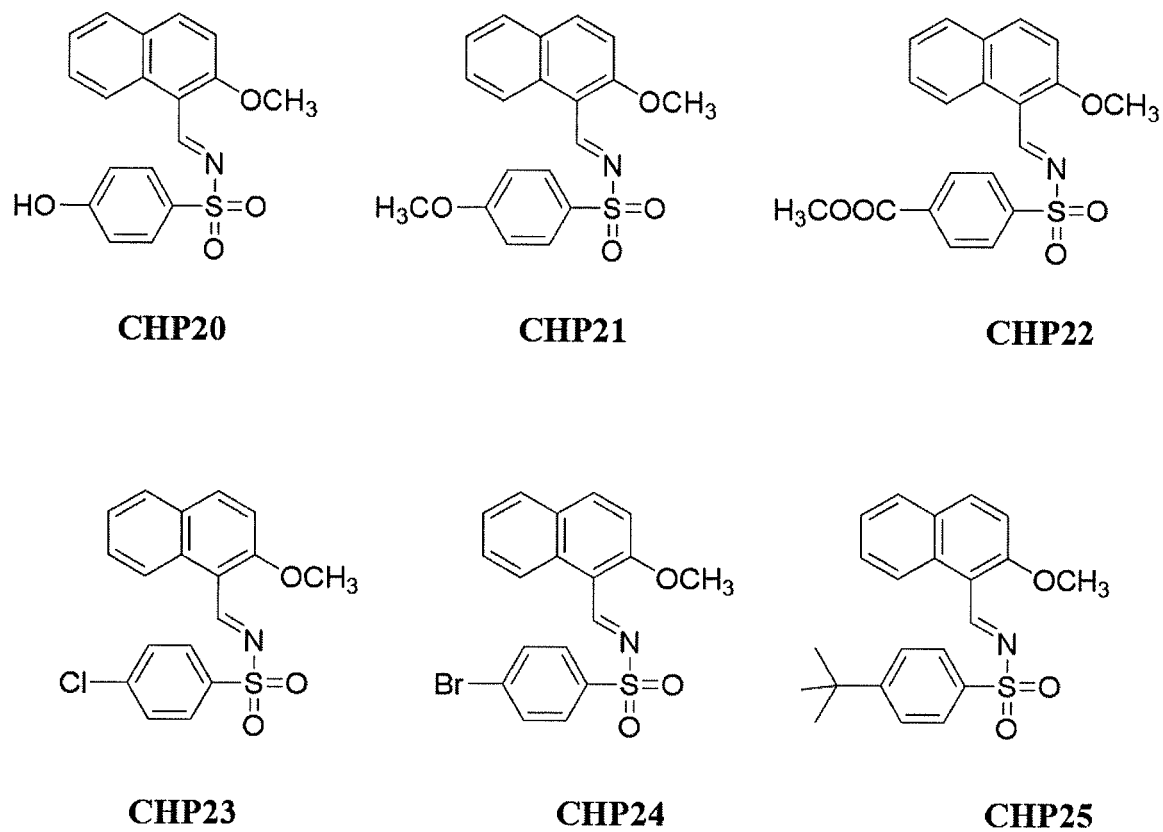
FIG. 6A shows compounds (CHP20-CHP25) tested for PARG inhibition and cell viability assays in Example 8.
FIG. 6B lists IC$_{50}$ and EC$_{50}$ values of compounds (CHP20-25) measured by colony formation assays.
Figure 7A:
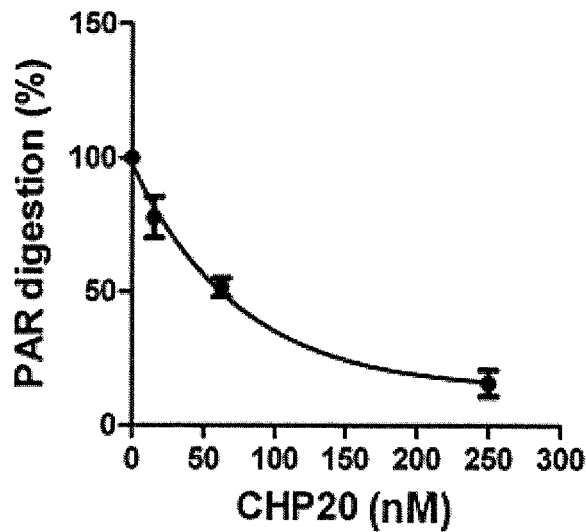
FIG. 7A indicates inhibition activity for PAR digestion by CHP20 measured by PAR digestion assay in Example 9.
Figure 7B:
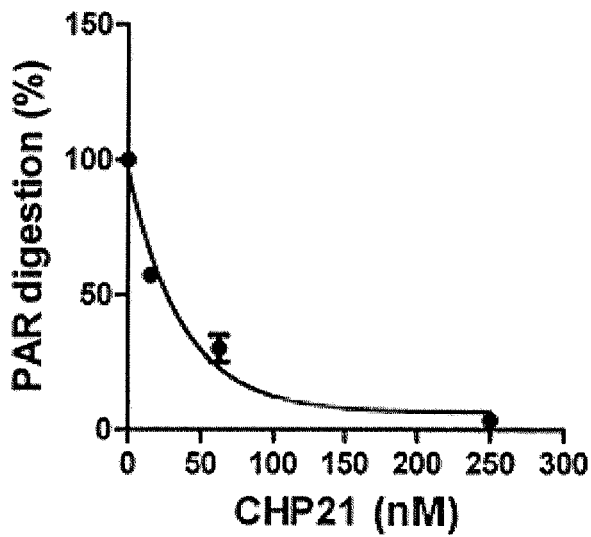
FIG. 7B indicates inhibition activity for PAR digestion by CHP21 measured by PAR digestion assay in Example 9.
Figure 7C:
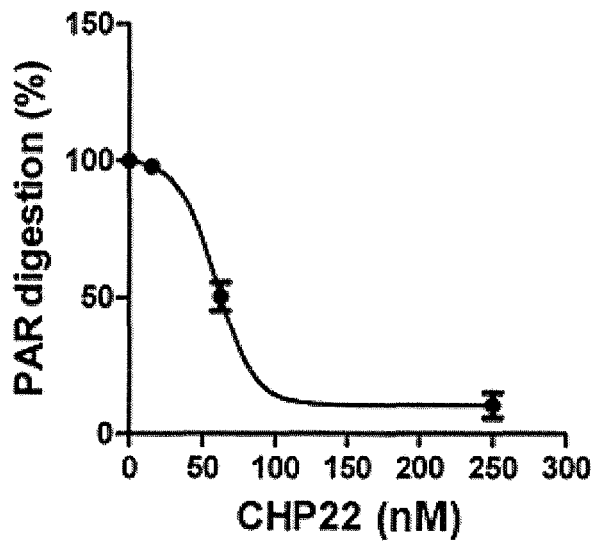
FIG. 7C indicates inhibition activity for PAR digestion by CHP22 measured by PAR digestion assay in Example 9.
Figure 7D:
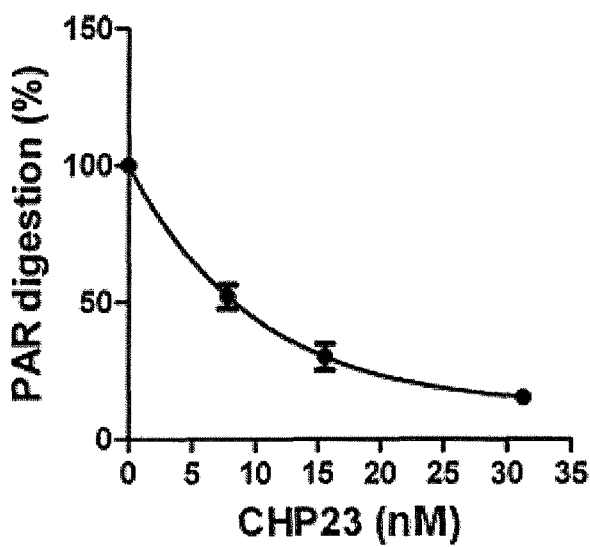
FIG. 7D indicates inhibition activity for PAR digestion by CHP23 measured by PAR digestion assay in Example 9.
Figure 7E:
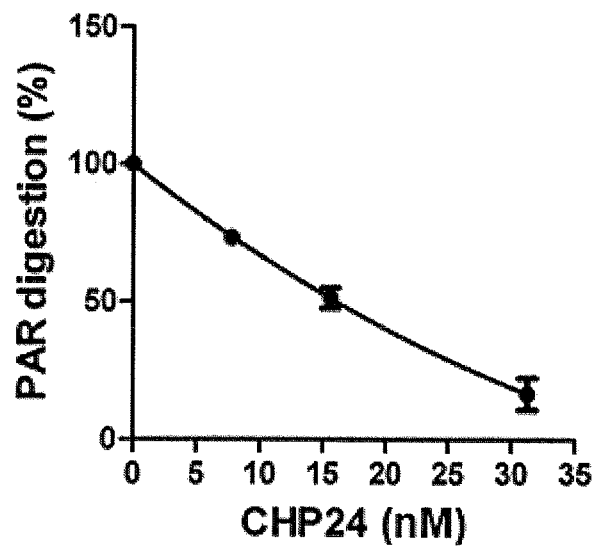
FIG. 7E indicates inhibition activity for PAR digestion by CHP24 measured by PAR digestion assay in Example 9.
Figure 7F:
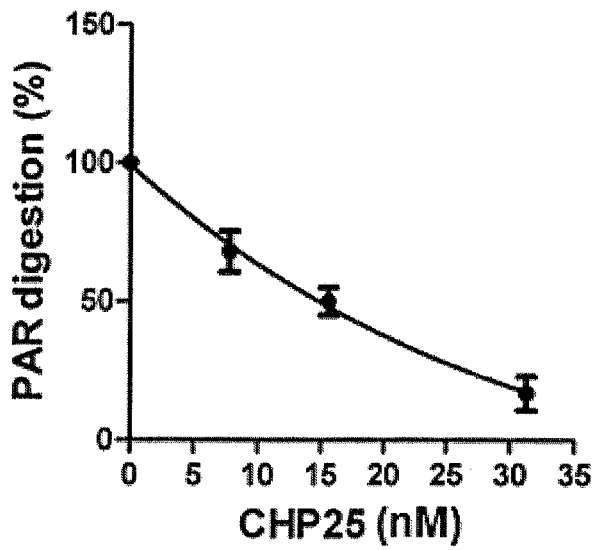
FIG. 7F indicates inhibition activity for PAR digestion by CHP25 measured by PAR digestion assay in Example 9.

The efficacy of CHP20-25 against PARG activity was examined by dot blot assays. PARG was incubated with PAR for 20 min at room temperature with or without inhibitors. PAR-digestion results were analyzed using dot blotting with anti-PAR antibody. $IC_{50}$ values of CHP20-25 were measured by dot blotting with anti-PAR antibody in a dose course of CHP20-25. Colony formation assays were performed using HCC1937 (BRCA1-mutant breast cancer cells) and PARPi-resistant UWB1.289 (BRCA1-mutant ovarian cancer cells) with 2.5-20 µM PARG inhibitors (CHP20-25, FIG. 6A). The $IC_{50}$ and $EC_{50}$ values of CHP20-25 were summarized in the table (FIG. 6B).

Example 9: PAR Digestion Assay

Recombinant PAR was purified from a biochemical assay using PARP1. The concentration of PAR was calculated as the ADP-ribose unit. Recombinant full length PARG was incubated with 10 µM PAR in the presence of DMSO (negative control) or small molecule compounds (CHP20-25) in a 10 µl reaction for 20 minutes at room temperature. Positive control only contains PAR in PBS. For dot blotting analysis, samples (1 µl) were spotted onto a nitrocellulose membrane. Then, the membrane was baked for 30 minutes at 60° C. and blocked with TBST buffer (0.15 M NaCl, 0.01 M Tris-HCl at pH 7.4, 0.1% Tween 20) supplemented with 5% milk for 30 minutes at room temperature. After washing with TBST, the membrane was incubated with anti-PAR monoclonal antibody (Trevigen) overnight at 4° C. Following standard western blot method, the signals were visualized by chemiluminescent detection and results are shown in FIG. 7A-FIG. 7F.

Example 10: Colony Formation Assay

HCC1937 and PARPi-resistant UWB1.289 (~1000 cells) were seeded into six-well plates and then treated by various doses of PARG inhibitors (CHP20-25). After a 14~21-d culture, the viable cells were fixed by methanol and stained with crystal violet. The number of colonies (>50 cells for each colony) was calculated.

Example 11: Colony Formation Assay

Suppressing de-PARylation traps massive PAR-dependent factor of DNA damage repair. Recruitment of PAR-dependent CHFR in U2OS cells without or with PARG inhibitors (COH34 and CHP20-25) treatments after laser scissor.

Example 12: Laser Microirradiation and Imaging of Cells

U2OS cells with transfection of GFP-CHFR were plated on glass-bottomed culture dishes (Mat Tek Corporation) and treated with or without 100 nM COH34 (control) or 1 µM CHP20-25. Laser microirradiation was performed using an IX 71 microscope (Olympus) coupled with the MicoPoint laser illumination and ablation system (Photonic Instruments, Inc.). A 337.1-nm laser diode (3.4 mW) transmitted through a specific dye cell and then yielded a 365-nm wavelength laser beam that was focused through 603 UPlanSApo/1.35 oil objective to yield a spot size of 0.5-1 mm. The time of cell exposure to the laser beam was ~3.5 nsec. The pulse energy was 170 mJ at 10 Hz. Images (FIG. 8) were taken by the same microscope with the CellSens software (Olympus).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of formula (VIII):

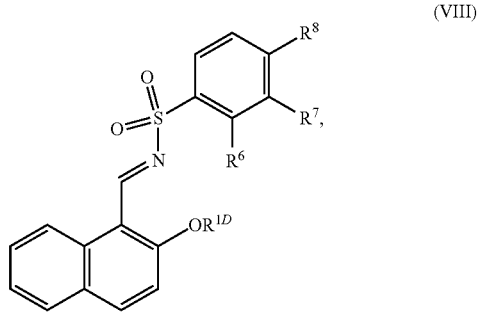

(VIII)

or a pharmaceutically acceptable salt thereof, wherein:
$R^{1D}$ is hydrogen or —CH₃;
$R^6$ is hydrogen or —C(O)—OR^{6C};
$R^7$ is hydrogen or halogen; and
$R^8$ is —OR^{8D}, —C(O)—OR^{8C}, or unsubstituted $C_2$-$C_4$ alkyl; and
$R^{6C}$, $R^{8C}$ and $R^{8D}$ are independently hydrogen or —CH₃.

2. A compound of formula (IX),

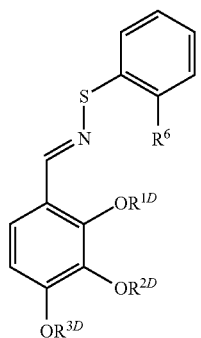

or a pharmaceutically acceptable salt thereof, wherein:
$R^{1D}$, $R^{2D}$, and $R^{3D}$ are independently hydrogen or unsubstituted $C_1$-$C_4$ alkyl; and
$R^6$ is hydrogen, halogen, —C(O)—$OR^{6C}$, —$OR^{6D}$, or unsubstituted $C_1$-$C_4$ alkyl; and
$R^{6C}$ and $R^{6D}$ are independently hydrogen or —$CH_3$.

3. The compound of claim 2, wherein:
$R^{1D}$, $R^{2D}$, and $R^{3D}$ are independently hydrogen or —$CH_3$.

4. The compound of claim 1, wherein the compound is:

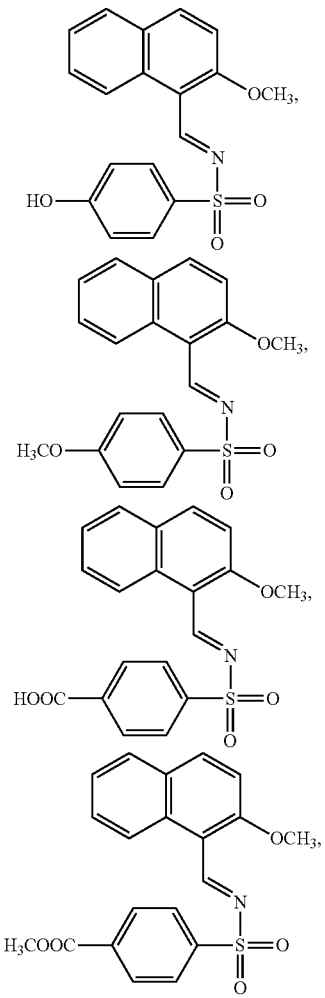

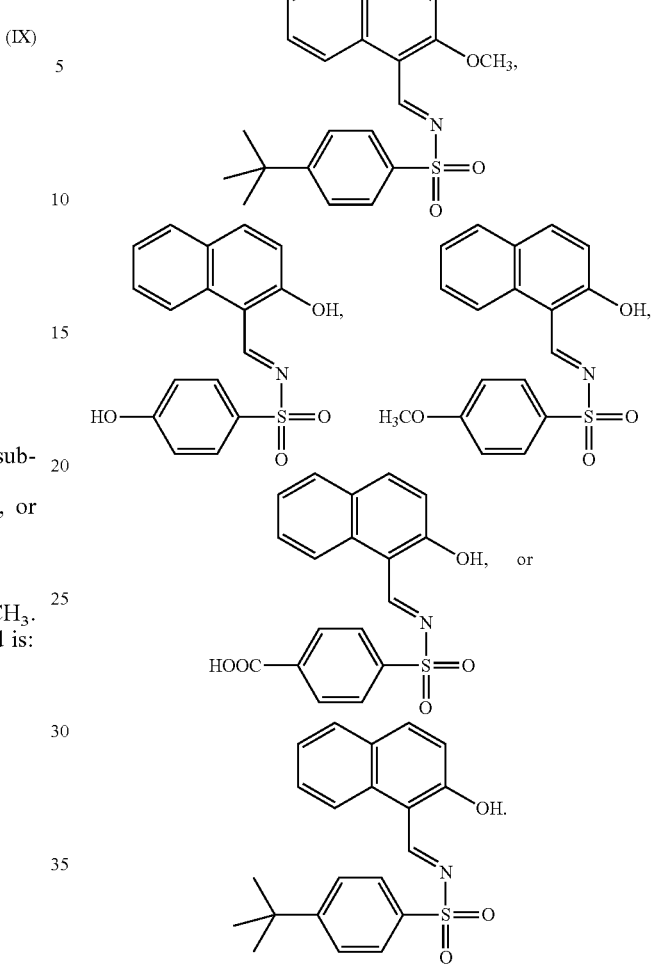

5. A method of treating cancer in a subject suffering therefrom, the method comprising administering to the subject an effective amount of a compound having formula (VIII),

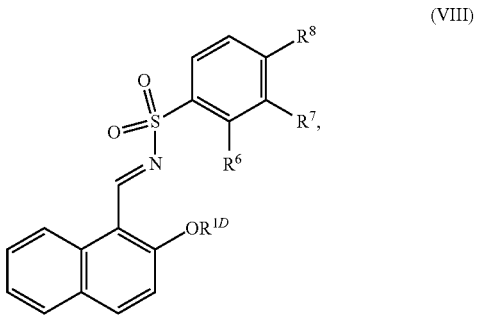

or a pharmaceutically acceptable salt thereof,
wherein:
$R^{1D}$ is hydrogen or —$CH_3$;
$R^6$ is hydrogen or —C(O)—$OR^{6C}$;
$R^7$ is hydrogen or halogen; and
$R^8$ is —$OR^{8D}$, —C(O)—$OR^{8C}$, or unsubstituted $C_2$-$C_4$ alkyl; and $R^{6C}$, $R^{8C}$, and $R^{8D}$ are independently hydrogen or —CH$_3$;
wherein the cancer is selected from: breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

6. A method of treating cancer in a subject suffering therefrom, the method comprising administering to the subject an effective amount of a compound having formula (IX):

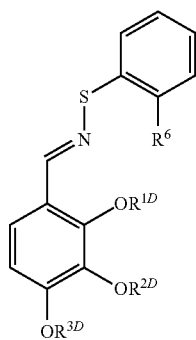

(IX)

or a pharmaceutically acceptable salt thereof, wherein:
$R^{1D}$, $R^{2D}$, and $R^{3D}$ are independently hydrogen or unsubstituted C$_1$-C$_4$ alkyl;
$R^6$ is hydrogen, halogen, —C(O)—OR$^{6C}$, —OR$^{6D}$, or unsubstituted C$_1$-C$_4$ alkyl, and
$R^{6C}$ and $R^{6D}$ are independently hydrogen or —CH$_3$;
wherein the cancer is selected from: breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

7. The method of claim 6, wherein:
$R^{1D}$, $R^{2D}$, and $R^{3D}$ are independently hydrogen or —CH$_3$.

8. The method of claim 5, wherein the compound is:

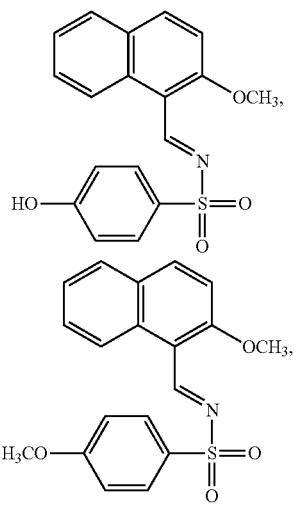

-continued

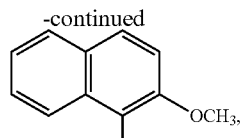

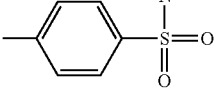

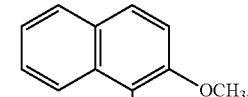

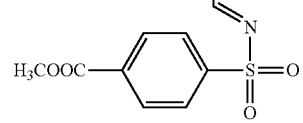

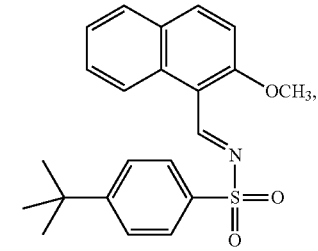

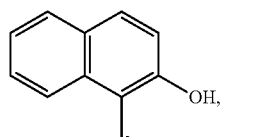 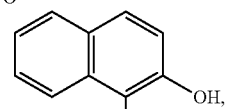

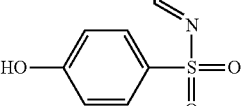

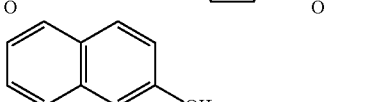

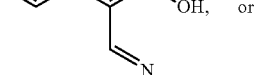, or

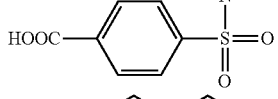

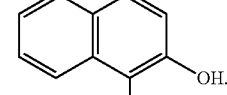

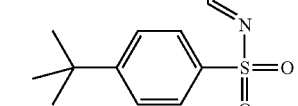

9. The method of claim 5, wherein the compound inhibits poly(ADP-ribose) glycohydrolase (PARG) in a cancer cell; wherein the cancer is selected from: breast cancer, ovarian cancer, lung cancer, pancreatic cancer, glioblastoma, uterine cancer, bladder cancer, esophagus cancer, gastric cancer, head and neck cancer, cholangiocarcinoma, mesothelioma, prostate cancer, colon carcinoma, fallopian tube cancer, lymphoma and leukemia.

10. A method of inhibiting a poly(ADP-ribose) glycohydrolase (PARG), the method comprising contacting the PARG with a compound having a formula (VIII) or (IX):

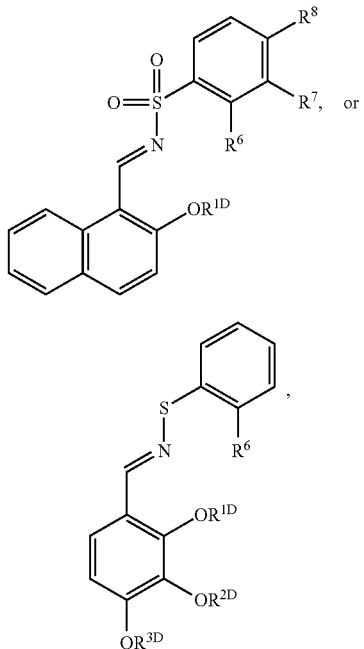

or a pharmaceutically acceptable salt thereof, wherein:
- $R^{1D}$ is hydrogen or —CH$_3$;
- $R^6$ is hydrogen or —C(O)—OR$^{6C}$;
- $R^7$ is hydrogen or halogen;
- $R^8$ is —OR$^{8D}$, —C(O)—OR$^{8C}$, or unsubstituted C$_2$-C$_4$ alkyl;
- $R^{6C}$, $R^{8C}$, and $R^{8D}$ are independently hydrogen or —CH$_3$; and
- $R^{2D}$, and $R^{3D}$ are independently hydrogen or unsubstituted C$_1$-C$_4$ alkyl.

11. A pharmaceutical composition comprising a pharmaceutically acceptable excipient and a compound having formula (VIII) or (IX),

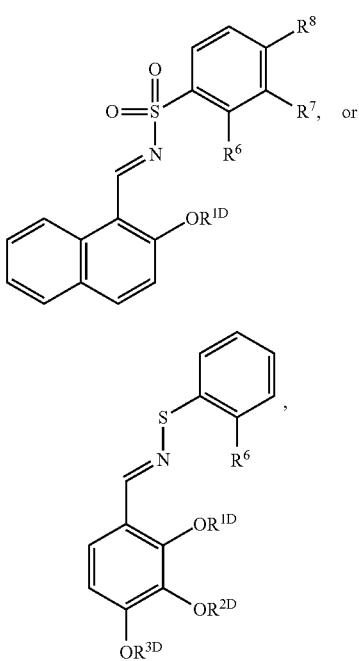

or a pharmaceutically acceptable salt thereof, wherein:
- $R^{1D}$ is hydrogen or —CH$_3$;
- $R^6$ is hydrogen or —C(O)—OR$^{6C}$;
- $R^7$ is hydrogen or halogen;
- $R^8$ is —OR$^{8D}$, —C(O)—OR$^{8C}$, or unsubstituted C$_2$-C$_4$ alkyl;
- $R^{6C}$, $R^{8C}$, and $R^{8D}$ are independently hydrogen or —CH$_3$; and
- $R^{2D}$, and $R^{3D}$ are independently hydrogen or unsubstituted C$_1$-C$_4$ alkyl.

* * * * *